United States Patent
Hanson et al.

(10) Patent No.: US 9,790,499 B2
(45) Date of Patent: Oct. 17, 2017

(54) FUNCTIONALLY-MODIFIED OLIGONUCLEOTIDES AND SUBUNITS THEREOF

(71) Applicant: Sarepta Therapeutics, Inc., Corvallis, OR (US)

(72) Inventors: Gunnar J. Hanson, Cambridge, MA (US); Dwight D. Weller, Corvallis, OR (US); Bao Zhong Cai, Corvallis, OR (US); Ming Zhou, Coppell, TX (US)

(73) Assignee: SAREPTA THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 15/007,017

(22) Filed: Jan. 26, 2016

(65) Prior Publication Data
US 2016/0376587 A1    Dec. 29, 2016

Related U.S. Application Data

(63) Continuation of application No. 14/358,992, filed as application No. PCT/US2012/065350 on Nov. 15, 2012, now Pat. No. 9,278,987.

(60) Provisional application No. 61/561,806, filed on Nov. 18, 2011.

(51) Int. Cl.
| | | |
|---|---|---|
| C12N 15/113 | (2010.01) | |
| C07H 21/00 | (2006.01) | |
| C07F 9/6558 | (2006.01) | |
| C07F 9/6561 | (2006.01) | |
| C07F 9/6584 | (2006.01) | |

(52) U.S. Cl.
CPC ........ *C12N 15/113* (2013.01); *C07F 9/65583* (2013.01); *C07F 9/65586* (2013.01); *C07F 9/65616* (2013.01); *C07F 9/65846* (2013.01); *C07H 21/00* (2013.01); *C12N 15/1131* (2013.01); *C12N 2310/11* (2013.01); *C12N 2310/314* (2013.01); *C12N 2310/3233* (2013.01); *C12N 2310/346* (2013.01); *C12N 2310/351* (2013.01); *C12N 2310/353* (2013.01); *C12N 2310/3513* (2013.01)

(58) Field of Classification Search
CPC .............. C07F 9/65583; C07F 9/65586; C07F 9/65616; C07F 9/65846; C07H 21/00
USPC ............................ 540/467, 542; 544/123, 82
See application file for complete search history.

(56) References Cited

U.S. PATENT DOCUMENTS

| | | |
|---|---|---|
| 5,034,506 A | 7/1991 | Summerton et al. |
| 5,138,045 A | 8/1992 | Cook et al. |
| 5,142,047 A | 8/1992 | Summerton et al. |
| 5,166,315 A | 11/1992 | Summerton et al. |
| 5,185,444 A | 2/1993 | Summerton et al. |
| 5,212,295 A | 5/1993 | Cook |
| 5,217,866 A | 6/1993 | Summerton et al. |
| 5,218,105 A | 6/1993 | Cook et al. |
| 5,223,168 A | 6/1993 | Holt |
| 5,378,825 A | 1/1995 | Cook et al. |
| 5,386,023 A | 1/1995 | Sanghvi et al. |
| 5,457,191 A | 10/1995 | Cook et al. |
| 5,459,255 A | 10/1995 | Cook et al. |
| 5,506,337 A | 4/1996 | Summerton et al. |
| 5,506,351 A | 4/1996 | McGee |
| 5,521,063 A | 5/1996 | Summerton et al. |
| 5,521,302 A | 5/1996 | Cook et al. |
| 5,539,082 A | 7/1996 | Nielsen et al. |
| 5,541,307 A | 7/1996 | Cook et al. |
| 5,554,746 A | 9/1996 | Ravikumar et al. |
| 5,571,902 A | 11/1996 | Ravikumar et al. |
| 5,576,302 A | 11/1996 | Cook et al. |
| 5,578,718 A | 11/1996 | Cook et al. |
| 5,580,767 A | 12/1996 | Cowsert et al. |
| 5,587,361 A | 12/1996 | Cook et al. |
| 5,587,469 A | 12/1996 | Cook et al. |
| 5,587,470 A | 12/1996 | Cook et al. |
| 5,599,797 A | 2/1997 | Cook et al. |
| 5,602,240 A | 2/1997 | De Mesmaeker et al. |
| 5,608,046 A | 3/1997 | Cook et al. |
| 5,610,289 A | 3/1997 | Cook et al. |
| 5,698,685 A | 12/1997 | Summerton et al. |
| 5,702,891 A | 12/1997 | Kolberg et al. |
| 5,734,039 A | 3/1998 | Calabretta et al. |
| 5,749,847 A | 5/1998 | Zewert et al. |
| 5,801,154 A | 9/1998 | Baracchini et al. |
| 5,892,023 A | 4/1999 | Pirotzky et al. |
| 5,955,318 A | 9/1999 | Simons et al. |

(Continued)

FOREIGN PATENT DOCUMENTS

| | | |
|---|---|---|
| JP | H05-504563 A | 7/1993 |
| JP | 2002-167441 A | 6/2002 |

(Continued)

OTHER PUBLICATIONS

Loke et al., "Characterization of Oligonucleotide transport into living cells," Proc. NaNatl.Acad. Sci USA 86(10):3474-3478, May 1989.

(Continued)

*Primary Examiner* — Kristin Vajda

(74) *Attorney, Agent, or Firm* — Brian C. Trinque; Lathrop Gage LLP

(57) ABSTRACT

Functionally-modified oligonucleotide analogs comprising modified intersubunit linkages and/or modified 3' and/or 5'-end groups are provided. The disclosed compounds are useful for the treatment of diseases where inhibition of protein expression or correction of aberrant mRNA splice products produces beneficial therapeutic effects.

16 Claims, 4 Drawing Sheets

(56) References Cited

U.S. PATENT DOCUMENTS

| | | |
|---|---|---|
| 6,030,954 A | 2/2000 | Wu et al. |
| 6,060,456 A | 5/2000 | Arnold, Jr. et al. |
| 6,133,246 A | 10/2000 | McKay et al. |
| 6,174,868 B1 | 1/2001 | Anderson et al. |
| 6,228,579 B1 | 5/2001 | Zyskind et al. |
| 6,239,265 B1 | 5/2001 | Cook |
| 6,245,747 B1 | 6/2001 | Porter et al. |
| 6,262,241 B1 | 7/2001 | Cook et al. |
| 6,306,993 B1 | 10/2001 | Rothbard et al. |
| 6,365,351 B1 | 4/2002 | Iversen |
| 6,391,542 B1 | 5/2002 | Anderson et al. |
| 6,495,663 B1 | 12/2002 | Rothbard et al. |
| 6,548,651 B1 | 4/2003 | Nielsen et al. |
| 6,677,153 B2 | 1/2004 | Iversen |
| 6,784,291 B2 | 8/2004 | Iversen et al. |
| 6,828,105 B2 | 12/2004 | Stein et al. |
| 6,841,542 B2 | 1/2005 | Bartelmez et al. |
| 7,049,431 B2 | 5/2006 | Iversen |
| 7,094,765 B1 | 8/2006 | Iversen et al. |
| 7,115,374 B2 | 10/2006 | Linnen |
| 7,402,574 B2 | 7/2008 | Iversen et al. |
| 7,507,196 B2 | 3/2009 | Stein et al. |
| 7,524,829 B2 | 4/2009 | Stein et al. |
| 7,582,615 B2 | 9/2009 | Neuman et al. |
| 7,625,873 B2 | 12/2009 | Geller et al. |
| 7,790,694 B2 | 9/2010 | Geller et al. |
| 7,807,801 B2 | 10/2010 | Iversen et al. |
| 7,838,657 B2 | 11/2010 | Singh et al. |
| 7,943,762 B2 | 5/2011 | Weller et al. |
| 8,030,291 B2 | 10/2011 | Stein et al. |
| 8,030,292 B2 | 10/2011 | Stein et al. |
| 8,067,569 B2 | 11/2011 | Iversen et al. |
| 8,076,476 B2 | 12/2011 | Reeves et al. |
| 8,084,433 B2 | 12/2011 | Iversen et al. |
| 8,129,352 B2 | 3/2012 | Iversen et al. |
| 8,168,604 B2 | 5/2012 | Stein et al. |
| 8,198,429 B2 | 6/2012 | Iversen et al. |
| 8,299,206 B2 | 10/2012 | Fox et al. |
| 8,329,668 B2 | 12/2012 | Stein et al. |
| 8,779,128 B2 | 7/2014 | Hanson et al. |
| 8,969,551 B2 | 3/2015 | Ueda |
| 9,278,987 B2 * | 3/2016 | Hanson .................. C07H 21/00 |
| 2003/0095953 A1 | 5/2003 | Cabot et al. |
| 2003/0166588 A1 | 9/2003 | Iversen et al. |
| 2003/0171335 A1 | 9/2003 | Stein et al. |
| 2003/0175767 A1 | 9/2003 | Davis et al. |
| 2003/0224353 A1 | 12/2003 | Stein et al. |
| 2004/0110296 A1 | 6/2004 | Vargeese et al. |
| 2004/0161844 A1 | 8/2004 | Baker et al. |
| 2004/0259108 A1 | 12/2004 | Linnen et al. |
| 2005/0096291 A1 | 5/2005 | Iversen et al. |
| 2005/0107312 A1 | 5/2005 | Keicher et al. |
| 2005/0176661 A1 | 8/2005 | Vaillant et al. |
| 2005/0234002 A1 | 10/2005 | Mourich et al. |
| 2006/0104989 A1 | 5/2006 | Edwards et al. |
| 2006/0148747 A1 | 7/2006 | Stein et al. |
| 2006/0149046 A1 | 7/2006 | Arar |
| 2006/0269911 A1 | 11/2006 | Iversen et al. |
| 2007/0004661 A1 | 1/2007 | Stein et al. |
| 2007/0021362 A1 | 1/2007 | Geller et al. |
| 2007/0037763 A1 | 2/2007 | Stein et al. |
| 2007/0066556 A1 | 3/2007 | Stein et al. |
| 2007/0082336 A1 | 4/2007 | Johnsson et al. |
| 2007/0265214 A1 | 11/2007 | Stein et al. |
| 2008/0160225 A1 | 7/2008 | Lowe et al. |
| 2008/0194463 A1 | 8/2008 | Weller et al. |
| 2009/0082547 A1 | 3/2009 | Iversen et al. |
| 2009/0131624 A1 | 5/2009 | Reeves et al. |
| 2009/0131632 A1 | 5/2009 | Fox et al. |
| 2010/0016215 A1 | 1/2010 | Moulton et al. |
| 2010/0105120 A1 | 4/2010 | Zebala |
| 2010/0105865 A1 | 4/2010 | Telford et al. |
| 2010/0130591 A1 | 5/2010 | Sazani et al. |
| 2010/0137408 A1 | 6/2010 | Geller et al. |
| 2010/0234280 A1 | 9/2010 | Geller et al. |
| 2010/0234281 A1 | 9/2010 | Weller et al. |
| 2011/0118334 A1 | 5/2011 | Iversen |
| 2011/0224283 A1 | 9/2011 | Iversen |
| 2012/0065169 A1 | 3/2012 | Hanson et al. |
| 2012/0122769 A1 | 5/2012 | Iversen |
| 2012/0289457 A1 | 11/2012 | Hanson |
| 2013/0288369 A1 | 10/2013 | Iversen |
| 2013/0289091 A1 | 10/2013 | Geller et al. |
| 2014/0024698 A1 | 1/2014 | Kole et al. |
| 2014/0213737 A1 | 7/2014 | Weller et al. |
| 2015/0073140 A1 | 3/2015 | Hanson et al. |

FOREIGN PATENT DOCUMENTS

| | | |
|---|---|---|
| JP | 2004-537517 A | 12/2004 |
| JP | 2008-509701 A | 4/2008 |
| JP | 2008-513012 A | 5/2008 |
| JP | 2010-505741 A | 2/2010 |
| JP | 2014-515762 A | 7/2014 |
| WO | 91/09033 A1 | 6/1991 |
| WO | 93/01286 A2 | 1/1993 |
| WO | 97/40854 A2 | 11/1997 |
| WO | 00/56740 A1 | 9/2000 |
| WO | 01/49775 A2 | 7/2001 |
| WO | 01/76636 A2 | 10/2001 |
| WO | 02/079467 A2 | 10/2002 |
| WO | 02/092616 A1 | 11/2002 |
| WO | 02/094250 A2 | 11/2002 |
| WO | 03/033657 A2 | 4/2003 |
| WO | 2004/097017 A2 | 11/2004 |
| WO | 2005/007805 A2 | 1/2005 |
| WO | 2005/030800 A2 | 4/2005 |
| WO | 2005/065268 A2 | 7/2005 |
| WO | 2005/115479 A2 | 12/2005 |
| WO | 2006/000057 A1 | 1/2006 |
| WO | 2006/033933 A2 | 3/2006 |
| WO | 2006/047683 A2 | 5/2006 |
| WO | 2006/050414 A2 | 5/2006 |
| WO | 2006/085973 A2 | 8/2006 |
| WO | 2006/086667 A2 | 8/2006 |
| WO | 2006/121951 A2 | 11/2006 |
| WO | 2007/002390 A2 | 1/2007 |
| WO | 2007/009094 A2 | 1/2007 |
| WO | 2007/030576 A2 | 3/2007 |
| WO | 2007/030691 A2 | 3/2007 |
| WO | 2007/103529 A2 | 9/2007 |
| WO | 2008/018795 A1 | 2/2008 |
| WO | 2008/036127 A2 | 3/2008 |
| WO | 2008/036406 A1 | 3/2008 |
| WO | 2009/064471 A1 | 5/2009 |
| WO | 2010/048586 A1 | 4/2010 |
| WO | 2010/120820 A1 | 10/2010 |
| WO | 2010/148249 A1 | 12/2010 |
| WO | 2011/060320 A1 | 5/2011 |
| WO | 2011/150408 A2 | 12/2011 |
| WO | 2012/150960 A1 | 11/2012 |
| WO | 2013/142087 A1 | 9/2013 |

OTHER PUBLICATIONS

Lopez de Quinto et al., "Involvement of the Aphthovirus RNA Region Located between the Two Functional AUGs in Start Codon Selection," Virology 255(2):324-336, 1999.

Lu et al., "Therapeutic dendritic-cell vaccine for chronic HIV-1 infection," Nature Medicine 10(12):1359-1365, Dec. 2004.

Lutkenhaus et al., "Bacterial Cell Division and the Z Ring," Annu. Rev. Biochem. 66:93-116, 1997.

Manoharan, "Oligonucleotide Conjugates as Potential Antisense Drugs with Improved Uptake, Biodistribution, Targeted Delivery, and Mechanism of Action," Antisense & Nucleic Acid Drug Development 12:103-128, 2002.

Markoff, "5'- and 3'-Noncoding Regions in Flavivirus RNA," Advances in Virus Research 59:177228, 2003.

Mellbye et al., "Variations in amino acid composition of antisense peptide-phosphorodiamidate morpholino oligomer affect potency against *Escherichia coli* in vitro and in vivo," Antimicrobial Agents and Chemotherapy 53(2):525-530, Feb. 2009.

(56) References Cited

OTHER PUBLICATIONS

Mertes et al., "Synthesis of Carbonate Analogs of Dinucleosides. 3'-Thymidinyl 5'-Thymidinyl Carbonate, 3'-Thymidinyl 5'-(5-Fluoro-2'-Deoxyuridinyl) Carbonate, and 3'-(5-Fluoro-2'-deoxyuridinyl) 5'-Thymidinyl Carbonate," J. Med. Chem. 12(1):154-157, 1969.
Meyer et al., "Arenaviruses: Geonomic RNAs, Transcription and Replication," Curr. Top. Microbiol. Immunol. 262:139-157, 2002.
Micklefield, "Backbone Modification of Nucleic Acids: Synthesis, Structure and Therapeutic Applications," Current Medicinal Chemistry 8:1157-1179, 2001.
Mitev et al., "Inhibition of Intracellular Growth of *Salmonella enteric* Serovar Typhimurium in Tissue Culture by Antisense Peptide-Phosphorodiamidate Morpholino Oligomer," Antimicrobial Agents and Chemotherapy 53(9):3700-3704, 2009.
Miyada et al., "[6] Oligonucleotide Hybridization Techniques," Methods in Enzymology 154:94-107, 1987.
Mohamadzadeh et al., "Dendritic cells: In the forefront of immunopathogenesis and vaccine development—A review," Journal of Immune Based Therapies and Vaccines 2(1):1-11, Jan. 13, 2004.
Morcos, "Achieving Efficient Delivery of Morpholino Oligos in Cultured Cells," Genesis 30:94-102, 2001.
Moulton et al., "Cellular Uptake of Antisense Morpholino Oligomers Conjugated to Arginine-Rich Peptides," Bioconjugate Chemistry 15:290-299, 2004.
Moulton et al., "Delivery of Antisense Phosphorodiamidate Morpholino Oligomers by Arginine-Rich Peptides", in Proceedings of the 226th ACS National Meeting, Abstract No. 75, American Chemical Society, New York, NY, Sep. 7-11, 2003, 2 pages.
Moulton et al., "HIV Tat peptide enhances cellular delivery of antisense morpholino oligomers," Antisense Nucleic Acid Drug Dev. 13(1):31-43, 2003.
Moulton et al., "Morpholinos and their peptide conjugates: Therapeutic promise and challenge for Duchenne muscular dystrophy," Biochimica et Biophysica Acta 1798:2296-2303, 2010.
Moulton et al., "Peptide-assisted delivery of steric-blocking antisense oligomers," Current Opinion in Molecular Therapeutics 5(2):123-132, 2003.
Nekhotiaeva et al., "Inhibition of *Staphylococcus aureus* Gene Expression and Growth Using Antisense Peptide Nucleic Acids," Molecular Therapy 10(4):652-659, 2004.
Nelson et al., "Arginine-Rich Peptide Conjugation to Morpholino Oligomers: Effects on Antisense Activity and Specificity," Bioconjugate Chem. 16:959-966, 2005.
Neuman et al., "Antisense Morpholino-Oligomers Directed against the 5' End of the Genome Inhibit Coronavirus Proliferation and Growth," Journal of Virology 78(11):5891-5899, 2004.
Nielsen et al., "Sequence-selective recognition of DNA by strand displacement with a thymine-substituted polyamide," Science 254(5037):1497-1500, 1991.
Nielsen, "Peptide nucleic acids as antibacterial agents via the antisense principle," Exp. Opin. Invest. Drugs 10 (2):331-341, 2001.
Nielsen, "Peptide nucleic acids: on the road to new gene therapeutic drugs," Pharmacol. Toxicol. 86(1):3-7, 2000.
Nikaido, "Transport across the bacterial outer membrane," J Bioenerg Biomembr 25(6):581-589, 1993.
Orr et al., "Patent review: Therapeutic applications for antisense oligonucleotides 1999-2000," Current Opinion in Molecular Therapeutics 2(3):325-331, 2000.
Orabona et al., "CD28 induces immunostimulatory signals in dendritic cells via CD80 and CD86," Nature Immunology. 5(11):1134-1142, Nov. 2004.
D'Ryan et al., "Rotavirus, Enteric, Adenoviruses, Norwalk Virus, and Other Gastroenteritis Tract Viruses," Chapter 22, Specter et al., (Eds.) Clinical Virology Manual, Elsevier, New York,1992, pp. 361-396.
Palu et al. "In pursuit of new developments diseases," Journal of Biotechnology 68:1-13, 1999.
Pardigon et al., "Cellular Proteins Bind to the 3' End of Sindbis Virus Minus-Strand RNA," Journal of Virology 66 (2):1007-1015, 1992.
Pardigon et al., "Multiple Binding Sites for Cellular Proteins in the 3' End of Sindbis Alphavirus Minus-Sense RNA," Journal of Virology 67(8):5003-5011, 1993.
Pari et al., "Potent antiviral activity of an antisense oligonucleotide complementary to the intron-exon boundary of human cytomegalovirus genes UL36 and UL37," Antimicrobial Agents and Chemotherapy 39(5):1157-1161, May 1995.
Partridge et al., "A Simple Method for Delivering Morpholino Antisense Oligos into the Cytoplasm of Cells," Antisense & Nucleic Acid Drug Dev. 6:169-175, 1996.
Paul, Aniko V., "Possible Unifying Mechanism of Picornavirus Genome Replication," B. L. Semler et al., (Eds.), Molecular Biology of Picornaviruses, ASM Press, Wastington, DC, 2002, Chap. 19, pp. 227-246.
Peters et al., "An Introduction to Ebola: The Virus and the Disease," J. Infect. Dis. 1 79(Suppl 1)ix-xvi, 1999.
Petersen et al., "Synthesis of thymidine dimers containing piperazine in the internucleoside linkage and their incorporation into oligodeoxynucleotides," Tetrahedron 51:2145-2154, 1995.
Polacco et al., "A mutant of *Escherichia coli* conditionally defective in the synthesis of holo-[acyl carrier protein]," J. Biol. Chem. 256(11):5750-5754, 1981.
Polyak et al., "5' termini of Pichinde arenavirus S RNAs and mRNAs contain nontemplated nucleotides," Journal of Virology 69(5):3211-3215, 1995.
Rahman et al., "Antibacterial Activity and Inhibition of Protein Synthesis in *Escherichia coli* by Antisense DNA Analogs," Antisense Research and Development 1(4):319-327, 1991.
Raviprakash et al., "Inhibition of Dengue Virus by Novel, Modified Antisense Oligonucleotides," Journal of Virology 69(1):69-74, 1995.
Roehl et al., "Poliovirus Infection Enhances the Formation of Two Ribonucleoprotein Complexes at the 3' End of Viral Negative-Strand RNA," Journal of Virology 69(5):2954-2961, 1995.
Roehl et al., "Processing of a Cellular Polypeptide by 3CD Proteinase is Required for Poliovirus Ribonucleoprotein Complex Formation," Journal of Virology 71(1):578-585, 1997.
Rothbard et al., "Arginine-Rich Molecular Transporters for Drug Delivery: Role of Backbone Spacing in Cellular Uptake," J. Med. Chem. 45:3612-3618, 2002.
Salomon et al., "Complexities of CD281B7: CTLA-4 Costimulatory Pathways in Autoimmunity and Transplantation," Annu. Rev. Immunol. 19:225-252, 2001.
Sanchez et al., "Sequence analysis of the Ebola virus genome: organization, genetic elements, and comparison with the genome of Marburg virus," Virus Research 29:215-240, 1993.
Sankar et al., "Antisense oligonucleotide inhibition of encephalomyocarditis virus RNA translation," Eur.J. Biochem. 184:39-45, 1989.
Sazani et al., "Systemically delivered antisense oligomers upregulate gene expression in mouse tissues," Nature Biotechnology 20:1228-1233, Dec. 2002.
Siprashvili et al., "Gene Transfer via Reversible Plasmid Condensation with Cysteine-Flanked, Internally Spaced Arginine-Rich Peptides," Human Gene Therapy 14:1225-1233, 2003.
Smith et al., "Antisense treatment of Caliciviridae: An emerging disease agent of animals and humans," Current Opinion in Molecular Therapeutics 4(2):177-184, 2002.
Smith et al., "Calicivirus Emergence from Ocean Reservoirs: Zoonotic and Interspecies Movements," Emerging Infectious Diseases 4(1):13-20, 1998.
Smith et al., "Secondary structure and hybridization accessibility of the hepatitis C virus negative strand RNA 5'-terminus," Journal of Viral Hepatitis 11:115-123, 2004.
Stein et al., "A Specificity Comparison of Four Antisense Types: Morpholino, 2'-0-Methyl RNA, DNA, and Phosphorothioate DNA," Antisense & Nucleic Acid Drug Development 7:151-157, 1997.

(56) References Cited

OTHER PUBLICATIONS

Stein et al., "Antisense Antiviral Agent and Method for Treating ssRNA Viral Infection," Office Action mailed Feb. 17, 2010, for Corresponding U.S. Appl. No. 11/431,968, 19 pages.
Stein et al., "Inhibition of Vesivirus Infections in Mammalian Tissue Culture with Antisense Morpholino Oligomers," Antisense & Nucleic Acid Drug Development 11:317-325, 2001.
Summerton et al., "Morpholino and phosphorothioate antisense oligomers compared in cell-free and in-cell systems," Antisense Nucleic Acid Drug Dev. 7(2):63-70, 1997.
Summerton et al., "Morpholino antisense oligomers: design, preparation, and properties," Antisense Nucleic Acid Drug Dev. 7(3):187-195, 1997.
Summerton, "Morpholino antisense oligomers: the case for an RNase H-independent structural type," Biochimica et Biophysica Acta 1489:141-158, 1999.
Summerton, "Morpholinos and PNAs Compared," Ch. 6 In; Peptide Nucleic Acids, Morpholinos, and Related Antisense Biomolecules. Eds.: Janson et al. Landes Publishers. pp. 89-113, 2006.
Tan et al., "Peptide Nucleic Acid Antisense Oligomer as a Therapeutic Strategy against Bacterial Infection: Proof of Principle Using Mouse Intraperitoneal Infection," Antimicrobial Agents and Chemotherapy 49(8):3203-3207, Aug. 2005.
Taylor et al., "Antisense oligonucleotides: a systematic high-throughput approach to target validation and gene function Determination," DDT 4(12):562-567, 1999.
Thiel et al., "Infectious RNA transcribed in vitro from a cDNA copy of the human coronavirus genome cloned in vaccinia virus," Journal of General Virology 82:1273-1281, 2001.
Tilley et al., "Antisense peptide-phosphorodiamidate morpholino oligomer conjugate: dose-response in mice infected with Escherichia coli," Journal of Antimicrobial Chemotherapy 59:6673, 2007.
Tilley et al., "Gene-Specific Effects of Antisense Phosphorodiamidate Morpholino Oligomer-Peptide Conjugates on Escherichia coli and Salmonella enteric Serovar Typhimurium in Pure Culture and in Tissue Culture," Antimicrobial Agents and Chemotherapy 50(8):2789-2796, Aug. 2006.
Toulme et al., "Targeting RNA structures by antisense oligonucleotides," Biochimie 78:663-673, 1996.
Uhlmann et al., "Antisense Oligonucleotides: A New Therapeutic Principle," Chemical Reviews 90(4):544-584, Jun. 1990.
Van der Merwe et al., "Molecular Interactions Mediating T Cell Antigen Recognition," Annu. Rev. Immunol. 21:659-684, 2003.
Vijayakrishnan et al., "An autoimmune disease-associated CTLA-4 splice variant lacking the B7 binding domain signals negatively in T cells," Immunity. 20(5):563-575, 2004.
Wages, Jr. et al. "Affinity Purification of RNA: Sequence-Specific Capture by Nonionic Morpholino Probes," BioTechniques 23:1116-1121, 1997.
Wang et al., "Assessment of the utilization of the antisense RNA strategy to Identify essential genes in heterologous bacteria," FEMS Microbiology Letters 220(2):171-176, 2003.
Wang et al., "Specific Inhibition of Coxsackievirus B3 Translation and Replication by Phosphorothioate Antisense Dligodeoxynucleotides," Antimicrobial Agents and Chemotherapy 45(4):1043-1052, 2001.
Wang et al., "Synthesis of Antisense Phosphothioate Oligodeoxynucleotides of Dengue Fever Virus and their Anti-Viral Activity," Progress of Biochemistry and Biophysics 24(1), 12 pages, 1997.
Warfield et al., "Gene-Specific Countermeasures against Ebola Virus Based on Antisense Phosphorodiamidate Morpholino Oligomers," PLoS Pathogens 2(1):5-13, 2006.
Warfield et al., "Role of Natural Killer Cells in Innate Protection Against Lethal Ebola Virus Infection," The Journal of Experimental Medicine 200(2):169-179, 2004.
Wasem et al., "Sensitizing antigen-specific CD8+ T cells for accelerated suicide causes immune incompetence," The Journal of Clinical Investigation 111(8):1191-1199, Apr. 2003.
Wei et al., "Human immunodeficiency virus type-1 reverse transcription can be inhibited in vitro by oligonucleotides that target both natural and synthetic tRNA primers," Nucleic Acids Research 28(16):3065-3074, 2000.
Weller et al., "Oligonucleotide Analogs Having Cationic Intersubunit Linkages," Advisory Action, mailed Oct. 28, 2010, U.S. Appl. No. 11/801,885, 6 pages.
Weller et al., "Oligonucleotide Analogs Having Cationic Intersubunit Linkages," Office Action, mailed Aug. 18, 2010, U.S. Appl. No. 11/801,885, 6 pages.
Vender et al., "The design, synthesis, and evaluation of molecules that enable or enhance cellular uptake: peptoid molecular transporters," PNAS 97(24):13003-13008, Nov. 21, 2000.
Wiersinga, "Beyond Antibiotics: New Horizons in Treating Burkholderia Species Infections," The Journal of Infectious Diseases 201(12), Jun. 2010, 2 pages.
Williams et al., "Cationic lipids reduce time and dose of c-myc antisense oligodeoxynucleotides required to specifically inhibit Burkitt's lymphoma cell growth," Leukemia 10:1980-1989, 1996.
Wilson et al., "Naturally Occurring Dicistronic Cricket Paralysis Virus RNA Is Regulated by Two Internal Ribosome Entry Sites," Molecular and Cellular Biology 20(14):4990-4999, Jul. 2000.
Wu et al., "Receptor-mediated in Vitro Gene Transformation by a Soluble DNA Carrier System," The Journal of Biological Chemistry 262(10):4429-4432, Apr. 5, 1987.
Wu et al., "Specific Inhibition of Hepatitis B Viral Gene Expression in Vitro by Targeted Antisense Oligonucleotides," The Journal of Biological Chemistry 267(18):12436-124-39, 1992.
Xu et al., "Viral haemorrhagic disease of rabbits in the People's Republic of China: epidemiology and virus characterisation," Rev. sci. tech. Off int. Epiz. 10(2):393-408, 1991.
Yakubov et al., "Mechanism of oligonucleotide uptake by cells: Involvement of specific receptors?," Proc. Natl. Acad. Sci. USA 86(17):6454-6458, 1989.
Youngblood et al., "Stability of Cell-Penetrating Peptide—Morpholino Oligomer Conjugates in Human Serum and in Cells," Bioconjugate Chem. 18:50-60, 2007.
Zhang et al, "RNA interference in mammalian cells by siRNAs modifiedwith morpholino nucleoside analogues," Bioorganic & Medicinal Chemistry, 17:2441-2446, 2009.
Zhang et al., "Antisense Oligonucleotide Inhibition of Hepatitis C Virus (HCV) Gene Expression in Livers of Mice Infected with an HCV-Vaccinia Virus Recombinant," Antimicrobial Agents and Chemotherapy 43(2):347-353, 1999.
Zhang et al., "Polar Allele Duplication for Transcriptional Analysis of Consecutive Essential Genes: Application to a Cluster of Escherichia coli Fatty Acid Biosynthetic Genes," Journal of Bacteriology 178(12):3614-3620, Jun. 1996.
Zollinger et al., "Meningococcal vaccines—present and future," Transactions of Royal Society of Tropical Medicine and Hygiene 85(Supp. 1):37-43, 1991.
Zuker, "Mfold web server for nucleic acid folding and hybridization prediction," Nucleic Acids Research 31(13):3406-3415, 2003.
Agrawal et al., "Antisense therapeutics: is it as simple as complementary base recognition?," Molecular Med. Today 6:72-81, 2000.
Agrawal et al., "Oligodeoxynucleoside phosphoramidates and phosphorothioates as inhibitors of human immunodeficiency virus," Proc. Natl. Acad. Sci. USA 85:7079-7083, 1988.
Agrawal et al., "Site-specific excision from RNA by RNase H and mixed-phosphate-backbone oligodeoxynucleotides," Proc. Natl. Acad. Sci. USA 87:1401-1405, 1990.
Agrawal, "Antisense oligonucleotides: towards clinical trials," Tibtech 14(10):376-387, 1996.
Akhtar et al., "Interactions of antisense DNA oligonucleotide analogs with phospholipid membranes (liposomes)," Nucleic Acids Research 19(20)5551-5559, 1991.
Anderson et al., "Distribution of Equilibrative, Nitrobenzylthioinosine-Sensitive Nucleoside Transporters (ENT1) in Brain," Journal of Neurochemistry 73(2):867-873, 1999.
Anderson et al., "Inhibition of Human Cytomegalovirus Immediate-Early Gene Expression by an Antisense Oligonucleotide Complementary to Immediate-Early RNA," Antimicrobial Agents and Chemotherapy 40(9):2004-2011, Sep. 1996.

(56) References Cited

OTHER PUBLICATIONS

Arya et al., "Triple-helix formation of DNA oligomers with methylthiourea-linked nucleosides (DNmt): A kinetic and thermodynamic analysis," Proc. Natl. Acad. Sci. USA 96:4384-4389, Apr. 1999.
Bailey et al., "Cationic oligonucleotides can mediate specific inhibition of gene expression in Xenopus oocytes," Nucleic Acids Research 26(21):4860-4867, 1998.
Banerjee et al., "Interaction of picornavirus 2C polypeptide with the viral negative-strand RNA," Journal of General Virology 82:2621-2627, 2001.
Banerjee et al., "Interaction of Poliovirus-Encoded 2C12BC Polypeptides with the 3' Terminus Negative-Strand Cloverleaf Requires an Intact Stem-Loop b," Virology 280:41-51, 2001.
Banerjee et al., "Poliovirus-Encoded 2C Polypeptide Specifically Binds to the 3'-Terminal Sequences of Viral Negative-Strand RNA," Journal of Virology 71(12):9570-9578, 1997.
Banerjee et al., "Specific Interaction of Hepatitis C Virus Protease1Helicase NS3 with the 3'Terminal Sequences of Viral Positive- and Negative-Strand RNA," Journal of Virology 75(4):1708-1721, 2001.
Barawkar et al., "Synthesis, biophysical properties, and nuclease resistance properties of mixed backbone oligodeoxynucleotides containing cationic internucleoside guanidinium linkages: Deoxynucleic guanidine1DNA chimeras," Proc. Natl. Acad. Sci. USA 95:11047-11052, Sep. 1998.
Basler et al., "The Ebola virus VP35 protein functions as a type I IFN antagonist," PNAS 97(22):12289-12294, Oct. 24, 2000.
Blommers et al., "An approach to the structure determination of nucleic acid analogues hybridized to RNA. NMR studies of a duplex between 2'-OMe RNA and an oligonucleotide containing a single amide backbone modification," Nucleic Acids Research 22(20):4187-4194, 1994.
Bonham et al., "An assessment of the antisense properties of RNase H-competent and steric-blocking oligomers," Nucleic Acids Research 23(7):1197-1203, 1995.
Borio et al., "Hemorrhagic Fever Viruses as Biological Weapons: Medical and Public Health Management," JAMA 287 (18):2391-2405, May 8, 2002.
Borriello et al., "Differential Expression of Alternate Mb7-2 Transcripts," The Journal of Immunology 155(12):5490-5497, 1995.
Boudvillain et al., "Transplatin-Modified Oligo(2'-O-methyl ribonucleotide)s: A New Tool for Selective Modulation of Gene Expression," Biochemistry 36(10):2925-2931, 1997.
Bramhill, "Bacterial Cell Division," Annu Rev Cell Dev Biol 13:395-424, 1997.
Branch, "A good antisense molecule is hard to find," TIBS 23:45-50, 1998.
Brasey et al., "The Leader of Human Immunodeficiency Virus Type 1 Genomic RNA Harbors an Internal Ribosome Entry Segment That Is Active during the G21M Phase of the Cell Cycle," Journal of Virology 77(7):3939-3949, Apr. 2003.
Bray et al., "A Mouse Model for Evaluation of Prophylaxis and Therapy of Ebola Hemorrhagic Fever," The Journal of Infectious Diseases 178:651-661, 1998.
Burnett et al., "The Evolving Field of Biodefence: Therapeutic Developments and Diagnostics," Natural ReviewsIDrug Discovery 4:281-297, Apr. 2005.
Chambers et al., "CTLA-4-Mediated Inhibition in Regulation of T Cell Responses: Mechanisms and Manipulation in Tumor Immunotherapy," Annu. Rev. Immunol. 19:565-594, 2001.
Chirila et al., "The use of Synthetic polymers for delivery of therapeutic antisense oligodeoxynucleotides," Biomaterials 23:321-342, 2002.
Clarke et al., "Organization and Expression of Calicivirus Genes," Journal of Infectious Diseases 181(Suppl 2):S309-S316, 2000.
Connolly et al., "Pathogenesis of Experimental Ebola Virus Infection in Guinea Pigs," The Journal of Infectious Diseases 179(Suppl 1):S203-S217, 1999.
Corey et al., "Morpholino antisense oligonucleotides: tools for investigating vertebrate development," Genome Biology 2(5):reviews 1015.1-1015.3, Apr. 26, 2001.
Crooke, Antisense Research and Applications, ed. Springer, 1999, Chapter 1, "Basic Principles of Antisense Therapeutics," pp. 1-50.
Cross et al., "Solution Structure of an RNA-DNA Hybrid Duplex Containing a 3'-Thioformacetal Linker and an RNA A-Tract," Biochemistry 36(14):4096-4107, 1997.
Dagle et al., "Targeted elimination of zygotic messages in Xenopus laevis embryos by modified oligonucleotides possessing terminal cationic linkages," Nucleic Acids Research 28(10):2153-2157, 2000.
Deas et al., "Inhibition of Flavivirus Infections by Antisense Oligomers Specifically Suppressing Viral Translation and RNA Replication," Journal of Virology 79(8):4599-4609, Apr. 2005.
Deere et al., "Antisense Phosphorodiamidate Morpholino Oligomer Length and Target Position Effects on Gene-Specific Inhibition in *Escherichia coli*," Antimicrobial Agents and Chemotherapy 49(1):249-255, Jan. 2005.
Dempcy et al., "Design and synthesis of deoxynucleic guanidine: A polycation analogue of DNA," Proc. Natl. Acad. Sci. USA 91:7864-7868, Aug. 1994.
Dempcy et al., "Design and synthesis of ribonucleic guanidine: A polycationic analog of RNA," Proc. Natl. Acad. Sci. USA 93:4326-4330, Apr. 1996.
Ding et al., "An oligodeoxyribonucleotide N3'—P5' phosphoramidate duplex forms an A-type helix in solution," Nucleic Acids Research 24(2):354-360, 1996.
Donachie, "The Cell Cycle of *Escherichia Coli*," Annu. Rev. Microbiol. 47:199-230, 1993.
Dryselius et al., "The Translation Start Codon Region Is Sensitive to Antisense PNA Inhibition in *Escherichia coli*," Oligonucleotides 13:427-433, 2003.
Egholm et al., "PNA hybridizes to complementary oligonucleotides obeying the Watson-Crick hydrogen-bonding rules," Nature 365(6446):566-568, 1993.
Egli et al., "Probing the Influence of Stereoelectronic Effects on the Biophysical Properties of Oligonucleotides: Comprehensive Analysis of the RNA Affinity, Nuclease Resistance, and Crystal Structure of Ten 2'-0-Ribonucleic Acid Modifications," Biochemistry 44:9045-9057, 2005.
Ex Parte Thumm, 132 USPQ 66, 1961, 3 pages.
Feigner et al., "Lipofection: A highly efficient, lipid-mediated DNA-transfection procedure," Proc. Natl. Acad. Sci. USA 84(21):7413-7417, Nov. 1987.
Feldmann et al., "Classification, structure, and replication of filoviruses," Curr. Top. Microbiol. Immunol. 235:1-21, 1999.
Feldmann et al., "Ebola virus: from discovery to vaccine," Nature Reviews 3(8):677-685, Aug. 2003.
Feldmann et al., "Molecular biology and evolution of filoviruses," Arch. Virol. 7(Suppl.):81-100, 1993.
Freier, "Methods of Selecting Sites in RNA for Antisense Targeting," Crooke (ed.), Antisense Drug Technology: Principles, Strategies, and Applications, CRC Press, New York, 1999, Chap. 5, pp. 107-118, 14 pages.
Gait et al., "Synthetic Analogues of Polynucleotides. Part XII. Synthesis of Thymidine Derivatives containing an Oxyacetamido- or an Oxyformamido-linkage instead of a Phosphodiester Group," J. Chem. Soc. 0(14):1684-1686, 1974.
Galloway et al., "A mutant of *Escherichia coli* defective in the first step of endotoxin biosynthesis," J. Biol. Chem. 265(11):6394-6402, 1990.
Gee et al., "Assessment of High-Affinity Hybridization, RNase H Cleavage, and Covalent Linkage in Translation Arrest by Antisense Oligonucleotides," Antisense & Nucleic Acid Drug Development 8(2):103-111, 1998.
Geisbert et al., "Ebola virus: new insights into disease aetiopathology and possible therapeutic interventions," Expert Reviews in Molecular Medicine 6(20):1-24, Sep. 21, 2004.
Geisbert et al., "Treatment of Ebola virus infection with a recombinant inhibitor of factor VIIa1tissue factor: a study in rhesus monkeys," The Lancet 362(9400):1953-1958, Dec. 13, 2003.

(56) References Cited

OTHER PUBLICATIONS

Geller et al., "Antisense Antibacterial Method and Compound," Office Action, mailed Sep. 29, 2010, U.S. Appl. No. 11/173,847, 25 pages.
Geller et al., "Antisense phosphorodiamidate morpholino oligomer inhibits viability of Escherichia coli in pure culture and in mouse peritonitis," Journal of Antimicrobial Chemotherapy 55:938-988, 2005.
Geller et al., "Inhibition of Gene Expression in Escherichia coil by Antisense Phosphorodiamidate Morpholino Oligomers," Antimicrobial Agents and Chemotherapy 47(10):3233-3239, Oct. 2003.
Geller et al., "Translocation of Pro-OmpA across Inner Membrane Vesicles of Escherichia coli Occurs in Two consecutive Energetically Distinct Steps," The Journal of Biological Chemistry 264(28):16465-16469, 1989.
GenBank Accession No. AF074613, retrieved Jul. 15, 2010, from http//www.ncbi.nlm.nih.gov/nuccore13822114. 45 pages.
GenBank Accession No. AJ007716, retrieved Jul. 15, 2010, from http://www.ncbi.nlm.nih.gov/nuccore14775309. 4 pages.
GenBank Accession No. X97542.1, retrieved Jul. 15, 2010, from http://www.ncbi.nlm.nih.gov/nuccore12244635. 4 pages.
GenBank Accession No. Y11275.1, retrieved Jul. 15, 2010, from http://www.ncbi.nlm.nih.gov/nuccore14127812. 4 pages.
GenBank Accession No. AB011549, retrieved Jul. 15, 2010, from http://www.ncbi.nlm.nih.gov/nuccore14589740. 35 pages.
Gerdes et al., "Experimental Determination and System Level Analysis of Essential Genes in Escherichia coli MG1655," Journal of Bacteriology 185(19):5673-5684, Oct. 2003.
Gilbert et al., "Sieve analysis: methods for assessing from vaccine trial data how vaccine efficacy varies with genotypic and phenotypic pathogen variation," J Clinical Epidemiology 54:68-85, 2001.
Gong et al., "Molecular Mechanisms in Morpholino-DNA Surface Hybridization," J. Am. Chem. Soc.132:9663-9671, 2010.
Good et al., "Antisense PNA Effects in Escherichia coli are limited by the outer-membrane LPS layer," Microbiology 149(Pt 10):2665-2670, 2000.
Good et al., "Bactericidal antisense effects of peptide-PNA conjugates," Nature Biotechnology 19(4):360-364, Apr. 2001.
Good et al., "Inhibition of translation and bacterial growth by peptide nucleic acid targeted to ribosomal RNA," Proc. Natl. Acad. Sci. USA 95(5):207302076, 1998.
Green et al., "Antisense Oligonucleotides: An Evolving Technology for the Modulation of Gene Expression in Human Disease," J. Am. Coll. Surg. 191:93-105, 2000.
Greenberg et al., "Antisense Phosphorodiamidate Morpholino Oligmers Targeted to an Essential Gene Inhibit Burkholderia cepacia Complex," The Journal of Infectious Diseases 201(12)18221830, Jun. 2010.
Gunnar et al., "Oligonucleotide Analogues Having Modified Intersubunit Linkages and/or Terminal Groups," U.S. Appl. No. 14/298,655, filed Jun. 6, 2014, 180 pages.
Gupta, "Molecular signaling in death receptor and mitochondrial pathways of apoptosis (Review)," International Journal of Oncology 22(1):15-20, 2003.
Hale et al., "Recruitment of ZipA to the Septal Ring of Escherichia coli is Dependent on FtsZ and Independent of FtsA," Journal of Bacteriology 181(1):167-176, Jan. 1999.
Hames et al. (eds.), "Nucleic acid hybridization: a practical approach," IRL Press, Oxford, England, pp. 107-108, 1985, 12 pages.
Hanecak et al., "Antisense Oligonucleotide Inhibition of Hepatitis C Virus Gene Expression in Transformed Hepatocytes," Journal of Virology 70(8):5203-5212, 1996.
Hanson et al., "Boronic Acid Conjugates of Oligonucleotide Analogues," filed Sep. 19, 2014, U.S. Appl. No. 14/386,720, 65 pages.
He et al., "A Comparison of in Vitro and in Vivo Stability in Mice of Two Morpholino Duplexes Differing in Chain Length," Bioconjugate Chem. 14:1018-1023, 2003.

Holland, Morse (ed.), Emerging Viruses, Oxford University Press US, New York, 1993, Chap. 19, "Replication Error, Duasispecies Populations, and Extreme Evolution Rates of RNA Viruses," pp. 203-218, 18 pages.
Hudziak et al., "Antiproliferative Effects of Steric Blocking Phosphorodiamidate Morpholino Antisense Agents Directed against c-myc," Antisense & Nucleic Acid Drug Dev. 10:163-176, 2000.
Hudziak et al., "Resistance of Morpholino Phosphorodiamidate Oligomers to Enzymatic Degradation," Antisense & Nucleic Acid Drug Development 6:267-272, 1996.
Hunt et al., "Identification of Burkholderia cenocepacia Genes Required for Bacterial Survival In Vivo," Infection and Immunity 72(7):4010-4022, 2004.
International Search Report (US), mailed Aug. 17, 2006, for PCT/US05/023553, 6 pages.
Iversen et al., "Antisense Antiviral Compound and Method for Treating ssRNA Viral Infection," Office Action, mailed Oct. 19, 2010, U.S. Appl. No. 11/432,031, 25 pages.
Iversen et al., "Splice-Region Antisense Composition and Method," Office Action, mailed on Apr. 23, 2010, U.S. Appl. No. 11/433,214, 17 pages.
Iversen, "Methods and Compositions for Manipulating Translation of Protein Isoforms from Alternative Initiation Start Sites," U.S. Appl. No. 14/232,858, filed Jan. 14, 2014, 166 pages.
Jackowski et al., "Ratio of active to inactive forms of acyl carrier protein in Escherichia coli," J. Biol. Chem. 258(24):15186-15191, 1983.
Jackson et al., "Escherichia coli 0157:H7 diarrhoea associated with well water and infected cattle on an Ontario farm," Epidemiol Infect 120(1)17-20, 1998.
Jaeger et al., "Improved predictions of secondary structures for RNA," Proc. Natl. Sci. USA 86:7706-7710, Oct. 1989.
Jahrling et al., "Evaluation of Immune Globulin and Recombiant Interferon-a2b for Treatment of Experimental Ebola Virus Infections," The Journal of Infectious Diseases 1 79(Suppl 1):S222-S234, 1999.
Jen et al., "Suppression of Gene Expression by Targeted Disruption of Messenger RNA: Available Options and current Strategies," Stem Cells 18:307-319, 2000.
Johannes et al., "Identification of eukaryotic mRNAs that are translated at reduced cap binding complex eIF4F concentrations using a cDNA microarray." PNAS 96(23):13118-13123, Nov. 9, 1999.
Jubin et al., "Hepatitis C Virus Internal Ribosome Entry Site (IRES) Stem Loop IIId Contains a Phylogenetically conserved GGG Triplet Essential for Translation and IRES Folding," Journal of Virology 74(22):10430-10437, Nov. 2000.
Kang et al., "Stacking Interactions of ApA Analogues with Modified Backbones," Biopolymers 32:1351-1363, 1992.
Knudsen et al., "Antisense properties of duplex- and triplex-forming PNAs," Nucleic Acids Res 24(3):494-500, 1996.
Kole et al., "Compound and Method for Treating Myotonic Dystrophy," U.S. Appl. No. 14/038,314, filed Sep. 26, 2013, 31 pages.
Lappalainen et al., "Cationic liposomes mediated delivery of antisense oligonucleotides targeted to HPV 16 E7 mRNA in CaSki cells," Antiviral Research 23:119-130, 1994.
Lesnikowski et al., "Octa(thymidine methanephosphonats) of partially defined stereochemistry: synthesis and effect of chirality at phosphorous on binding to pentadecadeoxyriboadenylic acid," Nucleic Acids Research 18(8):2109-2115, 1990.
Li et al., "Folate-Mediated Targeting of Antisense Oligodeoxynucleotides to Ovarian Cancer Cells," Pharmaceutical Research 15(10):1540-1546, 1998.
Linkletter et al., "Solid-phase synthesis of oligopurine deoxynucleic guanidine (DNG) and analysis of binding with DNA oligomers," Nucleic Acids Research 29(11):2370-2376, 2001.
Linkletter et al., "Solid-phase Synthesis of Positively Charged Deoxynucleic Guanidine (DNG) Modified Oligonucleotides Containing Neutral Urea Linkages: Effect of Charge Deletions on Binding and Fidelity," Bioorganic & Medicinal Chemistry 8:1893-1901, 2000.

* cited by examiner

SEQUENCE LISTING

```
<160> NUMBER OF SEQ ID NOS: 35

<210> SEQ ID NO 1
<211> LENGTH: 11
<212> TYPE: PRT
<213> ORGANISM: Artificial Sequence
<220> FEATURE:
<223> OTHER INFORMATION: Synthetic transport peptide
<220> FEATURE:
<221> NAME/KEY: misc_feature
<222> LOCATION: (10)..(10)
<223> OTHER INFORMATION: 6-aminohexanoic acid
<220> FEATURE:
<221> NAME/KEY: misc_feature
<222> LOCATION: (11)..(11)
<223> OTHER INFORMATION: beta-Alanine

<400> SEQUENCE: 1

Arg Phe Phe Arg Phe Phe Arg Phe Phe Xaa Xaa
1               5                   10

<210> SEQ ID NO 2
<211> LENGTH: 12
<212> TYPE: PRT
<213> ORGANISM: Artificial Sequence
```

```
<220> FEATURE:
<223> OTHER INFORMATION: Synthetic transport peptide
<220> FEATURE:
<221> NAME/KEY: misc_feature
<222> LOCATION: (11)..(11)
<223> OTHER INFORMATION: 6-aminohexanoic acid
<220> FEATURE:
<221> NAME/KEY: misc_feature
<222> LOCATION: (12)..(12)
<223> OTHER INFORMATION: beta-Alanine

<400> SEQUENCE: 2

Arg Thr Arg Thr Arg Phe Leu Arg Arg Thr Xaa Xaa
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic transport peptide
<220> FEATURE:
<221> NAME/KEY: misc_feature
<222> LOCATION: (11)..(11)
<223> OTHER INFORMATION: 6-aminohexanoic acid
<220> FEATURE:
<221> NAME/KEY: misc_feature
<222> LOCATION: (12)..(12)
<223> OTHER INFORMATION: beta-Alanine

<400> SEQUENCE: 3

Arg Phe Phe Arg Phe Phe Arg Phe Phe Arg Xaa Xaa
1               5                   10

<210> SEQ ID NO 4
<211> LENGTH: 12
<212> TYPE: PRT
<213> ORGANISM: Artificial Seqeunce
<220> FEATURE:
<223> OTHER INFORMATION: Synthetic transport peptide
<220> FEATURE:
<221> NAME/KEY: misc_feature
<222> LOCATION: (11)..(11)
<223> OTHER INFORMATION: 6-aminohexanoic acid
<220> FEATURE:
<221> NAME/KEY: misc_feature
<222> LOCATION: (12)..(12)
<223> OTHER INFORMATION: beta-Alanine

<400> SEQUENCE: 4

Lys Thr Arg Thr Lys Phe Leu Lys Lys Thr Xaa Xaa
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic transport peptide
<220> FEATURE:
<221> NAME/KEY: misc_feature
<222> LOCATION: (10)..(10)
<223> OTHER INFORMATION: 6-aminohexanoic acid
<220> FEATURE:
<221> NAME/KEY: misc_feature
<222> LOCATION: (11)..(11)
<223> OTHER INFORMATION: beta-Alanine

<400> SEQUENCE: 5

Lys Phe Phe Lys Phe Phe Lys Phe Phe Xaa Xaa
1               5                   10
```

```
<210> SEQ ID NO 6
<211> LENGTH: 12
<212> TYPE: PRT
<213> ORGANISM: Artificial Sequence
<220> FEATURE:
<223> OTHER INFORMATION: Synethetic transport peptide
<220> FEATURE:
<221> NAME/KEY: misc_feature
<222> LOCATION: (11)..(11)
<223> OTHER INFORMATION: 6-aminohexanoic acid
<220> FEATURE:
<221> NAME/KEY: misc_feature
<222> LOCATION: (12)..(12)
<223> OTHER INFORMATION: beta-Alanine

<400> SEQUENCE: 6

Lys Phe Phe Lys Phe Phe Lys Phe Phe Lys Xaa Xaa
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic transport peptide
<220> FEATURE:
<221> NAME/KEY: misc_feature
<222> LOCATION: (7)..(7)
<223> OTHER INFORMATION: 6-aminohexanoic acid
<220> FEATURE:
<221> NAME/KEY: misc_feature
<222> LOCATION: (8)..(8)
<223> OTHER INFORMATION: beta-Alanine

<400> SEQUENCE: 7

Arg Phe Phe Arg Phe Phe Xaa Xaa
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic transport peptide
<220> FEATURE:
<221> NAME/KEY: misc_feature
<222> LOCATION: (8)..(8)
<223> OTHER INFORMATION: 6-aminohexanoic acid
<220> FEATURE:
<221> NAME/KEY: misc_feature
<222> LOCATION: (9)..(9)
<223> OTHER INFORMATION: beta-Alanine

<400> SEQUENCE: 8

Arg Phe Phe Arg Phe Phe Arg Xaa Xaa
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic transport peptide
<220> FEATURE:
<221> NAME/KEY: misc_feature
<222> LOCATION: (2)..(3)
<223> OTHER INFORMATION: 6-aminohexanoic acid
<220> FEATURE:
<221> NAME/KEY: misc_feature
<222> LOCATION: (5)..(6)
<223> OTHER INFORMATION: 6-aminohexanoic acid
<220> FEATURE:
```

```
<221> NAME/KEY: misc_feature
<222> LOCATION: (8)..(9)
<223> OTHER INFORMATION: 6-aminohexanoic acid
<220> FEATURE:
<221> NAME/KEY: misc_feature
<222> LOCATION: (10)..(10)
<223> OTHER INFORMATION: beta-Alanine

<400> SEQUENCE: 9

Arg Xaa Xaa Arg Xaa Xaa Arg Xaa Xaa Xaa
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic transport peptide
<220> FEATURE:
<221> NAME/KEY: misc_feature
<222> LOCATION: (2)..(2)
<223> OTHER INFORMATION: 6-aminohexanoic acid
<220> FEATURE:
<221> NAME/KEY: misc_feature
<222> LOCATION: (5)..(5)
<223> OTHER INFORMATION: 6-aminohexanoic acid
<220> FEATURE:
<221> NAME/KEY: misc_feature
<222> LOCATION: (8)..(8)
<223> OTHER INFORMATION: 6-aminohexanoic acid
<220> FEATURE:
<221> NAME/KEY: misc_feature
<222> LOCATION: (11)..(11)
<223> OTHER INFORMATION: 6-aminohexanoic acid
<220> FEATURE:
<221> NAME/KEY: misc_feature
<222> LOCATION: (13)..(13)
<223> OTHER INFORMATION: 6-aminohexanoic acid
<220> FEATURE:
<221> NAME/KEY: misc_feature
<222> LOCATION: (14)..(14)
<223> OTHER INFORMATION: beta-Alanine

<400> SEQUENCE: 10

Arg Xaa Arg Arg Xaa Arg Arg Xaa Arg Xaa Arg Xaa Xaa
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic transport peptide

<400> SEQUENCE: 11

Arg Arg Arg Gln Arg Arg Lys Lys Arg Cys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic transport peptide

<400> SEQUENCE: 12

Arg Arg Arg Arg Arg Arg Arg Arg Arg Phe Phe Cys
1               5                   10

<210> SEQ ID NO 13
<211> LENGTH: 13
```

```
-continued

<212> TYPE: PRT
<213> ORGANISM: Artificial Sequence
<220> FEATURE:
<223> OTHER INFORMATION: Synthetic transport peptide
<220> FEATURE:
<221> NAME/KEY: misc_feature
<222> LOCATION: (3)..(3)
<223> OTHER INFORMATION: 6-aminohexanoic acid
<220> FEATURE:
<221> NAME/KEY: misc_feature
<222> LOCATION: (6)..(6)
<223> OTHER INFORMATION: 6-aminohexanoic acid
<220> FEATURE:
<221> NAME/KEY: misc_feature
<222> LOCATION: (9)..(9)
<223> OTHER INFORMATION: 6-aminohexanoic acid
<220> FEATURE:
<221> NAME/KEY: misc_feature
<222> LOCATION: (12)..(12)
<223> OTHER INFORMATION: 6-aminohexanoic acid
<220> FEATURE:
<221> NAME/KEY: misc_feature
<222> LOCATION: (13)..(13)
<223> OTHER INFORMATION: beta-Alanine

<400> SEQUENCE: 13

Arg Arg Xaa Arg Arg Xaa Arg Arg Xaa Arg Arg Xaa Xaa
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic transport peptide
<220> FEATURE:
<221> NAME/KEY: misc_feature
<222> LOCATION: (2)..(2)
<223> OTHER INFORMATION: 6-aminohexanoic acid
<220> FEATURE:
<221> NAME/KEY: misc_feature
<222> LOCATION: (5)..(5)
<223> OTHER INFORMATION: 6-aminohexanoic acid
<220> FEATURE:
<221> NAME/KEY: misc_feature
<222> LOCATION: (8)..(8)
<223> OTHER INFORMATION: 6-aminohexanoic acid
<220> FEATURE:
<221> NAME/KEY: misc_feature
<222> LOCATION: (11)..(11)
<223> OTHER INFORMATION: 6-aminohexanoic acid
<220> FEATURE:
<221> NAME/KEY: misc_feature
<222> LOCATION: (13)..(13)
<223> OTHER INFORMATION: 6-aminohexanoic acid
<220> FEATURE:
<221> NAME/KEY: misc_feature
<222> LOCATION: (14)..(14)
<223> OTHER INFORMATION: beta-Alanine

<400> SEQUENCE: 14

Arg Xaa Arg Arg Xaa Arg Arg Xaa Arg Arg Xaa Arg Xaa Xaa
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic transport peptide
<220> FEATURE:
<221> NAME/KEY: misc_feature
<222> LOCATION: (1)..(1)
<223> OTHER INFORMATION: 6-aminohexanoic acid
<220> FEATURE:
```

```
<221> NAME/KEY: misc_feature
<222> LOCATION: (4)..(4)
<223> OTHER INFORMATION: 6-aminohexanoic acid
<220> FEATURE:
<221> NAME/KEY: misc_feature
<222> LOCATION: (7)..(7)
<223> OTHER INFORMATION: 6-aminohexanoic acid
<220> FEATURE:
<221> NAME/KEY: misc_feature
<222> LOCATION: (10)..(10)
<223> OTHER INFORMATION: 6-aminohexanoic acid
<220> FEATURE:
<221> NAME/KEY: misc_feature
<222> LOCATION: (13)..(13)
<223> OTHER INFORMATION: 6-aminohexanoic acid
<220> FEATURE:
<221> NAME/KEY: misc_feature
<222> LOCATION: (14)..(14)
<223> OTHER INFORMATION: beta-Alanine

<400> SEQUENCE: 15

Xaa Arg Arg Xaa Arg Arg Xaa Arg Arg Xaa Arg Arg Xaa Xaa
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic transport peptide
<220> FEATURE:
<221> NAME/KEY: misc_feature
<222> LOCATION: (2)..(2)
<223> OTHER INFORMATION: 6-aminohexanoic acid
<220> FEATURE:
<221> NAME/KEY: misc_feature
<222> LOCATION: (4)..(4)
<223> OTHER INFORMATION: 6-aminohexanoic acid
<220> FEATURE:
<221> NAME/KEY: misc_feature
<222> LOCATION: (6)..(6)
<223> OTHER INFORMATION: 6-aminohexanoic acid
<220> FEATURE:
<221> NAME/KEY: misc_feature
<222> LOCATION: (8)..(8)
<223> OTHER INFORMATION: 6-aminohexanoic acid
<220> FEATURE:
<221> NAME/KEY: misc_feature
<222> LOCATION: (10)..(10)
<223> OTHER INFORMATION: 6-aminohexanoic acid
<220> FEATURE:
<221> NAME/KEY: misc_feature
<222> LOCATION: (12)..(12)
<223> OTHER INFORMATION: 6-aminohexanoic acid
<220> FEATURE:
<221> NAME/KEY: misc_feature
<222> LOCATION: (13)..(13)
<223> OTHER INFORMATION: beta-Alanine

<400> SEQUENCE: 16

Arg Xaa Arg Xaa Arg Xaa Arg Xaa Arg Xaa Arg Xaa Xaa
1               5                   10

<210> SEQ ID NO 17
<211> LENGTH: 15
<212> TYPE: PRT
<213> ORGANISM: Artificial Sequence
<220> FEATURE:
<223> OTHER INFORMATION: Synthetic transport peptide
<220> FEATURE:
<221> NAME/KEY: misc_feature
<222> LOCATION: (2)..(2)
<223> OTHER INFORMATION: 6-aminohexanoic acid
<220> FEATURE:
<221> NAME/KEY: misc_feature
```

```
<222> LOCATION: (4)..(4)
<223> OTHER INFORMATION: 6-aminohexanoic acid
<220> FEATURE:
<221> NAME/KEY: misc_feature
<222> LOCATION: (6)..(6)
<223> OTHER INFORMATION: 6-aminohexanoic acid
<220> FEATURE:
<221> NAME/KEY: misc_feature
<222> LOCATION: (8)..(8)
<223> OTHER INFORMATION: 6-aminohexanoic acid
<220> FEATURE:
<221> NAME/KEY: misc_feature
<222> LOCATION: (10)..(10)
<223> OTHER INFORMATION: 6-aminohexanoic acid
<220> FEATURE:
<221> NAME/KEY: misc_feature
<222> LOCATION: (12)..(12)
<223> OTHER INFORMATION: 6-aminohexanoic acid
<220> FEATURE:
<221> NAME/KEY: misc_feature
<222> LOCATION: (14)..(14)
<223> OTHER INFORMATION: 6-aminohexanoic acid
<220> FEATURE:
<221> NAME/KEY: misc_feature
<222> LOCATION: (15)..(15)
<223> OTHER INFORMATION: beta-Alanine

<400> SEQUENCE: 17

Arg Xaa Arg Xaa Arg Xaa Arg Xaa Arg Xaa Arg Xaa Arg Xaa Xaa
1               5                   10                  15

<210> SEQ ID NO 18
<211> LENGTH: 17
<212> TYPE: PRT
<213> ORGANISM: Artificial Sequence
<220> FEATURE:
<223> OTHER INFORMATION: Synthetic transport peptide
<220> FEATURE:
<221> NAME/KEY: misc_feature
<222> LOCATION: (2)..(2)
<223> OTHER INFORMATION: 6-aminohexanoic acid
<220> FEATURE:
<221> NAME/KEY: misc_feature
<222> LOCATION: (5)..(5)
<223> OTHER INFORMATION: 6-aminohexanoic acid
<220> FEATURE:
<221> NAME/KEY: misc_feature
<222> LOCATION: (8)..(8)
<223> OTHER INFORMATION: 6-aminohexanoic acid
<220> FEATURE:
<221> NAME/KEY: misc_feature
<222> LOCATION: (11)..(11)
<223> OTHER INFORMATION: 6-aminohexanoic acid
<220> FEATURE:
<221> NAME/KEY: misc_feature
<222> LOCATION: (14)..(14)
<223> OTHER INFORMATION: 6-aminohexanoic acid
<220> FEATURE:
<221> NAME/KEY: misc_feature
<222> LOCATION: (16)..(16)
<223> OTHER INFORMATION: 6-aminohexanoic acid
<220> FEATURE:
<221> NAME/KEY: misc_feature
<222> LOCATION: (17)..(17)
<223> OTHER INFORMATION: beta-Alanine

<400> SEQUENCE: 18

Arg Xaa Arg Arg Xaa Arg Arg Xaa Arg Arg Xaa Arg Arg Xaa Arg Xaa
1               5                   10                  15

Xaa

<210> SEQ ID NO 19
<211> LENGTH: 14
<212> TYPE: PRT
```

```
<213> ORGANISM: Artificial Sequence
<220> FEATURE:
<223> OTHER INFORMATION: Synthetic transport peptide
<220> FEATURE:
<221> NAME/KEY: misc_feature
<222> LOCATION: (2)..(2)
<223> OTHER INFORMATION: 6-aminohexanoic acid
<220> FEATURE:
<221> NAME/KEY: misc_feature
<222> LOCATION: (5)..(5)
<223> OTHER INFORMATION: beta-Alanine
<220> FEATURE:
<221> NAME/KEY: misc_feature
<222> LOCATION: (8)..(8)
<223> OTHER INFORMATION: 6-aminohexanoic acid
<220> FEATURE:
<221> NAME/KEY: misc_feature
<222> LOCATION: (11)..(11)
<223> OTHER INFORMATION: beta-Alanine
<220> FEATURE:
<221> NAME/KEY: misc_feature
<222> LOCATION: (13)..(13)
<223> OTHER INFORMATION: 6-aminohexanoic acid
<220> FEATURE:
<221> NAME/KEY: misc_feature
<222> LOCATION: (14)..(14)
<223> OTHER INFORMATION: beta-Alanine

<400> SEQUENCE: 19

Arg Xaa Arg Arg Xaa Arg Arg Xaa Arg Arg Xaa Arg Xaa Xaa
1               5                   10

<210> SEQ ID NO 20
<211> LENGTH: 5
<212> TYPE: PRT
<213> ORGANISM: Artificial Sequence
<220> FEATURE:
<223> OTHER INFORMATION: Synthetic transport peptide

<400> SEQUENCE: 20

Arg Arg Arg Arg Gly
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic transport peptide

<400> SEQUENCE: 21

Arg Arg Arg Arg Arg Gly
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic transport peptide

<400> SEQUENCE: 22

Arg Arg Arg Arg Arg Arg Gly
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic transport peptide
```

```
<400> SEQUENCE: 23

Arg Arg Arg Arg Arg Arg Gly
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic transport peptide

<400> SEQUENCE: 24

Arg Arg Arg Arg Arg Arg Arg Arg Gly
1               5

<210> SEQ ID NO 25
<211> LENGTH: 11
<212> TYPE: PRT
<213> ORGANISM: Artificial Sequence
<220> FEATURE:
<223> OTHER INFORMATION: Synthetic transport peptide

<400> SEQUENCE: 25

Arg Arg Arg Arg Arg Gly Arg Arg Arg Arg Gly
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic transport peptide

<400> SEQUENCE: 26

Arg Arg Arg Arg Arg Phe Phe Arg Arg Arg Gly
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic transport peptide

<400> SEQUENCE: 27

Arg Lys Lys Arg Arg Gln Arg Arg Arg Gly
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic transport peptide

<400> SEQUENCE: 28

Arg Arg Arg Gln Arg Arg Lys Lys Arg Gly
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic transport peptide
<220> FEATURE:
```

```
<221> NAME/KEY: misc_feature
<222> LOCATION: (2)..(2)
<223> OTHER INFORMATION: 6-aminohexanoic acid
<220> FEATURE:
<221> NAME/KEY: misc_feature
<222> LOCATION: (8)..(8)
<223> OTHER INFORMATION: 6-aminohexanoic acid

<400> SEQUENCE: 29

Arg Xaa Arg Arg Gly Gly Arg Xaa Arg Gly Gly
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic transport peptide
<220> FEATURE:
<221> NAME/KEY: misc_feature
<222> LOCATION: (2)..(2)
<223> OTHER INFORMATION: 6-aminohexanoic acid
<220> FEATURE:
<221> NAME/KEY: misc_feature
<222> LOCATION: (6)..(6)
<223> OTHER INFORMATION: 6-aminohexanoic acid
<220> FEATURE:
<221> NAME/KEY: misc_feature
<222> LOCATION: (8)..(8)
<223> OTHER INFORMATION: 6-aminohexanoic acid

<400> SEQUENCE: 30

Arg Xaa Arg Arg Arg Xaa Arg Xaa Arg Arg Gly
1               5                   10

<210> SEQ ID NO 31
<211> LENGTH: 5
<212> TYPE: PRT
<213> ORGANISM: Artificial Sequence
<220> FEATURE:
<223> OTHER INFORMATION: Synthetic transport peptide

<400> SEQUENCE: 31

Arg Arg Arg Arg Pro
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic transport peptide

<400> SEQUENCE: 32

Arg Arg Arg Arg Arg Pro
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic transport peptide

<400> SEQUENCE: 33

Arg Arg Arg Arg Arg Arg Pro
1               5

<210> SEQ ID NO 34
```

```
<211> LENGTH: 8
<212> TYPE: PRT
<213> ORGANISM: Artificial Sequence
<220> FEATURE:
<223> OTHER INFORMATION: Synthetic transport peptide

<400> SEQUENCE: 34

Arg Arg Arg Arg Arg Arg Arg Pro
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic transport peptide

<400> SEQUENCE: 35

Arg Arg Arg Arg Arg Arg Arg Arg Pro
1               5
```

FUNCTIONALLY-MODIFIED OLIGONUCLEOTIDES AND SUBUNITS THEREOF

This application is a continuation of U.S. application Ser. No. 14/358,992, now U.S. Pat. No. 9,278,987, filed on May 16, 2014, which is a is a National Stage Entry of PCT/US2012/065350, filed on Nov. 15, 2012, which claims priority to U.S. Provisional Application No. 61/561,806, filed on Nov. 18, 2011. The contents of each of these applications are incorporated herein in their entirety.

STATEMENT REGARDING SEQUENCE LISTING

The sequence listing associated with this application is provided in text format in lieu of a paper copy, and is hereby incorporated by reference into the specification. The name of the text file containing the sequence listing is 120178_498C1_SEQUENCE_LISTING.txt. The text file is about 13 KB, was created on Jan. 26, 2016, and is being submitted electronically via EFS-web.

BACKGROUND OF THE INVENTION

Technical Field

The present invention is generally related to oligonucleotide compounds (oligomers) useful as antisense compounds, and more particularly to oligomer compounds comprising modified intersubunit linkages and/or terminal groups, and the use of such oligomer compounds in antisense applications.

Description of the Related Art

Antisense oligomers are generally designed to bind in a sequence specific manner to DNA or RNA regions and alter the expression of disease-causing proteins. Requirements for successful implementation of antisense therapeutics include (a) stability in vivo, (b) sufficient membrane permeability and cellular uptake, and (c) a good balance of binding affinity and sequence specificity. Many oligonucleotide analogues have been developed in which the phosphodiester linkages of native DNA are replaced by other linkages that are resistant to nuclease degradation (see, e.g., Barawkar, D. A. et al., *Proc. Na't'l Acad. Sci. USA* 95(19):11047-52 (1998); Linkletter, B. A. et al., *Nucleic Acids Res.* 29(11): 2370-6 (2001); Micklefield, J., *Curr, Med, Chem,* 8(10):1157-79 (2001)). Antisense oligonucleotides having other various backbone modifications have also been prepared (Crooke, S. T., *Antisense Drug Technology: Principles, Strategies, and Applications*, New York, Marcel Dekker (2001); Micklefield, J., *Curr, Med, Chem,* 8(10):1157-79 (2001); Crooke, S. T., *Antisense Drug Technology*, Boca Raton, CRC Press (2008)). In addition, oligonucleotides have been modified by peptide conjugation in order to enhance cellular uptake (Moulton, H. M. et al., *Bioconjug Chem* 15(2):290-9 (2004); Nelson, M. H. et al., *Bioconjug. Chem.* 16(4):959-66 (2005); Moulton, H. M. et al., *Biochim Biophys Acta* (2010)).

The performance of such nucleic acid analogues as antisense or antigene drugs has been hampered by certain characteristics of the various analogues. For example, analogues with negatively charged linkages, including phosphorothioate-linked analogues, suffer from considerable electrostatic repulsion between the negative charges of the oligomer and the DNA or RNA target. The phosphorothioates also exhibit non-specific binding to other cellular components such as proteins. These attributes limit the therapeutic effectiveness of antisense oligomers comprised of native RNA, native DNA, and negatively charged analogues (Crooke, S. T., *Antisense Drug Technology: Principles, Strategies, and Applications*, New York, Marcel Dekker (2001); Crooke, S. T., *Antisense Drug Technology*, Boca Raton, CRC Press (2008)). The nonionic methylphosphonate-linked oligonucleotide analogues can be transported into cells by passive diffusion and/or fluid phase endocytosis, but their use is hampered by stereoisomeric complexity and poor solubility (Crooke, S. T., *Antisense Drug Technology: Principles, Strategies, and Applications*, New York, Marcel Dekker (2001); Micklefield, J., *Curr, Med, Chem,* 8(10):1157-79 (2001)).

Several groups have reported the synthesis of positively charged oligonucleotides (Bailey, C. P. et al. *Nucleic Acids Res.* 26(21):4860-7 (1998); Micklefield, J., *Curr, Med, Chem,* 8(10):1157-79 (2001); Egli, M. et al., *Biochemistry* 44(25):9045-57 (2005)). For example, a class of guanidinium linked nucleosides (designated DNG), formed by replacement of the phosphate linkages in DNA and RNA by achiral guanidino groups, has been reported (Dempcy, R. O. et al., *Proc. Nat'l Acad. Sci. USA* 91(17):7864-8 (1994); Dempcy, R. O. et al., *Proc. Nat'l Acad. Sci. USA* 93(9): 4326-30 (1996); Barawkar, D. A. et al., *Proc. Na't'l Acad. Sci. USA* 95(19):11047-52 (1998); Linkletter, B. A. et al., *Nucleic Acids Res.* 29(11):2370-6 (2001)). Oligomers linked with positively charged methylated thiourea linkages have also been reported (Arya, D. P. et al., *Proc. Nat'l Acad. Sci USA* 96(8): 4384-9 (1999)). Replacement of some of these linkages with neutral urea linkages has been reported to reduce the tendency of such positively charged oligomers towards non-sequence-specific binding (Linkletter, B. A. et al., *Bioorg. Med. Chem.* 8(8):1893-901 (2000)). Morpholino oligomers containing (1-piperazino) phosphinylideneoxy and (1-(4-(ω-guanidino-alkanoyl))-piperazino) phosphinylideneoxy linkages have been described previously (see e.g., WO2008036127).

Although significant progress has been made, there remains a need in the art for oligonucleotide analogues with improved antisense or antigene performance. Such improved antisense or antigene performance includes; stronger affinity for DNA and RNA without compromising sequence selectivity; improved pharmacokinetics and tissue distribution; improved cellular delivery and reliable and controllable in vivo distribution.

BRIEF SUMMARY OF THE INVENTION

Compounds of the present invention address these issues and provide improvements over existing antisense molecules in the art. Modification of the intersubunit linkages and/or conjugation of terminal moieties to the 5' and/or 3' terminus of an oligonucleotide analogue, for example a morpholino oligonucleotide, results in an antisense oligomer having superior properties. For example, in certain embodiments the disclosed oligomers have enhanced cell delivery, potency, and/or tissue distribution compared to other oligonucleotide analogues and/or can be effectively delivered to the target organs. These superior properties give rise to favorable therapeutic indices, reduced clinical dosing, and lower cost of goods.

In one embodiment, described herein are compounds comprising a backbone, the backbone comprising a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the compound can bind in a sequence-specific manner to a target nucleic acid.

In one aspect is a compound having the structure of Formula (I):

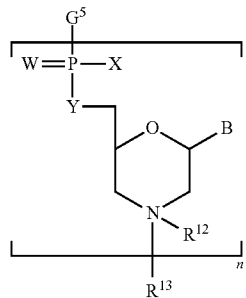

(I)

or a salt or isomer thereof,
wherein:
n is an integer from 1 to 50;
$G^5$ is halogen, OH, alkoxy, $OSO_2$(alkyl), $OSO_2$(aryl), or

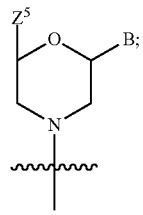

each B is an independently selected base pair moiety;
each Y is independently O or $NR^{10}$; optionally, $R^{10}$ and X8e are bonded together form a ring;
each W is independently S or O;
$Z^5$ is $-(L^{11})-(R^{15})$, $-(L^{11})-(L^5)-(R^{16})$, or $-(L^{11})-(L^{12})-(R^{17})$;
$L^{11}$ is selected from:

a)

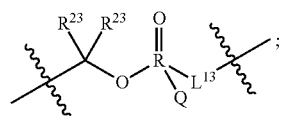

b)

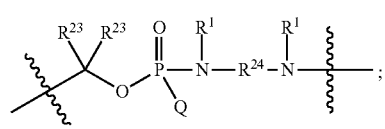

c)

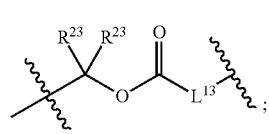

d)

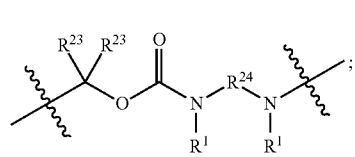

e)

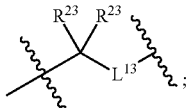

f)

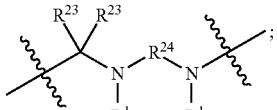

g)

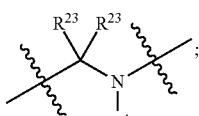

h)

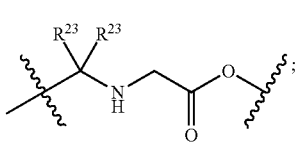

i)

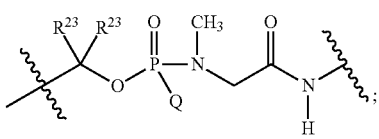

j)

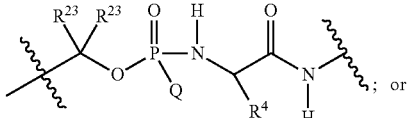

; or k)

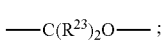

$—C(R^{23})_2O—$;

wherein $L^{13}$ is selected from:

a)

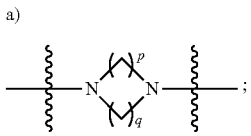

b)

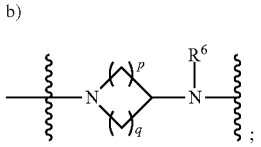

c)

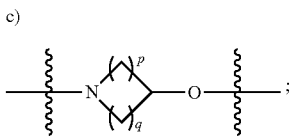

d)

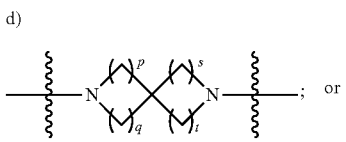

; or e)

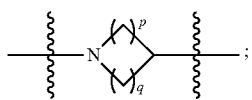

L$^{12}$ is a linker cleaveable under biological conditions selected from:
a) —(C$_1$-C$_{10}$ alkylene)-OC(O)O—CH$_2$O—;
b) —C(O)—(C$_1$-C$_{10}$ alkylene)-OC(O)O—CH$_2$O—;
c) —C(O)—(CH=CH)—C(O)O—CH$_2$O—;
d) —(C$_1$-C$_{10}$ alkylene)-S—S—CH$_2$CH$_2$O—; or
e) —C(O)—(C$_1$-C$_{10}$ alkylene)-S—S—CH$_2$CH$_2$O—;

L$^{15}$ is divalent radical selected from C$_1$-C$_{30}$ alkylene, C$_3$-C$_8$ cycloalkylene, C$_6$-C$_{30}$ arylene, —(C$_6$-C$_{30}$ arylene)-(C$_1$-C$_{30}$ alkylene)-, —(C$_1$-C$_{30}$ alkylene)-C(=O)—, —(C$_2$-C$_{30}$ alkoxy)-C(=O)—, -(3-18 membered heteroalkylene)-C(=O)—, —(C$_3$-C$_8$ cycloalkylene)-C(=O)—, —(C$_3$-C$_8$ cycloalkylene)-(C$_1$-C$_{30}$ alkylene)-C(=O)—, —(C$_1$-C$_{30}$ alkylene) (C$_3$-C$_8$ cycloalkylene)-C(=O)—, —(C$_6$-C$_{30}$ arylene)-C(=O)—, —(C$_6$-C$_{30}$ arylene)-(C$_1$-C$_{30}$ alkylene)-C(=O)—, —(C$_1$-C$_{30}$ alkylene)-(C$_6$-C$_{30}$ arylene)-C(=O)—, —(C$_1$-C$_{30}$ alkylene)-O—C(=O)—, —(C$_3$-C$_8$ cycloalkylene)-O—C(=O)—, —(C$_7$-C$_{30}$ arylene)-O—C(=O)—, —(C$_6$-C$_{30}$ arylene)-(C$_1$-C$_{30}$ alkylene)-O—C(=O)—, —(C$_6$-C$_{30}$ arylene)-(C$_1$-C$_{30}$ alkylene)-O—C(=O)—, —C(=O)OR$^{21}$, or —P(=O)(R$^{22}$)$_2$;

R$^{12}$ is an electron pair, with the provision that if R$^{13}$ is C$_1$-C$_{30}$ alkyl, then R$^{12}$ is an electron pair, an N-oxide, or C$_1$-C$_6$ alkyl;

each R$^{10}$ and R$^{13}$ is independently selected from hydrogen, a cell-penetrating peptide, a natural or non-natural amino acid, guanidinyl, amidinyl, heterocyclyl, C$_1$-C$_{30}$ alkyl, C$_3$-C$_8$ cycloalkyl; C$_6$-C$_{30}$ aryl, C$_7$-C$_{30}$ aralkyl, C$_1$-C$_{30}$ alkylcarbonyl, C$_3$-C$_8$ cycloalkylcarbonyl, C$_3$-C$_8$ cycloalkylalkylcarbonyl, C$_6$-C$_{30}$ arylcarbonyl, C$_7$-C$_{30}$ aralkylcarbonyl, C$_1$-C$_{30}$ alkyloxycarbonyl, C$_3$-C$_8$ cycloalkyloxycarbonyl, C$_7$-C$_{30}$ aryloxycarbonyl, C$_8$-C$_{30}$ aralkyloxycarbonyl, —C(=O)OR$^{21}$, —C(=O)NHR$^{21}$, or —P(=O)(R$^{22}$)$_2$;

R$^{15}$ is independently selected from a cell-penetrating peptide, a natural or non-natural amino acid, guanidinyl, amidinyl, heterocyclyl, C$_1$-C$_{30}$ alkyl, C$_3$-C$_8$ cycloalkyl; C$_6$-C$_{30}$ aryl, C$_7$-C$_{30}$ aralkyl, C$_1$-C$_{30}$ alkylcarbonyl, C$_3$-C$_8$ cycloalkylcarbonyl, C$_3$-C$_8$ cycloalkylalkylcarbonyl, C$_6$-C$_{30}$ arylcarbonyl, C$_7$-C$_{30}$ aralkylcarbonyl, C$_2$-C$_{30}$ alkyloxycarbonyl, C$_3$-C$_8$ cycloalkyloxycarbonyl, C$_7$-C$_{30}$ aryloxycarbonyl, C$_8$-C$_{30}$ aralkyloxycarbonyl, 3-18 membered alkoxyalkylcarbonyl, —SO$_2$R$^{21}$, —C(=O)OR$^{21}$, —P(=O)(OH)$_2$ or —P(=O)(R$^{22}$)$_2$;

R$^{16}$ is a solid support matrix suitable for solid phase synthesis of oligonucleotides;
R$^{17}$ is a drug, protein or toxin;
each R$^{21}$ is independently C$_1$-C$_{30}$ alkyl, or a 3-18 membered alkoxyalkyl group;
each R$^{22}$ is independently an C$_6$-C$_{12}$ aryloxy;
each R$^{23}$ is independently H or C$_1$-C$_6$ alkyl; or optionally two R$^{23}$ groups join to form a 3- to 8-membered ring;
R$^{24}$ is a C$_1$-C$_6$ alkylene;
Q is independently selected from X1, X2, X3, X4, X5, X6, X7, or X8;

each X is independently selected from X1, X2, X3, X4, X5, X6, X7, or X8 with the provision that at least one X is not X1;
wherein
X1 is N(CH$_3$)$_2$;
X2 is selected from:
a) —O-alkylene-CO$_2$H;
b) —O-alkylene-CHN$_4$;
c) —N(R$^1$)-alkylene-CO$_2$H;
d) —N(R$^1$)-alkylene-CHN$_4$;
e) -L1-CO-alkylene-CO$_2$H;
f) -L1-CO-alkylene-CHN$_4$;
g) -L1-CO-alkenylene-CO$_2$H;
h) -L1-CO-alkenylene-CHN$_4$;
i) -L1-CO-arylene-CO$_2$H;
j) -L1-CO-arylene-CHN$_4$;
k) -L1-CONH-alkylene-CO$_2$H;
l) -L1-CONH-alkylene-CHN$_4$;
m) -L1-CONH-arylene-CO$_2$H;
n) -L1-CONH-arylene-CHN$_4$;
o) -L1-SO$_2$-alkylene-CO$_2$H;
p) -L1-SO$_2$-alkylene-CHN$_4$;
q) -L1-SO$_2$-arylene-CO$_2$H;
r) -L1-SO$_2$-arylene-CHN$_4$;
s) -L1-alkylene-CO$_2$H;
t) -L1-alkylene-CHN$_4$;
u) -L1-arylene-CO$_2$H;
v) -L1-arylene-CHN$_4$; and
w) a protected form of any of the above X2 groups;
X3 is selected from:
a) -L1-alkyl;
b) -L1-heterocyclyl;
c) —O-alkylene-CNH—NH$_2$;
d) —N(R$^1$)-alkylene-CNH—NH$_2$;
e) -L1-CNH—NH$_2$;
f) -L1-alkylene-CNH—NH$_2$;
g) -L1-arylene-CNH—NH$_2$;
h) -L1-CO-alkylene-CNH—NH$_2$;
i) -L1-CO-alkenylene-CNH—NH$_2$;
j) -L1-CO-arylene-CNH—NH$_2$;
k) -L1-CONH-alkylene-CNH—NH$_2$;
l) -L1-CONH-arylene-CNH—NH$_2$;
m) -L1-SO$_2$-alkylene-CNH—NH$_2$;
n) -L1-SO$_2$-arylene-CNH—NH$_2$;
o) —O-alkylene-N(R$^1$)$_2$;
p) —N(R$^1$)-alkylene-N(R$^1$)$_2$;
q) -L1-N(R$^1$)$_2$;
r) -L1-alkylene-N(R$^1$)$_2$;
s) -L1-arylene-N(R$^1$)$_2$;
t) -L1-CO-alkylene-N(R$^1$)$_2$;
u) -L1-CO-alkenylene-N(R$^1$)$_2$;
v) -L1-CO-arylene-N(R$^1$)$_2$;
w) -L1-CONH-alkylene-N(R$^1$)$_2$;
x) -L1-CONH-arylene-N(R$^1$)$_2$;
y) -L1-SO$_2$-alkylene-N(R$^1$)$_2$;
z) —O-alkylene-N(R$^2$)$_3$;
aa) —N(R$^1$)-alkylene-N(R$^2$)$_3$;
bb) -L1-N(R$^2$)$_3$;
cc) -L1-alkylene-N(R$^2$)$_3$;
dd) -L1-arylene-N(R$^2$)$_3$;
ee) -L1-CO-alkylene-N(R$^2$)$_3$;
ff) -L1-CO-alkenylene-N(R$^2$)$_3$;
gg) -L1-CO-arylene-N(R$^2$)$_3$;
hh) -L1-CONH-alkylene-N(R$^2$)$_3$;
ii) -L1-CONH-arylene-N(R$^2$)$_3$;
jj) -L1-SO$_2$-alkylene-N(R$^2$)$_3$;
kk) —O-alkylene-heterocyclyl;

ll) —N(R¹)-alkylene-heterocyclyl;
mm) -L1-alkylene-heterocyclyl;
nn) -L1-arylene-heterocyclyl;
oo) -L1-CO-alkylene-heterocyclyl;
pp) -L1-CO-alkenylene-heterocyclyl;
qq) -L1-CO-arylene-heterocyclyl;
rr) -L1-CONH-alkylene-heterocyclyl;
ss) -L1-CONH-arylene-heterocyclyl;
tt) -L1-SO₂-alkylene-heterocyclyl;
uu) —O-alkylene-N(O)(R²)₂;
vv) —N(R¹)-alkylene-N(O)(R²)₂;
ww) -L1-N(O)(R²)₂;
xx) -L1-alkylene-N(O)(R²)₂₃;
yy) -L1-arylene-N(O)(R²)₂;
zz) -L1-CO-alkylene-N(O)(R²)₂;
aaa) -L1-CO-alkenylene-N(O)(R²)₂₃;
bbb) -L1-CO-arylene-N(O)(R²)₂;
ccc) -L1-CONH-alkylene-N(O)(R²)₂;
ddd) -L1-CONH-arylene-N(O)(R²)₂;
eee) -L1-SO₂-alkylene-N(O)(R²)₂;
fff) —O-alkylene-NH—CNH—NH₂;
ggg) —N(R¹)-alkylene-NH—CNH—NH₂;
hhh) -L1-NH—CNH—NH₂;
iii) -L1-alkylene-NH—CNH—NH₂;
jjj) -L1-arylene-NH—CNH—NH₂;
kkk) -L1-CO-alkylene-NH—CNH—NH₂;
lll) -L1-CO-alkenylene-NH—CNH—NH₂;
mmm) -L1-CO-arylene-NH—CNH—NH₂;
nnn) -L1-CONH-alkylene-NH—CNH—NH₂;
ooo) -L1-CONH-arylene-NH—CNH—NH₂;
ppp) -L1-SO₂-alkylene-NH—CNH—NH₂;
qqq) -L1-SO₂-arylene-NH—CNH—NH₂; and
rrr) a protected form of any of the above X3 groups;
with the provision that if X1 is present as N(CH₃)₂, and X7 is present as piperidinyl, then X3 is not

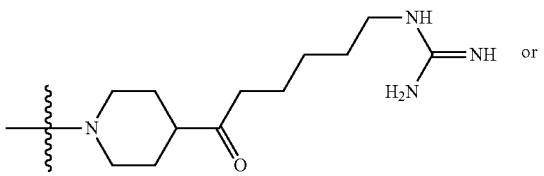

or

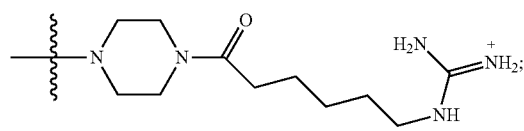

X4 is selected from:
a) —O-alkylene-aryl;
b) —N(R¹)-aryl;
c) —N(R¹)-alkylene-aryl;
d) -L1-CO-alkylene-aryl;
e) -L1-CO-alkenylene-aryl;
f) -L1-CO-arylene-aryl;
g) -L1-CONH-alkylene-aryl;
h) -L1-CONH-arylene-aryl;
i) -L1-SO₂-alkylene-aryl;
j) -L1-SO₂-arylene-aryl;
k) -L1-alkylene-aryl;
l) -L1-arylene-aryl;
m) —N(R¹)-alkylene-N(R¹)-aryl;
n) —N(R¹)-alkylene-N(R¹)CO-aryl;
o) —N(R¹)-alkylene-N(R¹)SO₂-aryl;
p) —N(R¹)-alkylene-N(R¹)CH₂-aryl;
q) -L1-aryl;
r) -L1-CO-aryl;
s) -L1-SO₂-aryl;
t) -L1-alkylene-P(aryl)₃;
u) -L1-CO-alkylene-P(aryl)₃;
v) -L1-SO₂-alkylene-P(aryl)₃; and
w) a protected form of any of the above X4 groups;
X5 is selected from:
a) —O-alkylene-heteroaryl;
b) —N(R¹)-alkylene-heteroaryl;
c) -L1-CO-alkylene-heteroaryl;
d) -L1-CO-alkenylene-heteroaryl;
e) -L1-CO-arylene-heteroaryl;
f) -L1-CONH-alkylene-heteroaryl;
g) -L1-CONH-arylene-heteroaryl;
h) -L1-SO₂-alkylene-heteroaryl;
i) -L1-SO₂-arylene-heteroaryl;
j) -L1-alkylene-heteroaryl;
k) -L1-arylene-heteroaryl;
l) —N(R¹)-alkylene-N(R¹)-heteroaryl;
m) —N(R¹)-alkylene-N(R¹)CO-heteroaryl;
n) —N(R¹)-alkylene-N(R¹)SO₂-heteroaryl;
o) —N(R¹)-alkylene-N(R¹)CH₂-heteroaryl;
p) -L1-heteroaryl; and
q) a protected form of any of the above X5 groups;
X6 is selected from:
a) —O-alkylene-(OCH₂CH₂)$_m$OH;
b) —O-alkylene-(OCH₂CH₂)$_m$OCH₃;
c) —N(R¹)-alkylene-(OCH₂CH₂)$_m$OH;
d) —N(R¹)-alkylene-(OCH₂CH₂)$_m$OCH₃;
e) —N(R¹)-arylene-(OCH₂CH₂)$_m$OH;
f) —N(R¹)-arylene-(OCH₂CH₂)$_m$OCH₃;
g) -L1-alkylene-(OCH₂CH₂)$_m$OH;
h) -L1-CO-alkylene-(OCH₂CH₂)$_m$OH;
i) -L1-CO-alkylene-(OCH₂CH₂)$_m$OCH₃;
j) -L1-SO₂-alkylene-(OCH₂CH₂)$_m$OH;
k) -L1-SO₂-alkylene-(OCH₂CH₂)$_m$OCH₃;
l) -L1-CO-arylene-(OCH₂CH₂)$_m$OH;
m) -L1-CO-arylene-(OCH₂CH₂)$_m$OCH₃;
n) -L1-SO₂-arylene-(OCH₂CH₂)$_m$OH;
o) -L1-SO₂-arylene-(OCH₂CH₂)$_m$OCH₃;
p) -L1-CO—(OCH₂CH₂)$_m$OH;
q) -L1-CO—(OCH₂CH₂)$_m$OCH₃;
r) —N(R¹)-(dibenzo-18-crown-6);
s) an aza-crown ether; and
t) a protected form of any of the above X6 groups;
X7 is selected from:
a) -heterocyclyl;
b) —N(R¹)(R³)
c) -L1-hydrogen;
d) -L1-alkyl;
e) -L1-CO-alkyl;
f) -L1-CONH-alkyl;
g) -L1-CON(alkyl)-alkyl;
h) -L1-SO₂-alkyl; and
i) a protected form of any of the above X7 groups;
with the provision that if X1 is present as N(CH₃)₂, and X3 is present as

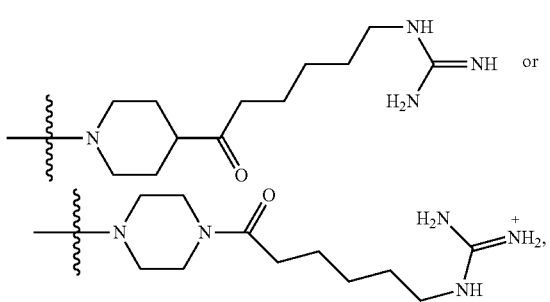

then X7 is not piperdinyl;
X8 is selected from:
a) -L1-CA;
b) -L1-dCA;
c) -L1-COCH$_2$(R$^4$)
d) -L1-COCH(R$^4$)NHCO$_2$-alkyl;
e) —OR$^5$, wherein R$^5$ and R$^{10}$ together form a ring;
f) a protected form of any of the above X8 groups;
each R$^1$ is independently hydrogen, alkyl, or a cell-penetrating peptide;
each R$^2$ is independently C$_1$-C$_{12}$ alkyl or optionally when two R$^2$ are C$_1$-C$_{12}$ alkyl, two R$^2$ are joined to form a heterocyclic ring;
each R$^3$ is independently C$_2$-C$_{18}$ alkyl, alkenyl, or alkynyl;
each R$^4$ is independently hydrogen, alkyl, hydroxyalkyl, sulfhydrylalkyl, or arylalkyl;
each R$^5$ is independently C$_1$-C$_{12}$ alkyl;
each R$^6$ is independently hydrogen or C$_1$-C$_{12}$ alkyl;
L1 is selected from:

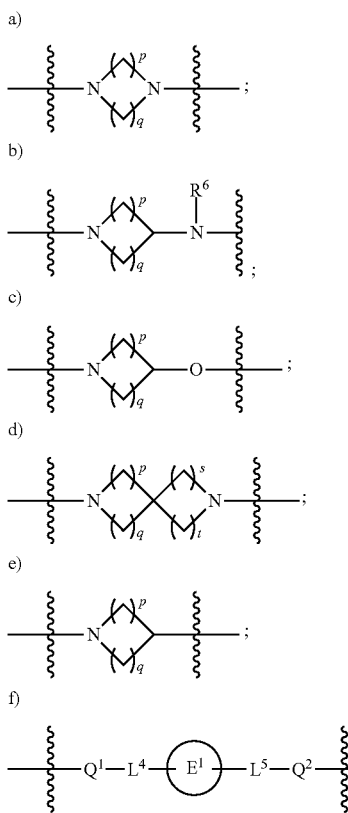

and g)

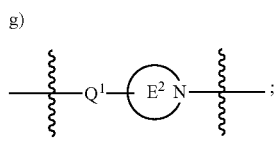

wherein
each Q$^1$ and Q$^2$ are each selected from a bond, —O— or —N(R$^6$)—;
each E$^1$ is independently selected from optionally substituted aryl or optionally substituted heteroaryl;
each E$^2$ is independently an optionally substituted nitrogen containing heteroaryl;
each L$^4$ and L$^5$ are each independently a bond, optionally substituted C$_1$-C$_6$ alkyl, or optionally substituted heteroalkyl; and
m, p, q, s, and t are each independently 1-4.

In another embodiment, the present disclosure provides a method of inhibiting production of a protein, the method comprising exposing a nucleic acid encoding the protein to an oligomer of the present disclosure.

In another embodiment, the disclosure is directed to a method of treating a disease in a subject, the method comprising administering a therapeutically effective amount of an oligomer. Methods of making the oligomers and methods for their use are also provided.

These and other aspects of the invention will be apparent upon reference to the following detailed description. To this end, various references are set forth herein which describe in more detail certain background information, procedures, compounds and/or compositions, and are each hereby incorporated by reference in their entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Definitions

Figure 1:
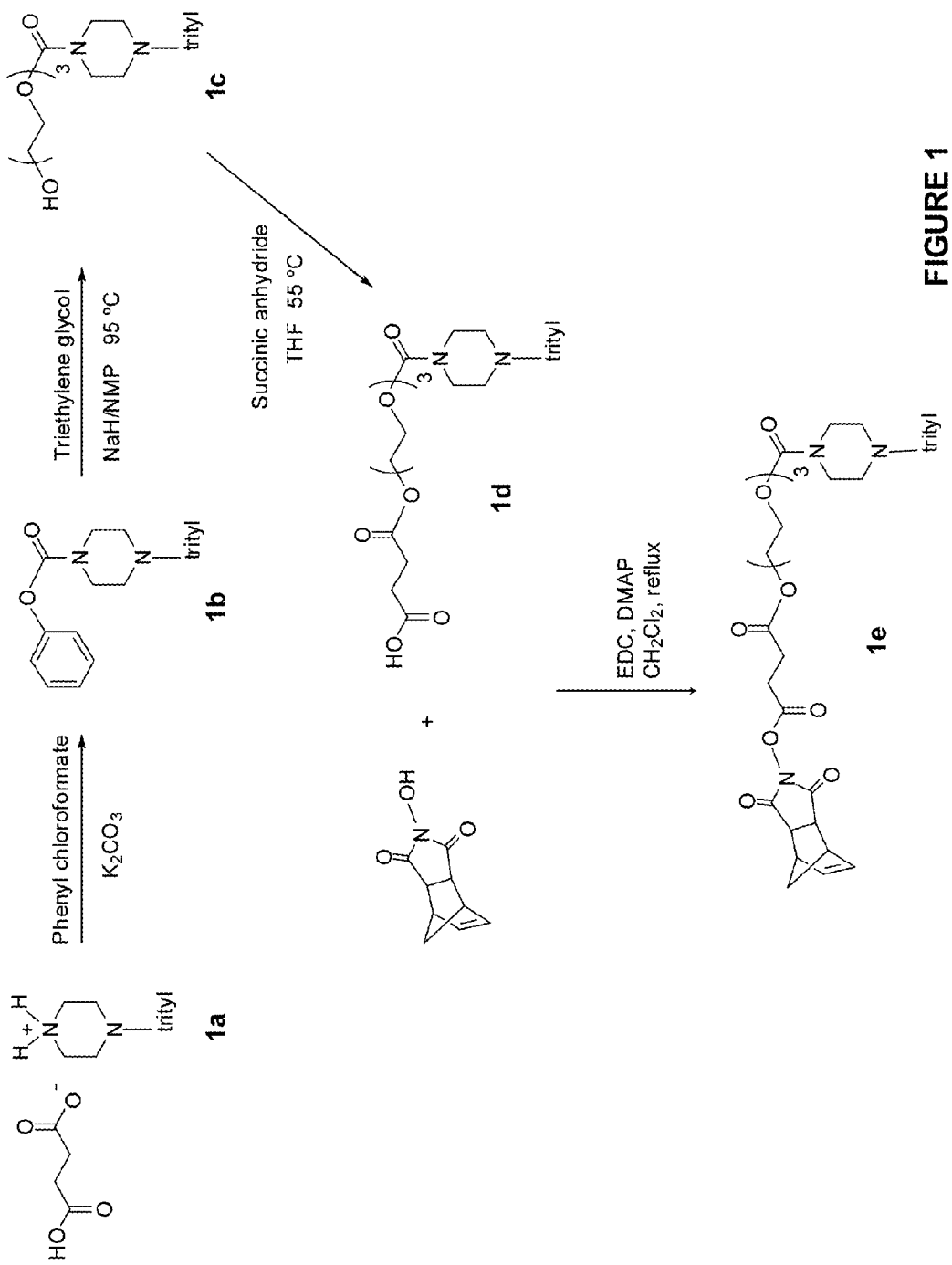
FIG. 1 illustrates preparation of a linker for solid-phase synthesis.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —$NH_2$ radical.

"Cyano" or "nitrile" refers to the —CN radical.

"Hydroxy" or "hydroxyl" refers to the —OH radical.

"Imino" refers to the =NH substituent.

"Guanidinyl" refers to the —NHC(=NH)$NH_2$ substituent.

"Amidinyl" refers to the —C(=NH)$NH_2$ substituent.

"Nitro" refers to the —$NO_2$ radical.

"Oxo" refers to the =O substituent.

"Thioxo" refers to the =S substituent.

"Cholate" or "CA" refers to the following structure:

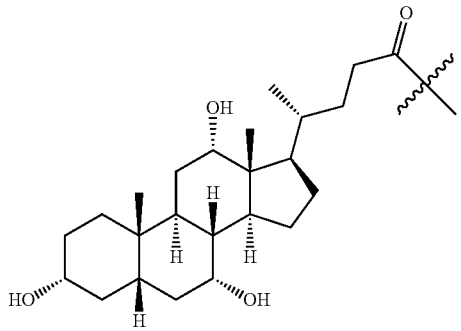

"Deoxycholate" or "dCA" refers to the following structure:

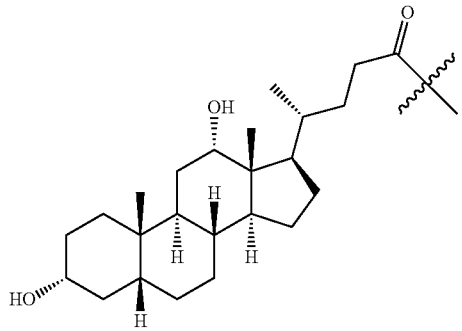

"Alkyl" refers to a straight or branched hydrocarbon chain radical which is saturated or unsaturated (i.e., contains one or more double and/or triple bonds), having from one to thirty carbon atoms, and which is attached to the rest of the molecule by a single bond. Alkyls comprising any number of carbon atoms from 1 to are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, but-2-ynyl, but-3-ynyl, pentynyl, hexynyl, and the like. Unless stated otherwise specifically in the specification, an alkyl group may be optionally substituted as described below.

"Alkylene" or "alkylene chain" refers to a straight or branched divalent hydrocarbon chain linking the rest of the molecule to a radical group. Alkylenes may be saturated or unsaturated (i.e., contains one or more double and/or triple bonds). Representative alkylenes include, but are not limited to, $C_1$-$C_{12}$ alkylene, $C_1$-$C_8$ alkylene, $C_1$-$C_6$ alkylene, $C_1$-$C_4$ alkylene, $C_1$-$C_3$ alkylene, $C_1$-$C_2$ alkylene, $C_1$ alkylene. Representative alkylene groups include, but are not limited to, methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted as described below.

"Alkoxy" refers to a radical of the formula —$OR_a$ where $R_a$ is an alkyl radical as defined. Unless stated otherwise specifically in the specification, an alkoxy group may be optionally substituted as described below.

"Alkoxyalkyl" refers to a radical of the formula —$R_bOR_a$ where $R_a$ is an alkyl radical as defined and where $R_b$ is an alkylene radical as defined. Unless stated otherwise specifically in the specification, an alkoxyalkyl group may be optionally substituted as described below.

"Alkoxyalkylcarbonyl" refers to a radical of the formula —C(=O)$R_b$O$R_a$ where $R_a$ is an alkyl radical as defined and where $R_b$ is an alkylene radical as defined. Unless stated otherwise specifically in the specification, an alkoxyalkylcarbonyl group may be optionally substituted as described below.

"Alkylcarbonyl" refers to a radical of the formula —C(=O)$R_a$ where $R_a$ is an alkyl radical as defined above. Unless stated otherwise specifically in the specification, an alkylcarbonyl group may be optionally substituted as described below.

"Alkyloxycarbonyl" refers to a radical of the formula —C(=O)O$R_a$ where $R_a$ is an alkyl radical as defined. Unless stated otherwise specifically in the specification, an alkyloxycarbonyl group may be optionally substituted as described below. Representative alkyloxycarbonyl groups include, but are not limited to —C(=O)OCH$_2$CH$_2$OH, —C(=O)OCH$_2$CH$_2$OCH$_2$CH$_2$OH, —C(=O)OCH$_2$CH$_2$OCH$_2$CH$_2$OCH$_2$CH$_2$OH, —C(=O)OCH$_2$CH$_2$OCH$_3$, —C(=O)OCH$_2$CH$_2$OCH$_2$CH$_2$OCH$_3$, or —C(=O)OCH$_2$CH$_2$OCH$_2$CH$_2$OCH$_2$CH$_2$OCH$_3$.

"Heteroalkylene" refers to an alkylene radical as described above where one or more carbon atoms of the alkylene is replaced with a O, N or S atom. Unless stated otherwise specifically in the specification, the heteroalkylene group may be optionally substituted as described below. Representative heteroalkylene groups include, but are not limited to —OCH$_2$CH$_2$O—, —OCH$_2$CH$_2$OCH$_2$CH$_2$O—, or —OCH$_2$CH$_2$OCH$_2$CH$_2$OCH$_2$CH$_2$O—.

"Alkylamino" refers to a radical of the formula —NH$R_a$ or —N$R_a R_a$ where each $R_a$ is, independently, an alkyl radical as defined above. Unless stated otherwise specifically in the specification, an alkylamino group may be optionally substituted as described below.

"Amidyl" refers to a radical of the formula —N(H)C(=O)—$R_a$ where $R_a$ is an alkyl or aryl radical as defined herein. Unless stated otherwise specifically in the specification, an amidyl group may be optionally substituted as described below.

"Amidinylalkyl" refers a radical of the formula —$R_b$—C(=NH)NH$_2$ where $R_b$ is an alkylene radical as defined above. Unless stated otherwise specifically in the specification, an amidinylalkyl group may be optionally substituted as described below.

"Amidinylalkylcarbonyl" refers a radical of the formula —C(=O)$R_b$—C(=NH)NH$_2$ where $R_b$ is an alkylene radical as defined above. Unless stated otherwise specifically in the specification, an amidinylalkylcarbonyl group may be optionally substituted as described below.

"Aminoalkyl" refers to a radical of the formula —$R_b$—N$R_a R_a$ where $R_b$ is an alkylene radical as defined above, and each $R_a$ is independently a hydrogen or an alkyl radical.

"Thioalkyl" refers to a radical of the formula —S$R_a$ where $R_a$ is an alkyl radical as defined above. Unless stated otherwise specifically in the specification, a thioalkyl group may be optionally substituted.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above. Examples of aralkyl include, but are not limited to, benzyl, diphenylmethyl, trityl and the like. Unless stated otherwise specifically in the specification, an aralkyl group may be optionally substituted.

"Arylcarbonyl" refers to a radical of the formula —C(=O)$R_c$ where $R_c$ is one or more aryl radicals as defined above, for example, phenyl. Unless stated otherwise specifically in the specification, an arylcarbonyl group may be optionally substituted.

"Aryloxycarbonyl" refers to a radical of the formula —C(=O)O$R_c$ where $R_c$ is one or more aryl radicals as defined above, for example, phenyl. Unless stated otherwise specifically in the specification, an aryloxycarbonyl group may be optionally substituted.

"Aralkylcarbonyl" refers to a radical of the formula —C(=O)$R_b$—$R_c$ where $R_b$ is an alkylene chain as defined above and R is one or more aryl radicals as defined above, for example, phenyl. Unless stated otherwise specifically in the specification, an aralkylcarbonyl group may be optionally substituted.

"Aralkyloxycarbonyl" refers to a radical of the formula —C(=O)O$R_b$—$R_c$ where $R_b$ is an alkylene chain as defined above and $R_c$ is one or more aryl radicals as defined above, for example, phenyl. Unless stated otherwise specifically in the specification, an aralkyloxycarbonyl group may be optionally substituted.

"Aryloxy" refers to a radical of the formula —O$R_c$ where $R_c$ is one or more aryl radicals as defined above, for example, phenyl. Unless stated otherwise specifically in the specification, an arylcarbonyl group may be optionally substituted.

"Cycloalkyl" refers to a stable, non-aromatic, monocyclic or polycyclic carbocyclic ring, which may include fused or bridged ring systems, which is saturated or unsaturated, and attached to the rest of the molecule by a single bond. Representative cycloalkyls include, but are not limited to, cycloalkyls having from three to fifteen carbon atoms, from three to ten carbon atoms, from three to eight carbon atoms, from three to six carbon atoms, from three to five carbon atoms, or three to four carbon atoms. Monocyclic cycloalkyl radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and 7,7-dimethyl-bicyclo[2.2.1]heptanyl. Unless otherwise stated specifically in the specification, a cycloalkyl group may be optionally substituted.

"Cycloalkylalkyl" refers to a radical of the formula —$R_b R_d$ where $R_b$ is an alkylene chain as defined above and $R_d$ is a cycloalkyl radical as defined above. Unless stated otherwise specifically in the specification, a cycloalkylalkyl group may be optionally substituted.

"Cycloalkylcarbonyl" refers to a radical of the formula —C(=O)$R_d$ where $R_d$ is a cycloalkyl radical as defined above. Unless stated otherwise specifically in the specification, a cycloalkylcarbonyl group may be optionally substituted.

Cycloalkyloxycarbonyl" refers to a radical of the formula —C(=O)O$R_d$ where $R_d$ is a cycloalkyl radical as defined above. Unless stated otherwise specifically in the specification, a cycloalkyloxycarbonyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Guanidinylalkyl" refers a radical of the formula —$R_b$—NHC(=NH)NH$_2$ where $R_b$ is an alkylene radical as defined above. Unless stated otherwise specifically in the specification, a guanidinylalkyl group may be optionally substituted as described below.

"Guanidinylalkylcarbonyl" refers a radical of the formula —C(=O)$R_b$—NHC(=NH)NH$_2$ where $R_b$ is an alkylene radical as defined above. Unless stated otherwise specifically in the specification, a guanidinylalkylcarbonyl group may be optionally substituted as described below.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Perhalo" or "perfluoro" refers to a moiety in which each hydrogen atom has been replaced by a halo atom or fluorine atom, respectively.

"Heterocyclyl" or "heterocyclic ring" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups (i.e., alkyl, alkylene, alkoxy, alkoxyalkyl, alkylcarbonyl, alkyloxycarbonyl, alkylamino, amidyl, amidinylalkyl, amidinylalkylcarbonyl, aminoalkyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, guanidinylalkyl, guanidinylalkylcarbonyl, haloalkyl, heterocyclyl and/or heteroaryl), may be further functionalized wherein at least one hydrogen atom is replaced by a bond to a non-hydrogen atom substituent. Unless stated specifically in the specification, a substituted group may include one or more substituents selected from: oxo, —CO$_2$H, nitrile, nitro, hydroxyl, thiooxy, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, heterocyclyl, heteroaryl, dialkylamines, arylamines, alkylarylamines, diarylamines, trialkylammonium (—N$^+$R$_3$), N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted" also means any of the above groups in which one or more hydrogen atoms are replaced with —C(=O)R$_g$, —C(=O)OR$_g$, —CH$_2$SO$_2$R$_g$, —CH$_2$SO$_2$NR$_g$R$_h$, —SH, —SR$_g$ or —SSR$_g$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen or sulfur atoms. For example, an alkyl group may be substituted with one or more internal oxygen atoms to form an ether or polyether group. Similarly, an alkyl group may be substituted with one or more internal sulfur atoms to form a thioether, disulfide, etc. Amidyl moieties may be substituted with up to 2 halo atoms, while other groups above may be substituted with one or more halo atoms. With the exception of alkyl groups, all other groups may also be substituted with amino or monoalkylamino. With the exception of alkyl and alkylcarbonyl groups, all other groups may also be substituted with guanidinyl or amidinyl. Optional substituents for any of the above groups also include arylphosphoryl, for example —$R_aP(Ar)_3$ wherein Ra is an alkylene and Ar is aryl moiety, for example phenyl.

The terms "antisense oligomer" or "antisense compound" are used interchangeably and refer to a sequence of subunits, each having a base carried on a backbone subunit composed of ribose or other pentose sugar or morpholino group, and where the backbone groups are linked by intersubunit linkages that allow the bases in the compound to hybridize to a target sequence in a nucleic acid (typically an RNA) by Watson-Crick base pairing, to form a nucleic acid:oligomer heteroduplex within the target sequence. The oligomer may have exact sequence complementarity to the target sequence or near complementarity. Such antisense oligomers are designed to block or inhibit translation of the mRNA containing the target sequence, and may be said to be "directed to" a sequence with which it hybridizes.

A "morpholino oligomer" or "PMO" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. An exemplary "morpholino" oligomer comprises morpholino subunit structures linked together by (thio)phosphoramidate or (thio)phosphorodiamidate linkages, joining the morpholino nitrogen of one subunit to the 5' exocyclic carbon of an adjacent subunit, each subunit comprising a purine or pyrimidine base-pairing moiety effective to bind, by base-specific hydrogen bonding, to a base in a polynucleotide. Morpholino oligomers (including antisense oligomers) are detailed, for example, in U.S. Pat. Nos. 5,698,685; 5,217,866; 5,142,047; 5,034,506; 5,166, 315; 5,185,444; 5,521,063; 5,506,337 and pending U.S. patent application Ser. Nos. 12/271,036; 12/271,040; and PCT publication number WO/2009/064471 all of which are incorporated herein by reference in their entirety.

"PMO+" refers to phosphorodiamidate morpholino oligomers comprising any number of (1-piperazino)phosphinylideneoxy, (1-(4-(ω-guanidino-alkanoyl))-piperazino) phosphinylideneoxy linkages that have been described previously (see e.g., PCT publication WO/2008/036127 which is incorporated herein by reference in its entirety.

"PMO-X" refers to phosphorodiamidate morpholino oligomers disclosed herein.

A "phosphoramidate" group comprises phosphorus having three attached oxygen atoms and one attached nitrogen atom, while a "phosphorodiamidate" group comprises phosphorus having two attached oxygen atoms and two attached nitrogen atoms.

"Thiophosphoramidate" or "thiophosphorodiamidate" linkages are phosphoramidate or phosphorodiamidate linkages, respectively, wherein one oxygen atom, typically the oxygen pendant to the backbone, is replaced with sulfur.

"Intersubunit linkage" refers to the linkage connecting two morpholino subunits.

"Charged", "uncharged", "cationic" and "anionic" as used herein refer to the predominant state of a chemical moiety at near-neutral pH, e.g., about 6 to 8. For example, the term may refer to the predominant state of the chemical moiety at physiological pH, that is, about 7.4.

"Lower alkyl" refers to an alkyl radical of one to six carbon atoms, as exemplified by methyl, ethyl, n-butyl, i-butyl, t-butyl, isoamyl, n-pentyl, and isopentyl. In certain embodiments, a "lower alkyl" group has one to four carbon atoms. In other embodiments a "lower alkyl" group has one to two carbon atoms; i.e. methyl or ethyl. Analogously, "lower alkenyl" refers to an alkenyl radical of two to six, preferably three or four, carbon atoms, as exemplified by allyl and butenyl.

A "non-interfering" substituent is one that does not adversely affect the ability of an antisense oligomer as described herein to bind to its intended target. Such substituents include small and/or relatively non-polar groups such as methyl, ethyl, methoxy, ethoxy, or fluoro.

An oligonucleotide or antisense oligomer "specifically hybridizes" to a target polynucleotide if the oligomer hybridizes to the target under physiological conditions, with a Tm greater than 37° C., greater than 45° C., preferably at least 50° C., and typically 60° C.-80° C. or higher. The "Tm" of an oligomer is the temperature at which 50% hybridizes to a complementary polynucleotide. Tm is determined under standard conditions in physiological saline, as described, for example, in Miyada et al., *Methods Enzymol.* 154:94-107 (1987). Such hybridization may occur with "near" or "substantial" complementary of the antisense oligomer to the target sequence, as well as with exact complementarity.

Polynucleotides are described as "complementary" to one another when hybridization occurs in an antiparallel configuration between two single-stranded polynucleotides. Complementarity (the degree that one polynucleotide is complementary with another) is quantifiable in terms of the proportion of bases in opposing strands that are expected to form hydrogen bonds with each other, according to generally accepted base-pairing rules.

A first sequence is an "antisense sequence" with respect to a second sequence if a polynucleotide whose sequence is the first sequence specifically binds to, or specifically hybridizes with, the second polynucleotide sequence under physiological conditions.

The term "targeting sequence" is the sequence in the oligonucleotide analog that is complementary (meaning, in addition, substantially complementary) to the target sequence in the RNA genome. The entire sequence, or only a portion, of the analog compound may be complementary to the target sequence. For example, in an analog having 20 bases, only 12-14 may be targeting sequences. Typically, the targeting sequence is formed of contiguous bases in the analog, but may alternatively be formed of non-contiguous sequences that when placed together, e.g., from opposite ends of the analog, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the presently described methods, that is, still be "complementary." Preferably, the oligonucleotide analog compounds employed in the presently described methods have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein. For purposes of complementary binding to an RNA target, and as discussed below, a guanine base may be complementary to either a cytosine or uracil RNA base.

A "heteroduplex" refers to a duplex between an oligonucleotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAse H, which are capable of cutting double-stranded RNA/RNA or RNA/DNA complexes.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane.

The terms "modulating expression" and/or "antisense activity" refer to the ability of an antisense oligomer to either enhance or, more typically, reduce the expression of a given protein, by interfering with the expression or translation of RNA. In the case of reduced protein expression, the antisense oligomer may directly block expression of a given gene, or contribute to the accelerated breakdown of the RNA transcribed from that gene. Morpholino oligomers as described herein are believed to act via the former (steric blocking) mechanism. Preferred antisense targets for steric blocking oligomers include the ATG start codon region, splice sites, regions closely adjacent to splice sites, and 5'-untranslated region of mRNA, although other regions have been successfully targeted using morpholino oligomers.

An "amino acid subunit" is preferably an α-amino acid residue (—CO—CHR—NH—); it may also be a β- or other amino acid residue (e.g. —CO—CH$_2$CHR—NH—), where R is an amino acid side chain.

The term "naturally occurring amino acid" refers to an amino acid present in proteins found in nature. The term "non-natural amino acids" refers to those amino acids not present in proteins found in nature; examples include beta-alanine (β-Ala) and 6-aminohexanoic acid (Ahx).

An "effective amount" or "therapeutically effective amount" refers to an amount of antisense oligomer administered to a mammalian subject, either as a single dose or as part of a series of doses, which is effective to produce a desired therapeutic effect, typically by inhibiting translation of a selected target nucleic acid sequence.

"Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

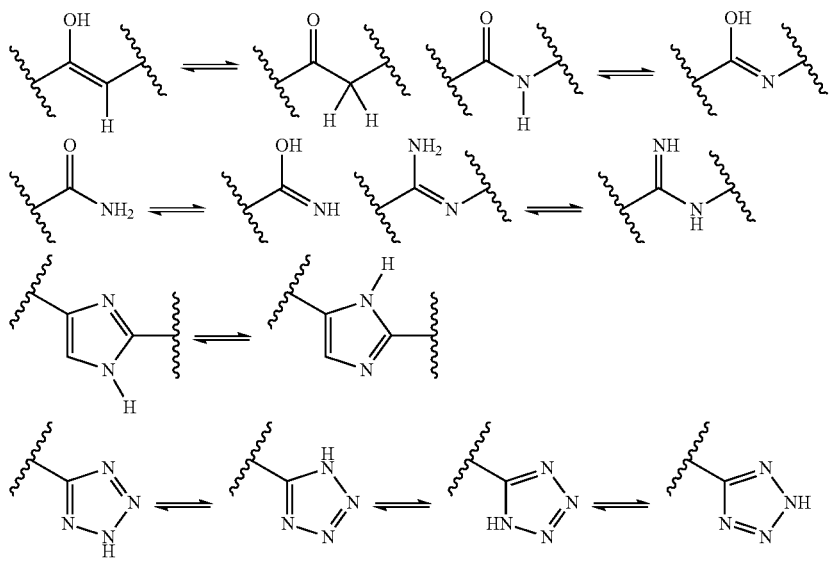

Antisense Oligomers

A. Oligomers with Modified Intersubunit Linkages

As noted above, one embodiment of the present disclosure is directed to oligomers comprising novel intersubunit linkages. In some embodiments, the oligomers have higher affinity for DNA and RNA than do the corresponding unmodified oligomers and demonstrate improved cell delivery, potency, and/or tissue distribution properties compared to oligomers having other intersubunit linkages. The structural features and properties of the various linkage types and oligomers are described in more detail in the following discussion.

Applicants have found that enhancement of antisense activity, biodistribution and/or other desirable properties can be optimized by preparing oligomers having various inter-subunit linkages. In one aspect is a compound having the structure of Formula (I):

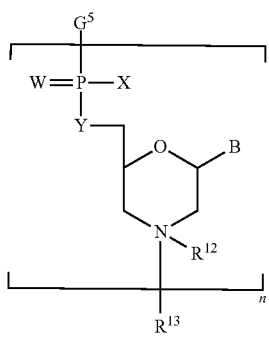

(I)

or a salt or isomer thereof,
wherein:
n is an integer from 1 to 50;
$G^5$ is halogen, OH, alkoxy, $OSO_2$(alkyl), $OSO_2$(aryl), or

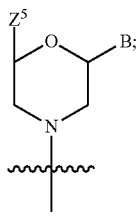

each B is an independently selected base pair moiety;
each Y is independently O or $NR^{10}$; optionally, $R^{10}$ and X8e are bonded together form a ring;
each W is independently S or O;
$Z^5$ is $-(L^{11})-(R^{15})$, $-(L^{11})-(L^{15})-(R^{16})$, or $-(L^{11})-(L^{12})-(R^{17})$;
$L^{11}$ is selected from:

a)
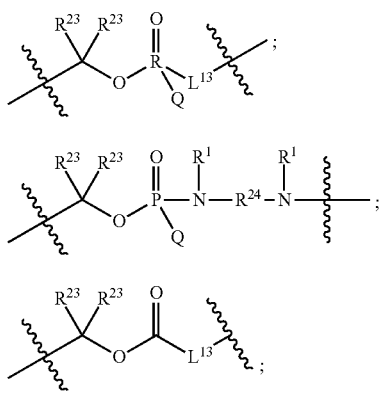

b)

c)

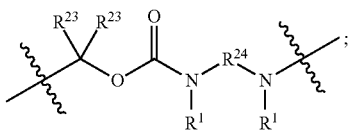  d)

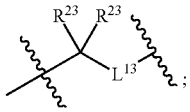  e)

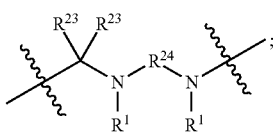  f)

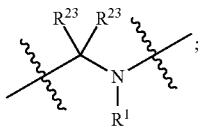  g)

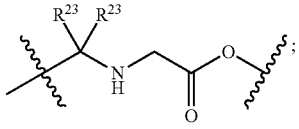  h)

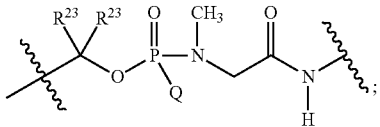  i)

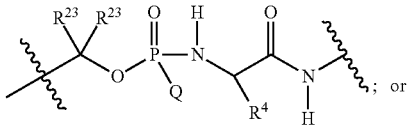  j)

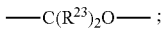  k)

wherein $L^{13}$ is selected from:

a)
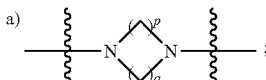

b)
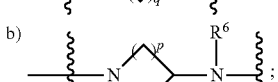

c)
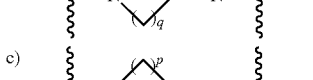

d)
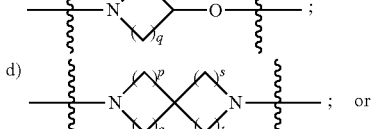 ; or e)
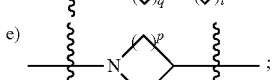

$L^{12}$ is a linker cleaveable under biological conditions selected from:
a) —($C_1$-$C_{10}$ alkylene)-OC(O)O—$CH_2$O—;
b) —C(O)—($C_1$-$C_{10}$ alkylene)-OC(O)O—$CH_2$O—;
c) —C(O)—(CH=CH)—C(O)O—$CH_2$O—;
d) —($C_1$-$C_{10}$ alkylene)-S—S—$CH_2CH_2$O—; or
e) C(O) ($C_1$-$C_{10}$ alkylene)-S—S—$CH_2CH_2$O—;

$L^{15}$ is divalent radical selected from $C_1$-$C_{30}$ alkylene, $C_3$-$C_8$ cycloalkylene, $C_6$-$C_{30}$ arylene, —($C_6$-$C_{30}$ arylene)-($C_1$-$C_{30}$ alkylene)-, —($C_1$-$C_{30}$ alkylene)-C(=O)—, —($C_2$-$C_{30}$ alkoxy)-C(=O)—, -(3-18 membered heteroalkylene)-C(=O)—, —($C_3$-$C_8$ cycloalkylene)-C(=O)—, —($C_3$-$C_8$ cycloalkylene)-($C_1$-$C_{30}$ alkylene)-C(=O)—, —($C_1$-$C_{30}$ alkylene) ($C_3$-$C_8$ cycloalkylene)-C(=O)—, —($C_6$-$C_{30}$ arylene)-C(=O)—, —($C_6$-$C_{30}$ arylene)-($C_1$-$C_{30}$ alkylene)-C(=O)—, —($C_1$-$C_{30}$ alkylene)-($C_6$-$C_{30}$ arylene)-C(=O)—, —($C_1$-$C_{30}$ alkylene)-O—C(=O)—, —($C_3$-$C_8$ cycloalkylene)-O—C(=O)—, —($C_7$-$C_{30}$ arylene)-O—C(=O)—, —($C_6$-$C_{30}$ arylene)-($C_1$-$C_{30}$ alkylene)-O—C(=O)—, —($C_6$-$C_{30}$ arylene)-($C_1$-$C_{30}$ alkylene)-O—C(=O)—, —C(=O)O$R^{21}$, or —P(=O)($R^{22}$)$_2$;

$R^{12}$ is an electron pair, with the provision that if $R^{13}$ is $C_1$-$C_{30}$ alkyl, then $R^{12}$ is an electron pair, an N-oxide, or $C_1$-$C_6$ alkyl;

each $R^{10}$ and $R^{13}$ is independently selected from hydrogen, a cell-penetrating peptide, a natural or non-natural amino acid, guanidinyl, amidinyl, heterocyclyl, $C_1$-$C_{30}$ alkyl, $C_3$-$C_8$ cycloalkyl; $C_6$-$C_{30}$ aryl, $C_7$-$C_{30}$ aralkyl, $C_1$-$C_{30}$ alkylcarbonyl, $C_3$-$C_8$ cycloalkylcarbonyl, $C_3$-$C_8$ cycloalkylalkylcarbonyl, $C_6$-$C_{30}$ arylcarbonyl, $C_7$-$C_{30}$ aralkylcarbonyl, $C_1$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, —C(=O)O$R^{21}$, —C(=O)NH$R^{21}$, or —P(=O)($R^{22}$)$_2$;

$R^{15}$ is independently selected from a cell-penetrating peptide, a natural or non-natural amino acid, guanidinyl, amidinyl, heterocyclyl, $C_1$-$C_{30}$ alkyl, $C_3$-$C_8$ cycloalkyl; $C_6$-$C_{30}$ aryl, $C_7$-$C_{30}$ aralkyl, $C_1$-$C_{30}$ alkylcarbonyl, $C_3$-$C_8$ cycloalkylcarbonyl, $C_3$-$C_8$ cycloalkylalkylcarbonyl, $C_6$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, 3-18 membered alkoxyalkylcarbonyl, —SO$_2$$R^{21}$, —C(=O)O$R^{21}$, —P(=O)(OH)$_2$ or —P(=O)($R^{22}$)$_2$;

$R^{16}$ is a solid support matrix suitable for solid phase synthesis of oligonucleotides;

$R^{17}$ is a drug, protein or toxin;

each $R^{21}$ is independently $C_1$-$C_{30}$ alkyl, or a 3-18 membered alkoxyalkyl group;

each $R^{22}$ is independently an $C_6$-$C_{12}$ aryloxy;

each $R^{23}$ is independently H or $C_1$-$C_6$ alkyl; or optionally two $R^{23}$ groups join to form a 3- to 8-membered ring;

$R^{24}$ is a $C_1$-$C_6$ alkylene;

Q is independently selected from X1, X2, X3, X4, X5, X6, X7, or X8;

each X is independently selected from X1, X2, X3, X4, X5, X6, X7, or X8 with the provision that at least one X is not X1;

wherein

X1 is N(CH$_3$)$_2$;

X2 is selected from:
a) —O-alkylene-CO$_2$H;
b) —O-alkylene-CHN$_4$;
c) —N($R^1$)-alkylene-CO$_2$H;
d) —N($R^1$)-alkylene-CHN$_4$;
e) -L1-CO-alkylene-CO$_2$H;
f) -L1-CO-alkylene-CHN$_4$;
g) -L1-CO-alkenylene-CO$_2$H;
h) -L1-CO-alkenylene-CHN$_4$;
i) -L1-CO-arylene-CO$_2$H;
j) -L1-CO-arylene-CHN$_4$;
k) -L1-CONH-alkylene-CO$_2$H;
l) -L1-CONH-alkylene-CHN$_4$;
m) -L1-CONH-arylene-CO$_2$H;
n) -L1-CONH-arylene-CHN$_4$;
o) -L1-SO$_2$-alkylene-CO$_2$H;
p) -L1-SO$_2$-alkylene-CHN$_4$
q) -L1-SO$_2$-arylene-CO$_2$H;
r) -L1-SO$_2$-arylene-CHN$_4$;
s) -L1-alkylene-CO$_2$H;
t) -L1-alkylene-CHN$_4$;
u) -L1-arylene-CO$_2$H;
v) -L1-arylene-CHN$_4$; and
w) a protected form of any of the above X2 groups;

X3 is selected from:
a) -L1-alkyl;
b) -L1-heterocyclyl;
c) —O-alkylene-CNH—NH$_2$;
d) —N($R^1$)-alkylene-CNH—NH$_2$;
e) -L1-CNH—NH$_2$;
f) -L1-alkylene-CNH—NH$_2$;
g) -L1-arylene-CNH—NH$_2$;
h) -L1-CO-alkylene-CNH—NH$_2$;
i) -L1-CO-alkenylene-CNH—NH$_2$;
j) -L1-CO-arylene-CNH—NH$_2$;
k) -L1-CONH-alkylene-CNH—NH$_2$;
l) -L1-CONH-arylene-CNH—NH$_2$;
m) -L1-SO$_2$-alkylene-CNH—NH$_2$;
n) -L1-SO$_2$-arylene-CNH—NH$_2$;
o) —O-alkylene-N($R^1$)$_2$;
p) —N($R^1$)-alkylene-N($R^1$)$_2$;
q) -L1-N($R^1$)$_2$;
r) -L1-alkylene-N($R^1$)$_2$;
s) -L1-arylene-N($R^1$)$_2$;
t) -L1-CO-alkylene-N($R^1$)$_2$;
u) -L1-CO-alkenylene-N($R^1$)$_2$;
v) -L1-CO-arylene-N($R^1$)$_2$;
w) -L1-CONH-alkylene-N($R^1$)$_2$;
x) -L1-CONH-arylene-N($R^1$)$_2$;
y) -L1-SO$_2$-alkylene-N($R^1$)$_2$;
z) —O-alkylene-N($R^2$)$_3$;
aa) —N($R^1$)-allylene-N($R^2$)$_3$;
bb) -L1-N($R^2$)$_3$;
cc) -L1-alkylene-N($R^2$)$_3$;
dd) -L1-arylene-N($R^2$)$_3$;
ee) -L1-CO-alkylene-N($R^2$)$_3$;
ff) -L1-CO-alkenylene-N($R^2$)$_3$;
gg) -L1-CO-arylene-N($R^2$)$_3$;
hh) -L1-CONH-alkylene-N($R^2$)$_3$;
ii) -L1-CONH-arylene-N($R^2$)$_3$;
jj) -L1-SO$_2$-alkylene-N($R^2$)$_3$;
kk) —O-alkylene-heterocyclyl;
ll) —N($R^1$)-alkylene-heterocyclyl;
mm) -L1-alkylene-heterocyclyl;
nn) -L1-arylene-heterocyclyl;
oo) -L1-CO-alkylene-heterocyclyl;
pp) -L1-CO-alkenylene-heterocyclyl;
qq) -L1-CO-arylene-heterocyclyl;
rr) -L1-CONH-alkylene-heterocyclyl;
ss) -L1-CONH-arylene-heterocyclyl;
tt) -L1-SO$_2$-alkylene-heterocyclyl;
uu) —O-alkylene-N(O)($R^2$)$_2$;
vv) —N($R^1$)-alkylene-N(O)($R^2$)$_2$;

ww) -L1-N(O)($R^2$)$_2$;
xx) -L1-alkylene-N(O)($R^2$)$_{23}$;
yy) -L1-arylene-N(O)($R^2$)$_2$;
zz) -L1-CO-alkylene-N(O)($R^2$)$_2$;
aaa) -L1-CO-alkenylene-N(O)($R^2$)$_{23}$;
bbb) -L1-CO-arylene-N(O)($R^2$)$_2$;
ccc) -L1-CONH-alkylene-N(O)($R^2$)$_2$;
ddd) -L1-CONH-arylene-N(O)($R^2$)$_2$;
eee) -L1-SO$_2$-alkylene-N(O)($R^2$)$_2$;
fff) —O-alkylene-NH—CNH—NH$_2$;
ggg) —N($R^1$)-alkylene-NH—CNH—NH$_2$;
hhh) -L1-NH—CNH—NH$_2$;
iii) -L1-alkylene-NH—CNH—NH$_2$;
jjj) -L1-arylene-NH—CNH—NH$_2$;
kkk) -L1-CO-alkylene-NH—CNH—NH$_2$;
lll) -L1-CO-alkenylene-NH—CNH—NH$_2$;
mmm) -L1-CO-arylene-NH—CNH—NH$_2$;
nnn) -L1-CONH-alkylene-NH—CNH—NH$_2$;
ooo) -L1-CONH-arylene-NH—CNH—NH$_2$;
ppp) -L1-SO$_2$-alkylene-NH—CNH—NH$_2$;
qqq) -L1-SO$_2$-arylene-NH—CNH—NH$_2$; and
rrr) a protected form of any of the above X3 groups;
with the provision that if X1 is present as N(CH$_3$)$_2$, and X7 is present as piperidinyl, then X3 is not

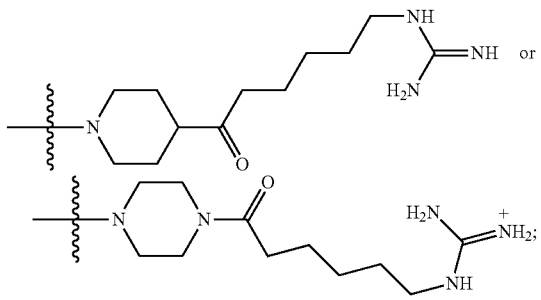

X4 is selected from:
a) —O-alkylene-aryl;
b) —N($R^1$)-aryl;
c) —N($R^1$)-alkylene-aryl;
d) -L1-CO-alkylene-aryl;
e) -L1-CO-alkenylene-aryl;
f) -L1-CO-arylene-aryl;
g) -L1-CONH-alkylene-aryl;
h) -L1-CONH-arylene-aryl;
i) -L1-SO$_2$-alkylene-aryl;
j) -L1-SO$_2$-arylene-aryl;
k) -L1-alkylene-aryl;
l) -L1-arylene-aryl;
m) —N($R^1$)-alkylene-N($R^1$)-aryl;
n) —N($R^1$)-alkylene-N($R^1$)CO-aryl;
o) —N($R^1$)-alkylene-N($R^1$)SO$_2$-aryl;
p) —N($R^1$)-alkylene-N($R^1$)CH$_2$-aryl;
q) -L1-aryl;
r) -L1-CO-aryl;
s) -L1-SO$_2$-aryl;
t) -L1-alkylene-P(aryl)$_3$;
u) -L1-CO-alkylene-P(aryl)$_3$;
v) -L1-SO$_2$-alkylene-P(aryl)$_3$; and
w) a protected form of any of the above X4 groups;
X5 is selected from:
a) —O-alkylene-heteroaryl;
b) —N($R^1$)-alkylene-heteroaryl;
c) -L1-CO-alkylene-heteroaryl;
d) -L1-CO-alkenylene-heteroaryl;
e) -L1-CO-arylene-heteroaryl;
f) -L1-CONH-alkylene-heteroaryl;
g) -L1-CONH-arylene-heteroaryl;
h) -L1-SO$_2$-alkylene-heteroaryl;
i) -L1-SO$_2$-arylene-heteroaryl;
j) -L1-alkylene-heteroaryl;
k) -L1-arylene-heteroaryl;
l) —N($R^1$)-alkylene-N($R^1$)-heteroaryl;
m) —N($R^1$)-alkylene-N($R^1$)CO-heteroaryl;
n) —N($R^1$)-alkylene-N($R^1$)SO$_2$-heteroaryl;
o) —N($R^1$)-alkylene-N($R^1$)CH$_2$-heteroaryl;
p) -L1-heteroaryl; and
q) a protected form of any of the above X5 groups;
X6 is selected from:
a) —O-alkylene-(OCH$_2$CH$_2$)$_m$OH;
b) —O-alkylene-(OCH$_2$CH$_2$)$_m$OCH$_3$;
c) —N($R^1$)-alkylene-(OCH$_2$CH$_2$)$_m$OH;
d) —N($R^1$)-alkylene-(OCH$_2$CH$_2$)$_m$OCH$_3$;
e) —N($R^1$)-arylene-(OCH$_2$CH$_2$)$_m$OH;
f) —N($R^1$)-arylene-(OCH$_2$CH$_2$)$_m$OCH$_3$;
g) -L1-alkylene-(OCH$_2$CH$_2$)$_m$OH;
h) -L1-CO-alkylene-(OCH$_2$CH$_2$)$_m$OH;
i) -L1-CO-alkylene-(OCH$_2$CH$_2$)$_m$OCH$_3$;
j) -L1-SO$_2$-alkylene-(OCH$_2$CH$_2$)$_m$OH;
k) -L1-SO$_2$-alkylene-(OCH$_2$CH$_2$)$_m$OCH$_3$;
l) -L1-CO-arylene-(OCH$_2$CH$_2$)$_m$OH;
m) -L1-CO-arylene-(OCH$_2$CH$_2$)$_m$OCH$_3$;
n) -L1-SO$_2$-arylene-(OCH$_2$CH$_2$)$_m$OH;
o) -L1-SO$_2$-arylene-(OCH$_2$CH$_2$)$_m$OCH$_3$;
p) -L1-CO—(OCH$_2$CH$_2$)$_m$OH;
q) -L1-CO—(OCH$_2$CH$_2$)$_m$OCH$_3$;
r) —N($R^1$)-(dibenzo-18-crown-6);
s) an aza-crown ether; and
t) a protected form of any of the above X6 groups;
X7 is selected from:
a) -heterocyclyl;
b) —N($R^1$)($R^3$)
c) -L1-hydrogen;
d) -L1-alkyl;
e) -L1-CO-alkyl;
f) -L1-CONH-alkyl;
g) -L1-CON(alkyl)-alkyl;
h) -L1-SO$_2$-alkyl; and
i) a protected form of any of the above X7 groups;
with the provision that if X1 is present as N(CH$_3$)$_2$, and X3 is present as

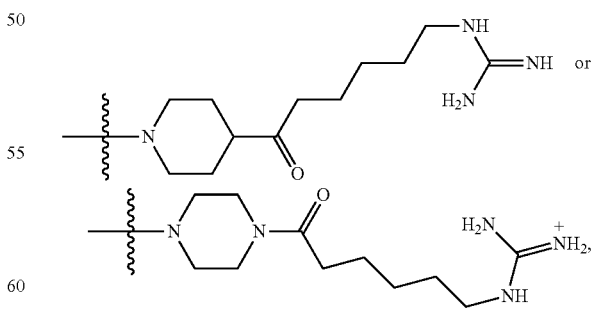

then X7 is not piperdinyl;
X8 is selected from:
a) -L1-CA;
b) -L1-dCA;
c) -L1-COCH$_2$($R^4$)

d) -L1-COCH(R$^4$)NHCO$_2$-alkyl;
e) —OR$^5$, wherein R$^5$ and R$^{10}$ together form a ring;
f) a protected form of any of the above X8 groups;

each R$^1$ is independently hydrogen, alkyl, or a cell-penetrating peptide;
each R$^2$ is independently C$_1$-C$_{12}$ alkyl or optionally when two R$^2$ are C$_1$-C$_{12}$ alkyl, two R$^2$ are joined to form a heterocyclic ring;
each R$^3$ is independently C$_2$-C$_{18}$ alkyl, alkenyl, or alkynyl;
each R$^4$ is independently hydrogen, alkyl, hydroxyalkyl, sulfhydrylalkyl, or arylalkyl;
each R$^5$ is independently C$_1$-C$_{12}$ alkyl;
each R$^6$ is independently hydrogen or C$_1$-C$_{12}$ alkyl;
L1 is selected from:

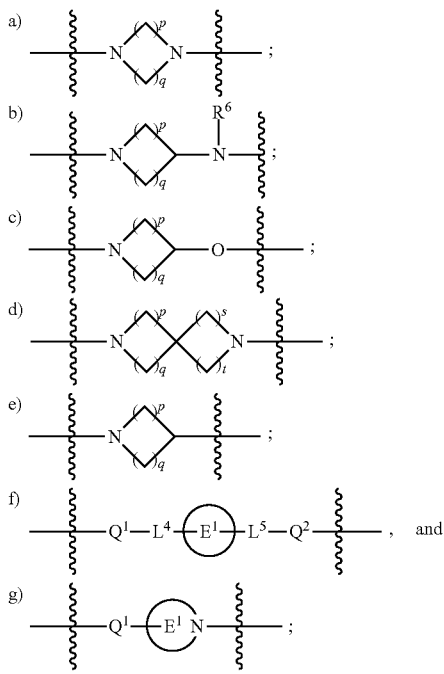

wherein
each Q$^1$ and Q$^2$ are each selected from a bond, —O— or —N(R$^6$)—;
each E$^1$ is independently selected from optionally substituted aryl or optionally substituted heteroaryl;
each E$^2$ is independently an optionally substituted nitrogen containing heteroaryl;
each L$^4$ and L$^5$ are each independently a bond, optionally substituted C$_1$-C$_6$ alkyl, or optionally substituted heteroalkyl; and
m, p, q, s, and t are each independently 1-4.

In some embodiments of Formula (I), Z$^5$ is -(L$^{11}$)-(R$^{15}$). In other embodiments, Z$^5$ is -(L$^{11}$)-(L$^{15}$)-(R$^{16}$). In another embodiments, Z$^5$ is -(L$^{12}$)-(R$^{17}$). In a further embodiment of Formula (I), each Y is independently O, NH, or NR$^{10}$. In a further embodiment of the aforementioned embodiments, each W is O. In yet a further embodiment, each R$^1$ is independently hydrogen or alkyl. In a further embodiment, each R$^2$ is independently C$_1$-C$_{12}$ alkyl. In yet a further embodiment, each X is independently selected from X1, X2, X3, X4, X5, X6, X7, or X8.

In one embodiment is a compound of Formula (I), wherein Z$^5$ is -(L$^{11}$)-(R$^{15}$), each Y is independently O, NH, or NR$^{10}$, each W is O, each R$^1$ is independently hydrogen or alkyl, each R$^2$ is independently C$_1$-C$_{12}$ alkyl, each X is independently selected from X1, X2, X3, X4, X5, X6, X7, or X8 and n is an integer from 1 to 35.

In another embodiment is a compound of Formula (I), wherein n is 1, Z$^5$ is -(L$^{11}$)-(R$^{15}$), each Y is independently O, NH, or NR$^{10}$, each W is O, each R$^1$ is independently hydrogen or alkyl, each R$^2$ is independently C$_1$-C$_{12}$ alkyl, and X is selected from X2, X3, X4, X5, X6, X7, or X8. In some embodiments of Formula (I) wherein n is 1, G$^5$ is halogen. In another embodiment, W is O. In another embodiment, Y is O. In another embodiment, R$^{13}$ is aralkyl. In another embodiment R$^{13}$ is an optionally substituted triphenylmethyl group.

In some embodiments is a compound of Formula (I), wherein n is 1, G$^5$ is halogen, W is O, Y is O, R$^{13}$ is an optionally substituted triphenylmethyl group, and X is X2. In some embodiments is a compound of Formula (I), wherein n is 1, G$^5$ is halogen, W is O, Y is O, R$^{13}$ is an optionally substituted triphenylmethyl group, and X is X3. In some embodiments is a compound of Formula (I), wherein n is 1, G$^5$ is halogen, W is O, Y is O, R$^{13}$ is an optionally substituted triphenylmethyl group, and X is X4. In some embodiments is a compound of Formula (I), wherein n is 1, G$^5$ is halogen, W is O, Y is O, R$^{13}$ is an optionally substituted triphenylmethyl group, and X is X5. In some embodiments is a compound of Formula (I), wherein n is 1, G$^5$ is halogen, W is O, Y is O, R$^{13}$ is an optionally substituted triphenylmethyl group, and X is X6. In some embodiments is a compound of Formula (I), wherein n is 1, G$^5$ is halogen, W is O, Y is O, R$^{13}$ is an optionally substituted triphenylmethyl group, and X is X7. In some embodiments is a compound of Formula (I), wherein n is 1, G$^5$ is halogen, W is O, Y is O, R$^{13}$ is an optionally substituted triphenylmethyl group, and X is X8.

In another embodiment is a compound of Formula (I) wherein G$^5$ is -(L$^{13}$)-(L$^{15}$)-(R$^{16}$). In another embodiment is a compound of Formula (I) wherein G$^5$ is -(L$^{13}$)-(R$^{15}$). In another embodiment is a compound of Formula (I) wherein G$^5$ is -(L$^{13}$)-(L$^{12}$)-(R$^{17}$).

In another embodiment is a compound of Formula (I) wherein n is an integer from 1 to 35 and G$^5$ is

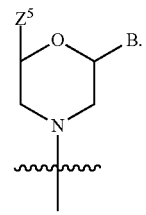

In another embodiment is a compound of Formula (I) wherein n is an integer from 1 to 35 and W is O. In another embodiment is a compound of Formula (I) wherein n is an integer from 1 to 35 and Y is O. In another embodiment is a compound of Formula (I) wherein n is an integer from 1 to 35, G$^5$ is

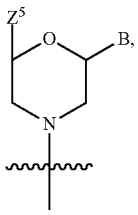

each W is O, each Y is O, and each X is independently selected from X1, X2, X3, X4, X5, X6, X7, or X8.

In another embodiment is a compound of Formula (I) wherein n is an integer from 1 to 35, $G^5$ is

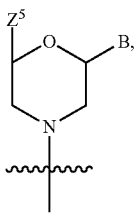

each W is O, each Y is O, and at least one X is X2. In some embodiments, at least one X2 is selected from —O-alkylene-$CO_2H$, —O-alkylene-$CHN_4$, —N($R^1$)-alkylene-$CO_2H$, and —N($R^1$)-alkylene-$CHN_4$. In some embodiments, at least one X2 is —O-alkylene-$CO_2H$. In some embodiments, at least one X2 is —O-alkylene-$CHN_4$. In some embodiments, at least one X2 is —N($R^1$)-alkylene-$CO_2H$. In some embodiments, at least one X2 is —N($R^1$)-alkylene-$CHN_4$. In some embodiments, at least one X2 is selected from —O-alkylene-$CO_2H$, —O-alkylene-$CHN_4$, —N($R^1$)-alkylene-$CO_2H$, and —N($R^1$)-alkylene-$CHN_4$, wherein -alkylene- is —$CH_2$—, —$CH_2CH_2$—, or —$CH_2CH_2CH_2$—. In further embodiments, at least one X2 is selected from —N(H)$CH_2CO_2H$, —N($CH_3$)$CH_2CO_2H$, —N($CH_2CH_3$)$CH_2CO_2H$, —N(H)$CH_2CH_2CO_2H$, and —N($CH_3$)$CH_2CH_2CO_2H$. In some embodiments, at least one X2 is —N(H)$CH_2CO_2H$. In some embodiments, at least one X2 is —N($CH_3$)$CH_2CO_2H$. In some embodiments, at least one X2 is —N($CH_2CH_3$)$CH_2CO_2H$. In some embodiments, at least one X2 is —N(H)$CH_2CH_2CO_2H$. In some embodiments, at least one X2 is —N($CH_3$)$CH_2CH_2CO_2H$. In further embodiments, at least one X2 is selected from -L1-CO-alkylene-$CO_2H$, -L1-CO-alkylene-$CHN_4$, -L1-CO-alkenylene-$CO_2H$, -L1-CO-alkenylene-$CHN_4$, -L1-CO-arylene-$CO_2H$, and -L1-CO-arylene-$CHN_4$. In some embodiments, at least one X2 is -L1-CO-alkylene-$CO_2H$. In some embodiments, at least one X2 is -L1-CO-alkylene-$CHN_4$. In some embodiments, at least one X2 is -L1-CO-alkenylene-$CO_2H$. In some embodiments, at least one X2 is -L1-CO-alkenylene-$CHN_4$. In some embodiments, at least one X2 is -L1-CO-arylene-$CO_2H$. In some embodiments at least one X2 is -L1-CO-arylene-$CHN_4$. In further embodiments, at least one X2 is selected from -L1-CO-alkylene-$CO_2H$, -L1-CO-alkylene-$CHN_4$, -L1-CO-alkenylene-$CO_2H$, -L1-CO-alkenylene-$CHN_4$, -L1-CO-arylene-$CO_2H$, and -L1-CO-arylene-$CHN_4$, wherein L1 is

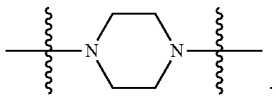

In yet further embodiments, at least one X2 is selected from -L1-CO-alkylene-$CO_2H$, -L1-CO-alkylene-$CHN_4$, -L1-CO-alkenylene-$CO_2H$, -L1-CO-alkenylene-$CHN_4$, -L1-CO-arylene-$CO_2H$, and -L1-CO-arylene-$CHN_4$, wherein L1 is

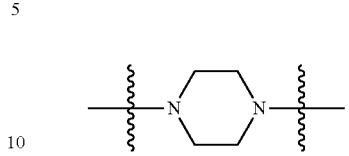

and -alkylene- is —$CH_2$—, —$CH_2CH_2$—, or —$CH_2CH_2CH_2$—. In another embodiment, at least one X2 is selected from -L1-CO-alkylene-$CO_2H$, -L1-CO-alkylene-$CHN_4$, -L1-CO-alkenylene-$CO_2H$, -L1-CO-alkenylene-$CHN_4$, -L1-CO-arylene-$CO_2H$, and -L1-CO-arylene-$CHN_4$, wherein L1 is

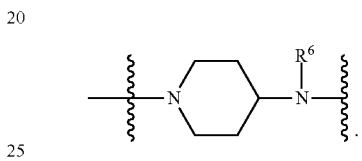

In another embodiment, at least one X2 is selected from -L1-CO-alkylene-$CO_2H$, -L1-CO-alkylene-$CHN_4$, -L1-CO-alkenylene-$CO_2H$, -L1-CO-alkenylene-$CHN_4$, -L1-CO-arylene-$CO_2H$, and -L1-CO-arylene-$CHN_4$, wherein L1 is

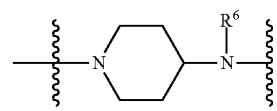

and -alkylene- is —$CH_2$—, —$CH_2CH_2$—, or —$CH_2CH_2CH_2$—.

In another embodiment is a compound of Formula (I) wherein n is an integer from 1 to 35, $G^5$ is

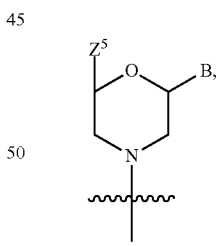

each W is O, each Y is O, at least one X is X2 and X2 is selected from:

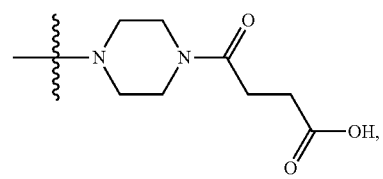

-continued
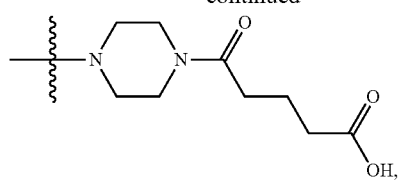
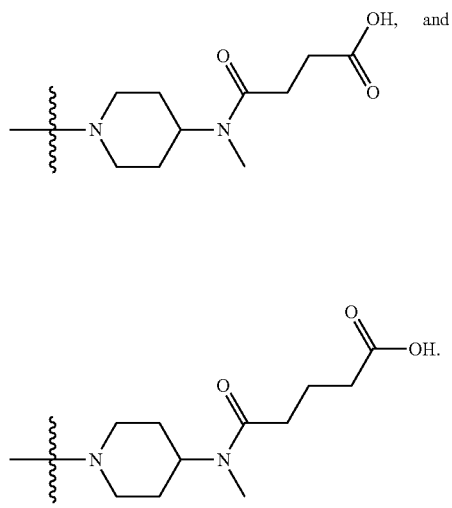
In some embodiments, at least one X2 is
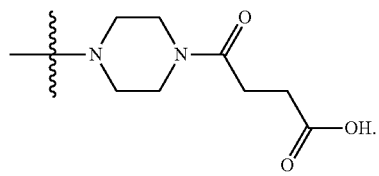 [SMILES: *N1CCN(C(=O)CCC(=O)O)CC1]
In some embodiments, at least one X2 is
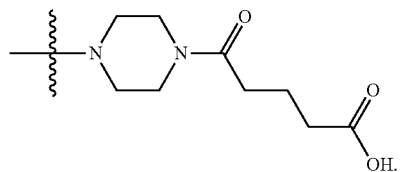 [SMILES: *N1CCN(C(=O)CCCC(=O)O)CC1]
In some embodiments, at least one X2 is
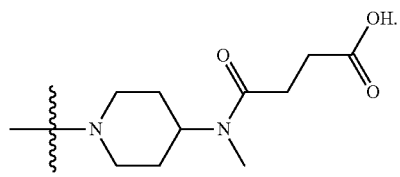 [SMILES: *N1CCC(N(C)C(=O)CCC(=O)O)CC1]
In some embodiments, at least one X2 is
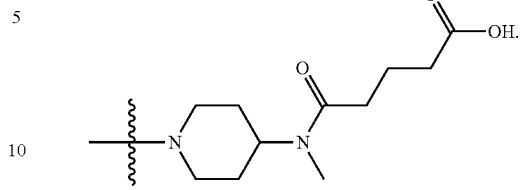
In another embodiment is a compound of Formula (I) wherein n is an integer from 1 to 35, $G^5$ is
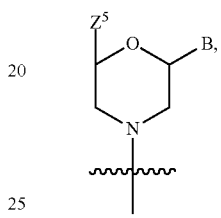
each W is O, each Y is O, at least one X is X2 and X2 is selected from:
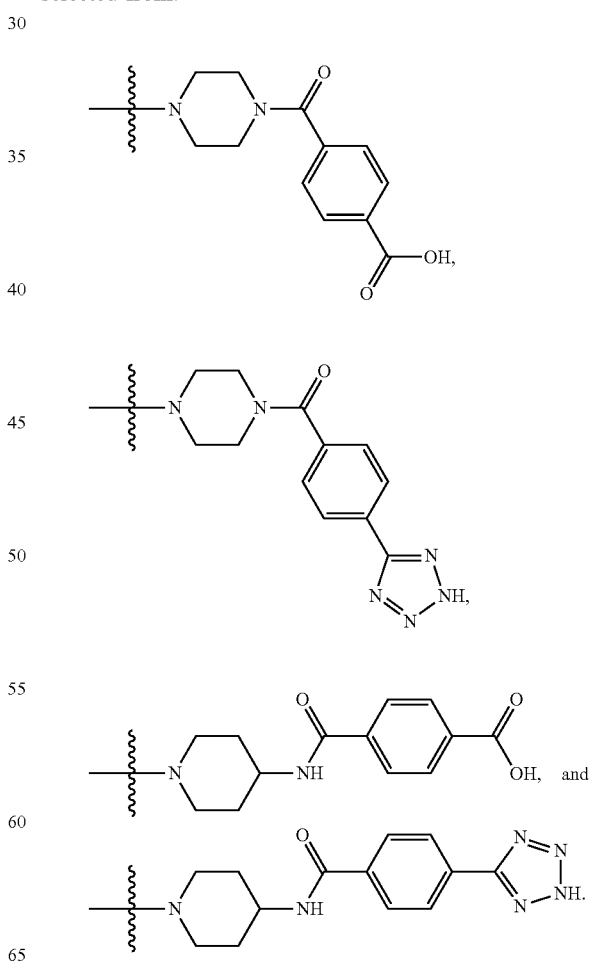

In some embodiments, at least one X2 is

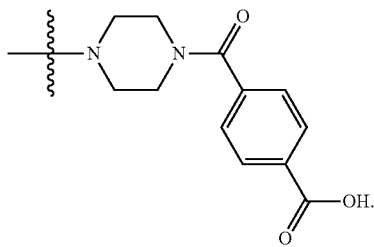 [SMILES: *N1CCN(C(=O)c2ccc(C(=O)O)cc2)CC1]

In some embodiments, at least one X2 is

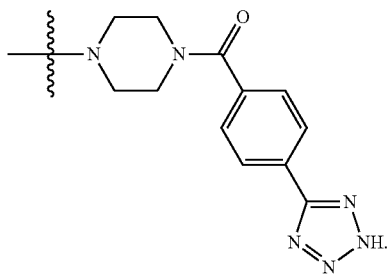 [SMILES: *N1CCN(C(=O)c2ccc(-c3nn[nH]n3)cc2)CC1]

In some embodiments, at least one X2 is

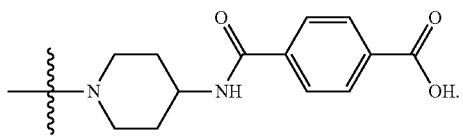 [SMILES: *N1CCC(NC(=O)c2ccc(C(=O)O)cc2)CC1]

In some embodiments, at least one X2 is

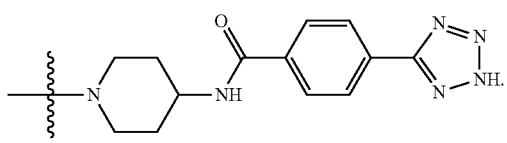 [SMILES: *N1CCC(NC(=O)c2ccc(-c3nn[nH]n3)cc2)CC1]

In another embodiment is a compound of Formula (I) wherein n is an integer from 1 to 35, $G^5$ is

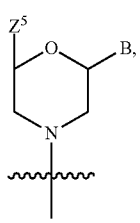

each W is O, each Y is O, at least one X is X2, and X2 is selected from -L1-CONH-alkylene-CO$_2$H, -L1-CONH-alkylene-CHN$_4$, -L1-CONH-arylene-CO$_2$H, and -L1-CONH-arylene-CHN$_4$. In some embodiments, X2 is -L1-CONH-alkylene-CO$_2$H. In some embodiments, X2 is -L1-CONH-alkylene-CHN$_4$. In some embodiments, X2 is -L1-CONH-arylene-CO$_2$H. In some embodiments, X2 is -L1-CONH-arylene-CHN$_4$. In another embodiment, X2 is selected from -L1-CONH-alkylene-CO$_2$H, -L1-CONH-alkylene-CHN$_4$, -L1-CONH-arylene-CO$_2$H, and -L1-CONH-arylene-CHN$_4$, wherein L1 is

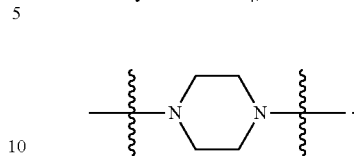

In another embodiment, X2 is selected from -L1-CONH-alkylene-CO$_2$H, -L1-CONH-alkylene-CHN$_4$, -L1-CONH-arylene-CO$_2$H, and -L1-CONH-arylene-CHN$_4$, wherein L1 is

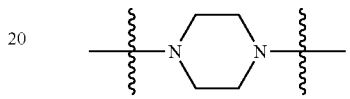

and -alkylene- is —CH$_2$—, —CH$_2$CH$_2$—, or —CH$_2$CH$_2$CH$_2$—. In another embodiment, X2 is selected from -L1-CONH-alkylene-CO$_2$H, -L1-CONH-alkylene-CHN$_4$, -L1-CONH-arylene-CO$_2$H, and -L1-CONH-arylene-CHN$_4$, wherein L1 is

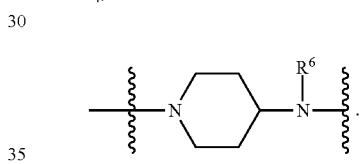

In another embodiment, X2 is selected from -L1-CONH-alkylene-CO$_2$H, -L1-CONH-alkylene-CHN$_4$, -L1-CONH-arylene-CO$_2$H, and -L1-CONH-arylene-CHN$_4$, wherein L1 is

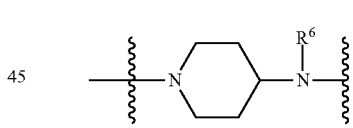

and -alkylene- is —CH$_2$—, —CH$_2$CH$_2$—, or —CH$_2$CH$_2$CH$_2$—.

In another embodiment is a compound of Formula (I) wherein n is an integer from 1 to 35, $G^5$ is

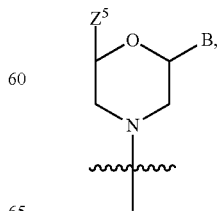

each W is O, each Y is O, at least one X is X2 and X2 is selected from:

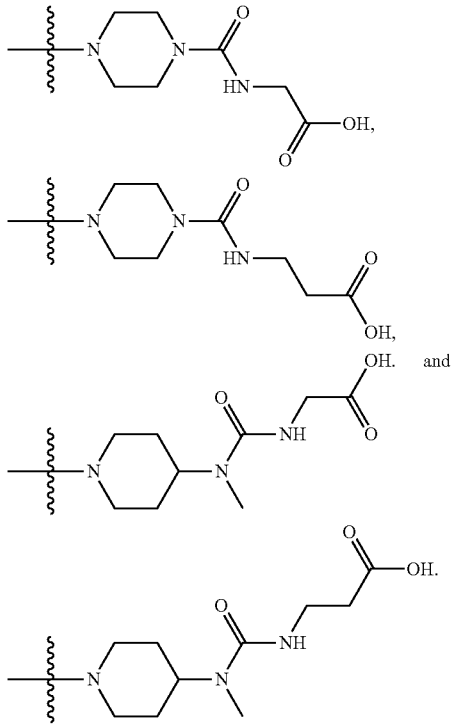

In some embodiments, at least one X2 is

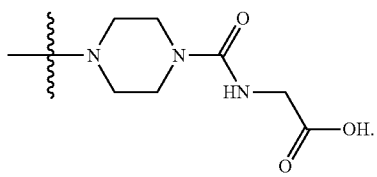

In some embodiments, at least one X2 is

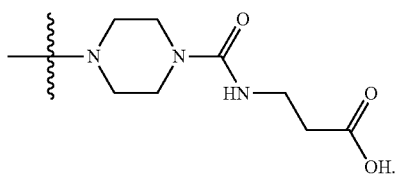 [SMILES: *N1CCN(C(=O)NCCC(=O)O)CC1]

In some embodiments, at least one X2 is

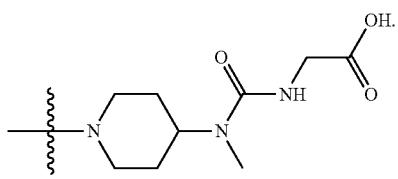

In some embodiments, at least one X2 is

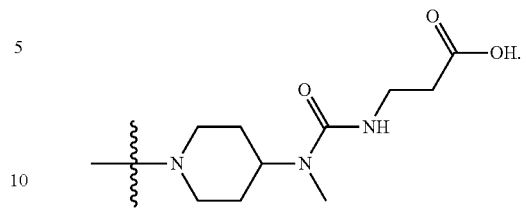

In another embodiment is a compound of Formula (I) wherein n is an integer from 1 to 35, $G^5$ is

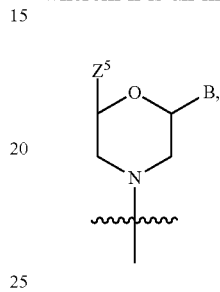

each W is O, each Y is O, at least one X is X2, and X2 is selected from -L1-SO$_2$-alkylene-CO$_2$H, -L1-SO$_2$-alkylene-CHN$_4$, -L1-SO$_2$-arylene-CO$_2$H, and -L1-SO$_2$-arylene-CHN$_4$. In some embodiments, X2 is -L1-SO$_2$-alkylene-CO$_2$H. In some embodiments, X2 is L1-SO$_2$-alkylene-CHN$_4$. In some embodiments, X2 is -L1-SO$_2$-arylene-CO$_2$H. In some embodiments, X2 is -L1-SO$_2$-arylene-CHN$_4$. In another embodiment, X2 is selected from -L1-SO$_2$-alkylene-CO$_2$H, -L1-SO$_2$-alkylene-CHN$_4$, -L1-SO$_2$-arylene-CO$_2$H, and -L1-SO$_2$-arylene-CHN$_4$, wherein L1 is

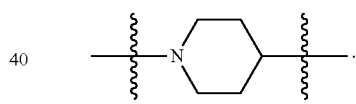

In another embodiment, X2 is selected from -L1-SO$_2$-alkylene-CO$_2$H, -L1-SO$_2$-alkylene-CHN$_4$, -L1-SO$_2$-arylene-CO$_2$H, and -L1-SO$_2$-arylene-CHN$_4$, wherein L1 is

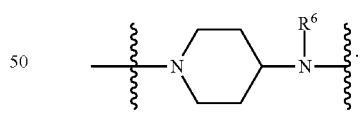

In another embodiment is a compound of Formula (I) wherein n is an integer from 1 to 35, $G^5$ is

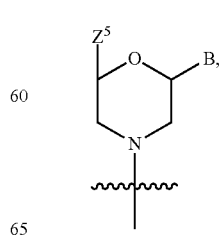

each W is O, each Y is O, at least one X is X2 and X2 is selected from:
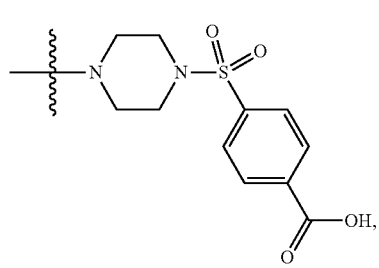 [SMILES: *N1CCN(S(=O)(=O)c2ccc(C(=O)O)cc2)CC1]
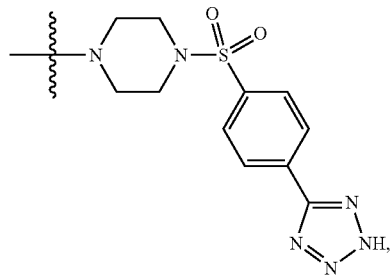
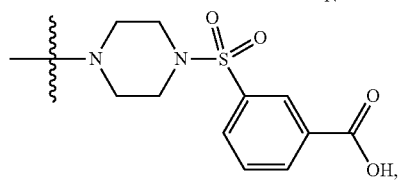
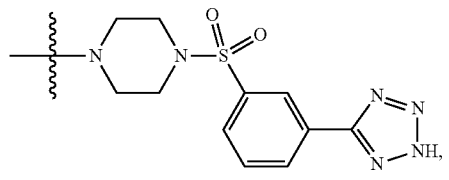
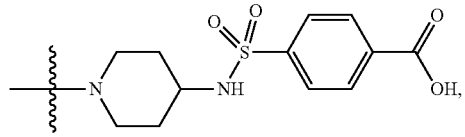
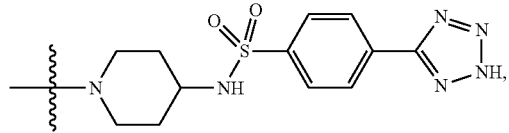
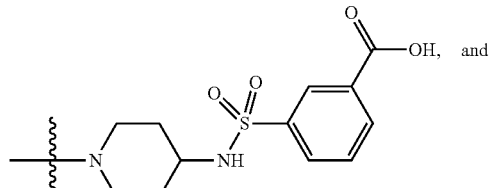
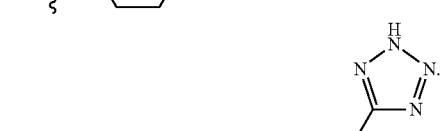
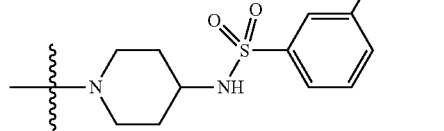
In some embodiments, at least one X2 is
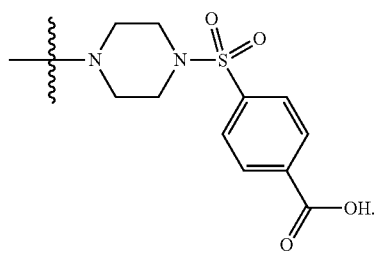
In some embodiments, at least one X2 is
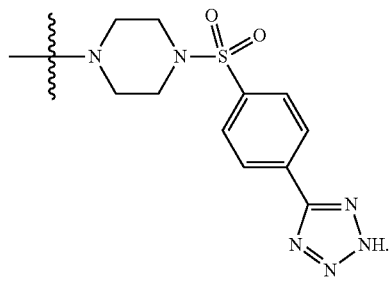 [SMILES: *N1CCN(S(=O)(=O)c2ccc(-c3nn[nH]n3)cc2)CC1]
In some embodiments, at least one X2 is
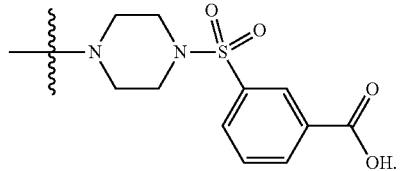 [SMILES: *N1CCN(S(=O)(=O)c2cccc(C(=O)O)c2)CC1]
In some embodiments, at least one X2 is
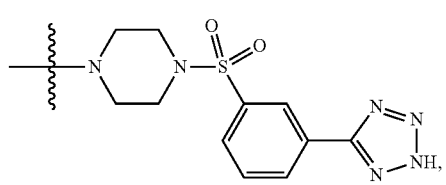 [SMILES: *N1CCN(S(=O)(=O)c2cccc(-c3nn[nH]n3)c2)CC1]
In some embodiments, at least one X2 is
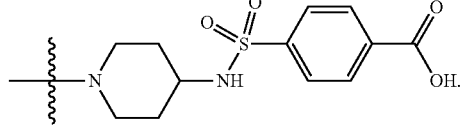

In some embodiments, at least one X2 is

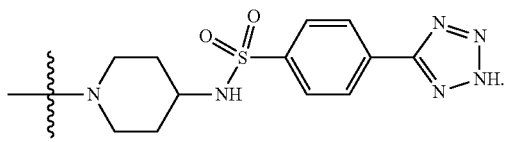 [SMILES: *N1CCC(NS(=O)(=O)c2ccc(-c3nn[nH]n3)cc2)CC1]

In some embodiments, at least one X2 is

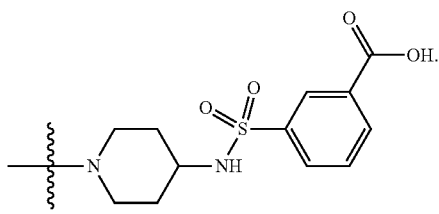 [SMILES: *N1CCC(NS(=O)(=O)c2cccc(C(=O)O)c2)CC1]

In some embodiments, at least one X2 is

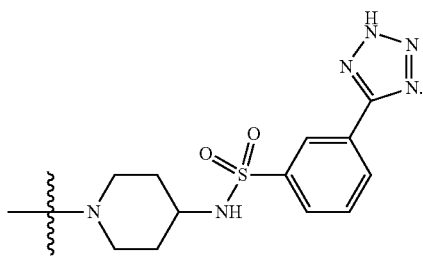 [SMILES: *N1CCC(NS(=O)(=O)c2cccc(-c3nn[nH]n3)c2)CC1]

In another embodiment is a compound of Formula (I) wherein n is an integer from 1 to 35, $G^5$ is

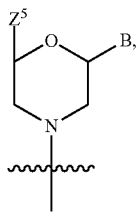

each W is O, each Y is O, at least one X is X2, and X2 is selected from -L1-alkylene-$CO_2H$, -L1-alkylene-$CHN_4$, -L1-arylene-$CO_2H$, and -L1-arylene-$CHN_4$. In some embodiments, X2 is -L1-alkylene-$CO_2H$. In some embodiments, X2 is -L1-alkylene-$CHN_4$. In some embodiments, X2 is -L1-arylene-$CO_2H$. In some embodiments, X2 is -L1-arylene-$CHN_4$. In some embodiments, X2 is selected from -L1-alkylene-$CO_2H$, -L1-alkylene-$CHN_4$, -L1-arylene-$CO_2H$, and -L1-arylene-$CHN_4$. In another embodiment, X2 is selected from -L1-alkylene-$CO_2H$, -L1-alkylene-$CHN_4$, -L1-arylene-$CO_2H$, and -L1-arylene-$CHN_4$, wherein L1 is

In another embodiment, X2 is selected from -L1-alkylene-$CO_2H$, -L1-alkylene-$CHN_4$, -L1-arylene-$CO_2H$, and -L1-arylene-$CHN_4$, wherein L1 is

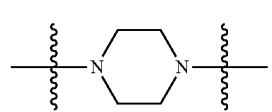

and -alkylene- is —$CH_2$—, —$CH_2CH_2$—, or —$CH_2CH_2CH_2$—. In another embodiment, X2 is selected from -L1-alkylene-$CO_2H$, -L1-alkylene-$CHN_4$, -L1-arylene-$CO_2H$, and -L1-arylene-$CHN_4$, wherein L1 is

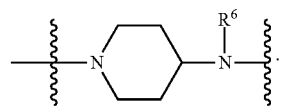

In another embodiment, X2 is selected from -L1-alkylene-$CO_2H$, -L1-alkylene-$CHN_4$, -L1-arylene-$CO_2H$, and -L1-arylene-$CHN_4$, wherein L1 is

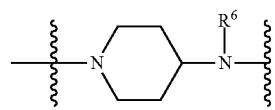

and -alkylene- is —$CH_2$—, —$CH_2CH_2$—, or —$CH_2CH_2CH_2$—.

In another embodiment is a compound of Formula (I) wherein n is an integer from 1 to 35, $G^5$ is

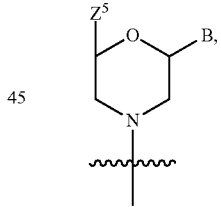

each W is O, each Y is O, at least one X is X2 and X2 is selected from:

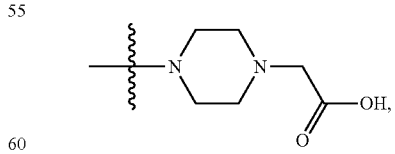

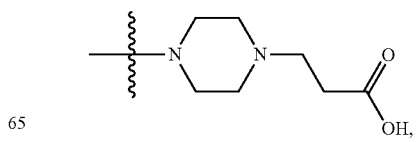

-continued

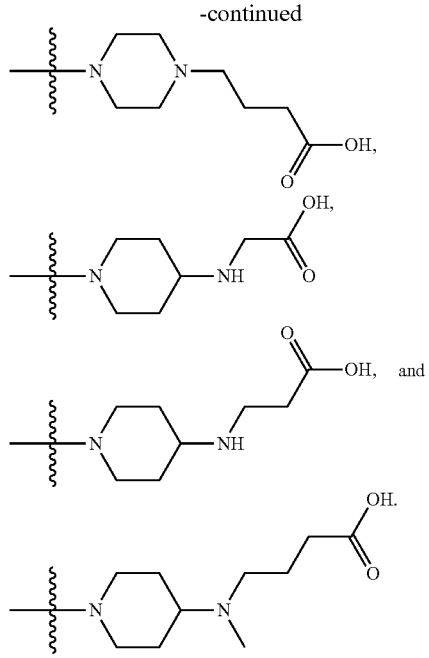

In some embodiments, at least one X2 is

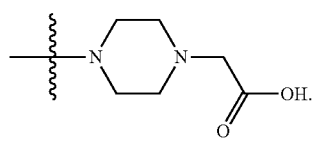

In some embodiments, at least one X2 is

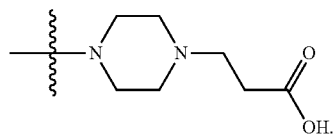 [SMILES: *N1CCN(CCC(=O)O)CC1]

In some embodiments, at least one X2 is

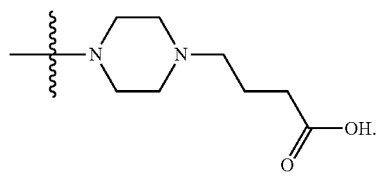 [SMILES: *N1CCN(CCCC(=O)O)CC1]

In some embodiments, at least one X2 is

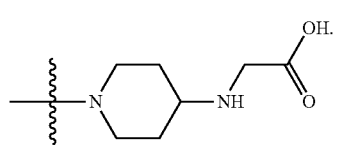 [SMILES: *N1CCC(NCC(=O)O)CC1]

In some embodiments, at least one X2 is

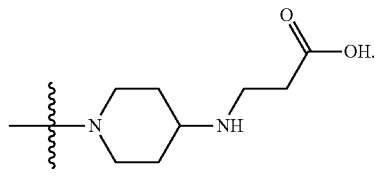 [SMILES: *N1CCC(NCCC(=O)O)CC1]

In some embodiments, at least one X2 is

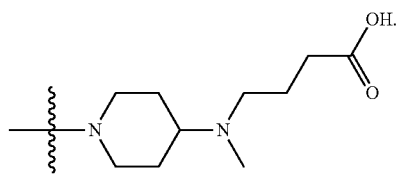 [SMILES: *N1CCC(N(C)CCCC(=O)O)CC1]

In another embodiment is a compound of Formula (I) wherein n is an integer from 1 to 35, $G^5$ is

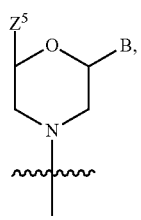

each W is O, each Y is O, at least one X is X2 and X2 is selected from:

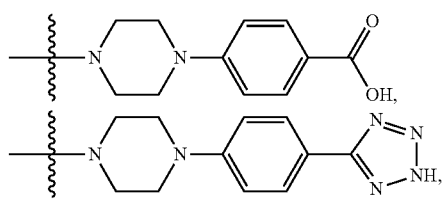

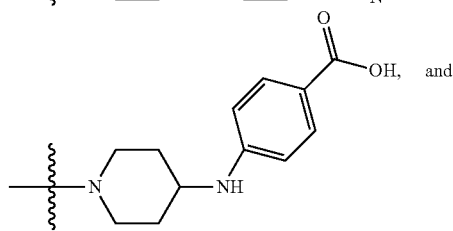

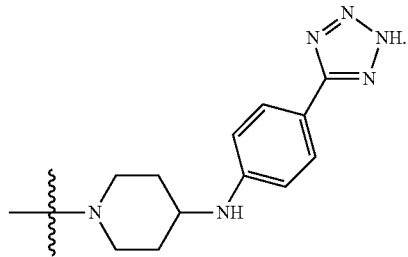

In some embodiments, at least one X2 is

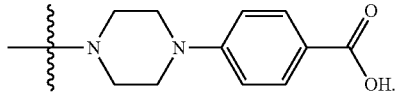

In some embodiments, at least one X2 is

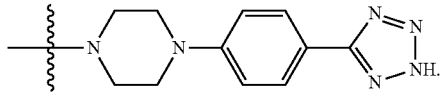

In some embodiments, at least one X2 is

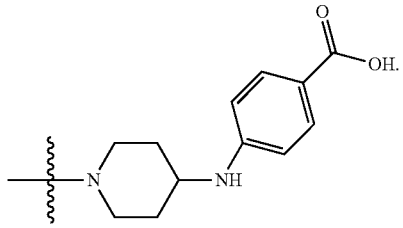 [SMILES: *N1CCC(Nc2ccc(C(=O)O)cc2)CC1]

In some embodiments, at least one X2 is

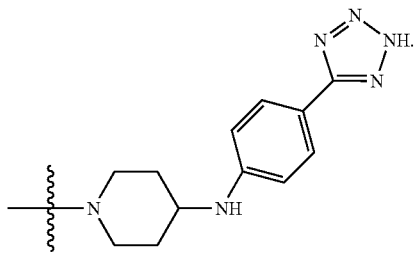 [SMILES: *N1CCC(Nc2ccc(-c3nn[nH]n3)cc2)CC1]

In any of the aforementioned embodiments of Formula (I) wherein at least one X is X2 is another embodiment wherein n is an integer from 30-35. In further embodiments of the aforementioned embodiments of Formula (I) wherein at least one X is X2, n is an integer from 25-29. In further embodiments of the aforementioned embodiments of Formula (I) wherein at least one X is X2, n is an integer from 20-24. In further embodiments of any of the aforementioned embodiments of Formula (I) wherein at least one X is X2, n is an integer from 15-19. In further embodiments of the aforementioned embodiments of Formula (I) wherein at least one X is X2, n is an integer from 10-14. In further embodiments of the aforementioned embodiments of Formula (I) wherein at least one X is X2, n is an integer from 5-9. In yet further embodiments of the aforementioned embodiments of Formula (I) wherein at least one X is X2, n is an integer from 1-4.

In another embodiment is a compound of Formula (I) wherein n is an integer from 1 to 35, $G^5$ is

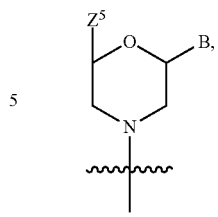

each W is O, each Y is O, and at least one X is X3. In further embodiments at least one X3 is selected from -L1-alkyl and -L1-heterocyclyl. In some embodiments at least one X3 is -L1-alkyl. In yet another embodiment, at least one X3 is -L1-alkyl and -L1 is

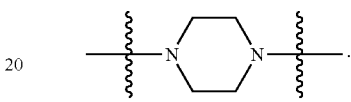

In another embodiment, at least one X3 is -L1-alkyl and L1 is

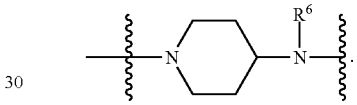

In another embodiment, at least one X3 is -L1-alkyl and L1 is

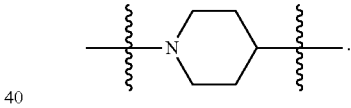

In a further embodiment of the aforementioned embodiments wherein at least one X is X3, alkyl is methyl, ethyl, propyl, and isopropyl. In another embodiment, alkyl is $CF_3$. In another embodiment, alkyl is CN.

In another embodiment is a compound of Formula (I) wherein n is an integer from 1 to 35, $G^5$ is

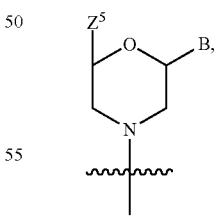

each W is O, each Y is O, at least one X is X3 and X3 is selected from:

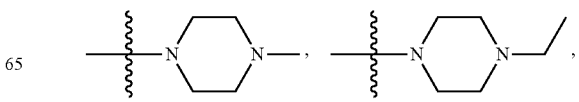

-continued

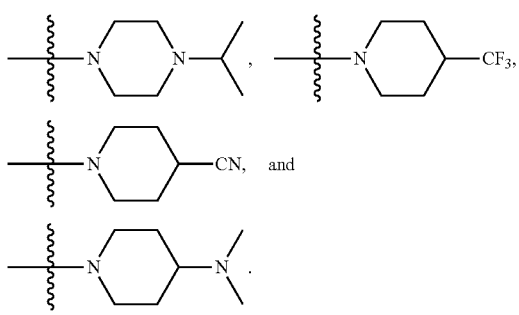

In some embodiments, at least one X is X3 and X3 is

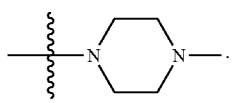

In some embodiments, at least one X is X3 and X3 is

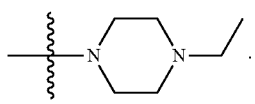 [SMILES: *N1CCN(CC)CC1]

In some embodiments, at least one X is X3 and X3 is

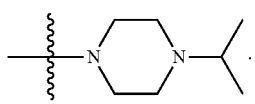 [SMILES: *N1CCN(C(C)C)CC1]

In some embodiments, at least one X is X3 and X3 is

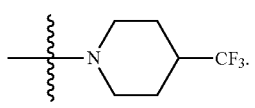 [SMILES: *N1CCC(C(F)(F)F)CC1]

In some embodiments, at least one X is X3 and X3 is

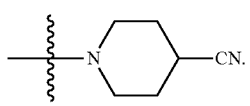

In some embodiments, at least one X is X3 and X3 is

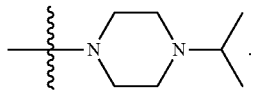 [SMILES: *N1CCN(C(C)C)CC1]

In another embodiment is a compound of Formula (I) wherein n is an integer from 1 to 35, $G^5$ is

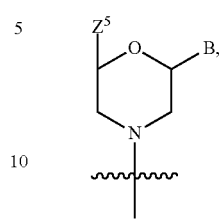

each W is O, each Y is O, at least one X is X3, and X3 is -L1-heterocyclyl. In yet another embodiment, at least one X3 is -L1-heterocyclyl and L1 is

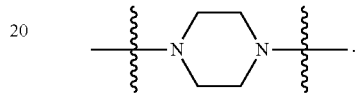

In another embodiment, at least one X3 is -L1-heterocyclyl and L1 is

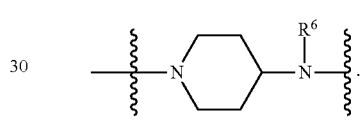

In another embodiment, at least one X3 is -L1-heterocyclyl and L1 is

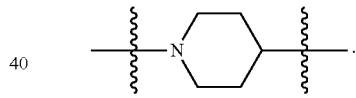

In another embodiment of the aforementioned embodiments wherein at least one X is X3, heterocyclyl is pyrrolidine, tetrahydrofuran, piperidine, morpholine, piperazine, pyrrole, furan, thiophene, pyrazole, imidazole, oxazole, isoxazole, pyridine, and pyrimidine. In a further embodiment, heterocyclyl is pyrrolidine. In a further embodiment, heterocyclyl is piperidine. In a further embodiment, heterocyclyl is morpholine. In a further embodiment, heterocyclyl is piperazine. In a further embodiment, heterocyclyl is pyridine. In a further embodiment, heterocyclyl is pyrimidine.

In another embodiment is a compound of Formula (I) wherein n is an integer from 1 to 35, $G^5$ is

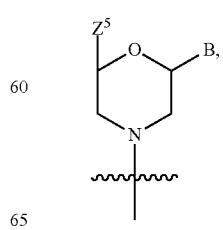

each W is O, each Y is O, at least one X is X3 and X3 is selected from:

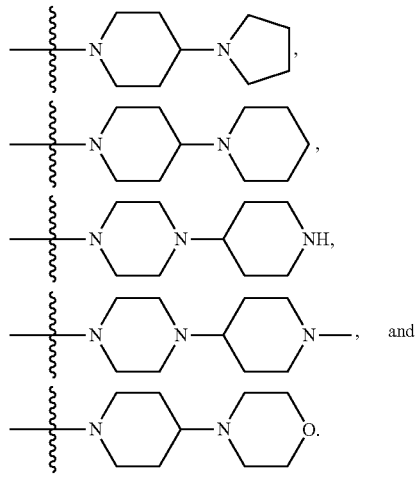
and

In some embodiments, at least one X is X3 and X3 is

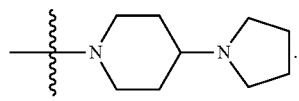 [SMILES: *N1CCC(N2CCCC2)CC1]

In some embodiments, at least one X is X3 and X3 is

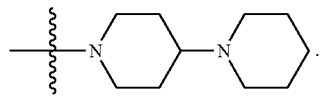 [SMILES: *N1CCC(N2CCOCC2)CC1]

In some embodiments, at least one X is X3 and X3 is

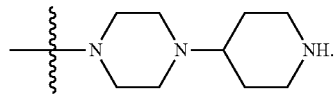

In some embodiments, at least one X is X3 and X3 is

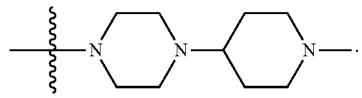

In some embodiments, at least one X is X3 and X3 is

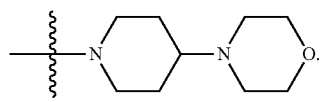

In another embodiment is a compound of Formula (I) wherein n is an integer from 1 to 35, $G^5$ is

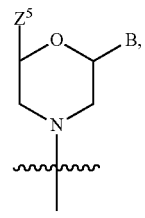

each W is O, each Y is O, at least one X is X3, and X3 is selected from —O-alkylene-CNH—NH$_2$, —N(R$^1$)-alkylene-CNH—NH$_2$, —O—alkylene-N(R$^1$)$_2$, —N(R$^1$)-alkylene-N(R$^1$)$_2$, —O-alkylene-N(R$^2$)$_3$, —N(R$^1$)-alkylene-N(R$^2$)$_3$, —O-alkylene-heterocyclyl, —N(R$^1$)-alkylene-heterocyclyl, —O-alkylene-N(O)(R$^2$)$_2$, —N(R$^1$)-alkylene-N(O)(R$^2$)$_2$, —O-alkylene-NH—CNH—NH$_2$, and —N(R$^1$)-alkylene-NH—CNH—NH$_2$. In a further embodiment, at least one X3 is selected from —O-alkylene-CNH—NH$_2$, —N(R$^1$)-alkylene-CNH—NH$_2$, —O-alkylene-N(R$^1$)$_2$, —N(R$^1$)-alkylene-N(R$^1$)$_2$, —O-alkylene-N(R$^2$)$_3$, —N(R$^1$)-alkylene-N(R$^2$)$_3$, —O-alkylene-heterocyclyl, —N(R$^1$)-alkylene-heterocyclyl, —O-alkylene-N(O)(R$^2$)$_2$, —N(R$^1$)-alkylene-N(O)(R$^2$)$_2$, —O-alkylene-NH—CNH—NH$_2$, and —N(R$^1$)-alkylene-NH—CNH—NH$_2$ wherein -alkylene- is —CH$_2$CH$_2$— or —CH$_2$CH$_2$CH$_2$—. In a further embodiment, at least one X3 is selected from —O-alkylene-CNH—NH$_2$, —O-alkylene-N(R$^1$)$_2$, —O-alkylene-N(R$^2$)$_3$, —O-alkylene-heterocyclyl, —O—alkylene-N(O)(R$^2$)$_2$, and —O-alkylene-NH—CNH—NH$_2$. In yet a further embodiment, at least one X3 is selected from —N(R$^1$)-alkylene-CNH—NH$_2$, —N(R$^1$)-alkylene-N(R$^1$)$_2$, —N(R$^1$)-alkylene-N(R$^2$)$_3$, —N(R$^1$)-alkylene-heterocyclyl, —N(R$^1$)-alkylene-N(O)(R$^2$)$_2$, and —N(R$^1$)-alkylene-NH—CNH—NH$_2$ wherein -alkylene- is —CH$_2$CH$_2$— or —CH$_2$CH$_2$CH$_2$—. In some of the above embodiments, at least one X3 is —O-alkylene-CNH—NH$_2$. In some of the above embodiments, at least one X3 is —N(R$^1$)-alkylene-CNH—NH$_2$. In some of the above embodiments, at least one X3 is —O-alkylene-N(R$^1$)$_2$. In some of the above embodiments, at least one X3 is —N(R$^1$)-alkylene-N(R$^1$)$_2$. In some of the above embodiments, at least one X3 is —O-alkylene-N(R$^2$)$_3$. In some of the above embodiments, at least one X3 is —N(R$^1$)-alkylene-N(R$^2$)$_3$. In some of the above embodiments, at least one X3 is —O-alkylene-heterocyclyl. In some of the above embodiments, at least one X3 is —N(R$^1$)-alkylene-heterocyclyl. In some of the above embodiments, at least one X3 is —O-alkylene-N(O)(R$^2$)$_2$. In some of the above embodiments, at least one X3 is —N(R$^1$)-alkylene-N(O)(R$^2$)$_2$. In some of the above embodiments, at least one X3 is —O-alkylene-NH—CNH—NH$_2$. In some of the above embodiments, at least one X3 is —N(R$^1$)-alkylene-NH—CNH—NH$_2$.

In another embodiment is a compound of Formula (I) wherein n is an integer from 1 to 35, $G^5$ is

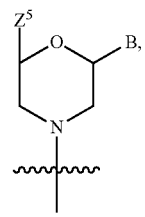

each W is O, each Y is O, at least one X is X3 and X3 is selected from

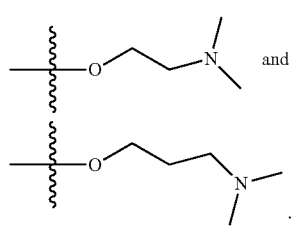

In some embodiments, at least one X is X3 and X3 is

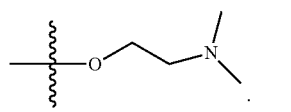

In some embodiments, at least one X is X3 and X3 is

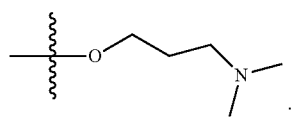 [SMILES: *OCCCN(C)C]

In further embodiments, at least one X is X3 and X3 is selected from

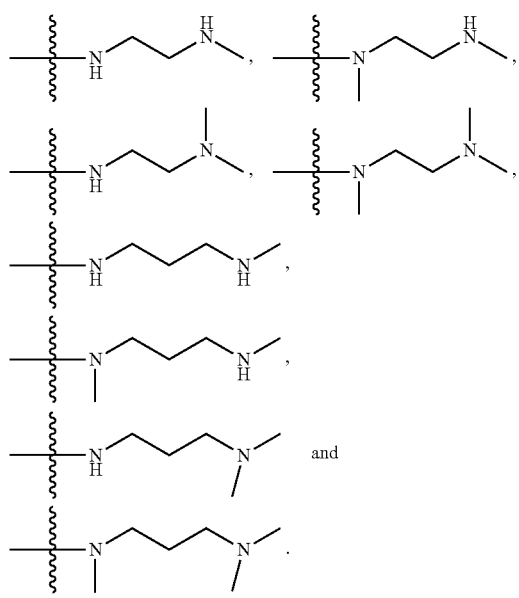

In some embodiments, at least one X is X3 and X3 is

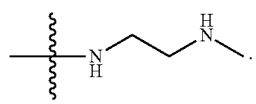

In some embodiments, at least one X is X3 and X3 is

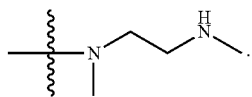 [SMILES: *N(C)CCNC]

In some embodiments, at least one X is X3 and X3 is

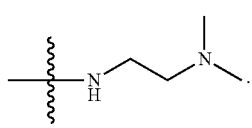 [SMILES: *NCCN(C)C]

In some embodiments, at least one X is X3 and X3 is

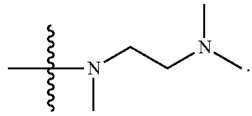

In some embodiments, at least one X is X3 and X3 is

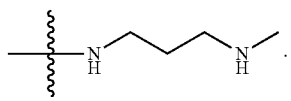 [SMILES: *NCCCNC]

In some embodiments, at least one X is X3 and X3 is

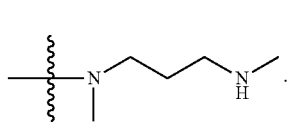

In some embodiments, at least one X is X3 and X3 is

In some embodiments, at least one X is X3 and X3 is

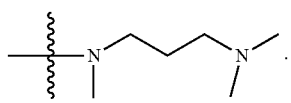 [SMILES: *N(C)CCCN(C)C]

In another embodiment is a compound of Formula (I) wherein n is an integer from 1 to 35, $G^5$ is

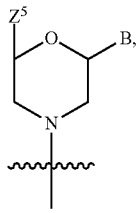

each W is O, each Y is O, at least one X is X3, and X3 is selected from -L1-CNH—NH$_2$, -L1-alkylene-CNH—NH$_2$, -L1-arylene-CNH—NH$_2$, -L1-alkylene-N(R$^1$)$_2$, -L1-arylene-N(R$^1$)$_2$, -L1-alkylene-N(R$^2$)$_3$, -L1-arylene-N(R$^2$)$_3$, -L1-alkylene-heterocyclyl, -L1-arylene-heterocyclyl, -L1-alkylene-N(O)(R$^2$)$_2$, -L1-arylene-N(O)(R$^2$)$_2$, -L1-alkylene-NH—CNH—NH$_2$, and -L1-arylene-NH—CNH—NH$_2$. In a further embodiment, at least one X3 is selected from -L1-arylene-CNH—NH$_2$, -L1-arylene-N(R$^1$)$_2$, -L1-arylene-N(R$^2$)$_3$, -L1-arylene-heterocyclyl, -L1-arylene-N(O)(R$^2$)$_2$, and -L1-arylene-NH—CNH—NH$_2$. In some embodiments, at least one X3 is -L1-arylene-CNH—NH$_2$. In some embodiments, at least one X3 is -L1-arylene-N(R$^1$)$_2$. In some embodiments, at least one X3 is -L1-arylene-N(R$^2$)$_3$. In some embodiments, at least one X3 is -L1-arylene-heterocyclyl. In some embodiments, at least one X3 is -L1-arylene-N(O)(R$^2$)$_2$. In some embodiments, at least one X3 is -L1-arylene-NH—CNH—NH$_2$. In a further embodiment of the aforementioned embodiments, L1 is

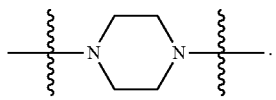

In yet a further embodiment of the aforementioned embodiments, L1 is

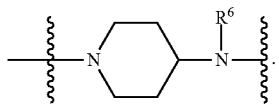

In another embodiment is a compound of Formula (I) wherein n is an integer from 1 to 35, $G^5$ is

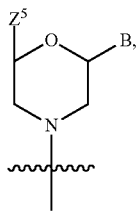

each W is O, each Y is O, at least one X is X3, and X3 is selected from -L1-CNH—NH$_2$, -L1-alkylene-CNH—NH$_2$, -L1-alkylene-N(R$^1$)$_2$, -L1-alkylene-N(R$^2$)$_3$, -L1-alkylene-heterocyclyl, -L1-alkylene-N(O)(R$^2$)$_2$, and -L1-alkylene-NH—CNH—NH$_2$. In a further embodiment, at least one X3 is selected from -L1-CNH—NH$_2$, -L1-alkylene-CNH—NH$_2$, and -L1-alkylene-NH—CNH—NH$_2$. In yet a further embodiment, at least one X3 is selected from -L1-alkylene-N(R$^1$)$_2$, -L1-alkylene-N(R$^2$)$_3$, -L1-alkylene-heterocyclyl, and -L1-alkylene-N(O)(R$^2$)$_2$. In some embodiments, at least one X3 is -L1-CNH—NH$_2$. In some embodiments, at least one X3 is -L1-alkylene-CNH—NH$_2$. In some embodiments, at least one X3 is -L1-alkylene-NH—CNH—NH$_2$. In some embodiments, at least one X3 is -L1-alkylene-N(R$^1$)$_2$. In some embodiments, at least one X3 is -L1-alkylene-N(R$^2$)$_3$. In some embodiments, at least one X3 is -L1-alkylene-heterocyclyl. In some embodiments, at least one X3 is -L1-alkylene-N(O)(R$^2$)$_2$. In a further embodiment of the aforementioned embodiments, L1 is

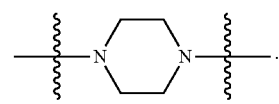

In another embodiment of the aforementioned embodiments, L1 is

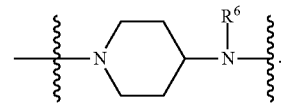

In yet a further embodiment of the aforementioned embodiments, -alkylene- is —CH$_2$CH$_2$— or —CH$_2$CH$_2$CH$_2$—. In some embodiments of the aforementioned embodiments, -alkylene- is —CH$_2$CH$_2$—. In some embodiments of the aforementioned embodiments, -alkylene- is —CH$_2$CH$_2$CH$_2$—.

In another embodiment is a compound of Formula (I) wherein n is an integer from 1 to 35, $G^5$ is

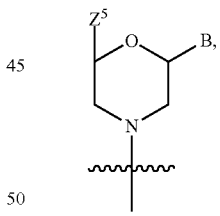

each W is O, each Y is O, at least one X is X3 and X3 is selected from

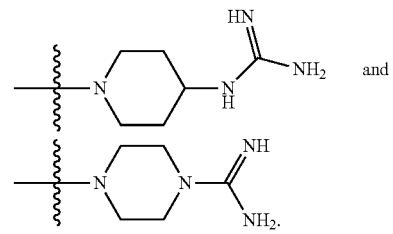

In some embodiments, at least one X3 is

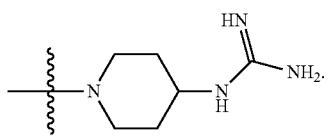 [SMILES: *N1CCC(NC(=N)N)CC1]

In some embodiments, at least one X3 is

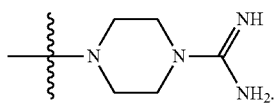

In another embodiment is a compound of Formula (I) wherein n is an integer from 1 to 35, $G^5$ is

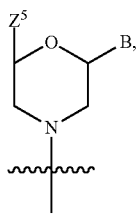

each W is O, each Y is O, at least one X is X3 and X3 is selected from

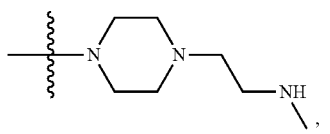

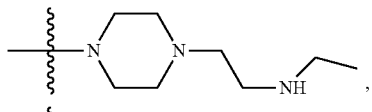

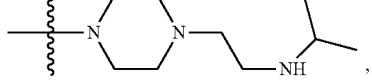

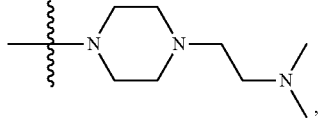

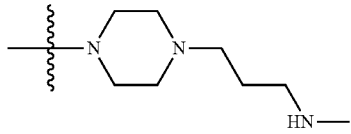

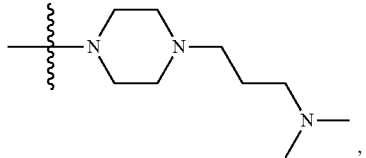

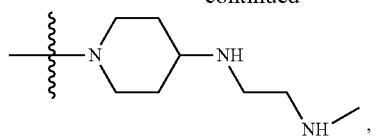

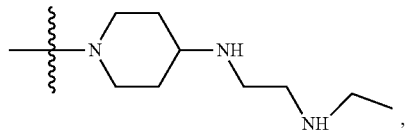

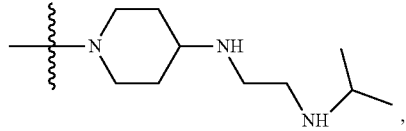

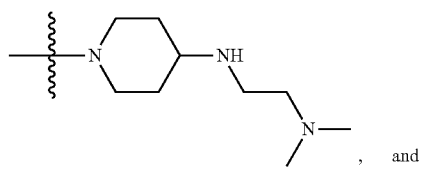

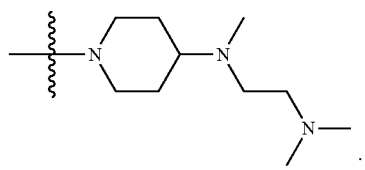, and

In some embodiments, at least one X3 is

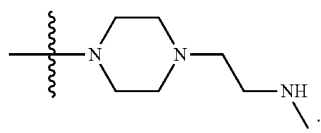

In some embodiments, at least one X3 is

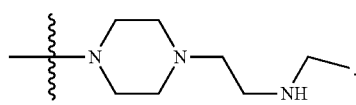

In some embodiments, at least one X3 is

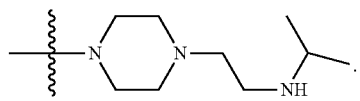

In some embodiments, at least one X3 is

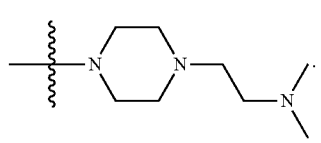

In some embodiments, at least one X3 is

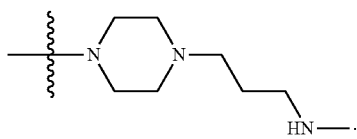 [SMILES: *N1CCN(CCCNC)CC1]

In some embodiments, at least one X3 is

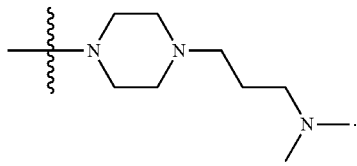 [SMILES: *N1CCN(CCCN(C)C)CC1]

In some embodiments, at least one X3 is

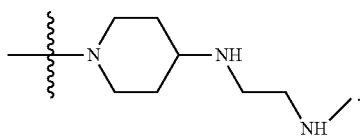 [SMILES: *N1CCC(NCCNC)CC1]

In some embodiments, at least one X3 is

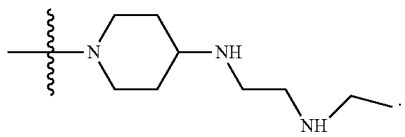 [SMILES: *N1CCC(NCCNCC)CC1]

In some embodiments, at least one X3 is

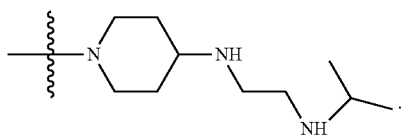 [SMILES: *N1CCC(NCCNC(C)C)CC1]

In some embodiments, at least one X3 is

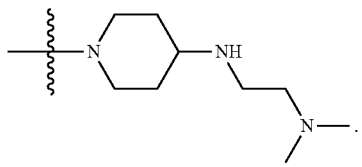 [SMILES: *N1CCC(NCCN(C)C)CC1]

In some embodiments, at least one X3 is

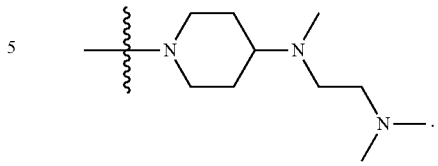

In another embodiment is a compound of Formula (I) wherein n is an integer from 1 to 35, $G^5$ is

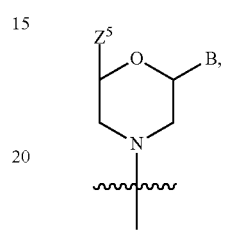

each W is O, each Y is O, at least one X is X3, and X3 is selected from -L1-CO-alkylene-CNH—$NH_2$, -L1-CO-alkenylene-CNH—$NH_2$, -L1-CO-arylene-CNH—$NH_2$, -L1-CONH-alkylene-CNH—$NH_2$, -L1-CONH-arylene-CNH—$NH_2$, -L1-$SO_2$-alkylene-CNH—$NH_2$, -L1-$SO_2$-arylene-CNH—$NH_2$, -L1-CO-alkylene-N($R^1$)$_2$, -L1-CO-alkenylene-N($R^1$)$_2$, -L1-CO-arylene-N($R^1$)$_2$, -L1-CONH-alkylene-N($R^1$)$_2$, -L1-CONH-arylene-N($R^1$)$_2$, -L1-$SO_2$-alkylene-N($R^1$)$_2$, -L1-CO-alkylene-N($R^2$)$_3$, -L1-CO-alkenylene-N($R^2$)$_3$, -L1-CO-arylene-N($R^2$)$_3$, -L1-CONH-alkylene-N($R^2$)$_3$, -L1-CONH-arylene-N($R^2$)$_3$, -L1-$SO_2$-alkylene-N($R^2$)$_3$, -L1-CO-alkylene-heterocyclyl, -L1-CO-alkenylene-heterocyclyl, -L1-CO-arylene-heterocyclyl, -L1-CONH-alkylene-heterocyclyl, -L1-CONH-arylene-heterocyclyl, -L1-$SO_2$-alkylene-heterocyclyl, -L1-CO-alkylene-N(O)($R^2$)$_2$, -L1-CO-alkenylene-N(O)($R^2$)$_2$, -L1-CO-arylene-N(O)($R^2$)$_2$, -L1-CONH-alkylene-N(O)($R^2$)$_2$, -L1-CONH-arylene-N(O)($R^2$)$_2$, -L1-$SO_2$-alkylene-N(O)($R^2$)$_2$, -L1-CO-alkylene-NH—CNH—$NH_2$, -L1-CO-alkenylene-NH—CNH—$NH_2$, -L1-CO-arylene-NH—CNH—$NH_2$, -L1-CONH-alkylene-NH—CNH—$NH_2$, -L1-CONH-arylene-NH—CNH—$NH_2$, -L1-$SO_2$-alkylene-NH—CNH—$NH_2$, and -L1-$SO_2$-arylene-NH—CNH—$NH_2$. In a further embodiment, at least one X3 is selected from -L1-CO-arylene-CNH—$NH_2$, -L1-CONH-arylene-CNH—$NH_2$, -L1-$SO_2$-arylene-CNH—$NH_2$, -L1-CO-arylene-N($R^1$)$_2$, -L1-CONH-arylene-N($R^1$)$_2$, -L1-CO-arylene-N($R^2$)$_3$, -L1-CONH-arylene-N($R^2$)$_3$, -L1-CO-arylene-heterocyclyl, -L1-CONH-arylene-heterocyclyl, -L1-CO-arylene-N(O)($R^2$)$_2$, -L1-CONH-arylene-N(O)($R^2$)$_2$, -L1-CO-arylene-NH—CNH—$NH_2$, -L1-CONH-arylene-NH—CNH—$NH_2$, and -L1-$SO_2$-arylene-NH—CNH—$NH_2$. In some embodiments, at least one X3 is -L1-CO-arylene-CNH—$NH_2$. In some embodiments, at least one X3 is -L1-CONH-arylene-CNH—$NH_2$. In some embodiments, at least one X3 is -L1-$SO_2$-arylene-CNH—$NH_2$. In some embodiments, at least one X3 is -L1-CO-arylene-N($R^1$)$_2$. In some embodiments, at least one X3 is -L1-CONH-arylene-N($R^1$)$_2$. In some embodiments, at least one X3 is -L1-CO-arylene-N($R^2$)$_3$. In some embodiments, at least one X3 is -L1-CONH-arylene-N($R^2$)$_3$. In some embodiments, at least one X3 is -L1-CO-arylene-heterocyclyl. In some embodiments, at least one X3 is -L1-CONH-arylene-heterocyclyl. In some embodiments, at least one X3 is -L1-CO-arylene-N(O)(R²)₂. In some embodiments, at least one X3 is -L1-CONH-arylene-N(O)(R²)₂. In some embodiments, at least one X3 is -L1-CO-arylene-NH—CNH—NH₂. In some embodiments, at least one X3 is -L1-CONH-arylene-NH—CNH—NH₂. In some embodiments, at least one X3 is -L1-SO₂-arylene-NH—CNH—NH₂. In a further embodiment of the aforementioned embodiments, L1 is

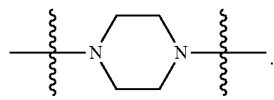

In another embodiment of the aforementioned embodiments, L1 is

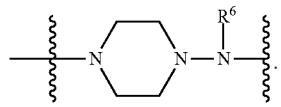

In another embodiment is a compound of Formula (I) wherein n is an integer from 1 to 35, G⁵ is

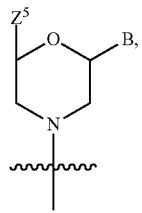

each W is O, each Y is O, at least one X is X3 and X3 is selected from

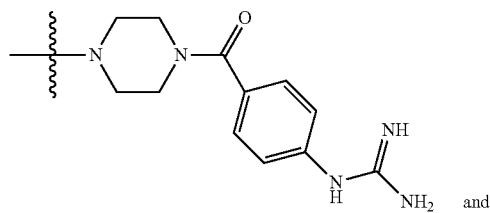

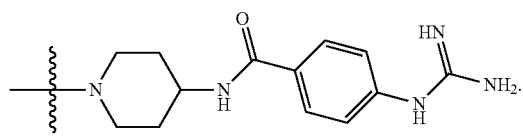

In some embodiments, at least one X3 is

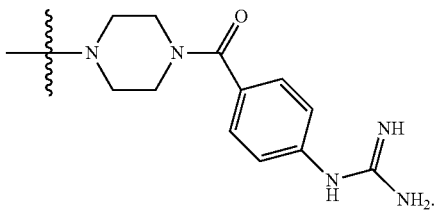 [SMILES: *N1CCN(C(=O)c2ccc(NC(=N)N)cc2)CC1]

In some embodiments, at least one X3 is

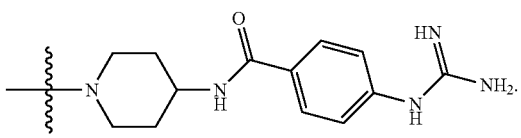 [SMILES: *N1CCC(NC(=O)c2ccc(NC(=N)N)cc2)CC1]

In another embodiment is a compound of Formula (I) wherein n is an integer from 1 to 35, G⁵ is

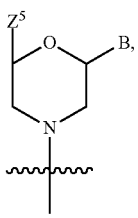

each W is O, each Y is O, at least one X is X3, and X3 is selected from -L1-CO-alkylene-CNH—NH₂, -L1-CO-alkenylene-CNH—NH₂, -L1-CONH-alkylene-CNH—NH₂, -L1-SO₂-alkylene-CNH—NH₂, -L1-CO-alkylene-N(R¹)₂, -L1-CO-alkenylene-N(R¹)₂, -L1-CONH-alkylene-N(R¹)₂, -L1-SO₂-alkylene-N(R¹)₂, -L1-CO-alkylene-N(R²)₃, -L1-CO-alkenylene-N(R²)₃, -L1-CONH-alkylene-N(R²)₃, -L1-SO₂-alkylene-N(R²)₃, -L1-CO-alkylene-heterocyclyl, -L1-CO-alkenylene-heterocyclyl, -L1-CONH-alkylene-heterocyclyl, -L1-SO₂-alkylene-heterocyclyl, -L1-CO-alkylene-N(O)(R²)₂, -L1-CO-alkenylene-N(O)(R²)₂, -L1-CONH-alkylene-N(O)(R²)₂, -L1-SO₂-alkylene-N(O)(R²)₂, -L1-CO-alkylene-NH—CNH—NH₂, -L1-CO-alkenylene-NH—CNH—NH₂, -L1-CONH-alkylene-NH—CNH—NH₂, and -L1-SO₂-alkylene-NH—CNH—NH₂. In a further embodiment, at least one X3 is selected from -L1-SO₂-alkylene-CNH—NH₂, -L1-SO₂-alkylene-N(R¹)₂, -L1-SO₂-alkylene-N(R²)₃, -L1-SO₂-alkylene-heterocyclyl, -L1-SO₂-alkylene-N(O)(R²)₂, and -L1-SO₂-alkylene-NH—CNH—NH₂. In some embodiments, at least one X3 is -L1-SO₂-alkylene-CNH—NH₂. In some embodiments, at least one X3 is -L1-SO₂-alkylene-N(R¹)₂. In some embodiments, at least one X3 is -L1-SO₂-alkylene-N(R²)₃. In some embodiments, at least one X3 is -L1-SO₂-alkylene-heterocyclyl. In some embodiments, at least one X3 is -L1-SO₂-alkylene-N(O)(R²)₂. In some embodiments, at least one X3 is -L1-SO₂-alkylene-NH—CNH—NH₂. In a further embodiment of the aforementioned embodiments, L1 is

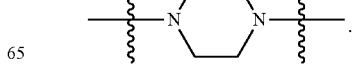

In another embodiment of the aforementioned embodiments, L1 is

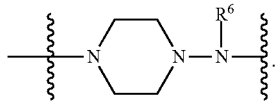

In another embodiment is a compound of Formula (I) wherein n is an integer from 1 to 35, $G^5$ is

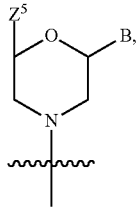

each W is O, each Y is O, at least one X is X3, and X3 is selected from -L1-CO-alkylene-CNH—NH$_2$, -L1-CO-alkenylene-CNH—NH$_2$, -L1-CONH-alkylene-CNH—NH$_2$, -L1-CO-alkylene-N(R$^1$)$_2$, -L1-CO-alkenylene-N(R$^1$)$_2$, -L1-CONH-alkylene-N(R$^1$)$_2$, -L1-CO-alkylene-N(R$^2$)$_3$, -L1-CO-alkenylene-N(R$^2$)$_3$, -L1-CONH-alkylene-N(R$^2$)$_3$, -L1-CO-alkylene-heterocyclyl, -L1-CO-alkenylene-heterocyclyl, -L1-CONH-alkylene-heterocyclyl, -L1-CO-alkylene-N(O)(R$^2$)$_2$, -L1-CO-alkenylene-N(O)(R$^2$)$_2$, -L1-CONH-alkylene-N(O)(R$^2$)$_2$, -L1-CO-alkylene-NH—CNH—NH$_2$, -L1-CO-alkenylene-NH—CNH—NH$_2$, and -L1-CONH-alkylene-NH—CNH—NH$_2$. In a further embodiment, at least one X3 is selected from -L1-CO-alkenylene-CNH—NH$_2$, -L1-CO-alkenylene-N(R$^1$)$_2$, -L1-CO-alkenylene-N(R$^2$)$_3$, -L1-CO-alkenylene-heterocyclyl, -L1-CO-alkenylene-N(O)(R$^2$)$_2$, and -L1-CO-alkenylene-NH—CNH—NH$_2$. In some embodiments, at least one X3 is -L1-CO-alkenylene-CNH—NH$_2$. In some embodiments, at least one X3 is -L1-CO-alkenylene-N(R$^1$)$_2$. In some embodiments, at least one X3 is -L1-CO-alkenylene-N(R$^2$)$_3$. In some embodiments, at least one X3 is -L1-CO-alkenylene-heterocyclyl. In some embodiments, at least one X3 is -L1-CO-alkenylene-N(O)(R$^2$)$_2$. In some embodiments, at least one X3 is -L1-CO-alkenylene-NH—CNH—NH$_2$. In a further embodiment of the aforementioned embodiments, L1 is

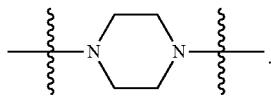

In another embodiment of the aforementioned embodiments, L1 is

In another embodiment is a compound of Formula (I) wherein n is an integer from 1 to 35, $G^5$ is

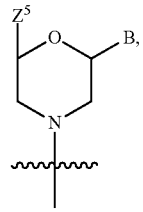

each W is O, each Y is O, at least one X is X3, and X3 is selected from -L1-CO-alkylene-CNH—NH$_2$, -L1-CONH-alkylene-CNH—NH$_2$, -L1-CO-alkylene-N(R$^1$)$_2$, -L1-CONH-alkylene-N(R$^1$)$_2$, -L1-CO-alkylene-N(R$^2$)$_3$, -L1-CONH-alkylene-N(R$^2$)$_3$, -L1-CO-alkylene-heterocyclyl, -L1-CONH-alkylene-heterocyclyl, -L1-CO-alkylene-N(O)(R$^2$)$_2$, -L1-CONH-alkylene-N(O)(R$^2$)$_2$, -L1-CO-alkylene-NH—CNH—NH$_2$, and -L1-CONH-alkylene-NH—CNH—NH$_2$. In a further embodiment, at least one X3 is selected from -L1-CO-alkylene-CNH—NH$_2$, -L1-CO-alkylene-N(R$^1$)$_2$, -L1-CO-alkylene-N(R$^2$)$_3$, -L1-CO-alkylene-heterocyclyl, -L1-CO-alkylene-N(O)(R$^2$)$_2$, and -L1-CO-alkylene-NH—CNH—NH$_2$. In some embodiments, at least one X3 is -L1-CO-alkylene-CNH—NH$_2$. In some embodiments, at least one X3 is -L1-CO-alkylene-N(R$^1$)$_2$. In some embodiments, at least one X3 is -L1-CO-alkylene-N(R$^2$)$_3$. In some embodiments, at least one X3 is -L1-CO-alkylene-heterocyclyl. In some embodiments, at least one X3 is -L1-CO-alkylene-N(O)(R$^2$)$_2$. In some embodiments, at least one X3 is -L1-CO-alkylene-NH—CNH—NH$_2$. In a further embodiment of the aforementioned embodiments, L1 is

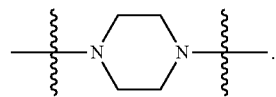

In another embodiment of the aforementioned embodiments, L1 is

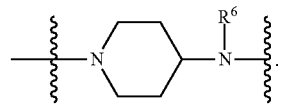

In yet a further embodiment of the aforementioned embodiments, -alkylene- is —CH$_2$—, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—. In some embodiments of the aforementioned embodiments, -alkylene- is —CH$_2$—. In some embodiments of the aforementioned embodiments, -alkylene- is —CH$_2$CH$_2$—. In some embodiments of the aforementioned embodiments, -alkylene- is —CH$_2$CH$_2$CH$_2$—. In some embodiments of the aforementioned embodiments, -alkylene- is —CH$_2$CH$_2$CH$_2$CH$_2$—. In some embodiments of the aforementioned embodiments, -alkylene- is —CH$_2$CH$_2$CH$_2$CH$_2$CH$_2$—.

In another embodiment is a compound of Formula (I) wherein n is an integer from 1 to 35, $G^5$ is

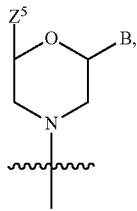

each W is O, each Y is O, at least one X is X3 and X3 is selected from

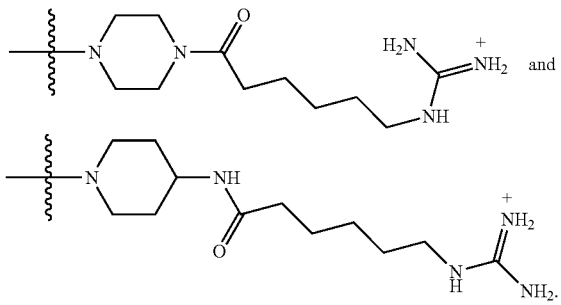

In some embodiments, at least one X3 is

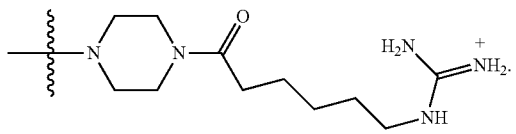

In some embodiments, at least one X3 is

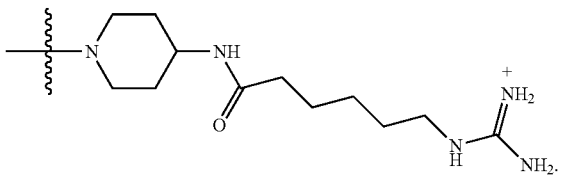 [SMILES: *N1CCC(NC(=O)CCCCCNC(=N)N)CC1]

In another embodiment is a compound of Formula (I) wherein n is an integer from 1 to 35, $G^5$ is

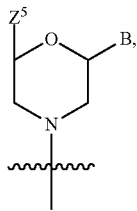

each W is O, each Y is O, at least one X is X3, and X3 is selected from -L1-CO-alkylene-CNH—$NH_2$, -L1-CONH-alkylene-CNH—$NH_2$, -L1-CO-alkylene-N($R^1$)$_2$, -L1-CONH-alkylene-N($R^1$)$_2$, -L1-CO-alkylene-N($R^2$)$_3$, -L1-CONH-alkylene-N($R^2$)$_3$, -L1-CO-alkylene-heterocyclyl, -L1-CONH-alkylene-heterocyclyl, -L1-CO-alkylene-N(O)($R^2$)$_2$, -L1-CONH-alkylene-N(O)($R^2$)$_2$, -L1-CO-alkylene-NH—CNH—$NH_2$, and -L1-CONH-alkylene-NH—CNH—$NH_2$. In a further embodiment, at least one X3 is selected from -L1-CO-alkylene-CNH—$NH_2$, -L1-CO-alkylene-N($R^1$)$_2$, -L1-CO-alkylene-N($R^2$)$_3$, -L1-CO-alkylene-heterocyclyl, -L1-CO-alkylene-N(O)($R^2$)$_2$, and -L1-CO-alkylene-NH—CNH—$NH_2$. In some embodiments, at least one X3 is -L1-CO-alkylene-CNH—$NH_2$. In some embodiments, at least one X3 is -L1-CO-alkylene-N($R^1$)$_2$. In some embodiments, at least one X3 is -L1-CO-alkenylene-N($R^2$)$_3$. In some embodiments, at least one X3 is -L1-CO-alkenylene-heterocyclyl. In some embodiments, at least one X3 is -L1-CO-alkenylene-N(O)($R^2$)$_2$. In some embodiments, at least one X3 is -L1-CO-alkenylene-NH—CNH—$NH_2$. In a further embodiment of the aforementioned embodiments, L1 is

In another embodiment of the aforementioned embodiments, L1 is

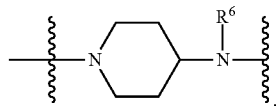

In yet a further embodiment of the aforementioned embodiments, -alkylene- is —$CH_2CH_2$—, —$CH_2CH_2CH_2$—, —$CH_2CH_2CH_2CH_2$—, and —$CH_2CH_2CH_2CH_2CH_2$—. In some embodiments of the aforementioned embodiments, -alkylene- is —$CH_2CH_2$—. In some embodiments of the aforementioned embodiments, -alkylene- is —$CH_2CH_2CH_2$—. In some embodiments of the aforementioned embodiments, -alkylene- is —$CH_2CH_2CH_2CH_2$—. In some embodiments of the aforementioned embodiments, -alkylene- is —$CH_2CH_2CH_2CH_2CH_2$—.

In another embodiment is a compound of Formula (I) wherein n is an integer from 1 to 35, $G^5$ is

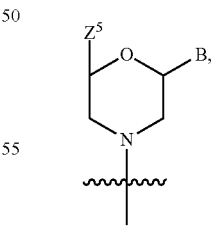

each W is O, each Y is O, at least one X is X3, and X3 is selected from -L1-N($R^1$)$_2$, -L1-N($R^2$)$_3$, -L1-N(O)($R^2$)$_2$, and -L1-NH—CNH—$NH_2$. In some embodiments, at least one X3 is -L1-N($R^1$)$_2$. In some embodiments, at least one X3 is -L1-N($R^2$)$_3$. In some embodiments, at least one X3 is -L1-N(O)($R^2$)$_2$. In some embodiments, at least one X3 is -L1-NH—CNH—$NH_2$. In further embodiments at least one X3 is selected from:

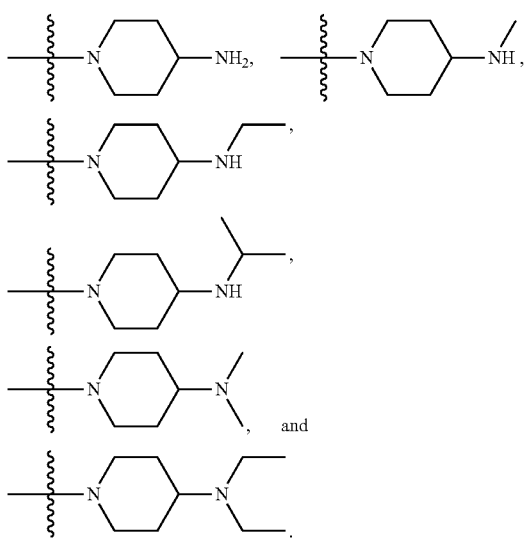

In some embodiments, at least one X3 is

In some embodiments, at least one X3 is

In some embodiments, at least one X3 is

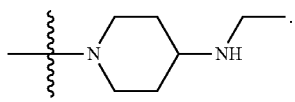

In some embodiments at least one X3 is

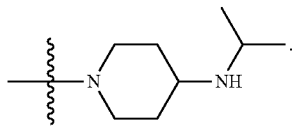 [SMILES: *N1CCC(NC(C)C)CC1]

In some embodiments, at least one X3 is

In some embodiments, at least one X3 is

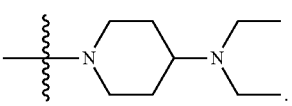

In yet further embodiments at least one X3 is selected from

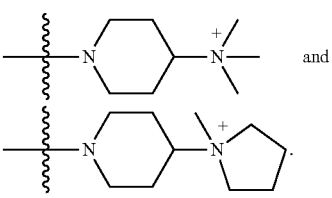

In some embodiments, at least one X3 is

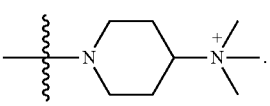

In some embodiments, at least one X3 is

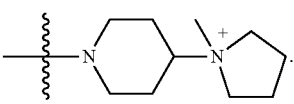

In any of the aforementioned embodiments of Formula (I) wherein at least one X is X3 is another embodiment wherein n is an integer from 30-35. In further embodiments of the aforementioned embodiments of Formula (I) wherein at least one X is X3, n is an integer from 25-29. In further embodiments of the aforementioned embodiments of Formula (I) wherein at least one X is X3, n is an integer from 20-24. In further embodiments of any of the aforementioned embodiments of Formula (I) wherein at least one X is X3, n is an integer from 15-19. In further embodiments of the aforementioned embodiments of Formula (I) wherein at least one X is X3, n is an integer from 10-14. In further embodiments of the aforementioned embodiments of Formula (I) wherein at least one X is X3, n is an integer from 5-9. In yet further embodiments of the aforementioned embodiments of Formula (I) wherein at least one X is X3, n is an integer from 1-4.

In another embodiment the X3 group is provided in a protected form. In another embodiment the protected form comprises a protected nitrogen. In another embodiment the protected nitrogen is protected with a trifluoroacetyl group.

In another embodiment is a compound of Formula (I) wherein n is an integer from 1 to 35, $G^5$ is

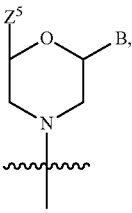

each W is O, each Y is O, and at least one X is X4. In further embodiments at least one X4 is selected from —O-alkylene-aryl, —N(R¹)-aryl, —N(R¹)-alkylene-aryl, —N(R¹)-alkylene-N(R¹)-aryl, —N(R¹)-alkylene-N(R¹)CO-aryl, —N(R¹)-alkylene-N(R¹)SO₂-aryl, and —N(R¹)-alkylene-N(R¹)CH₂-aryl. In a further embodiment, at least one X4 is —O-alkylene-aryl.

In another embodiment is a compound of Formula (I) wherein n is an integer from 1 to 35, G⁵ is

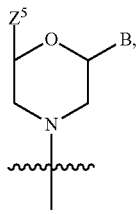

each W is O, each Y is O, at least one X is X4, and at least one X4 is selected from —N(R¹)-aryl, —N(R¹)-alkylene-aryl, —N(R¹)-alkylene-N(R¹)-aryl, —N(R¹)-alkylene-N(R¹)CO-aryl, —N(R¹)-alkylene-N(R¹)SO₂-aryl, and —N(R¹)-alkylene-N(R¹)CH₂-aryl. In a further embodiment, at least one X4 is —N(R¹)-aryl. In yet a further embodiment, at least one X4 is

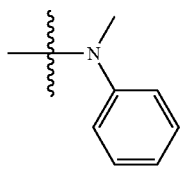 and 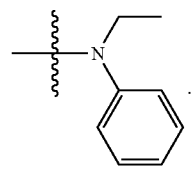

In some embodiments, at least one X4 is

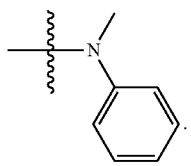 [SMILES: *N(C)c1ccccc1]

In some embodiments, at least one X4 is

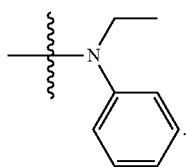 [SMILES: *N(CC)c1ccccc1]

In another embodiment is a compound of Formula (I) wherein n is an integer from 1 to 35, G⁵ is

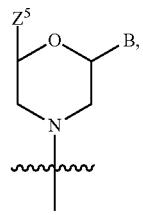

each W is O, each Y is O, at least one X is X4, and at least one X4 is —N(R¹)-alkylene-aryl. In further embodiments, -alkylene- is —CH₂—, —CH(CH₃)—, —CH₂CH₂—, and —CH₂CH₂CH₂—. In some embodiments, -alkylene- is —CH₂—. In some embodiments, -alkylene- is —CH(CH₃)—. In some embodiments, -alkylene- is —CH₂CH₂—. In some embodiments, -alkylene- is —CH₂CH₂CH₂—. In a further embodiment, at least one X4 is selected from:

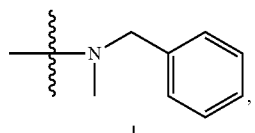 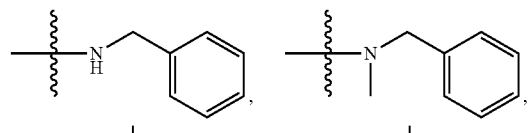

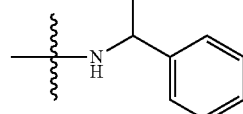 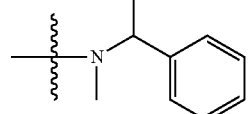

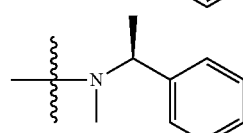 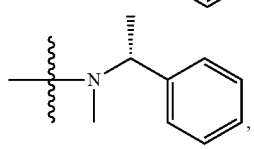

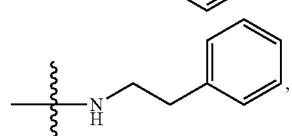, and

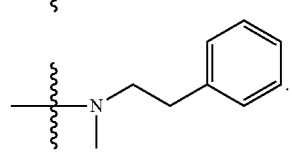

In some embodiments, at least one X4 is

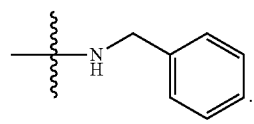 [SMILES: *NCc1ccccc1]

In some embodiments, at least one X4 is

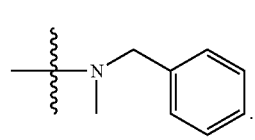

In some embodiments, at least one X4 is

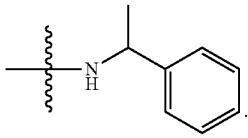 [SMILES: *NC(C)c1ccccc1]

In some embodiments, at least one X4 is

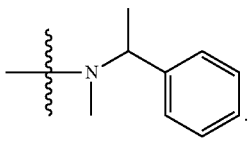 [SMILES: *N(C)C(C)c1ccccc1]

In some embodiments, at least one X4 is

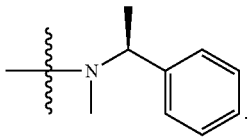 [SMILES: *N(C)[C@@H](C)c1ccccc1]

In some embodiments, at least one X4 is

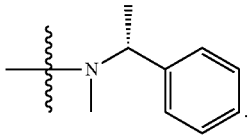 [SMILES: *N(C)[C@H](C)c1ccccc1]

In some embodiments, at least one X4 is

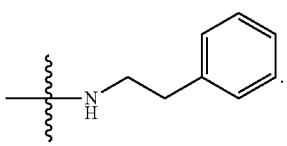 [SMILES: *NCCc1ccccc1]

In some embodiments, at least one X4 is

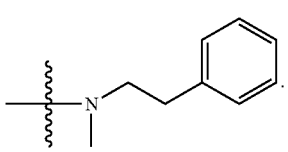 [SMILES: *N(C)CCc1ccccc1]

In another embodiment is a compound of Formula (I) wherein n is an integer from 1 to 35, $G^5$ is

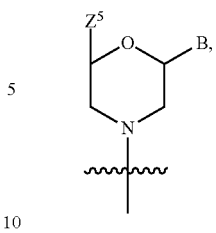

each W is O, each Y is O, at least one X is X4, and at least one X4 is selected from —N($R^1$)-alkylene-N($R^1$)-aryl, and —N($R^1$)-alkylene-N($R^1$)$CH_2$-aryl. In some embodiments, at least one X4 is —N($R^1$)-alkylene-N($R^1$)-aryl. In some embodiments, at least one X4 is —N($R^1$)-alkylene-N($R^1$)$CH_2$-aryl. In further embodiments, at least one X4 is selected from

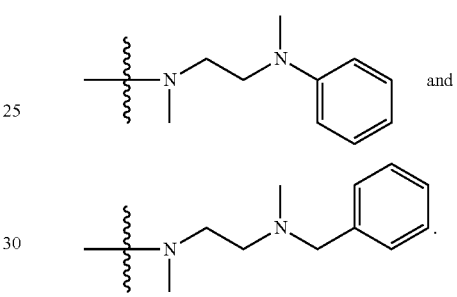

In some embodiments, at least one X4 is

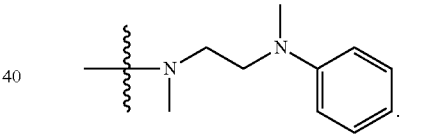

In some embodiments, at least one X4 is

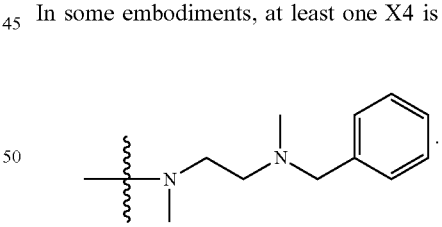

In yet a further embodiment, at least one X4 is selected from —N($R^1$)-alkylene-N($R^1$)CO-aryl and —N($R^1$)-alkylene-N($R^1$)$SO_2$-aryl. In further embodiments, at least one X4 is selected from

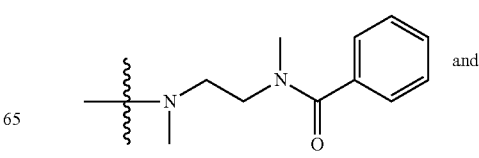

In some embodiments, at least one X4 is

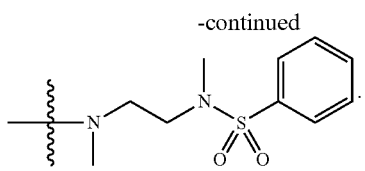

In some embodiments, at least one X4 is

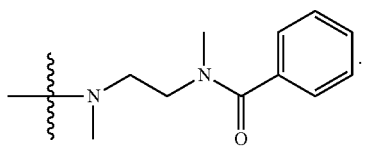 [SMILES: *N(C)CCN(C)C(=O)c1ccccc1]

In some embodiments, at least one X4 is

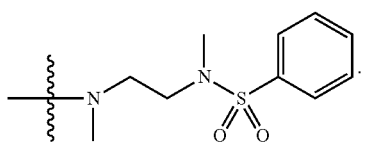 [SMILES: *N(C)CCN(C)S(=O)(=O)c1ccccc1]

In a further embodiment of the aforementioned embodiments, -alkylene- is selected from —CH₂CH₂—, —CH₂CH₂CH₂—, —CH₂CH₂CH₂CH₂—, and —CH₂CH₂CH₂CH₂CH₂—. In some embodiments of the aforementioned embodiments, -alkylene- is —CH₂CH₂—. In some embodiments of the aforementioned embodiments, -alkylene- is —CH₂CH₂CH₂—. In some embodiments of the aforementioned embodiments, -alkylene- is —CH₂CH₂CH₂CH₂—. In some embodiments of the aforementioned embodiments, -alkylene- is —CH₂CH₂CH₂CH₂CH₂—.

In another embodiment is a compound of Formula (I) wherein n is an integer from 1 to 35, $G^5$ is

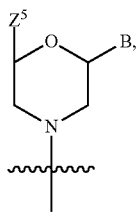

each W is O, each Y is O, at least one X is X4, and at least one X4 is selected from -L1-CO-alkylene-aryl, -L1-CO-alkenylene-aryl, -L1-CO-arylene-aryl, -L1-CONH-alkylene-aryl, -L1-CONH-arylene-aryl, -L1-SO₂-alkylene-aryl, -L1-SO₂-arylene-aryl, -L1-CO-aryl, -L1-SO₂-aryl, -L1-CO-alkylene-P(aryl)₃, and -L1-SO₂-alkylene-P(aryl)₃. In a further embodiment, at least one X4 is -L1-SO₂-alkylene-P(aryl)₃. In a further embodiment, at least one X4 is -L1-CO-alkylene-P(aryl)₃. In a further embodiment, at least one X4 is selected from -L1-CO-alkylene-aryl, -L1-CO-alkenylene-aryl, -L1-CO-arylene-aryl, -L1-CONH-alkylene-aryl, -L1-CONH-arylene-aryl, -L1-SO₂-alkylene-aryl, -L1-SO₂-arylene-aryl, -L1-CO-aryl, and -L1-SO₂-aryl. In a further embodiment, at least one X4 is selected from -L1-SO₂-alkylene-aryl, -L1-SO₂-arylene-aryl, and -L1-SO₂-aryl. In some embodiments, at least one X4 is -L1-SO₂-alkylene-aryl. In some embodiments, at least one X4 is -L1-SO₂-arylene-aryl. In some embodiments, at least one X4 is -L1-SO₂-aryl. In yet a further embodiment, at least one X4 is selected from -L1-CO-alkylene-aryl, -L1-CO-alkenylene-aryl, -L1-CO-arylene-aryl, -L1-CONH-alkylene-aryl, -L1-CONH-arylene-aryl, and -L1-CO-aryl. In a further embodiment, at least one X4 is selected from -L1-CONH-alkylene-aryl and -L1-CONH-arylene-aryl. In some embodiments, at least one X4 is -L1-CONH-alkylene-aryl. In some embodiments, at least one X4 is -L1-CONH-arylene-aryl. In yet a further embodiment, at least one X4 is selected from -L1-CO-alkylene-aryl, -L1-CO-alkenylene-aryl, -L1-CO-arylene-aryl, and -L1-CO-aryl. In some embodiments, at least one X4 is -L1-CO-alkylene-aryl. In some embodiments, at least one X4 is -L1-CO-alkenylene-aryl. In some embodiments, at least one X4 is -L1-CO-arylene-aryl. In some embodiments, at least one X4 is -L1-CO-aryl. In a further embodiment of the aforementioned embodiments, L1 is

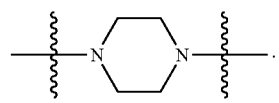

In another embodiment of the aforementioned embodiments, L1 is

In another embodiment is a compound of Formula (I) wherein n is an integer from 1 to 35, $G^5$ is

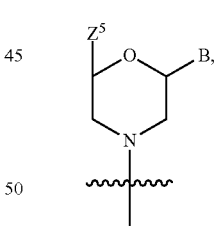

each W is O, each Y is O, at least one X is X4, and X4 is selected from

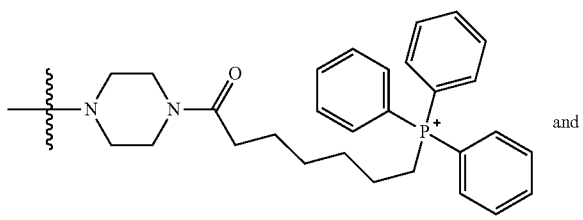

and

-continued
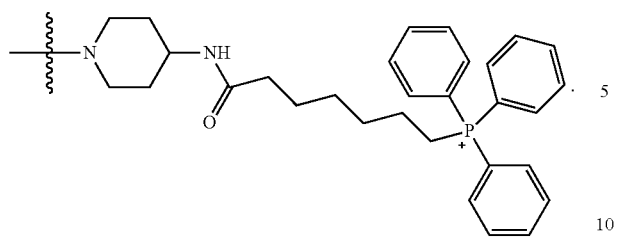
In some embodiments, at least one X4 is
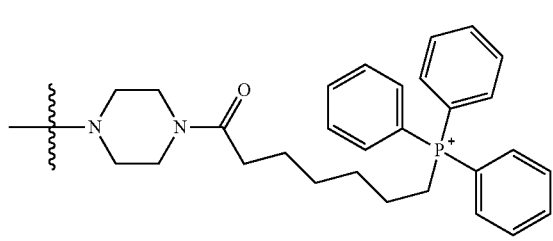
In some embodiments, at least one X4 is
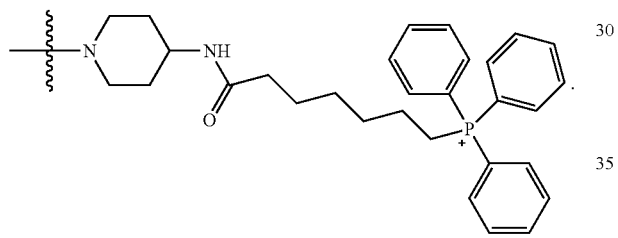
In a further embodiment, at least one X4 is selected from
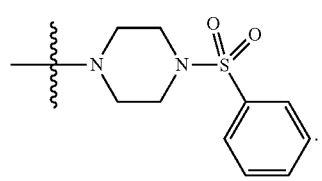 [SMILES: *N1CCN(S(=O)(=O)c2ccccc2)CC1]
and
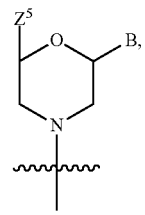
In some embodiments, at least one X4 is
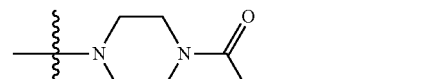
In another embodiment is a compound of Formula (I) wherein n is an integer from 1 to 35, $G^5$ is
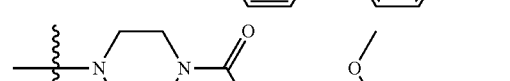
each W is O, each Y is O, at least one X is X4, and X4 is selected from:
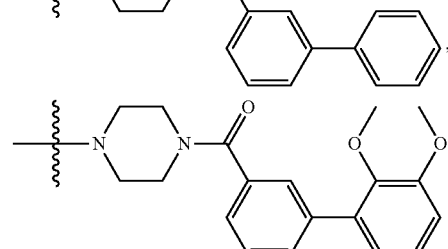
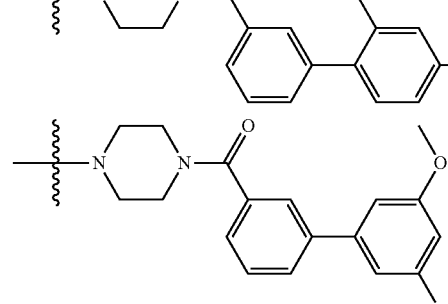
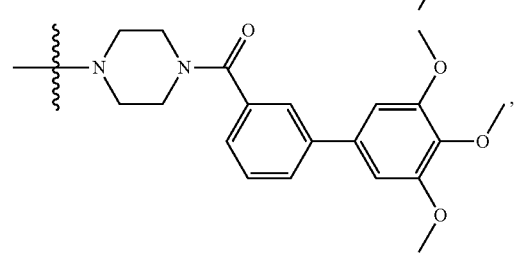

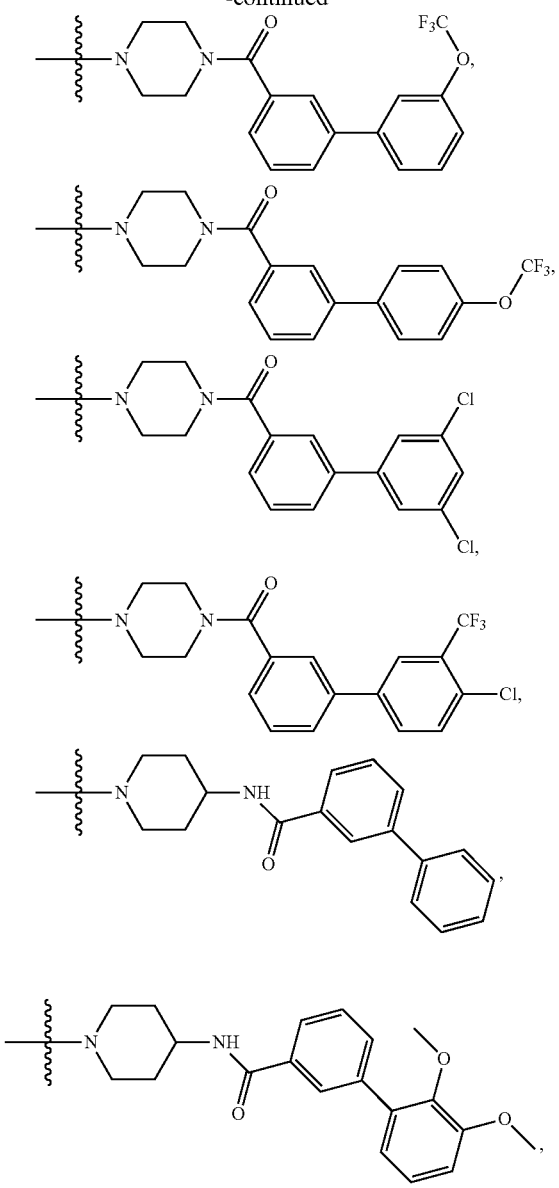
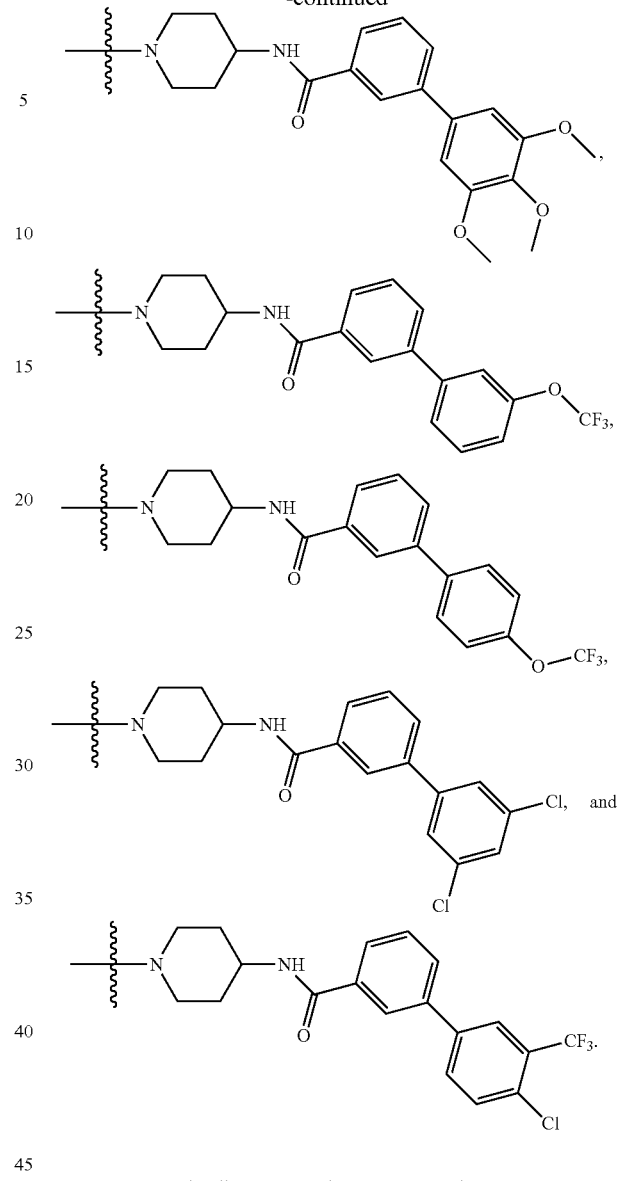
In some embodiments, at least one X4 is
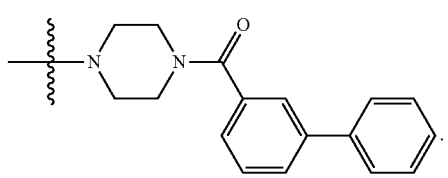 [SMILES: *N1CCN(C(=O)c2cccc(-c3ccccc3)c2)CC1]
In some embodiments, at least one X4 is
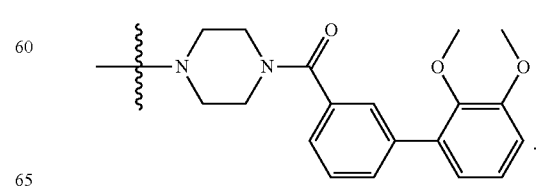

In some embodiments, at least one X4 is
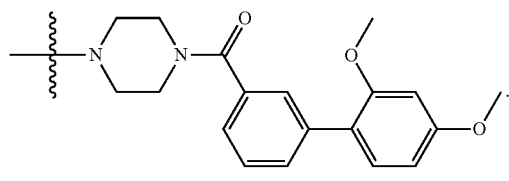 [SMILES: *N1CCN(C(=O)c2cccc(-c3ccc(OC)cc3OC)c2)CC1]
In some embodiments, at least one X4 is
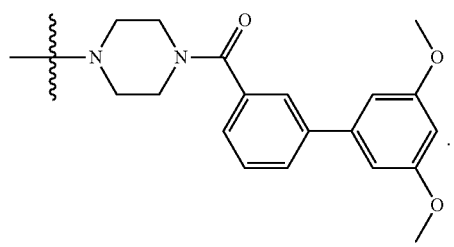 [SMILES: *N1CCN(C(=O)c2cccc(-c3cc(OC)cc(OC)c3)c2)CC1]
In some embodiments, at least one X4 is
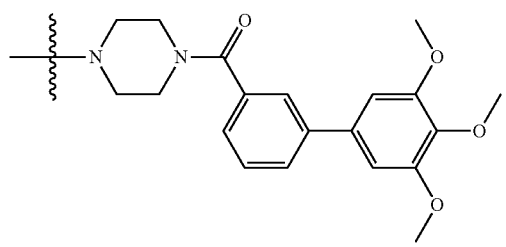
In some embodiments, at least one X4 is
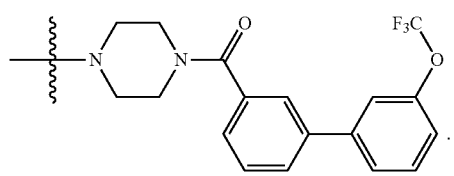 [SMILES: *N1CCN(C(=O)c2cccc(-c3cccc(OC(F)(F)F)c3)c2)CC1]
In some embodiments, at least one X4 is
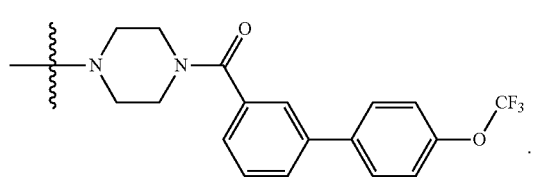 [SMILES: *N1CCN(C(=O)c2cccc(-c3ccc(OC(F)(F)F)cc3)c2)CC1]
In some embodiments, at least one X4 is
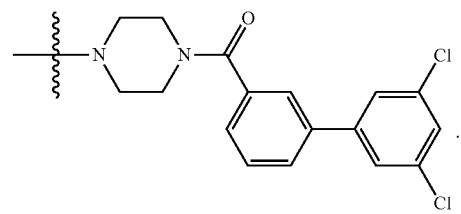 [SMILES: *N1CCN(C(=O)c2cccc(-c3cc(Cl)cc(Cl)c3)c2)CC1]
In some embodiments, at least one X4 is
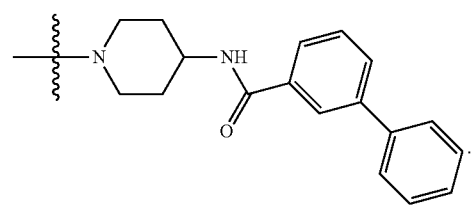 [SMILES: *N1CCC(NC(=O)c2cccc(-c3ccccc3)c2)CC1]
In some embodiments, at least one X4 is
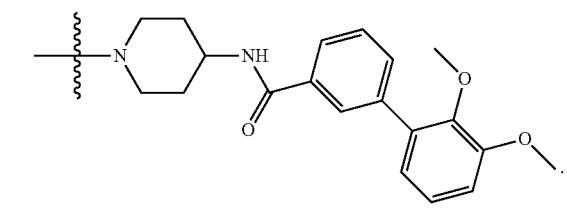 [SMILES: *N1CCC(NC(=O)c2cccc(-c3cccc(OC)c3OC)c2)CC1]
In some embodiments, at least one X4 is
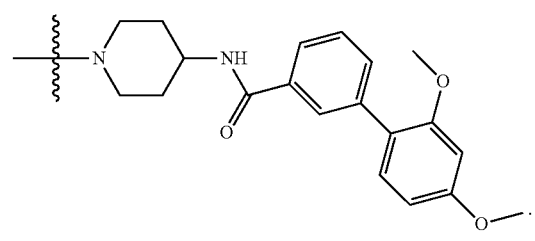 [SMILES: *N1CCC(NC(=O)c2cccc(-c3ccc(OC)cc3OC)c2)CC1]

In some embodiments, at least one X4 is

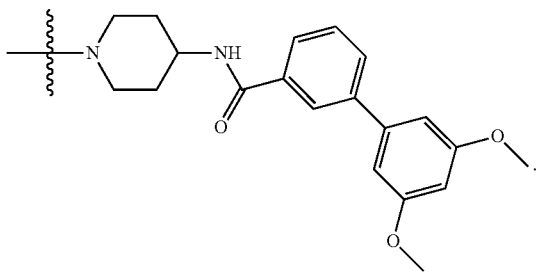 [SMILES: *N1CCC(NC(=O)c2cccc(-c3cc(OC)cc(OC)c3)c2)CC1]

In some embodiments, at least one X4 is

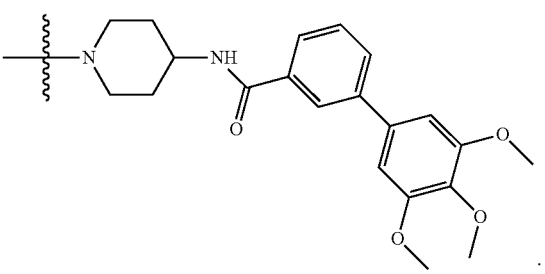 [SMILES: *N1CCC(NC(=O)c2cccc(-c3cc(OC)c(OC)c(OC)c3)c2)CC1]

In some embodiments, at least one X4 is

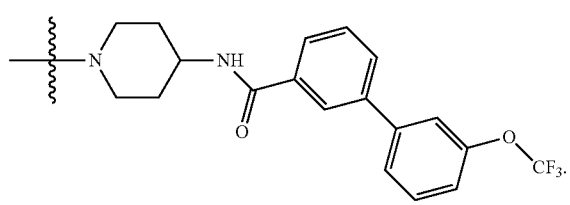 [SMILES: *N1CCC(NC(=O)c2cccc(-c3cccc(OC(F)(F)F)c3)c2)CC1]

In some embodiments, at least one X4 is

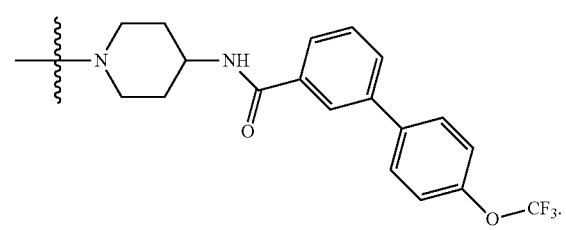 [SMILES: *N1CCC(NC(=O)c2cccc(-c3ccc(OC(F)(F)F)cc3)c2)CC1]

In some embodiments, at least one X4 is

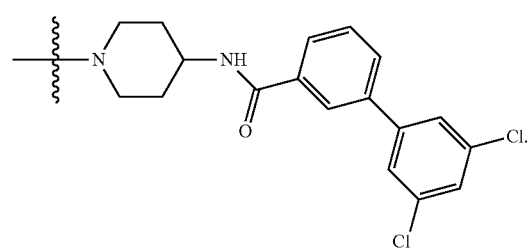 [SMILES: *N1CCC(NC(=O)c2cccc(-c3cc(Cl)cc(Cl)c3)c2)CC1]

In some embodiments, at least one X4 is

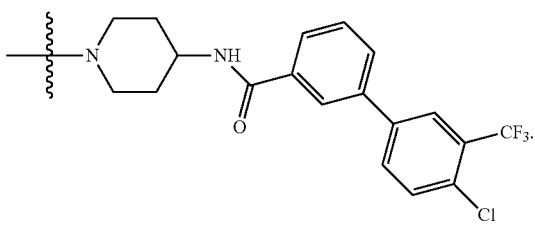 [SMILES: *N1CCC(NC(=O)c2cccc(-c3ccc(Cl)c(C(F)(F)F)c3)c2)CC1]

In a further embodiment, at least one X4 is selected from

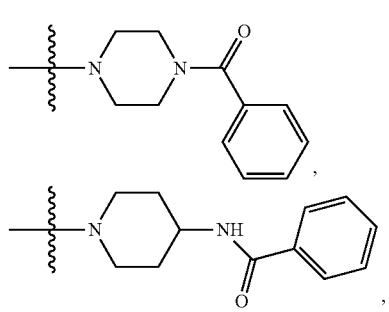

and

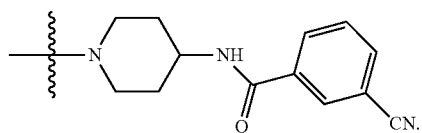 [SMILES: *N1CCC(NC(=O)c2cccc(C#N)c2)CC1]

In some embodiments, at least one X4 is

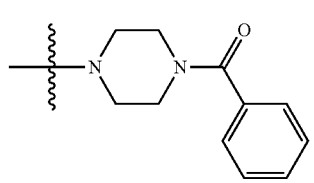

In some embodiments, at least one X4 is

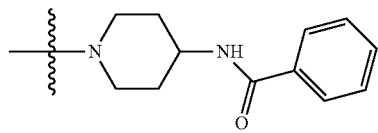

In some embodiments, at least one X4 is

In another embodiment is a compound of Formula (I) wherein n is an integer from 1 to 35, $G^5$ is

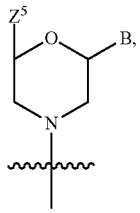

each W is O, each Y is O, at least one X is X4, and at least one X4 is selected from -L1-alkylene-aryl, -L1-arylene-aryl, -L1-aryl, and -L1-alkylene-P(aryl)$_3$. In some embodiments, at least one X4 is -L1-alkylene-aryl. In some embodiments, at least one X4 is -L1-arylene-aryl. In some embodiments, at least one X4 is -L1-aryl. In some embodiments, at least one X4 is -L1-alkylene-P(aryl)$_3$. In a further embodiment, at least one X4 is selected from

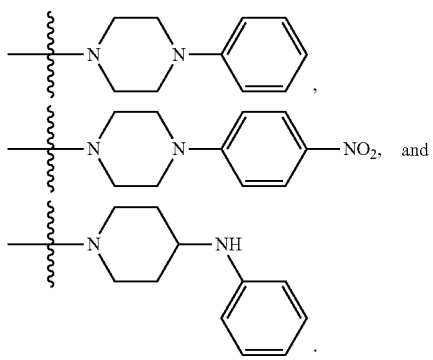

In some embodiments, at least one X4 is

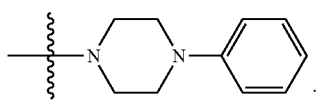

In some embodiments, at least one X4 is

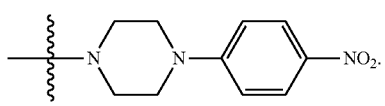

In some embodiments, at least one X4 is

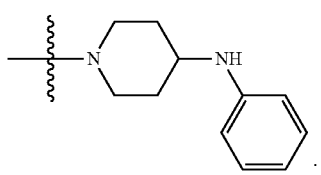 [SMILES: *N1CCC(Nc2ccccc2)CC1]

In any of the aforementioned embodiments of Formula (I) wherein at least one X is X4 is another embodiment wherein n is an integer from 30-35. In further embodiments of the aforementioned embodiments of Formula (I) wherein at least one X is X4, n is an integer from 25-29. In further embodiments of the aforementioned embodiments of Formula (I) wherein at least one X is X4, n is an integer from 20-24. In further embodiments of any of the aforementioned embodiments of Formula (I) wherein at least one X is X4, n is an integer from 15-19. In further embodiments of the aforementioned embodiments of Formula (I) wherein at least one X is X4, n is an integer from 10-14. In further embodiments of the aforementioned embodiments of Formula (I) wherein at least one X is X4, n is an integer from 5-9. In yet further embodiments of the aforementioned embodiments of Formula (I) wherein at least one X is X4, n is an integer from 1-4.

In another embodiment is a compound of Formula (I) wherein n is an integer from 1 to 35, $G^5$ is

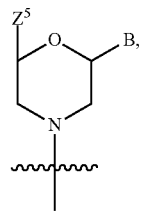

each W is O, each Y is O, and at least one X is X5. In further embodiments at least one X5 is selected from —O-alkylene-heteroaryl, —N($R^1$)-alkylene-heteroaryl, —N($R^1$)-alkylene-N($R^1$)-heteroaryl, —N($R^1$)-alkylene-N($R^1$)CO-heteroaryl, —N($R^1$)-alkylene-N($R^1$)SO$_2$-heteroaryl, and —N($R^1$)-alkylene-N($R^1$)CH$_2$-heteroaryl. In yet further embodiments, at least one X5 is selected from —N($R^1$)-alkylene-heteroaryl, —N($R^1$)-alkylene-N($R^1$)-heteroaryl, —N($R^1$)-alkylene-N($R^1$)CO-heteroaryl, —N($R^1$)-alkylene-N($R^1$)SO$_2$-heteroaryl, and —N($R^1$)-alkylene-N($R^1$)CH$_2$-heteroaryl.

In another embodiment is a compound of Formula (I) wherein n is an integer from 1 to 35, $G^5$ is

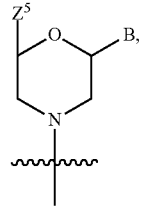

each W is O, each Y is O, at least one X is X5, and at least one X5 is —N($R^1$)-alkylene-heteroaryl. In a further embodiment, at least one X5 is —O-alkylene-heteroaryl. In yet further embodiments, -alkylene- is —CH$_2$—, —CH(CH$_3$)—, —CH$_2$CH$_2$—, and —CH$_2$CH$_2$CH$_2$—. In some embodiments, -alkylene- is —CH$_2$—. In some embodiments, -alkylene- is —CH(CH$_3$)—. In some embodiments, -alkylene- is —CH$_2$CH$_2$—. In some embodiments, -alkylene- is —CH$_2$CH$_2$CH$_2$ In another embodiment is a compound of Formula (I) wherein n is an integer from 1 to 35, $G^5$ is

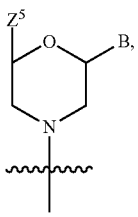

each W is O, each Y is O, at least one X is X5, and at least one X5 is selected from —N(R¹)-alkylene-heteroaryl, —N(R¹)-alkylene-N(R¹)-heteroaryl, —N(R¹)-alkylene-N(R¹)CO-heteroaryl, —N(R¹)-alkylene-N(R¹)SO₂-heteroaryl, and —N(R¹)-alkylene-N(R¹)CH₂-heteroaryl. In some embodiments, at least one X5 is —N(R¹)-alkylene-heteroaryl. In some embodiments, at least one X5 is —N(R¹)-alkylene-N(R¹)-heteroaryl. In some embodiments, at least one X5 is —N(R¹)-alkylene-N(R¹)CO-heteroaryl. In some embodiments, at least one X5 is —N(R¹)-alkylene-N(R¹)SO₂-heteroaryl. In some embodiments, at least one X5 is —N(R¹)-alkylene-N(R¹)CH₂-heteroaryl. In a further embodiment of the aforementioned embodiments, -alkylene- is selected from —CH₂CH₂—, —CH₂CH₂CH₂—, —CH₂CH₂CH₂CH₂—, and —CH₂CH₂CH₂CH₂CH₂—. In some embodiments of the aforementioned embodiments, -alkylene- is —CH₂CH₂—. In some embodiments of the aforementioned embodiments, -alkylene- is —CH₂CH₂CH₂—. In some embodiments of the aforementioned embodiments, -alkylene- is —CH₂CH₂CH₂CH₂—. In some embodiments of the aforementioned embodiments, -alkylene- is —CH₂CH₂CH₂CH₂CH₂—.

In another embodiment is a compound of Formula (I) wherein n is an integer from 1 to 35, $G^5$ is

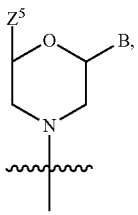

each W is O, each Y is O, at least one X is X5, and at least one X5 is selected from -L1-heteroaryl, -L1-alkylene-heteroaryl, -L1-arylene-heteroaryl, -L1-CO-alkylene-heteroaryl, -L1-CO-alkenylene-heteroaryl, -L1-CO-arylene-heteroaryl, -L1-CONH-alkylene-heteroaryl, -L1-CONH-arylene-heteroaryl, -L1-SO₂-alkylene-heteroaryl, -L1-SO₂-arylene-heteroaryl. In a further embodiment at least one X5 is selected from -L1-SO₂-alkylene-heteroaryl and -L1-SO₂-arylene-heteroaryl. In some embodiments, at least one X5 is -L1-SO₂-alkylene-heteroaryl. In some embodiments, at least one X5 is -L1-SO₂-arylene-heteroaryl. In a further embodiment at least one X5 is selected from -L1-CONH-alkylene-heteroaryl and -L1-CONH-arylene-heteroaryl. In some embodiments, at least one X5 is -L1-CONH-alkylene-heteroaryl. In some embodiments, at least one X5 is -L1-CONH-arylene-heteroaryl. In a further embodiment at least one X5 is selected from -L1-CO-alkylene-heteroaryl, -L1-CO-alkenylene-heteroaryl, and -L1-CO-arylene-heteroaryl. In some embodiments, at least one X5 is -L1-CO-alkylene-heteroaryl. In some embodiments, at least one X5 is -L1-CO-alkenylene-heteroaryl. In some embodiments, at least one X5 is -L1-CO-alkenylene-heteroaryl. In a further embodiment of the aforementioned embodiments, L1 is

In another embodiment of the aforementioned embodiments, L1 is

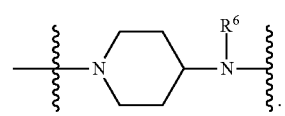

In yet a further embodiment of the aforementioned embodiments, -alkylene- is selected from —CH₂—, —CH(CH₃)—, —CH₂CH₂— and —CH₂CH₂CH₂—. In some embodiments of the aforementioned embodiments, -alkylene- is —CH₂—. In some embodiments of the aforementioned embodiments, -alkylene- is —CH(CH₃)—. In some embodiments of the aforementioned embodiments, -alkylene- is —CH₂CH₂—. In some embodiments of the aforementioned embodiments, -alkylene- is —CH₂CH₂CH₂—. In some embodiments, at least one X5 is -L1-heteroaryl. In a further embodiment, at least one X5 is selected from

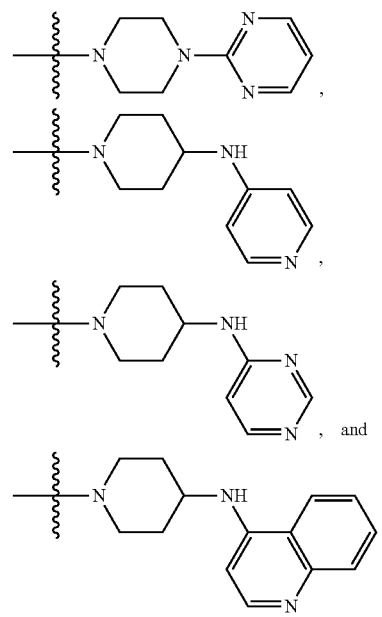

In some embodiments, at least one X is X5 and X5 is

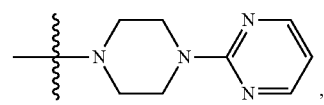 [SMILES: *N1CCN(c2ncccn2)CC1]

In some embodiments at least one X5 is

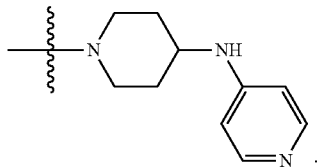 [SMILES: *N1CCC(Nc2ccncc2)CC1]

In some embodiments at least one X5 is

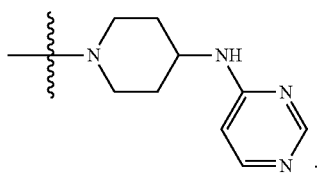

In some embodiments at least one X5 is

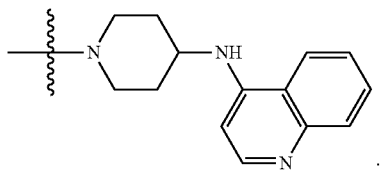 [SMILES: *N1CCC(Nc2ccnc3ccccc23)CC1]

In another embodiment is a compound of Formula (I) wherein n is an integer from 1 to 35, $G^5$ is

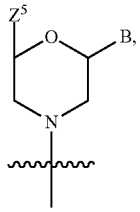

each W is O, each Y is O, at least one X is X5, and at least one X5 is selected from -L1-alkylene-heteroaryl and -L1-arylene-heteroaryl. In some embodiments at least one X5 is -L1-arylene-heteroaryl. In some embodiments at least one X5 is -L1-alkylene-heteroaryl. In a further embodiment, at least one X5 is selected from

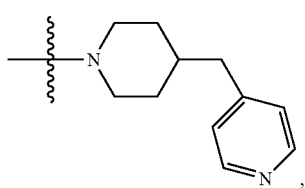

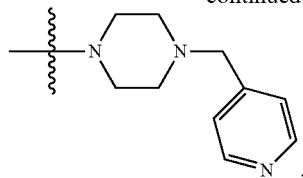

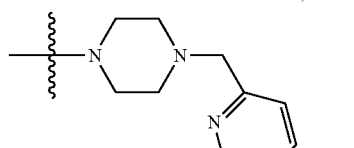

, and

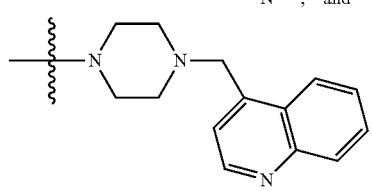

In some embodiments at least one X5 is

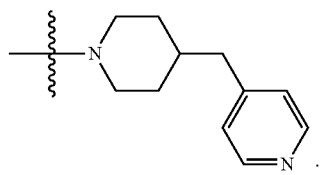

In some embodiments at least one X5 is

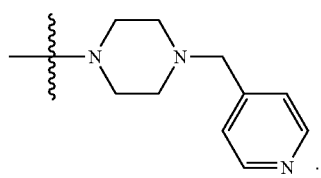

In some embodiments at least one X5 is

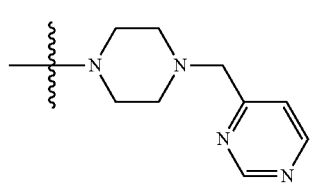

In some embodiments at least one X5 is

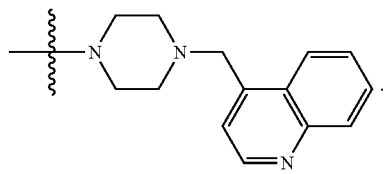 [SMILES: *N1CCN(Cc2ccnc3ccccc23)CC1]

In any of the aforementioned embodiments of Formula (I) wherein at least one X is X5 is another embodiment wherein n is an integer from 30-35. In further embodiments of the aforementioned embodiments of Formula (I) wherein at least one X is X5, n is an integer from 25-29. In further embodiments of the aforementioned embodiments of Formula (I) wherein at least one X is X5, n is an integer from 20-24. In further embodiments of any of the aforementioned embodiments of Formula (I) wherein at least one X is X5, n is an integer from 15-19. In further embodiments of the aforementioned embodiments of Formula (I) wherein at least one X is X5, n is an integer from 10-14. In further embodiments of the aforementioned embodiments of Formula (I) wherein at least one X is X5, n is an integer from 5-9. In yet further embodiments of the aforementioned embodiments of Formula (I) wherein at least one X is X5, n is an integer from 1-4.

In another embodiment is a compound of Formula (I) wherein n is an integer from 1 to 35, $G^5$ is

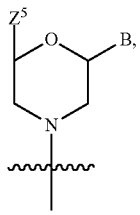

each W is O, each Y is O, and at least one X is X6. In further embodiments at least one X6 is selected from —O-alkylene-O(CH$_2$CH$_2$)$_m$OH, —O-alkylene-O(CH$_2$CH$_2$)$_m$OCH$_3$, —N(R$^1$)-alkylene-O(CH$_2$CH$_2$)$_m$OH, —N(R$^1$)-alkylene-O(CH$_2$CH$_2$)$_m$OCH$_3$, —N(R$^1$)-arylene-O(CH$_2$CH$_2$)$_m$OH, and —N(R$^1$)-arylene-O(CH$_2$CH$_2$)$_m$OCH$_3$. In further embodiments, at least one X6 is selected from —O-alkylene-O(CH$_2$CH$_2$)$_m$OH and —O-alkylene-O(CH$_2$CH$_2$)$_m$OCH$_3$. In some embodiments, at least one X6 is —O-alkylene-O(CH$_2$CH$_2$)$_m$OH. In some embodiments, at least one X6 is —O-alkylene-O(CH$_2$CH$_2$)$_m$OCH$_3$. In further embodiments, at least one X6 is selected from —N(R$^1$)-alkylene-O(CH$_2$CH$_2$)$_m$OH, —N(R$^1$)-alkylene-O(CH$_2$CH$_2$)$_m$OCH$_3$, —N(R$^1$)-arylene-O(CH$_2$CH$_2$)$_m$OH, and —N(R$^1$)-arylene-O(CH$_2$CH$_2$)$_m$OCH$_3$. In yet further embodiments, at least one X6 is selected from —N(R$^1$)-alkylene-O(CH$_2$CH$_2$)$_m$OH and —N(R$^1$)-alkylene-O(CH$_2$CH$_2$)$_m$OCH$_3$. In some embodiments, at least one X6 is —N(R$^1$)-alkylene-O(CH$_2$CH$_2$)$_m$OH. In some embodiments, at least one X6 is —N(R$^1$)-alkylene-O(CH$_2$CH$_2$)$_m$OCH$_3$. In further embodiments, at least one X6 is selected from —N(R$^1$)-arylene-O(CH$_2$CH$_2$)$_m$OH and —N(R$^1$)-arylene-O(CH$_2$CH$_2$)$_m$OCH$_3$. In some embodiments, at least one X6 is —N(R$^1$)-arylene-O(CH$_2$CH$_2$)$_m$OH. In some embodiments, at least one X6 is —N(R$^1$)-arylene-O(CH$_2$CH$_2$)$_m$OCH$_3$. In yet a further embodiment of the aforementioned embodiments, -alkylene- is selected from —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—. In some embodiments of the aforementioned embodiments, -alkylene- is —CH$_2$CH$_2$—. In some embodiments of the aforementioned embodiments, -alkylene- is —CH$_2$CH$_2$CH$_2$—. In some embodiments of the aforementioned embodiments, -alkylene- is —CH$_2$CH$_2$CH$_2$CH$_2$—. In some embodiments of the aforementioned embodiments, -alkylene- is —CH$_2$CH$_2$CH$_2$CH$_2$—.

In another embodiment is a compound of Formula (I) wherein n is an integer from 1 to 35, $G^5$ is

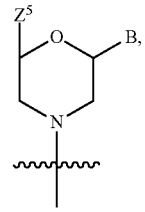

each W is O, each Y is O, at least one X is X6, and X6 is selected from -L1-alkylene-(OCH$_2$CH$_2$)$_m$OH, -L1-CO-alkylene-O(CH$_2$CH$_2$)$_m$OH, -L1-CO-alkylene-O(CH$_2$CH$_2$)$_m$OCH$_3$, -L1-SO$_2$-alkylene-O(CH$_2$CH$_2$)$_m$OH, -L1-SO$_2$-alkylene-O(CH$_2$CH$_2$)$_m$OCH$_3$, -L1-CO-arylene-O(CH$_2$CH$_2$)$_m$OH, -L1-CO-arylene-O(CH$_2$CH$_2$)$_m$OCH$_3$, -L1-SO$_2$-arylene-O(CH$_2$CH$_2$)$_m$OH, and -L1-SO$_2$-arylene-O(CH$_2$CH$_2$)$_m$OCH$_3$. In a further embodiment, at least one X6 is selected from -L1-SO$_2$-alkylene-O(CH$_2$CH$_2$)$_m$OH, -L1-SO$_2$-alkylene-O(CH$_2$CH$_2$)$_m$OCH$_3$, -L1-SO$_2$-arylene-O(CH$_2$CH$_2$)$_m$OH, and -L1-SO$_2$-arylene-O(CH$_2$CH$_2$)$_m$OCH$_3$. In yet a further embodiment, at least one X6 is selected from -L1-SO$_2$-alkylene-O(CH$_2$CH$_2$)$_m$OH and -L1-SO$_2$-alkylene-O(CH$_2$CH$_2$)$_m$OCH$_3$. In some embodiments, at least one X6 is -L1-SO$_2$-alkylene-O(CH$_2$CH$_2$)$_m$OH. In some embodiments, at least one X6 is -L1-SO$_2$-alkylene-O(CH$_2$CH$_2$)$_m$OCH$_3$. In a further embodiment, at least one X6 is selected from -L1-SO$_2$-arylene-O(CH$_2$CH$_2$)$_m$OH and -L1-SO$_2$-arylene-O(CH$_2$CH$_2$)$_m$OCH$_3$. In some embodiments, at least one X6 is -L1-SO$_2$-arylene-O(CH$_2$CH$_2$)$_m$OH. In some embodiments, at least one X6 is -L1-SO$_2$-arylene-O(CH$_2$CH$_2$)$_m$OCH$_3$. In a further embodiment, at least one X6 is selected from -L1-alkylene-(OCH$_2$CH$_2$)$_m$OH, -L1-CO-alkylene-O(CH$_2$CH$_2$)$_m$OH, -L1-CO-alkylene-O(CH$_2$CH$_2$)$_m$OCH$_3$, -L1-CO-arylene-O(CH$_2$CH$_2$)$_m$OH, and -L1-CO-arylene-O(CH$_2$CH$_2$)$_m$OCH$_3$. In some embodiments, at least one X6 is -L1-alkylene-(OCH$_2$CH$_2$)$_m$OH. In yet a further embodiment, at least one X6 is selected from -L1-CO-alkylene-O(CH$_2$CH$_2$)$_m$OH and -L1-CO-alkylene-O(CH$_2$CH$_2$)$_m$OCH$_3$. In some embodiments, at least one X6 is -L1-CO-alkylene-O(CH$_2$CH$_2$)$_m$OH. In some embodiments, at least one X6 is -L1-CO-alkylene-O(CH$_2$CH$_2$)$_m$OCH$_3$. In a further embodiment, at least one X6 is selected from -L1-CO-arylene-O(CH$_2$CH$_2$)$_m$OH and -L1-CO-arylene-O(CH$_2$CH$_2$)$_m$OCH$_3$. In some embodiments, at least one X6 is -L1-CO-arylene-O(CH$_2$CH$_2$)$_m$OH. In some embodiments, at least one X6 is -L1-CO-arylene-O(CH$_2$CH$_2$)$_m$OCH$_3$. In a further embodiment of the aforementioned embodiments, L1 is

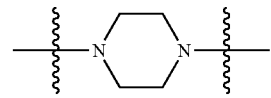

In another embodiment of the aforementioned embodiments, L1 is

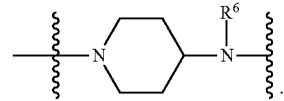

In yet a further embodiment of the aforementioned embodiments, -alkylene- is selected from —CH₂CH₂—, —CH₂CH₂CH₂—, —CH₂CH₂CH₂CH₂—, and —CH₂CH₂CH₂CH₂CH₂—. In some embodiments of the aforementioned embodiments, -alkylene- is —CH₂CH₂—. In some embodiments of the aforementioned embodiments, -alkylene- is —CH₂CH₂CH₂—. In some embodiments of the aforementioned embodiments, -alkylene- is —CH₂CH₂CH₂CH₂—. In some embodiments of the aforementioned embodiments, -alkylene- is —CH₂CH₂CH₂CH₂CH₂—. In some embodiments of the aforementioned embodiments, m is 1. In some embodiments of the aforementioned embodiments, m is 2. In some embodiments of the aforementioned embodiments, m is 3.

In another embodiment is a compound of Formula (I) wherein n is an integer from 1 to 35, G⁵ is

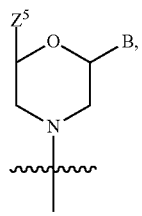

each W is O, each Y is O, at least one X is X6, and at least one X6 is selected from -L1-alkylene-(OCH₂CH₂)$_m$OH. In some embodiments, at least one X6 is

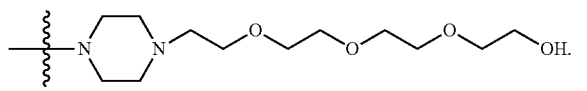 [SMILES: *N1CCN(CCOCCOCCOCCO)CC1]

In some embodiments, at least one X6 is

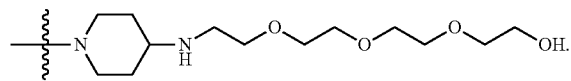

In another embodiment is a compound of Formula (I) wherein n is an integer from 1 to 35, G⁵ is

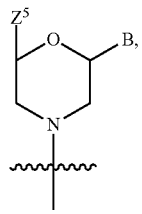

each W is O, each Y is O, at least one X is X6, and X6 is selected from -L1-CO—O(CH₂CH₂)$_m$OH and -L1-CO—O(CH₂CH₂)$_m$OCH₃. In a further embodiment, at least one X6 is -L1-CO—O(CH₂CH₂)$_m$OH. In yet a further embodiment, at least one X6 is -L1-CO—O(CH₂CH₂)$_m$OCH₃.

In another embodiment is a compound of Formula (I) wherein n is an integer from 1 to 35, G⁵ is

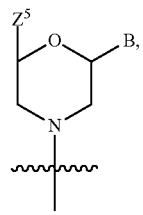

each W is O, each Y is O, at least one X is X6 and X6 is selected from —N(R¹)-(dibenzo-18-crown-6) and an aza-crown ether. In some embodiments, at least one X6 is —N(R¹)-(dibenzo-18-crown-6). In some embodiments, at least one X6 is an aza-crown ether. In further embodiments, at least one X is X6 and X6 is selected from:

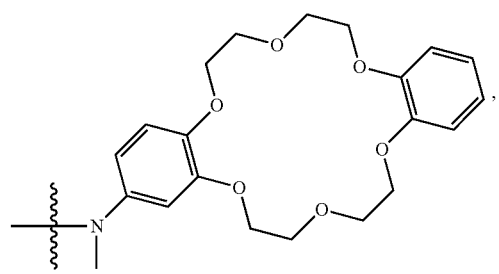 [SMILES: *N(C)c1ccc2c(c1)OCCOCCOc1ccccc1OCCOCCO2]

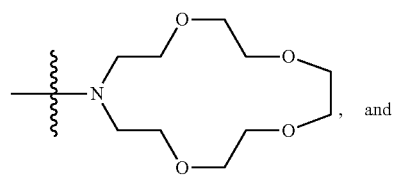

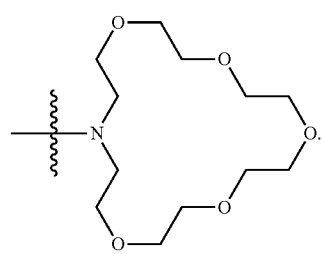 [SMILES: *N1CCOCCOCCOCCOCCOCC1]

In some embodiments, at least one X6 is

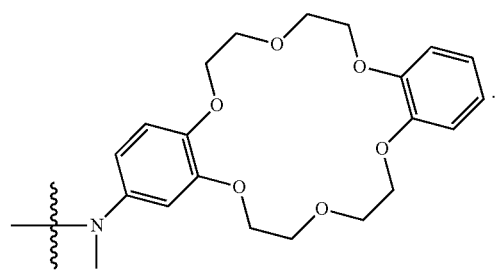

In some embodiments, at least one X6 is

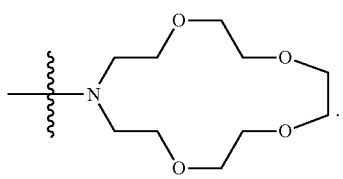

In some embodiments, at least one X6 is

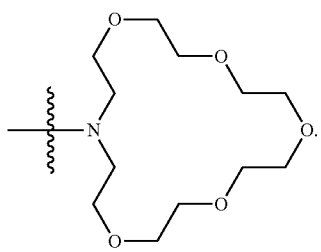

In any of the aforementioned embodiments of Formula (I) wherein at least one X is X6 is another embodiment wherein n is an integer from 30-35. In further embodiments of the aforementioned embodiments of Formula (I) wherein at least one X is X6, n is an integer from 25-29. In further embodiments of the aforementioned embodiments of Formula (I) wherein at least one X is X6, n is an integer from 20-24. In further embodiments of any of the aforementioned embodiments of Formula (I) wherein at least one X is X6, n is an integer from 15-19. In further embodiments of the aforementioned embodiments of Formula (I) wherein at least one X is X6, n is an integer from 10-14. In further embodiments of the aforementioned embodiments of Formula (I) wherein at least one X is X6, n is an integer from 5-9. In yet further embodiments of the aforementioned embodiments of Formula (I) wherein at least one X is X6, n is an integer from 1-4.

In another embodiment is a compound of Formula (I) wherein n is an integer from 1 to 35, $G^5$ is

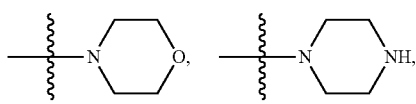

each W is O, each Y is O, and at least one X is X7. In a further embodiment, at least one X7 is a heterocycle. In a further embodiment, at least one X is X7 and X7 is selected from:

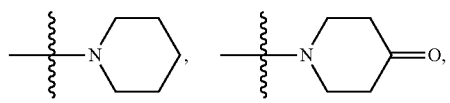

-continued

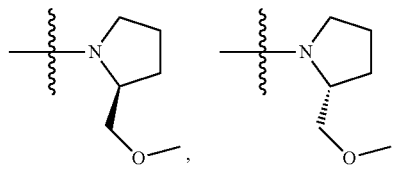

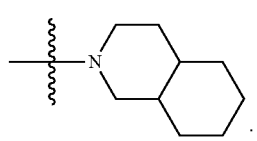

In some embodiments, at least one X7 is

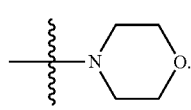

In some embodiments, at least one X7 is

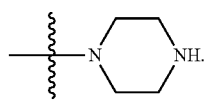

In some embodiments, at least one X7 is

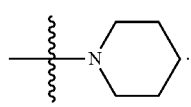

In some embodiments, at least one X7 is

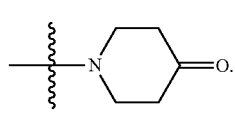

In some embodiments, at least one X7 is

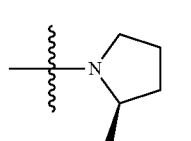

In some embodiments, at least one X7 is

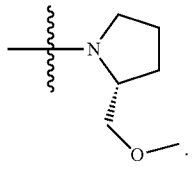

In some embodiments, at least one X7 is

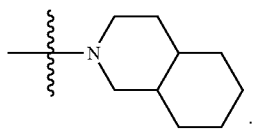 [SMILES: *N1CCC2CCCCC2C1]

In another embodiment is a compound of Formula (I) wherein n is an integer from 1 to 35, $G^5$ is

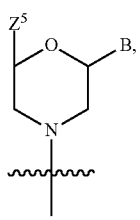

each W is O, each Y is O, at least one X is X7, and at least one X7 is —N(R$^1$)(R$^3$). In a further embodiment, at least one X7 is selected from:

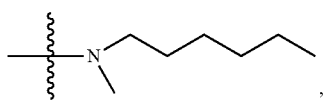 [SMILES: *N(C)CCCCCC]

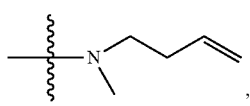

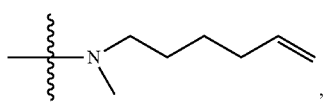 [SMILES: *N(C)CCCCC=C]

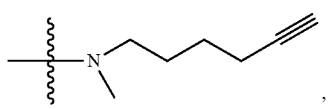 [SMILES: *N(C)CCCCC#C]

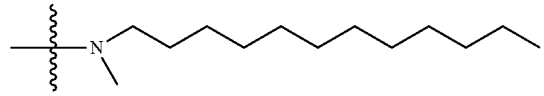

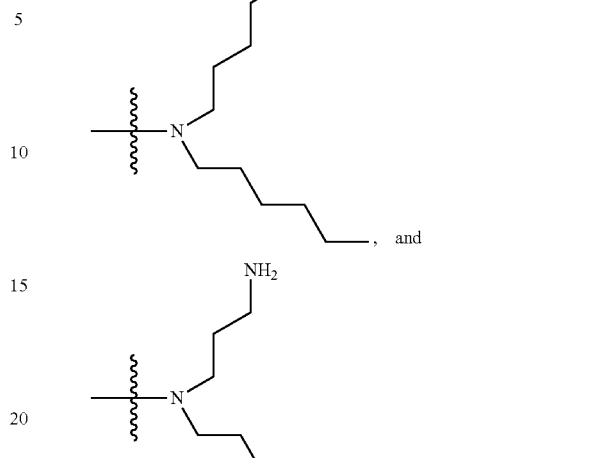

, and

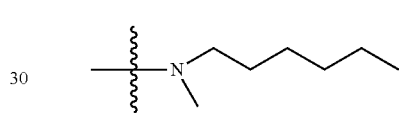

In some embodiments, at least one X7 is

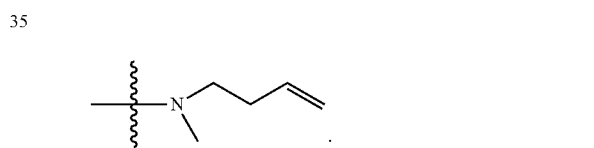

In some embodiments, at least one X7 is

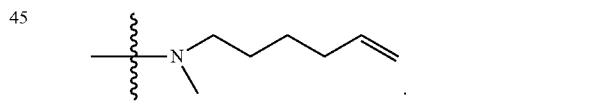

In some embodiments, at least one X7 is

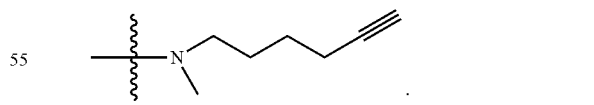

In some embodiments, at least one X7 is

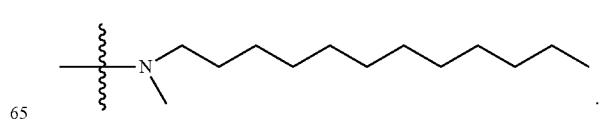

In some embodiments, at least one X7 is

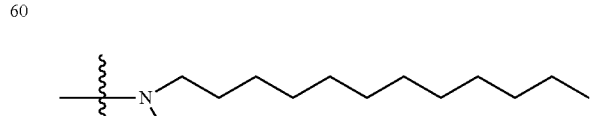

In some embodiments, at least one X7 is

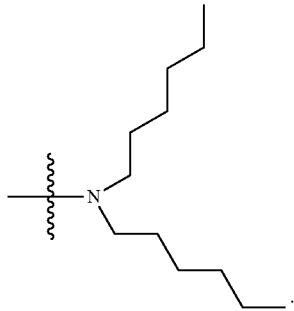 [SMILES: *N(CCCCCC)CCCCCC]

In some embodiments, at least one X7 is

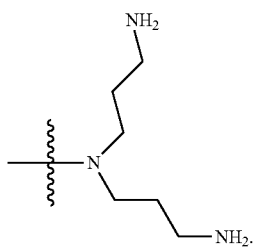 [SMILES: *N(CCCN)CCCN]

In another embodiment is a compound of Formula (I) wherein n is an integer from 1 to 35, $G^5$ is

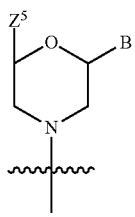

each W is O, each Y is O, at least one X is X7, and at least one X7 is —N($R^1$)($R^3$). In a further embodiment, at least one X7 is selected from -L1-CO-alkyl, -L1-CONH-alkyl, -L-CON(alkyl)-alkyl, and -L1-SO$_2$-alkyl. In a further embodiment, at least one X7 is -L1-CO-alkyl. In a further embodiment, at least one X7 is -L-CONH-alkyl. In a further embodiment, at least one X7 is -L1-CON(alkyl)-alkyl. In a further embodiment, at least one X7 is -L1-SO$_2$-alkyl.

In another embodiment is a compound of Formula (I) wherein n is an integer from 1 to 35, $G^5$ is

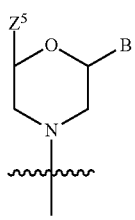

each W is O, each Y is O, at least one X is X7, and at least one X7 is selected from:

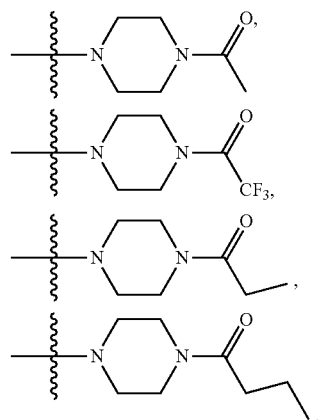

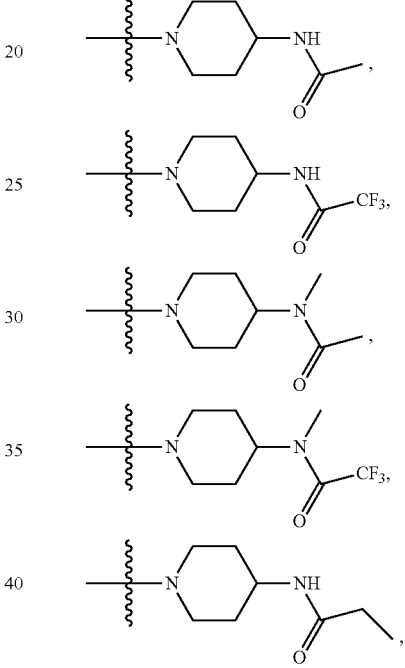

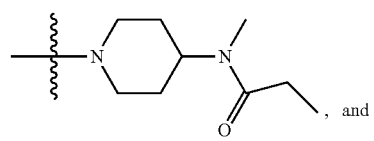

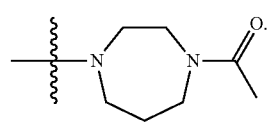

, and

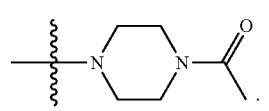

In some embodiments, at least one X7 is

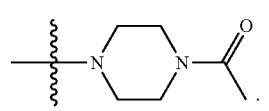

In some embodiments, at least one X7 is

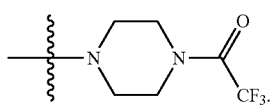

In some embodiments, at least one X7 is

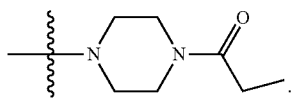

In some embodiments, at least one X7 is

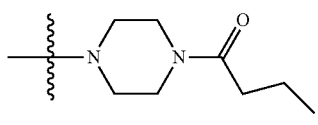

In some embodiments, at least one X7 is

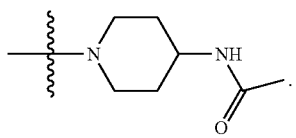 [SMILES: *N1CCC(NC(C)=O)CC1]

In some embodiments, at least one X7 is

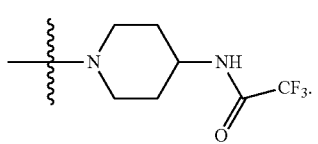 [SMILES: *N1CCC(NC(=O)C(F)(F)F)CC1]

In some embodiments, at least one X7 is

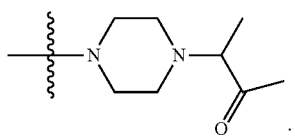 [SMILES: *N1CCN(C(C)C(C)=O)CC1]

In some embodiments, at least one X7 is

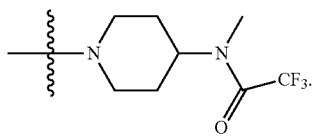 [SMILES: *N1CCC(N(C)C(=O)C(F)(F)F)CC1]

In some embodiments, at least one X7 is

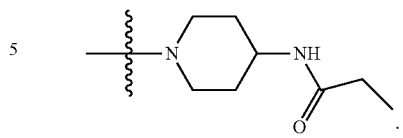

In some embodiments, at least one X7 is

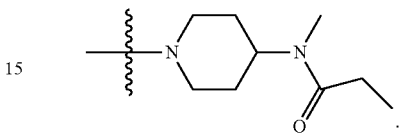

In some embodiments, at least one X7 is

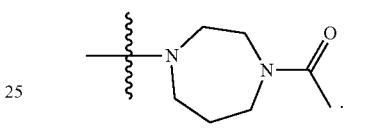

In another embodiment is a compound of Formula (I) wherein n is an integer from 1 to 35, $G^5$ is

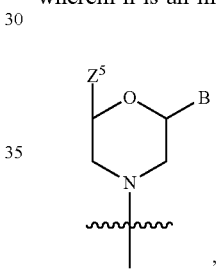

each W is O, each Y is O, at least one X is X7, and at least one X7 is —N(R$^1$)(R$^3$). In a further embodiment, at least one X7 is selected from:

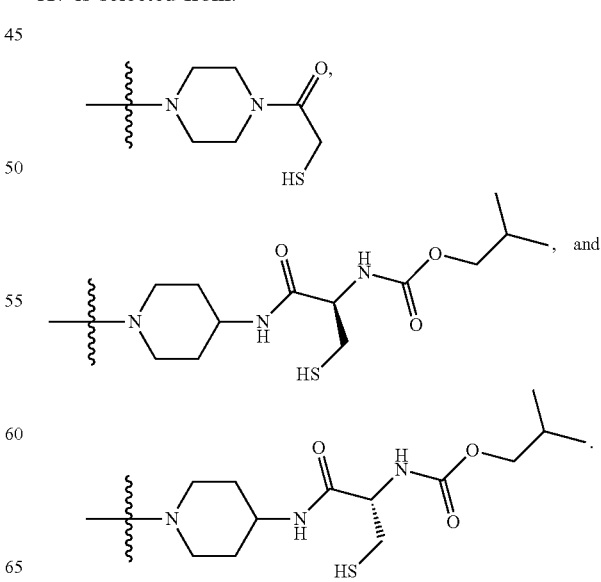

In some embodiments, at least one X7 is

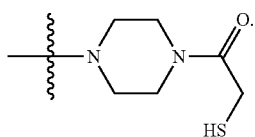

In some embodiments, at least one X7 is

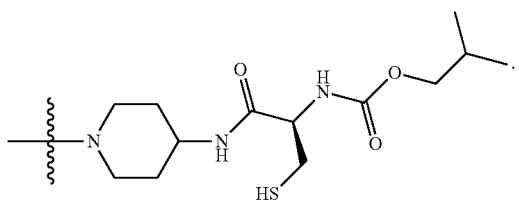 [SMILES: *N1CCC(NC(=O)[C@H](CS)NC(=O)OCC(C)C)CC1]

In some embodiments, at least one X7 is

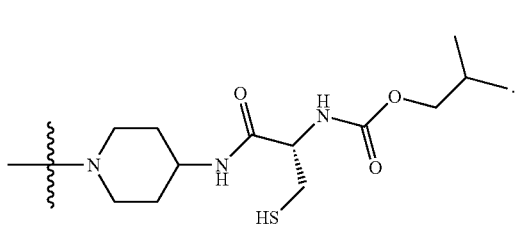 [SMILES: *N1CCC(NC(=O)[C@@H](CS)NC(=O)OCC(C)C)CC1]

In any of the aforementioned embodiments of Formula (I) wherein at least one X is X7 is another embodiment wherein n is an integer from 30-35. In further embodiments of the aforementioned embodiments of Formula (I) wherein at least one X is X7, n is an integer from 25-29. In further embodiments of the aforementioned embodiments of Formula (I) wherein at least one X is X7, n is an integer from 20-24. In further embodiments of any of the aforementioned embodiments of Formula (I) wherein at least one X is X7, n is an integer from 15-19. In further embodiments of the aforementioned embodiments of Formula (I) wherein at least one X is X7, n is an integer from 10-14. In further embodiments of the aforementioned embodiments of Formula (I) wherein at least one X is X7, n is an integer from 5-9. In yet further embodiments of the aforementioned embodiments of Formula (I) wherein at least one X is X7, n is an integer from 1-4.

In another embodiment is a compound of Formula (I) wherein n is an integer from 1 to 35, $G^5$ is

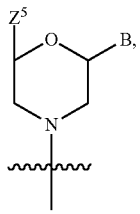

each W is O, each Y is O, and at least one X is X8. In a further embodiment, at least one X8 is -L1-CA. In a further embodiment, at least one X8 is -L1-dCA. In a further embodiment, at least one X8 is selected from -L1-COCH$_2$(R$^4$) and -L1-COCH(R$^4$)NHCO$_2$-alkyl. In some embodiments, at least one X8 is -L1-COCH$_2$(R$^4$). In some embodiments, at least one X8 is -L1-COCH(R$^4$)NHCO$_2$-alkyl.

In another embodiment is a compound of Formula (I) wherein n is an integer from 1 to 35, $G^5$ is

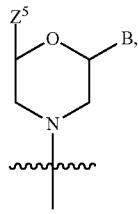

each W is O, at least one Y is NR$_{10}$, at least one X is X8, at least one X8 is —OR$^5$, and R$_5$ and R$^{10}$ together form a ring. In a further embodiment, the ring formed is selected from:

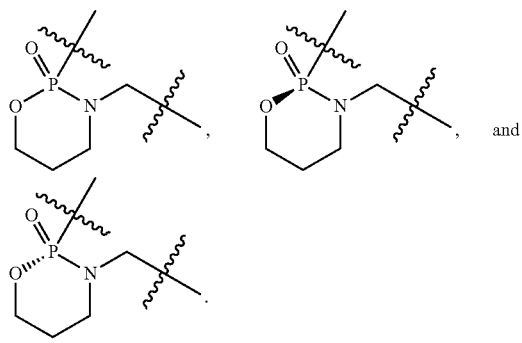

and

In some embodiments, the ring formed is

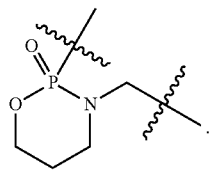 [SMILES: *CN1CCCOP1(*)=O]

In some embodiments, the ring formed is

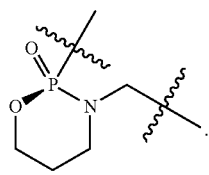 [SMILES: *CN1CCCO[P@]1(*)=O]

In some embodiments, the ring formed is

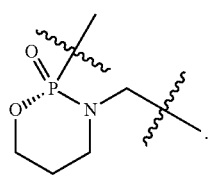 [SMILES: *CN1CCCO[P@@]1(*)=O]

In any of the aforementioned embodiments of Formula (I) wherein at least one X is X8 is another embodiment wherein n is an integer from 30-35. In further embodiments of the aforementioned embodiments of Formula (I) wherein at least one X is X8, n is an integer from 25-29. In further embodiments of the aforementioned embodiments of Formula (I) wherein at least one X is X8, n is an integer from 20-24. In further embodiments of any of the aforementioned embodiments of Formula (I) wherein at least one X is X8, n is an integer from 15-19. In further embodiments of the aforementioned embodiments of Formula (I) wherein at least one X is X8, n is an integer from 10-14. In further embodiments of the aforementioned embodiments of Formula (I) wherein at least one X is X8, n is an integer from 5-9. In yet further embodiments of the aforementioned embodiments of Formula (I) wherein at least one X is X8, n is an integer from 1-4.

In another embodiment is the compound of Formula (I) wherein L1 is selected from:

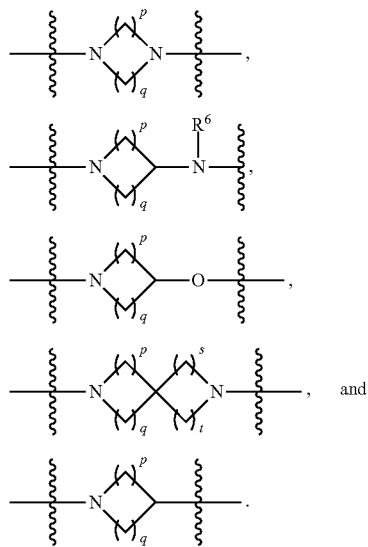

and

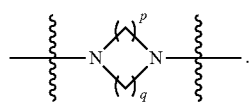

In another embodiment is the compound of Formula (I) wherein L1 is

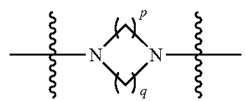

wherein p is 2 and q is 2. In another embodiment is the compound wherein p is 3 and q is 2.

In another embodiment is the compound of Formula (I) wherein L1 is

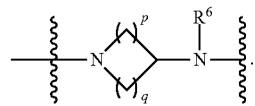

In another embodiment is the compound of Formula (I) wherein L1 is

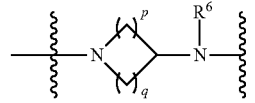

wherein p is 1 and is 2. In another embodiment is the compound wherein p is 1 and q is 2. In another embodiment is the compound wherein p is 3 and q is 2.

In another embodiment is the compound of Formula (I) wherein L1 is

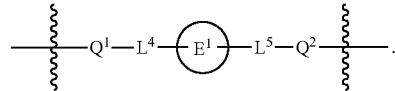

In another embodiment is the compound of Formula (I) wherein L1 is

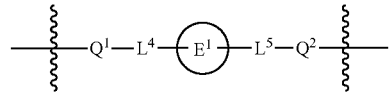

wherein $Q^1$ is —N($R^6$)—.

In another embodiment is the compound of Formula (I) wherein L1 is

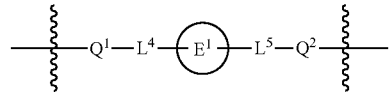

wherein $Q^2$ is —N($R^6$)—.

In another embodiment is the compound of Formula (I) wherein L1 is

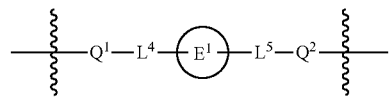

wherein $E^1$ is phenyl.

In another embodiment is the compound of Formula (I) wherein L1 is

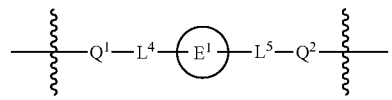

wherein $E^1$ is heteroaryl.

In another embodiment is the compound of Formula (I) wherein L1 is

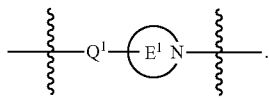

In another embodiment is the compound of Formula (I) wherein L1 is

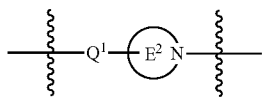

wherein $Q^1$ is —N($R^6$)—.

In another embodiment is the compound of Formula (I) wherein L1 is

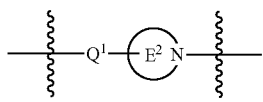

wherein $E^2$ is pyrrolyl. In another embodiment is the compound of Formula (I) wherein $E^2$ is imidazolyl. In another embodiment is the compound of Formula (I) wherein $E^2$ is triazinyl. In another embodiment is the compound of Formula (I) wherein $E^2$ is imidazolyl.

In another embodiment is the compound of Formula (I) wherein W is O, and Y is NH.

In another embodiment is the compound of Formula (I) wherein W is O, and Y is $NR^{10}$. In another embodiment is the compound of Formula (I) wherein W is O, and Y is $NR^{10}$, wherein $R^{10}$ and X8e together form a ring. In another embodiment is the compound of Formula (I) wherein $R^{10}$ and X8e together for a structure selected from

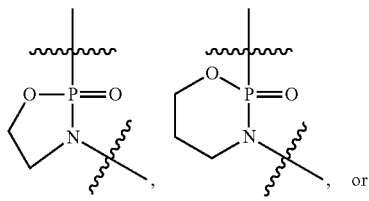

, or

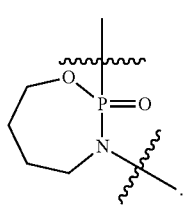

.

In another embodiment is the compound of Formula (I), wherein $L^{11}$ is

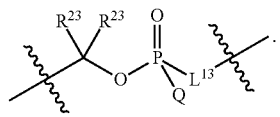

.

In another embodiment is the compound of Formula (I), wherein $L^{11}$ is

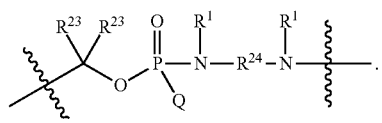

.

In another embodiment is the compound of Formula (I), wherein $L^{11}$ is

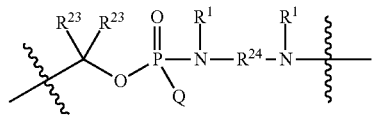

and $R^{24}$ is a $C_2$-$C_4$ alkylene. In another embodiment is the compound of Formula (I), wherein $L^{11}$ is

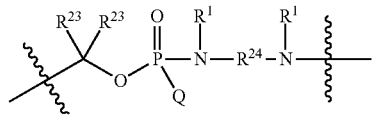

and wherein $R^{24}$ is ethylene or propylene, and $R^1$ is hydrogen or methyl.

In another embodiment is the compound of Formula (I), wherein $L^{11}$ is

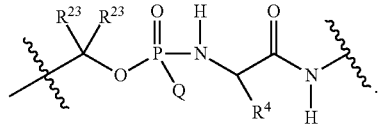

.

In another embodiment is the compound of Formula (I), wherein $L^{11}$ is

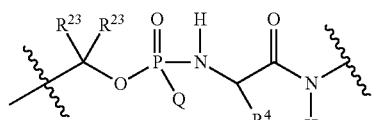

and $R^4$ is hydrogen or methyl. In another embodiment is the compound of Formula (I), wherein $L^{11}$ is

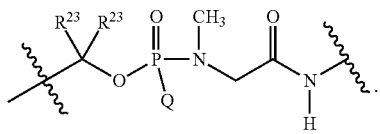

In another embodiment is the compound of Formula (I), wherein $L^{13}$ is

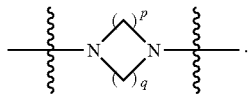

In another embodiment is the compound of Formula (I), wherein $L^{13}$ is

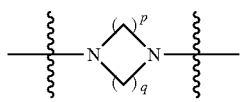

and wherein p is 2, and q is 2. In another embodiment is the compound of Formula (I), wherein $L^{13}$ is

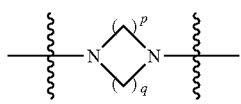

and wherein p is 2, and q is 3. In another embodiment is the compound of Formula (I), wherein $L^{13}$ is

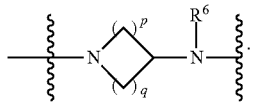

In another embodiment is the compound of Formula (I), wherein $L^{13}$ is

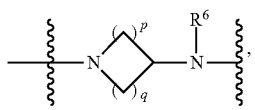

p and q are independently selected from 1 or 2, and $R^6$ is $CH_3$. In another embodiment is the compound of Formula (I), wherein $L^{13}$ is

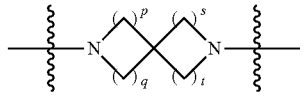

In another embodiment is the compound of Formula (I), wherein $L^{13}$ is

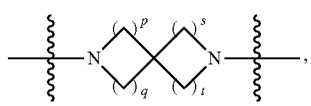

and p, q, s and t are independently selected from 1 or 2. In another embodiment is the compound of Formula (I), wherein Q is X1. In another embodiment is the compound of Formula (I), wherein $R^{23}$ is hydrogen, methyl or both $R^{23}$ groups together form a cyclopropyl, cyclobutyl, cyclopentyl or cyclohexyl ring. In another embodiment is the compound of Formula (I), wherein $R^{23}$ is hydrogen or methyl.

In another embodiment is the compound of Formula (I), wherein Q is X2. In another embodiment is the compound of Formula (I), wherein Q is X3. In another embodiment is the compound of Formula (I), wherein Q is X4. In another embodiment is the compound of Formula (I), wherein Q is X5. In another embodiment is the compound of Formula (I), wherein Q is X6. In another embodiment is the compound of Formula (I), wherein Q is X7. In another embodiment is the compound of Formula (I), wherein Q is X8.

In another embodiment is the compound of Formula (I), wherein $Z^5$ is $—C(R^{23})_2OP(=O)(OH)_2$. In another embodiment is the compound of Formula (I), wherein $R^{23}$ is hydrogen.

In another embodiment is the compound of Formula (I), wherein $Z^5$ is $-(L^{11})-(R^{15})$ and the $R^{15}$ is $C_1-C_{30}$ alkyl, $C_1-C_{30}$ alkylcarbonyl, $C_2-C_{30}$ alkyloxycarbonyl, or a 3-18 membered alkoxyalkylcarbonyl. In another embodiment is the compound of Formula (I), wherein $Z^5$ is $-(L^{11})-(R^{15})$ and the $R^{15}$ is a $C_2-C_{30}$ alkyloxycarbonyl. In another embodiment is the compound of Formula (I), wherein $Z^5$ is $-(L^{11})-(R^{15})$ and the $R^{15}$ is selected from $—C(=O)OCH_2CH_2OH$, $—C(=O)OCH_2CH_2OCH_2CH_2OH$, or $—C(=O)OCH_2CH_2OCH_2CH_2OCH_2CH_2OH$. In another embodiment is the compound of Formula (I), wherein $Z^5$ is $-(L^{11})-(R^{15})$ and the $R^{15}$ is $—C(=O)OCH_2CH_2OCH_2CH_2OCH_2CH_2OH$.

In another embodiment is the compound of Formula (I), wherein $Z^5$ is $-(L^{11})-(R^{15})$ and the $R^{15}$ is a cell-penetrating peptide. In another embodiment is the compound of Formula (I), wherein $R^{15}$ is a cell-penetrating peptide and the cell-penetrating peptide is linked through a aminohexanoic acid-derived linker. In another embodiment is the compound of Formula (I), wherein $R^{15}$ is a cell-penetrating peptide and the cell-penetrating peptide is linked through a aminohexanoic acid-derived linker comprising the structure:

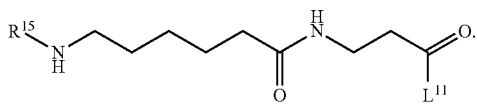

In another embodiment is the compound of Formula (I), wherein $Z^5$ is selected from:

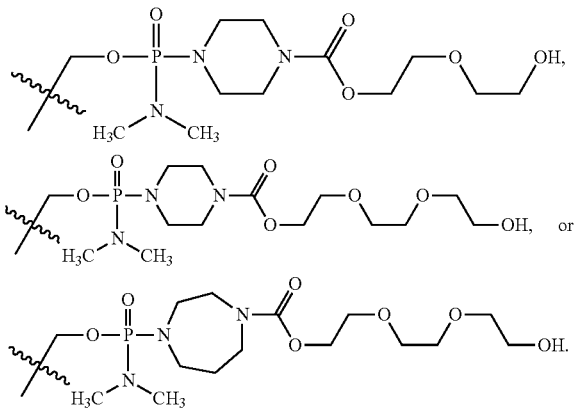

In another embodiment is the compound of Formula (I), wherein $Z^5$ is

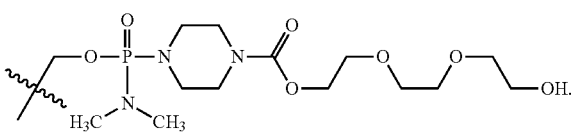

In another embodiment is the compound of Formula (I), wherein $Z^5$ is -($L^{11}$)-($L^{15}$)-($R^{16}$).

In another embodiment is the compound of Formula (I), wherein $L^{11}$ is

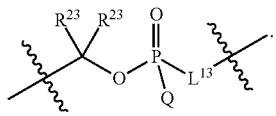

In another embodiment is the compound of Formula (I), wherein $L^{11}$ is

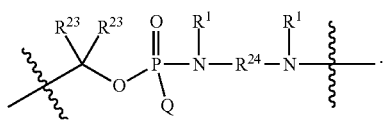

In another embodiment is the compound of Formula (I), wherein $L^{11}$ is

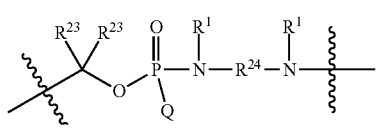

and $R^{24}$ is a $C_2$-$C_4$ alkylene. In another embodiment is the compound of Formula (I), wherein $L^{11}$ is

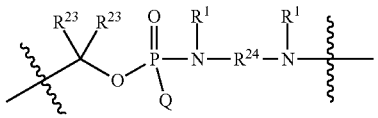

and wherein $R^{24}$ is ethylene or propylene, and $R^1$ is hydrogen or methyl.

In another embodiment is the compound of Formula (I), wherein $L^{11}$ is

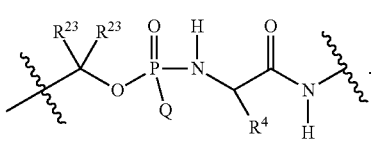

In another embodiment is the compound of Formula (I), wherein $L^{11}$ is

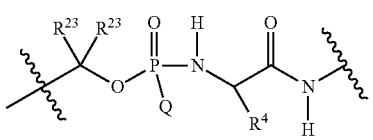

and $R^4$ is hydrogen or methyl. In another embodiment is the compound of Formula (I), wherein $L^{11}$ is

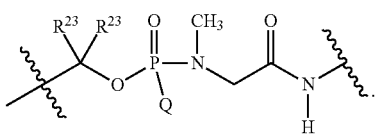

In another embodiment is the compound of Formula (I), wherein $L^{13}$ is

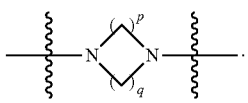

In another embodiment is the compound of Formula (I), wherein $L^{13}$ is

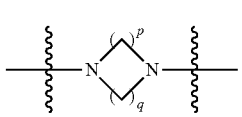

and wherein p is 2, and q is 2. In another embodiment is the compound of Formula (I), wherein $L^{13}$ is

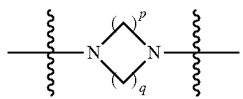

and wherein p is 2, and q is 3. In another embodiment is the compound of Formula (I), wherein $L^{13}$ is

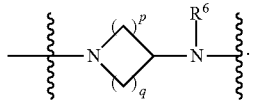

In another embodiment is the compound of Formula (I), wherein $L^{13}$ is

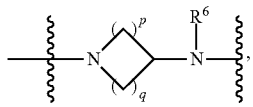

p and q are independently selected from 1 or 2, and $R^6$ is $CH_3$. In another embodiment is the compound of Formula (I), wherein $L^{13}$ is

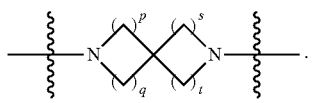

In another embodiment is the compound of Formula (I), wherein $L^{13}$ is

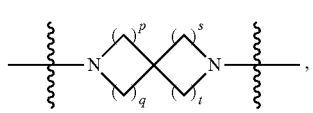

and p, q, s and t are independently selected from 1 or 2. In another embodiment is the compound of Formula (I), wherein Q is X1. In another embodiment is the compound of Formula (I), wherein $R^{23}$ is hydrogen, methyl or both $R^{23}$ groups together form a cyclopropyl, cyclobutyl, cyclopentyl or cyclohexyl ring. In another embodiment is the compound of Formula (I), wherein $R^{23}$ is hydrogen or methyl.

In another embodiment is the compound of Formula (I), wherein Q is X2. In another embodiment is the compound of Formula (I), wherein Q is X3. In another embodiment is the compound of Formula (I), wherein Q is X4. In another embodiment is the compound of Formula (I), wherein Q is X5. In another embodiment is the compound of Formula (I), wherein Q is X6. In another embodiment is the compound of Formula (I), wherein Q is X7. In another embodiment is the compound of Formula (I), wherein Q is X8.

In another embodiment is the compound of Formula (I), wherein $Z^5$ is -($L^{11}$)-(L15)-($R^{16}$), and $L^{15}$ is selected from —($C_1$-$C_{30}$ alkylene)-C(=O)—, or —($C_2$-$C_{30}$ alkoxy)-C(=O)—. In another embodiment is the compound of Formula (I), wherein $Z^5$ is -($L^{11}$)-(L15)-($R^{16}$), and $L^{15}$ is selected from —($C_2$-$C_{30}$ alkoxy)-C(=O)—.

In another embodiment is the compound of Formula (I), wherein $Z^5$ is -($L^{11}$)-($L^{15}$)-($R^{16}$) and is represented by the structure:

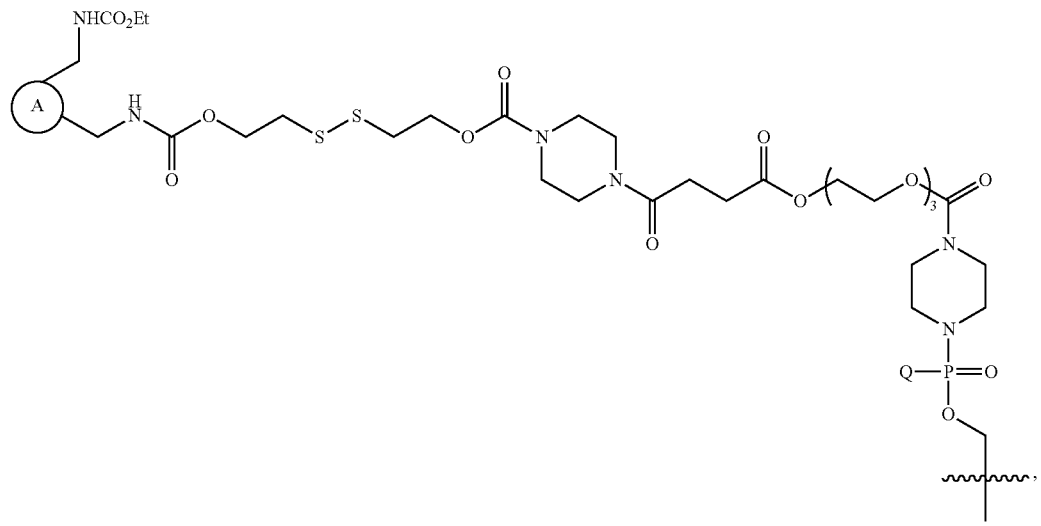

wherein group A is aminomethyl polystyrene resin.

In another embodiment is the compound of Formula (I), wherein $Z^5$ is -($L^{11}$)-($L^{15}$)-($R^{16}$) and $R^{16}$ is represented by the structure:

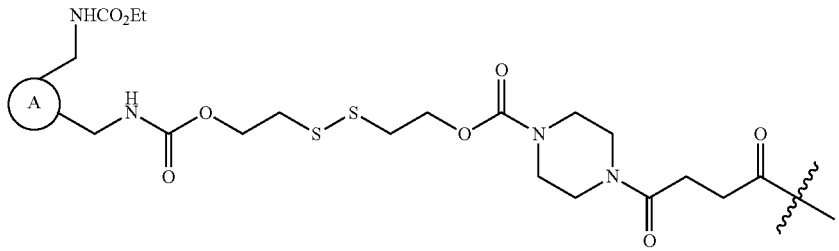

wherein group A is aminomethyl polystyrene resin.

In another embodiment is the compound of Formula (I), wherein $Z^5$ is -($L^{11}$)-($L^{15}$)-($R^{16}$) and $L^{15}$ is represented by the structure:

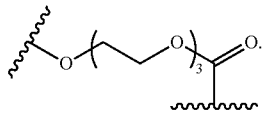

In another embodiment is the compound of Formula (I) wherein $R^{12}$ is an electron pair.

In another embodiment is the compound of Formula (I) wherein $R^{13}$ is a $C_1$-$C_{30}$ alkyl and $R^{12}$ is a $C_1$-$C_6$ alkyl. In another embodiment is the compound of Formula (I) wherein $R^{13}$ is a methyl group and $R^{12}$ is a methyl group.

In another embodiment is the compound of Formula (I) wherein $R^{13}$ is hydrogen.

In another embodiment is the compound of Formula (I) wherein $R^{13}$ is $C_1$-$C_{30}$ alkyl. In another embodiment is the compound of Formula (I) wherein $R^{13}$ is $C_1$-$C_{10}$ alkyl. In another embodiment is the compound of Formula (I) wherein $R^{13}$ is $C_1$-$C_6$ alkyl. In another embodiment is the compound of Formula (I) wherein $R^{13}$ is selected from prenyl, geranyl, farnesyl or geranylgeranyl.

In another embodiment is the compound of Formula (I) wherein $R^{13}$ is a cell-penetrating peptide.

In another embodiment is the compound of Formula (I) wherein $R^{13}$ is a guanidinyl or amidinyl group.

In another embodiment is the compound of Formula (I) wherein $R^{13}$ is a $C_3$-$C_8$ cycloalkyl.

In another embodiment is the compound of Formula (I) wherein $R^{13}$ is a $C_1$-$C_{30}$ alkylcarbonyl. In another embodiment is the compound of Formula (I) wherein $R^{13}$ is a $C_1$-$C_{15}$ alkylcarbonyl. In another embodiment is the compound of Formula (I) wherein $R^{13}$ is a $C_1$-$C_{10}$ alkylcarbonyl. In another embodiment is the compound of Formula (I) wherein $R^{13}$ is a $C_1$-$C_8$ alkylcarbonyl. In another embodiment is the compound of Formula (I) wherein $R^{13}$ is a $C_1$-$C_5$ alkylcarbonyl. In another embodiment is the compound of Formula (I) wherein $R^{13}$ is a $C_1$-$C_4$ alkylcarbonyl. In another embodiment is the compound of Formula (I) wherein $R^{13}$ is a $C_1$-$C_2$ alkylcarbonyl. In another embodiment is the compound of Formula (I) wherein $R^{13}$ is a $C_1$ alkylcarbonyl. In another embodiment is the compound of Formula (I) wherein $R^{13}$ is $CH_3CO$—.

In another embodiment is the compound of Formula (I) wherein $R^{13}$ is a $C_1$-$C_{15}$ alkylcarbonyl. In another embodiment is the compound of Formula (I) wherein $R^{13}$ is a $C_1$-$C_{30}$ alkyloxycarbonyl. In another embodiment is the compound of Formula (I) wherein $R^{13}$ is a $C_1$-$C_{10}$ alkyloxycarbonyl. In another embodiment is the compound of Formula (I) wherein $R^{13}$ is a $C_1$-$C_5$ alkyloxycarbonyl. In another embodiment is the compound of Formula (I) wherein $R^{13}$ is a $C_1$-$C_3$ alkyloxycarbonyl. In another embodiment is the compound of Formula (I) wherein $R^{13}$ is a $C_1$ alkyloxycarbonyl. In another embodiment is the compound of Formula (I) wherein $R^{13}$ is a $CH_3OCO$—. In another embodiment is the compound of Formula (I) wherein $R^{13}$ is a —C(=O)OCH$_2$CH$_2$OH, —C(=O)OCH$_2$CH$_2$OCH$_2$CH$_2$OH, or —C(=O)OCH$_2$CH$_2$OCH$_2$CH$_2$OCH$_2$CH$_2$OH.

In another embodiment is the compound of Formula (I) wherein $R^{13}$ is —C(=O)NHR$^{21}$. In another embodiment is the compound of Formula (I) wherein $R^{13}$ is —C(=O)NHR$^{21}$ and $R^{21}$ is methyl.

Table 1 provides, by way of example only, representative linkages for compounds of Formula (I)

TABLE 1
Representative Intersubunit Linkages (X-groups)
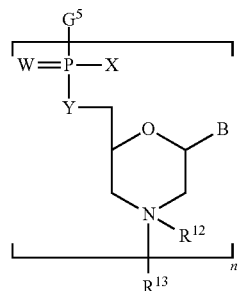
| No. | X |
| --- | --- |
| 1 | 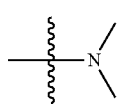 |
| 2 | 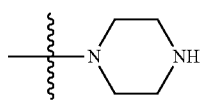 |
| 3 | 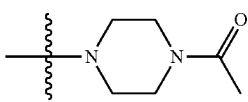 |
| 4 | 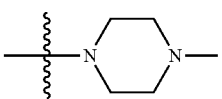 |
| 5 | 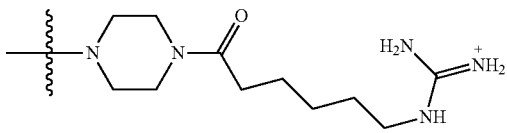 [SMILES: *N1CCN(C(=O)CCCCCNC(=N)N)CC1] |
| 6 | 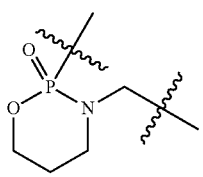 [SMILES: *CN1CCCOP1(*)=O] |
| 7 | 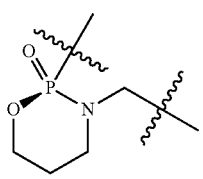 [SMILES: *CN1CCCO[P@]1(*)=O] |
| 8 | 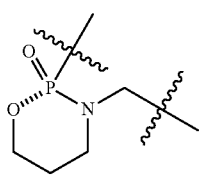 |

113 114
TABLE 1-continued
Representative Intersubunit Linkages (X-groups)
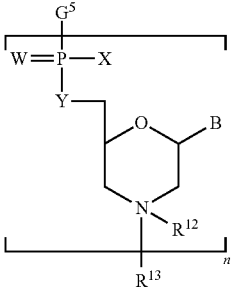
| No. | X |
|---|---|
| 9 | 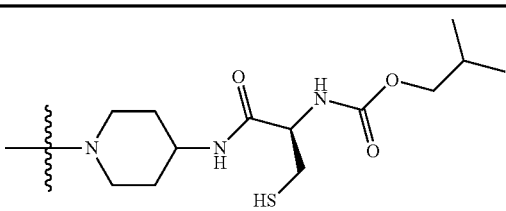 |
| 10 | 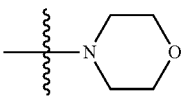 |
| 11 | 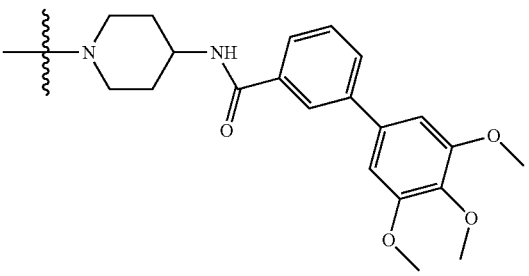 [SMILES: *N1CCC(NC(=O)c2cccc(-c3cc(OC)c(OC)c(OC)c3)c2)CC1] |
| 12 | 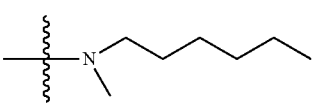 [SMILES: *N(C)CCCCCC] |
| 13 | 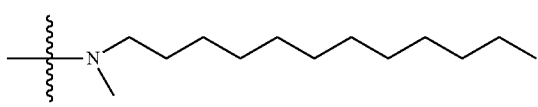 [SMILES: *N(C)CCCCCCCCCCCC] |
| 14 | 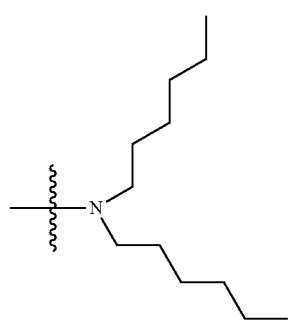 [SMILES: *N(CCCCCC)CCCCCC] |
| 15 | 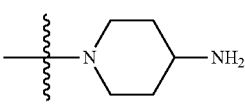 |

TABLE 1-continued
Representative Intersubunit Linkages (X-groups)
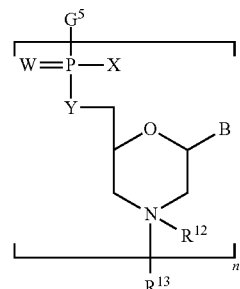
| No. | X |
| --- | --- |
| 16 | 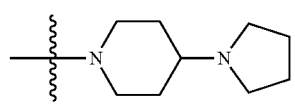 [SMILES: *N1CCC(N2CCCC2)CC1] |
| 17 | 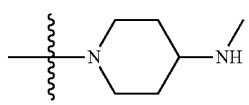 |
| 18 | 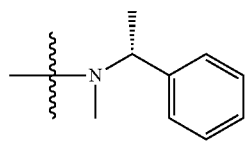 [SMILES: *N(C)[C@H](C)c1ccccc1] |
| 19 | 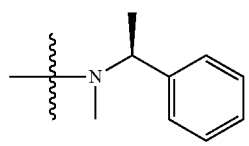 [SMILES: *N(C)[C@@H](C)c1ccccc1] |
| 20 | 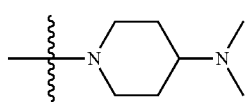 |
| 21 | 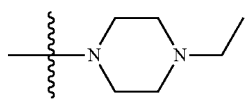 |
| 22 | 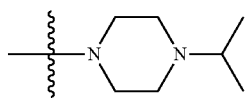 |
| 23 | 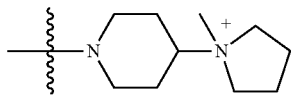 |
| 24 | 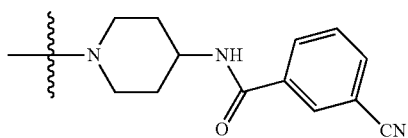 [SMILES: *N1CCC(NC(=O)c2cccc(C#N)c2)CC1] |

TABLE 1-continued
Representative Intersubunit Linkages (X-groups)
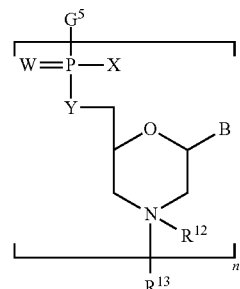
| No. | X |
|---|---|
| 25 | 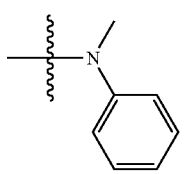 [SMILES: *N(C)c1ccccc1] |
| 26 | 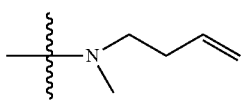 [SMILES: *N(C)CCC=C] |
| 27 | 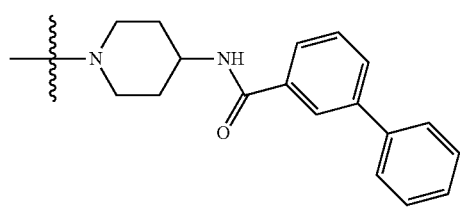 [SMILES: *N1CCC(NC(=O)c2cccc(-c3ccccc3)c2)CC1] |
| 28 | 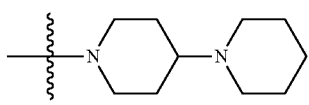 [SMILES: *N1CCC(N2CCCCC2)CC1] |
| 29 | 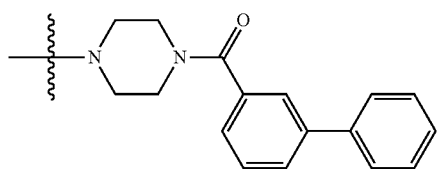 [SMILES: *N1CCN(C(=O)c2cccc(-c3ccccc3)c2)CC1] |
| 30 | 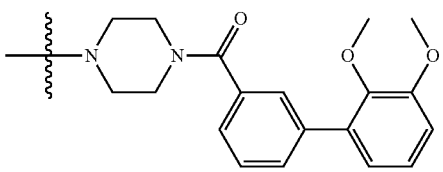 [SMILES: *N1CCN(C(=O)c2cccc(-c3cccc(OC)c3OC)c2)CC1] |
| 31 | 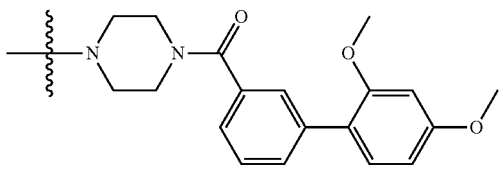 [SMILES: *N1CCN(C(=O)c2cccc(-c3ccc(OC)cc3OC)c2)CC1] |

TABLE 1-continued
Representative Intersubunit Linkages (X-groups)
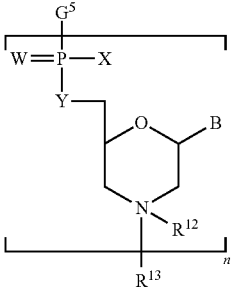
| No. | X |
|---|---|
| 32 | 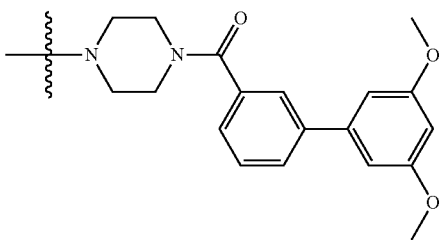 [SMILES: *N1CCN(C(=O)c2cccc(-c3cc(OC)cc(OC)c3)c2)CC1] |
| 33 | 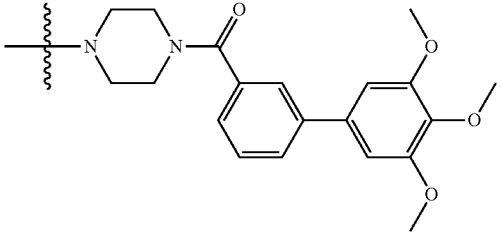 [SMILES: *N1CCN(C(=O)c2cccc(-c3cc(OC)c(OC)c(OC)c3)c2)CC1] |
| 34 | 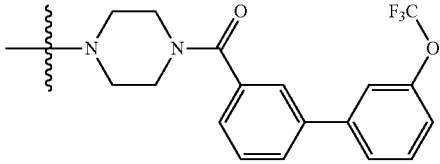 [SMILES: *N1CCN(C(=O)c2cccc(-c3cccc(OC(F)(F)F)c3)c2)CC1] |
| 35 | 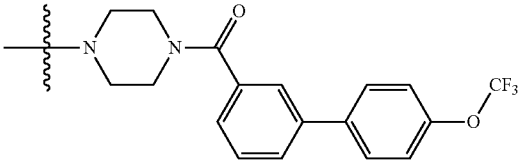 [SMILES: *N1CCN(C(=O)c2cccc(-c3ccc(OC(F)(F)F)cc3)c2)CC1] |
| 36 | 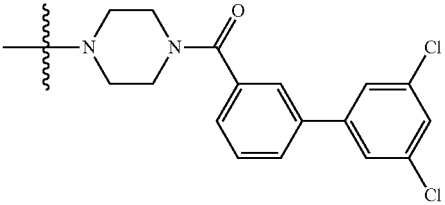 [SMILES: *N1CCN(C(=O)c2cccc(-c3cc(Cl)cc(Cl)c3)c2)CC1] |
| 37 | 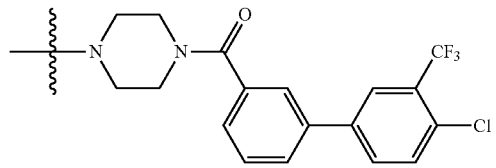 [SMILES: *N1CCN(C(=O)c2cccc(-c3ccc(Cl)c(C(F)(F)F)c3)c2)CC1] |

TABLE 1-continued
Representative Intersubunit Linkages (X-groups)
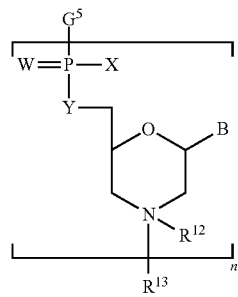
| No. | X |
|---|---|
| 38 | 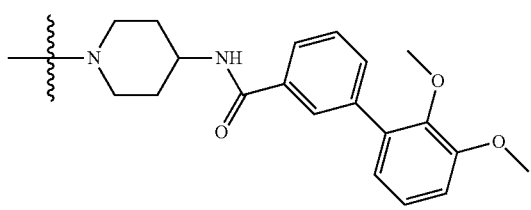 [SMILES: *N1CCC(NC(=O)c2cccc(-c3cccc(OC)c3OC)c2)CC1] |
| 39 | 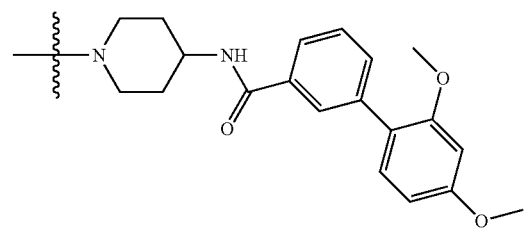 [SMILES: *N1CCC(NC(=O)c2cccc(-c3ccc(OC)cc3OC)c2)CC1] |
| 40 | 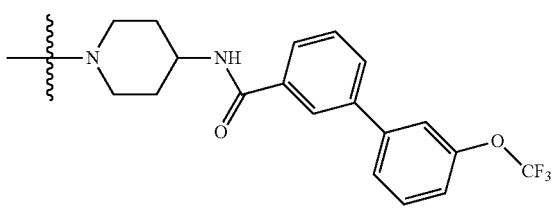 [SMILES: *N1CCC(NC(=O)c2cccc(-c3cccc(OC(F)(F)F)c3)c2)CC1] |
| 41 | 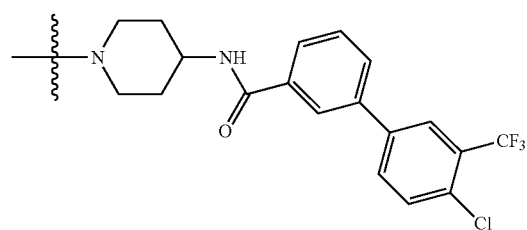 [SMILES: *N1CCC(NC(=O)c2cccc(-c3ccc(Cl)c(C(F)(F)F)c3)c2)CC1] |
| 42 | 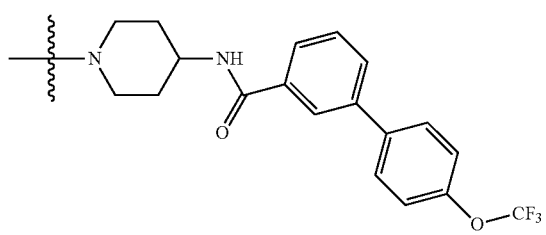 [SMILES: *N1CCC(NC(=O)c2cccc(-c3ccc(OC(F)(F)F)cc3)c2)CC1] |

TABLE 1-continued
Representative Intersubunit Linkages (X-groups)
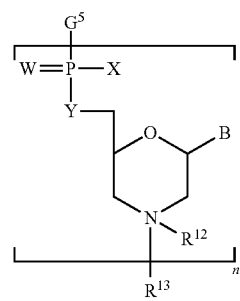
| No. | X |
|---|---|
| 43 | 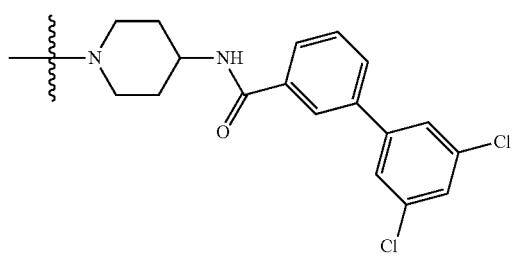 [SMILES: *N1CCC(NC(=O)c2cccc(-c3cc(Cl)cc(Cl)c3)c2)CC1] |
| 44 | 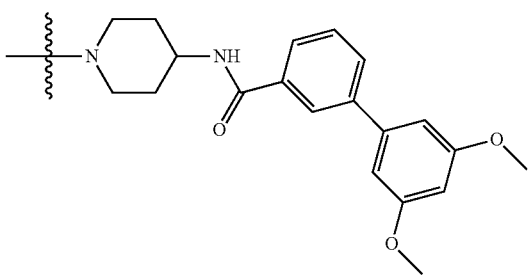 [SMILES: *N1CCC(NC(=O)c2cccc(-c3cc(OC)cc(OC)c3)c2)CC1] |
| 45 | 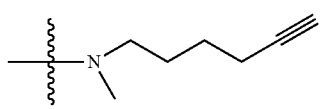 [SMILES: *N(C)CCCCC#C] |
| 46 | 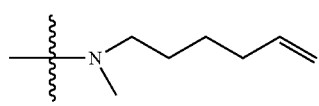 [SMILES: *N(C)CCCCC=C] |
| 47 | 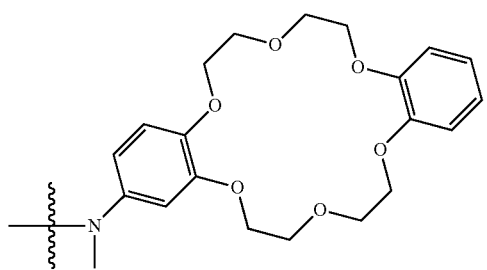 [SMILES: *N(C)c1ccc2c(c1)OCCOCCOc1ccccc1OCCOCCO2] |
| 48 | 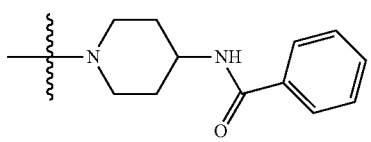 [SMILES: *N1CCC(NC(=O)c2ccccc2)CC1] |

TABLE 1-continued
Representative Intersubunit Linkages (X-groups)
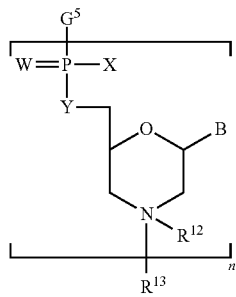
| No. | X |
|---|---|
| 49 | 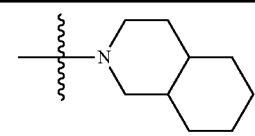 |
| 50 | 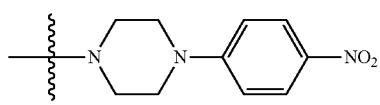 |
| 51 | 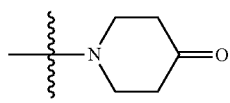 [SMILES: *N1CCC(=O)CC1] |
| 52 | 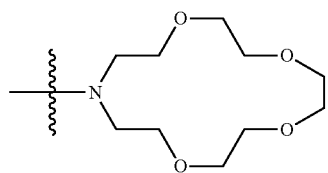 [SMILES: *N1CCOCCOCCOCCOCC1] |
| 53 | 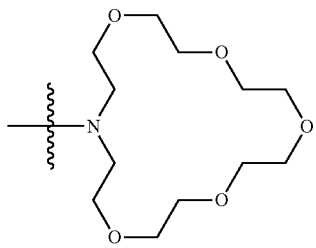 [SMILES: *N1CCOCCOCCOCCOCCOCC1] |
| 54 | 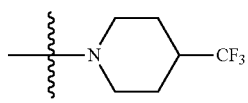 |
| 55 | 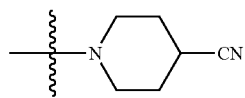 |
| 56 | 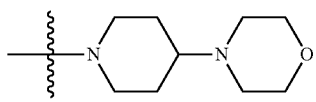 |
| 57 | 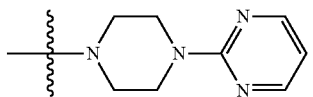 |

TABLE 1-continued
Representative Intersubunit Linkages (X-groups)
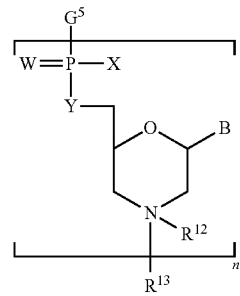
| No. | X |
|---|---|
| 58 | 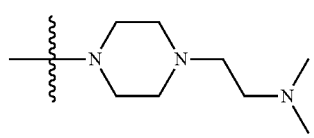 |
| 59 | 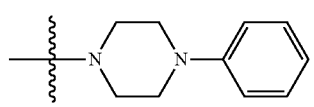 |
| 60 | 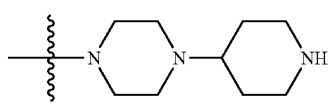 |
| 61 | 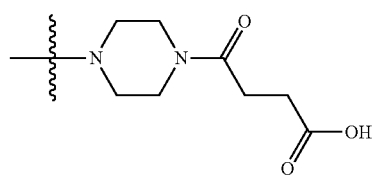 |
| 62 | 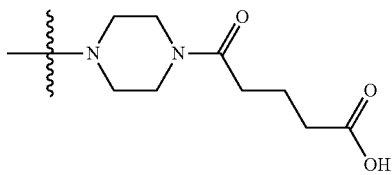 [SMILES: *N1CCN(C(=O)CCCC(=O)O)CC1] |
| 63 | 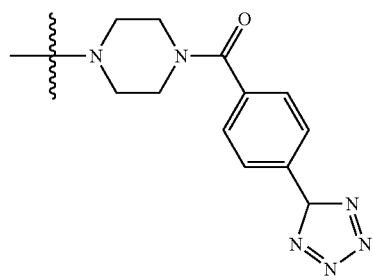 [SMILES: *N1CCN(C(=O)c2ccc(C3N=NN=N3)cc2)CC1] |
| 64 | 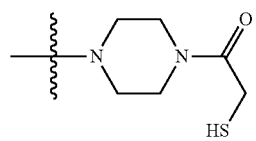 [SMILES: *N1CCN(C(=O)CS)CC1] |

TABLE 1-continued
Representative Intersubunit Linkages (X-groups)
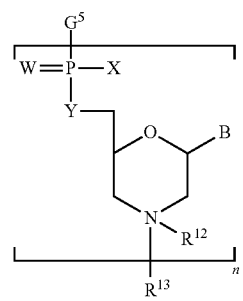
| No. | X |
|---|---|
| 65 | 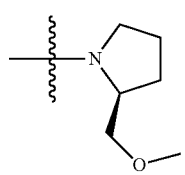 [SMILES: *N1CCC[C@H]1COC] |
| 66 | 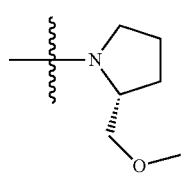 [SMILES: *N1CCC[C@@H]1COC] |
| 67 | 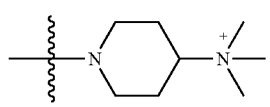 |
| 68 | 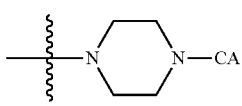 CA = cholate |
| 69 | 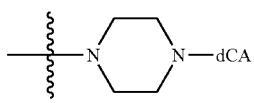 dCA = deoxycholate |
| 70 | 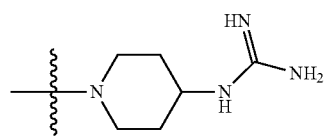 [SMILES: *N1CCC(NC(=N)N)CC1] |
| 71 | 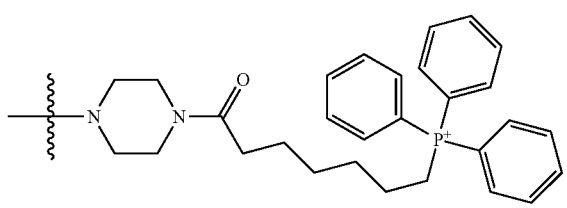 [SMILES: *N1CCN(C(=O)CCCCCC[P+](c2ccccc2)(c2ccccc2)c2ccccc2)CC1] |

TABLE 1-continued
Representative Intersubunit Linkages (X-groups)
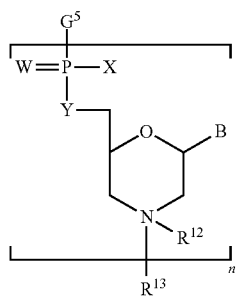
| No. | X |
|---|---|
| 72 | 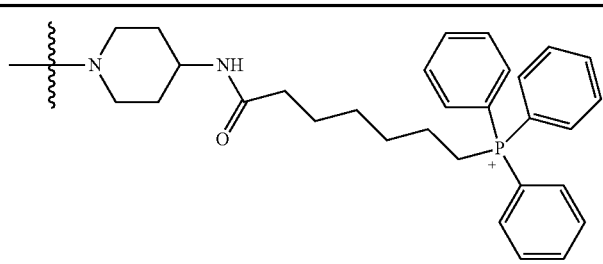 |
| 73 | —N(H)CH$_2$CO$_2$H |
| 74 | —N(CH$_3$)CH$_2$CO$_2$H |
| 75 | —N(CH$_2$CH$_3$)CH$_2$CO$_2$H |
| 76 | —N(H)CH$_2$CH$_2$CO$_2$H, |
| 77 | —N(CH$_3$)CH$_2$CH$_2$CO$_2$H |
| 78 | 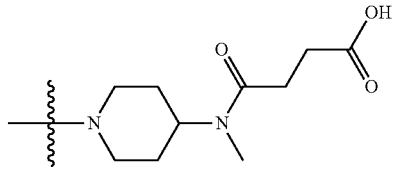 [SMILES: *N1CCC(N(C)C(=O)CCC(=O)O)CC1] |
| 79 | 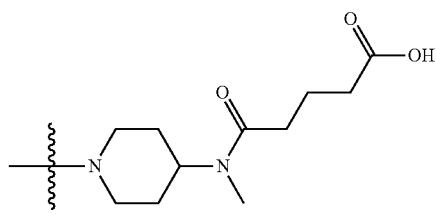 [SMILES: *N1CCC(N(C)C(=O)CCCC(=O)O)CC1] |
| 80 | 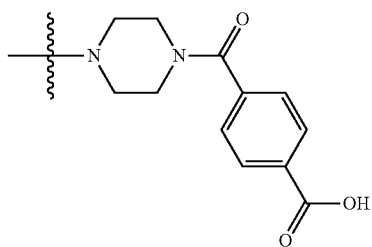 [SMILES: *N1CCN(C(=O)c2ccc(C(=O)O)cc2)CC1] |
| 81 | 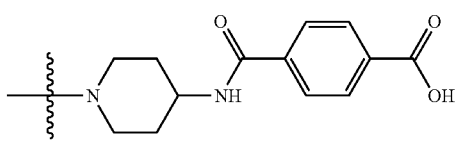 [SMILES: *N1CCC(NC(=O)c2ccc(C(=O)O)cc2)CC1] |

TABLE 1-continued
Representative Intersubunit Linkages (X-groups)
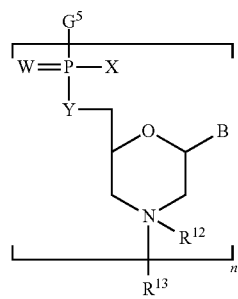
| No. | X |
|---|---|
| 82 | 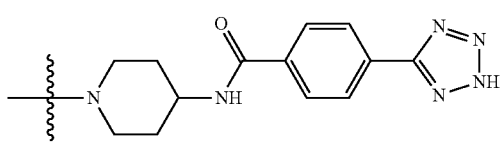 [SMILES: *N1CCC(NC(=O)c2ccc(-c3nn[nH]n3)cc2)CC1] |
| 83 | 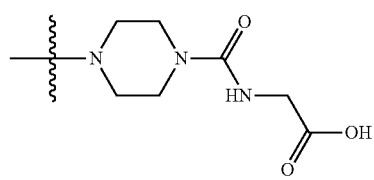 [SMILES: *N1CCN(C(=O)NCC(=O)O)CC1] |
| 84 | 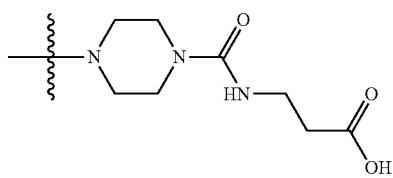 [SMILES: *N1CCN(C(=O)NCCC(=O)O)CC1] |
| 85 | 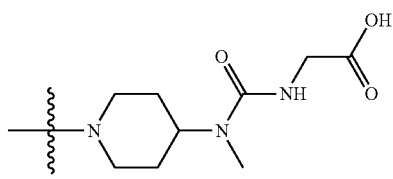 [SMILES: *N1CCC(N(C)C(=O)NCC(=O)O)CC1] |
| 86 | 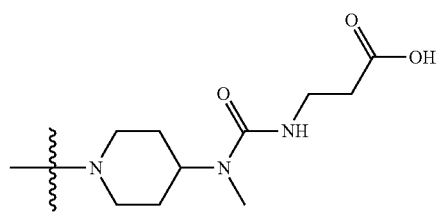 [SMILES: *N1CCC(N(C)C(=O)NCCC(=O)O)CC1] |
| 87 | 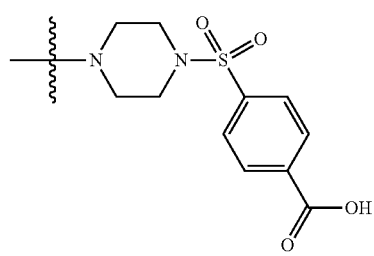 [SMILES: *N1CCN(S(=O)(=O)c2ccc(C(=O)O)cc2)CC1] |

TABLE 1-continued
Representative Intersubunit Linkages (X-groups)
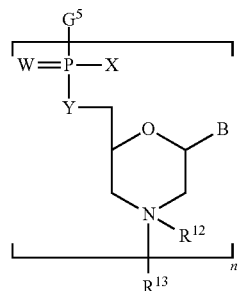
| No. | X |
|---|---|
| 88 | 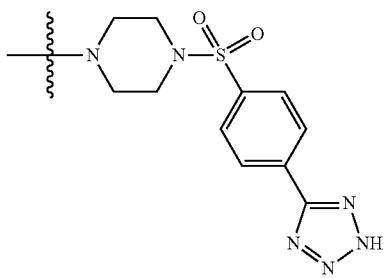 [SMILES: *N1CCN(S(=O)(=O)c2ccc(-c3nn[nH]n3)cc2)CC1] |
| 89 | 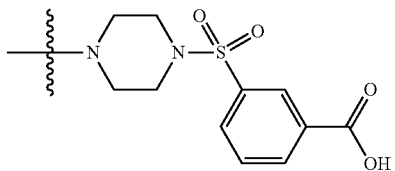 [SMILES: *N1CCN(S(=O)(=O)c2cccc(C(=O)O)c2)CC1] |
| 90 | 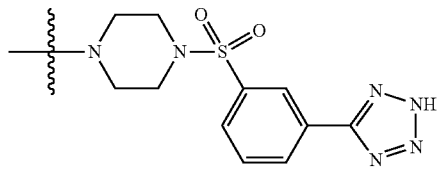 [SMILES: *N1CCN(S(=O)(=O)c2cccc(-c3nn[nH]n3)c2)CC1] |
| 91 | 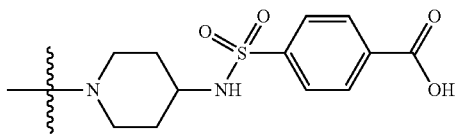 [SMILES: *N1CCC(NS(=O)(=O)c2ccc(C(=O)O)cc2)CC1] |
| 92 | 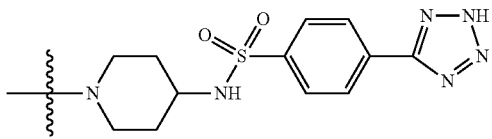 [SMILES: *N1CCC(NS(=O)(=O)c2ccc(-c3nn[nH]n3)cc2)CC1] |
| 93 | 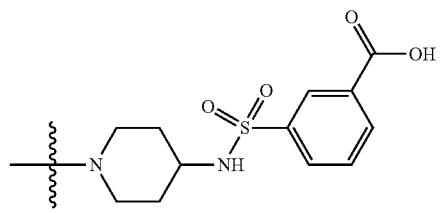 [SMILES: *N1CCC(NS(=O)(=O)c2cccc(C(=O)O)c2)CC1] |

TABLE 1-continued
Representative Intersubunit Linkages (X-groups)
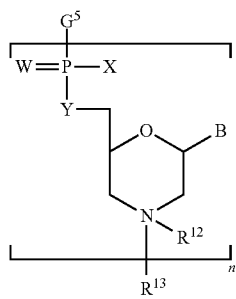
| No. | X |
|---|---|
| 94 | 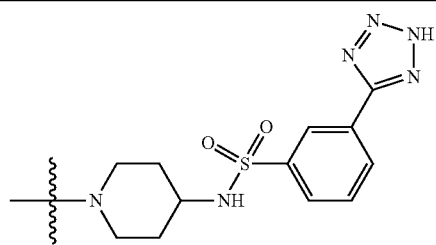 |
| 95 | 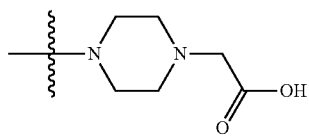 [SMILES: *N1CCN(CC(=O)O)CC1] |
| 96 | 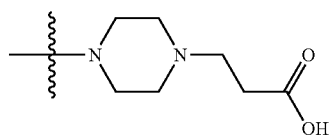 [SMILES: *N1CCN(CCC(=O)O)CC1] |
| 97 | 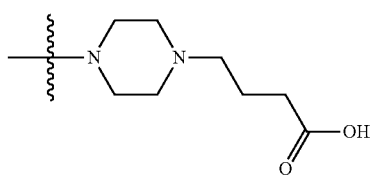 [SMILES: *N1CCN(CCCC(=O)O)CC1] |
| 98 | 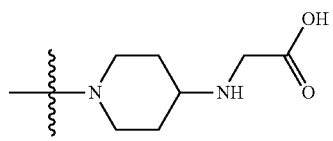 [SMILES: *N1CCC(NCC(=O)O)CC1] |
| 99 | 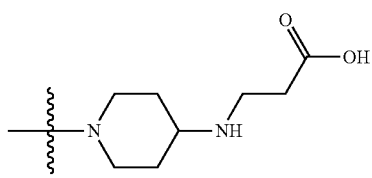 [SMILES: *N1CCC(NCCC(=O)O)CC1] |
| 100 | 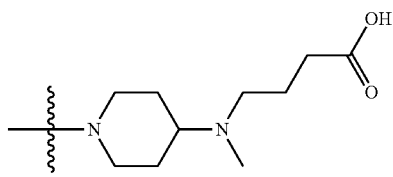 [SMILES: *N1CCC(N(C)CCCC(=O)O)CC1] |

TABLE 1-continued
Representative Intersubunit Linkages (X-groups)
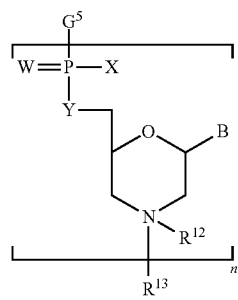
| No. | X |
|---|---|
| 101 | 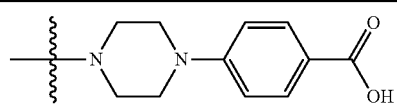 |
| 102 | 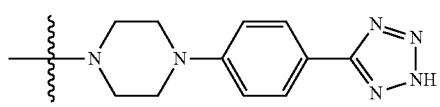 |
| 103 | 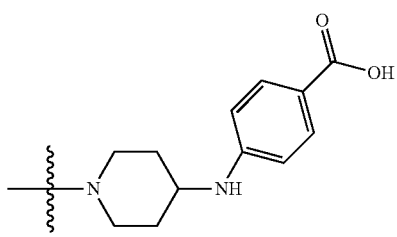 [SMILES: *N1CCC(Nc2ccc(C(=O)O)cc2)CC1] |
| 104 | 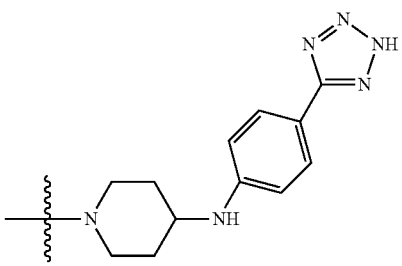 [SMILES: *N1CCC(Nc2ccc(-c3nn[nH]n3)cc2)CC1] |
| 105 | 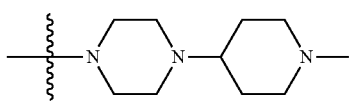 |
| 106 | 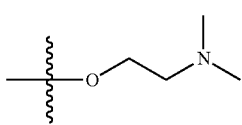 [SMILES: *OCCN(C)C] |
| 107 | 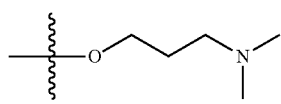 [SMILES: *OCCCN(C)C] |
| 108 | 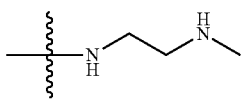 [SMILES: *NCCNC] |

TABLE 1-continued
Representative Intersubunit Linkages (X-groups)
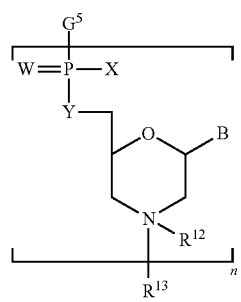
| No. | X |
| --- | --- |
| 109 | |
| 110 | |
| 111 | |
| 112 | |
| 113 | |
| 114 | |
| 115 | |
| 116 | |
| 117 | |
| 118 | |

TABLE 1-continued
Representative Intersubunit Linkages (X-groups)
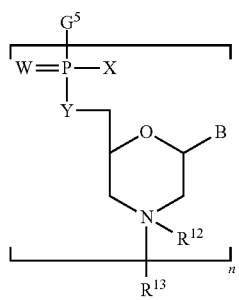
| No. | X |
|---|---|
| 119 | 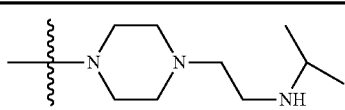 |
| 120 | 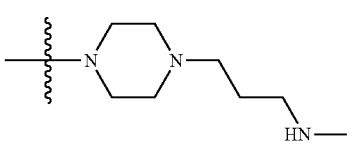 |
| 121 | 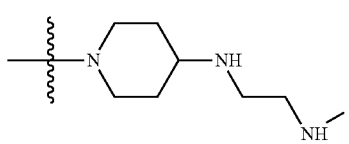 [SMILES: *N1CCC(NCCNC)CC1] |
| 122 | 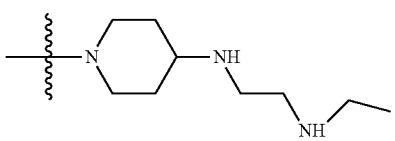 |
| 123 | 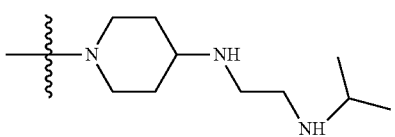 [SMILES: *N1CCC(NCCNC(C)C)CC1] |
| 124 | 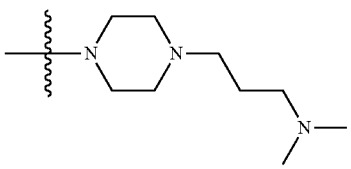 [SMILES: *N1CCN(CCCN(C)C)CC1] |
| 125 | 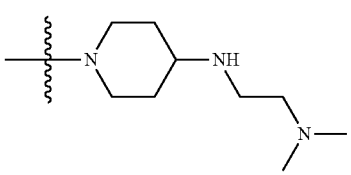 |
| 126 | 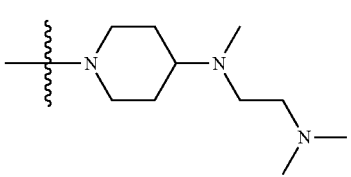 [SMILES: *N1CCC(N(C)CCN(C)C)CC1] |

TABLE 1-continued
Representative Intersubunit Linkages (X-groups)
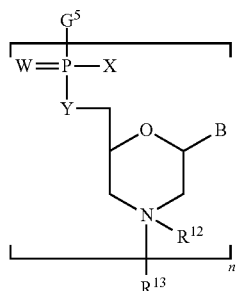
| No. | X |
|---|---|
| 127 | |
| 128 | |
| 129 | |
| 130 | |
| 131 | |
| 132 | |
| 133 | |
| 134 | |

TABLE 1-continued
Representative Intersubunit Linkages (X-groups)
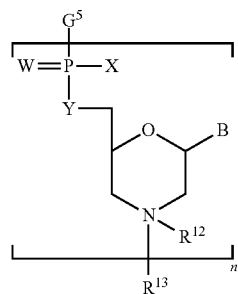
| No. | X |
|---|---|
| 135 | 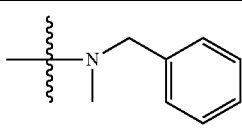 |
| 136 | 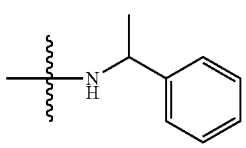 |
| 137 | 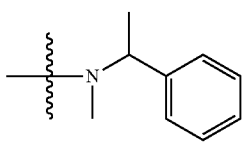 [SMILES: *N(C)C(C)c1ccccc1] |
| 138 | 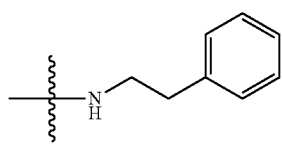 [SMILES: *NCCc1ccccc1] |
| 139 | 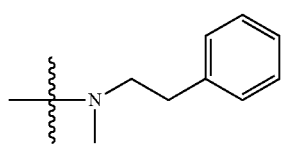 [SMILES: *N(C)CCc1ccccc1] |
| 140 | 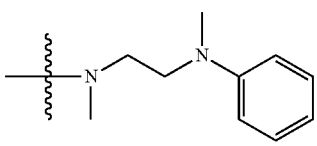 [SMILES: *N(C)CCN(C)c1ccccc1] |
| 141 | 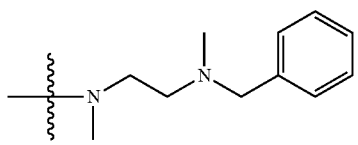 [SMILES: *N(C)CCN(C)Cc1ccccc1] |
| 142 | 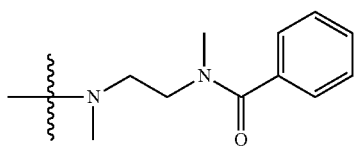 [SMILES: *N(C)CCN(C)C(=O)c1ccccc1] |

TABLE 1-continued
Representative Intersubunit Linkages (X-groups)
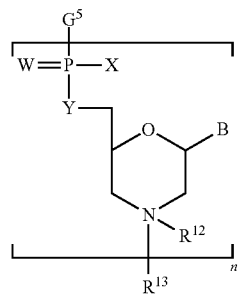
| No. | X |
|---|---|
| 143 | 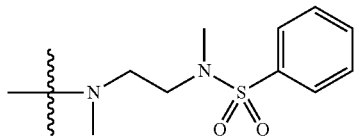 [SMILES: *N(C)CCN(C)S(=O)(=O)c1ccccc1] |
| 144 | 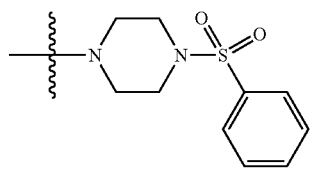 [SMILES: *N1CCN(S(=O)(=O)c2ccccc2)CC1] |
| 145 | 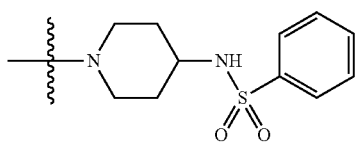 [SMILES: *N1CCC(NS(=O)(=O)c2ccccc2)CC1] |
| 146 | 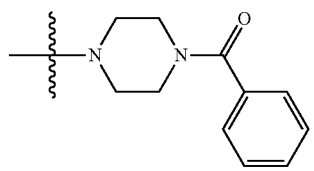 [SMILES: *N1CCN(C(=O)c2ccccc2)CC1] |
| 147 | 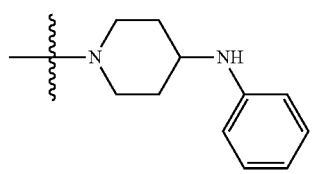 |
| 148 | 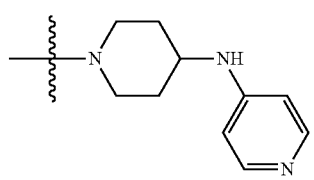 [SMILES: *N1CCC(Nc2ccncc2)CC1] |
| 149 | 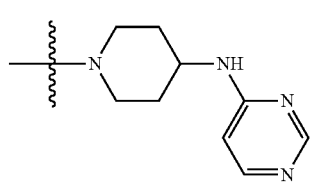 [SMILES: *N1CCC(Nc2ccncn2)CC1] |

TABLE 1-continued
Representative Intersubunit Linkages (X-groups)
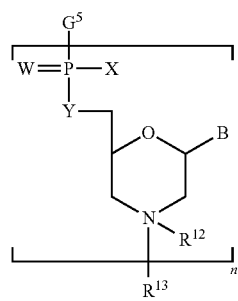
| No. | X |
|---|---|
| 150 | 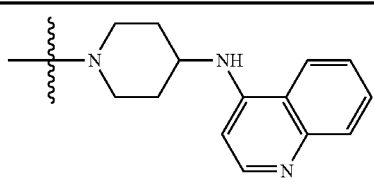 |
| 151 | 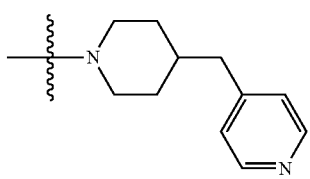 |
| 152 | 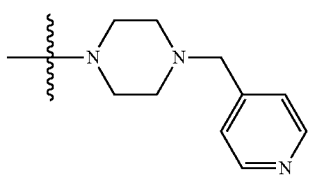 |
| 153 | 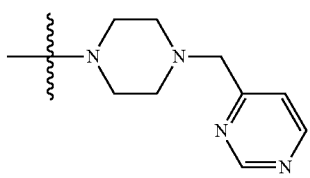 |
| 154 | 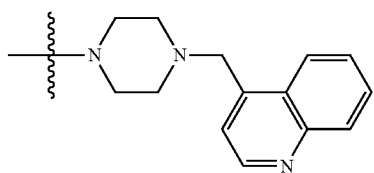 [SMILES: *N1CCC(Nc2ccnc3ccccc23)CC1] |
| 155 | 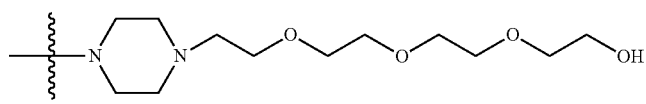 |
| 156 | 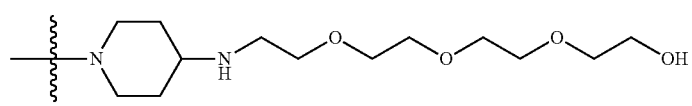 [SMILES: *N1CCC(NCCOCCOCCOCCO)CC1] |
| 157 | 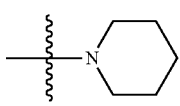 |

TABLE 1-continued
Representative Intersubunit Linkages (X-groups)
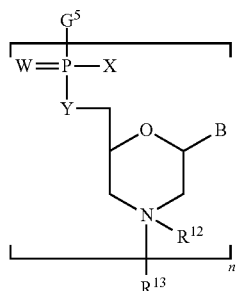
| No. | X |
|---|---|
| 158 | piperazine-N-C(=O)CF₃ |
| 159 | piperazine-N-C(=O)CH₂CH₃ |
| 160 | piperazine-N-C(=O)CH₂CH₂CH₃ |
| 161 | homopiperazine-N-C(=O)CH₃ |
| 162 | piperidine-4-NH-C(=O)CH₃ |
| 163 | piperidine-4-N(CH₃)-C(=O)CH₃ |
| 164 | piperidine-4-NH-C(=O)CF₃ |
| 165 | piperidine-4-N(CH₃)-C(=O)CF₃ |
| 166 | piperidine-4-NH-C(=O)CH₂CH₃ |

155

TABLE 1-continued

Representative Intersubunit Linkages (X-groups)

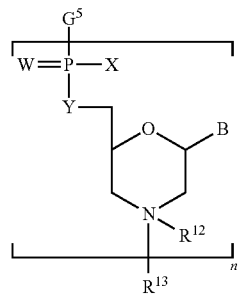

| No. | X |
|---|---|
| 167 | 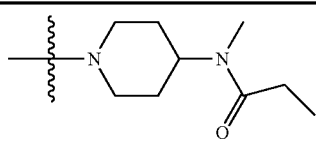 |
| 168 | 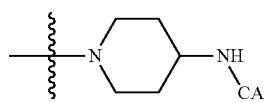 |
| 169 | 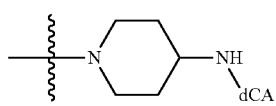 |
| 170 | 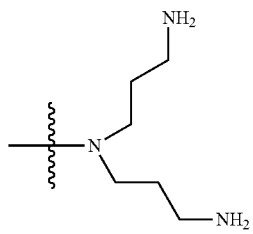 [SMILES: *N(CCCN)CCCN] |
| 171 | 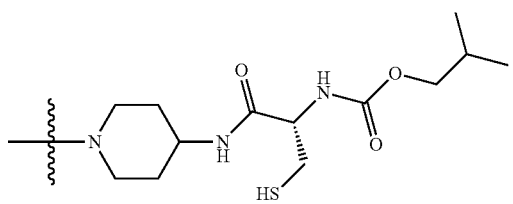 [SMILES: *N1CCC(NC(=O)[C@@H](CS)NC(=O)OCC(C)C)CC1] |

B. Oligomers with Modified Terminal Groups

As noted above, the present disclosure also provides an oligomer comprising modified terminal groups. Applicants have found that modification of the 3' and/or 5' end of the oligomer with various chemical moieties provides beneficial therapeutic properties (e.g., enhanced cell delivery, potency, and/or tissue distribution, etc.) to the oligomers. In various embodiments, the modified terminal groups comprise a hydrophobic moiety, while in other embodiments the modified terminal groups comprise a hydrophilic moiety. The modified terminal groups may be present with or without the linkages described above. For example, in some embodiments, the oligomers comprise one or more modified terminal group and modified intersubunit linkages. Combinations of modified terminal groups and modified linkages also provide favorable therapeutic properties to the oligomers. In some embodiments the modified terminal group is a peptide transporter as described herein.

In another embodiment is the compound of Formula (I), wherein $L^{11}$ is

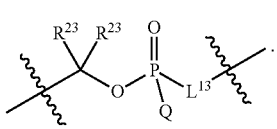

In another embodiment is the compound of Formula (I), wherein $L^{11}$ is

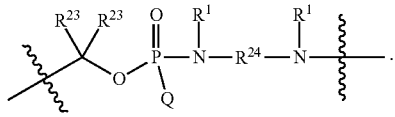

In another embodiment is the compound of Formula (I), wherein $L^{11}$ is

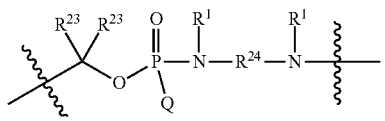

and $R^{24}$ is a $C_2$-$C_4$ alkylene. In another embodiment is the compound of Formula (I), wherein $L^{11}$ is

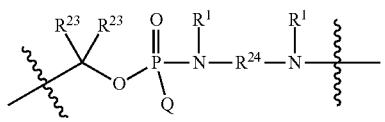

and wherein $R^{24}$ is ethylene or propylene, and $R^1$ is hydrogen or methyl.

In another embodiment is the compound of Formula (I), wherein $L^{11}$ is

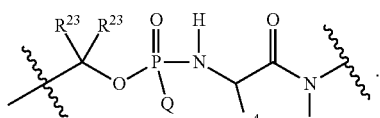

In another embodiment is the compound of Formula (I), wherein $L^{11}$ is

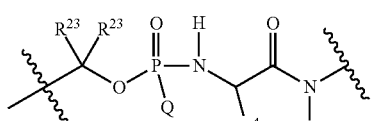

$R^4$ is hydrogen or methyl. In another embodiment is the compound of Formula (I), wherein $L^{11}$ is

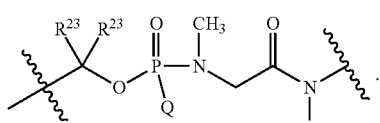

In another embodiment is the compound of Formula (I), wherein $L^{13}$ is

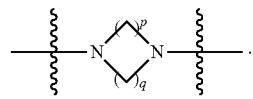

In another embodiment is the compound of Formula (I), wherein $L^{13}$ is

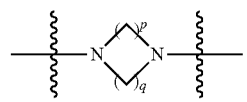

and wherein p is 2, and q is 2. In another embodiment is the compound of Formula (I), wherein $L^{13}$ is

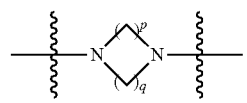

and wherein p is 2, and q is 3. In another embodiment is the compound of Formula (I), wherein $L^{13}$ is

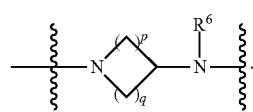

In another embodiment is the compound of Formula (I), wherein $L^{13}$ is

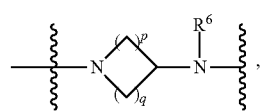

p and q are independently selected from 1 or 2, and $R^6$ is $CH_3$. In another embodiment is the compound of Formula (I), wherein $L^{13}$ is

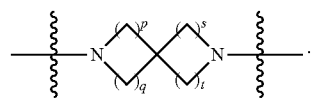

In another embodiment is the compound of Formula (I), wherein $L^{13}$ is

and p, q, s and t are independently selected from 1 or 2. In another embodiment is the compound of Formula (I), wherein $R^1$ is methyl. In another embodiment is the compound of Formula (I), wherein $R^{23}$ is hydrogen, methyl or both $R^{23}$ groups together form a cyclopropyl, cyclobutyl, cyclopentyl or cyclohexyl ring. In another embodiment is the compound of Formula (I), wherein $R^{23}$ is hydrogen or methyl.

In another embodiment is the compound of Formula (I), wherein $Z^5$ is —C($R^{23}$)$_2$OP(=O)(OH)$_2$. In another embodiment is the compound of Formula (I), wherein $R^{23}$ is hydrogen.

In another embodiment is the compound of Formula (I), wherein $Z^5$ is -($L^{11}$)-($R^{15}$) and the $R^{15}$ is $C_1$-$C_{30}$ alkyl, $C_1$-$C_{30}$ alkylcarbonyl, $C_2$-$C_{30}$ alkyloxycarbonyl, or a 3-18 membered alkoxyalkylcarbonyl. In another embodiment is the compound of Formula (I), wherein $Z^5$ is -($L^{11}$)-($R^{15}$) and the $R^{15}$ is a $C_2$-$C_{30}$ alkyloxycarbonyl. In another embodiment is the compound of Formula (I), wherein $Z^5$ is -($L^{11}$)-($R^{15}$) and the $R^{15}$ is selected from —C(=O)OCH$_2$CH$_2$OH, —C(=O)OCH$_2$CH$_2$OCH$_2$CH$_2$OH, or —C(=O)OCH$_2$CH$_2$OCH$_2$CH$_2$OCH$_2$CH$_2$OH. In another embodiment is the compound of Formula (I), wherein $Z^5$ is -($L^{11}$)-($R^{15}$) and the $R^{15}$ is —C(=O)OCH$_2$CH$_2$OCH$_2$CH$_2$OCH$_2$CH$_2$OH.

In another embodiment is the compound of Formula (I), wherein $Z^5$ is selected from:

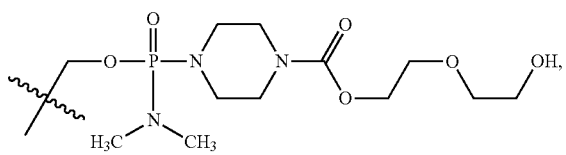

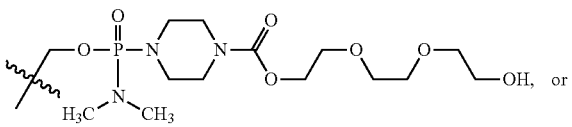

In another embodiment is the compound of Formula (I), wherein $Z^5$ is

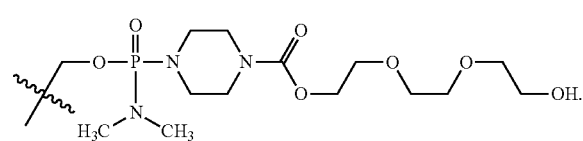

In another embodiment is the compound of Formula (I) wherein $R^{12}$ is an electron pair.

In another embodiment is the compound of Formula (I) wherein $R^{13}$ is a $C_1$-$C_{30}$ alkyl and $R^{12}$ is a $C_1$-$C_6$ alkyl. In another embodiment is the compound of Formula (I) wherein $R^{13}$ is a methyl group and $R^{12}$ is a methyl group.

In another embodiment is the compound of Formula (I) wherein $R^{13}$ is hydrogen.

In another embodiment is the compound of Formula (I) wherein $R^{13}$ is $C_1$-$C_{30}$ alkyl. In another embodiment is the compound of Formula (I) wherein $R^{13}$ is $C_1$-$C_{10}$ alkyl. In another embodiment is the compound of Formula (I) wherein $R^{13}$ is $C_1$-$C_6$ alkyl. In another embodiment is the compound of Formula (I) wherein $R^{13}$ is selected from prenyl, geranyl, farnesyl or geranylgeranyl.

In another embodiment is the compound of Formula (I) wherein $R^{13}$ is a cell-penetrating peptide.

In another embodiment is the compound of Formula (I) wherein $R^{13}$ is a guanidinyl or amidinyl group.

In another embodiment is the compound of Formula (I) wherein $R^{13}$ is a $C_3$-$C_8$ cycloalkyl.

In another embodiment is the compound of Formula (I) wherein $R^{13}$ is a $C_1$-$C_{30}$ alkylcarbonyl. In another embodiment is the compound of Formula (I) wherein $R_{13}$ is a $C_1$-$C_{15}$ alkylcarbonyl. In another embodiment is the compound of Formula (I) wherein $R^{13}$ is a $C_1$-$C_{10}$ alkylcarbonyl. In another embodiment is the compound of Formula (I) wherein $R^{13}$ is a $C_1$-$C_8$ alkylcarbonyl. In another embodiment is the compound of Formula (I) wherein $R^{13}$ is a $C_1$-$C_5$ alkylcarbonyl. In another embodiment is the compound of Formula (I) wherein $R^{13}$ is a $C_1$-$C_4$ alkylcarbonyl. In another embodiment is the compound of Formula (I) wherein $R^{13}$ is a $C_1$-$C_2$ alkylcarbonyl. In another embodiment is the compound of Formula (I) wherein $R^3$ is a $C_1$ alkylcarbonyl. In another embodiment is the compound of Formula (I) wherein $R^{13}$ is CH$_3$CO—.

In another embodiment is the compound of Formula (I) wherein $R^{13}$ is a $C_1$-$C_{15}$ alkylcarbonyl. In another embodiment is the compound of Formula (I) wherein $R^{13}$ is a $C_1$-$C_{30}$ alkyloxycarbonyl. In another embodiment is the compound of Formula (I) wherein $R^{13}$ is a $C_1$-$C_{10}$ alkyloxycarbonyl. In another embodiment is the compound of Formula (I) wherein $R^{13}$ is a $C_1$-$C_5$ alkyloxycarbonyl. In another embodiment is the compound of Formula (I) wherein $R^{13}$ is a $C_1$-$C_3$ alkyloxycarbonyl. In another embodiment is the compound of Formula (I) wherein $R^{13}$ is a $C_1$ alkyloxycarbonyl. In another embodiment is the compound of Formula (I) wherein $R^{13}$ is a CH$_3$OCO—. In another embodiment is the compound of Formula (I) wherein $R^{13}$ is a —C(O)CH$_2$CH$_2$CO$_2$H. In another embodiment is the compound of Formula (I) wherein $R^{13}$ is a —C(=O)OCH$_2$CH$_2$OH, —C(=O)OCH$_2$CH$_2$OCH$_2$CH$_2$OH, or —C(=O)OCH$_2$CH$_2$OCH$_2$CH$_2$OCH$_2$CH$_2$OH.

In another embodiment is the compound of Formula (I) wherein $R^{13}$ is —C(=O)NHR$^{21}$. In another embodiment is the compound of Formula (I) wherein $R^{13}$ is —C(=O)NHR$^{21}$ and $R^{21}$ is methyl.

In some other embodiments, only the 3' terminus of the oligomer is conjugated to one of the groups noted above. In some other embodiments, only the 5' terminus of the oligomer is conjugated to one of the groups noted above. In other embodiments, both the 3' and 5' termini comprise one of the groups noted above. The terminal group for either the 5' terminus, the 3' terminus, or both, may be selected from any one of the groups noted above or any of the specific groups illustrated in Table 2.

TABLE 2
Representative Terminal Groups
| No. | Name | Structure |
|---|---|---|
| 1 | Trimethoxybenzoyl | 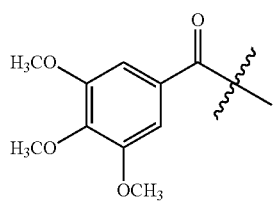 [SMILES: *C(=O)c1cc(OC)c(OC)c(OC)c1] |
| 2 | 9-fluorene-carboxyl | 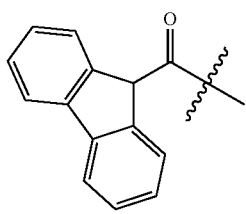 [SMILES: *C(=O)C1c2ccccc2-c2ccccc21] |
| 3 | 4-carbazolylbenzoyl | 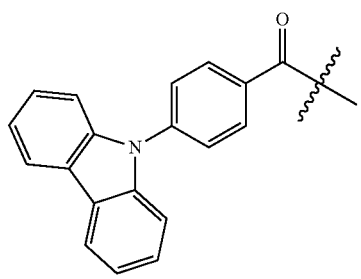 [SMILES: *C(=O)c1ccc(-n2c3ccccc3c3ccccc32)cc1] |
| 4 | 4-indazolylonebenzoyl | 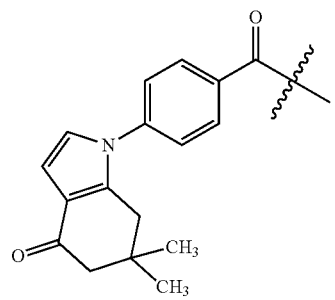 [SMILES: *C(=O)c1ccc(-n2ccc3c2CC(C)(C)CC3=O)cc1] |
| 5 | Farnesyl | 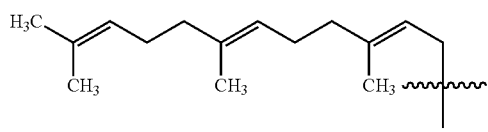 [SMILES: *C/C=C(\C)CC/C=C(\C)CCC=C(C)C] |
| 6 | Geranyl | 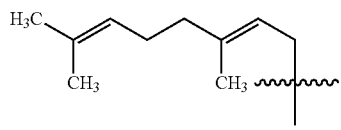 [SMILES: *C/C=C(\C)CCC=C(C)C] |
| 7 | Prenyl | 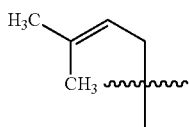 |

TABLE 2-continued
Representative Terminal Groups
| No. | Name | Structure |
|---|---|---|
| 8 | Diphenylacetyl | 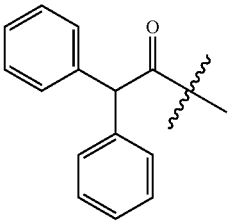 [SMILES: *C(=O)C(c1ccccc1)c1ccccc1] |
| 9 | Chlorodiphenylacetyl | 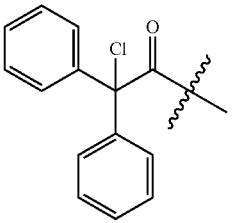 [SMILES: *C(=O)C(Cl)(c1ccccc1)c1ccccc1] |
| 10 | Hydroxydiphenylacetyl | 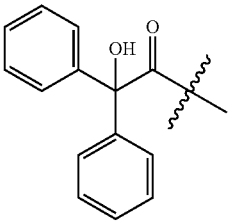 [SMILES: *C(=O)C(O)(c1ccccc1)c1ccccc1] |
| 11 | Triphenylpropionyl | 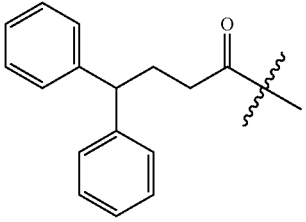 [SMILES: *C(=O)CCC(c1ccccc1)c1ccccc1] |
| 12 | Triphenylpropyl | 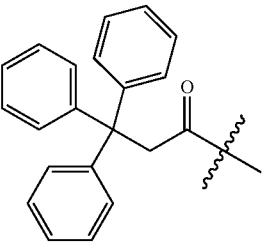 [SMILES: *C(=O)CC(c1ccccc1)(c1ccccc1)c1ccccc1] |
| 13 | Triphenylacetyl | 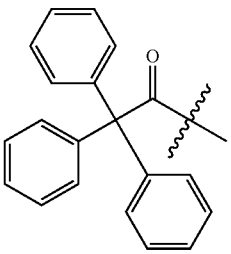 [SMILES: *C(=O)C(c1ccccc1)(c1ccccc1)c1ccccc1] |

TABLE 2-continued
Representative Terminal Groups
| No. | Name | Structure |
|---|---|---|
| 14 | Trityl (Tr) | 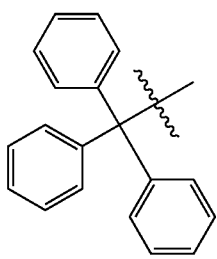 [SMILES: *C(c1ccccc1)(c1ccccc1)c1ccccc1] |
| 15 | Methoxytrityl (MeOTr) | 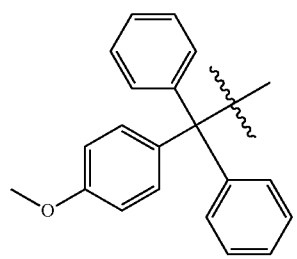 [SMILES: *C(c1ccccc1)(c1ccccc1)c1ccc(OC)cc1] |
| 16 | Methylsuccinimidyl-cyclohexoyl | 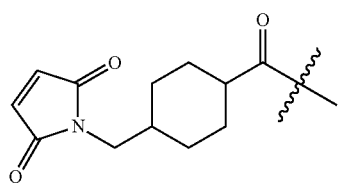 [SMILES: *C(=O)C1CCC(CN2C(=O)C=CC2=O)CC1] |
| 17 | Thioacetyl | 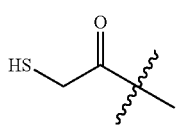 |
| 18 | COCH$_2$CH$_2$SSPy | 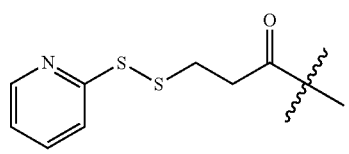 [SMILES: *C(=O)CCSSc1ccccn1] |
| 19 | Guanidinyl | 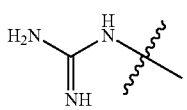 |
| 20 | Trimethylglycine | 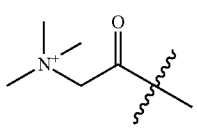 [SMILES: *C(=O)C[N+](C)(C)C] |
| 21 | Lauroyl | 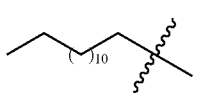 |
| 22 | Triethyleneglycoloyl (EG3) | 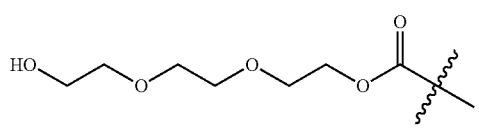 [SMILES: *C(=O)OCCOCCOCCO] |

TABLE 2-continued
Representative Terminal Groups
| No. | Name | Structure |
|-----|------|-----------|
| 23 | Succinicacetyl | 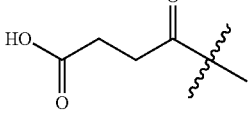 |
| 24 | Diphenylphosphoryl | 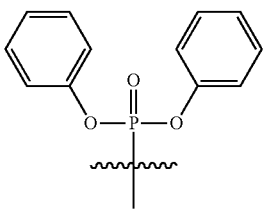 [SMILES: *P(=O)(Oc1ccccc1)Oc1ccccc1] |
| 25 | Piperidin-4-yl | 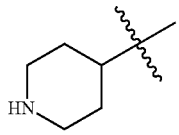 [SMILES: *C1CCNCC1] |
| 26 | Tritylpiperidin-4-yl | 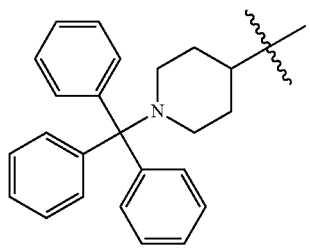 [SMILES: *C1CCN(C(c2ccccc2)(c2ccccc2)c2ccccc2)CC1] |
| 27 | Boc-Piperidin-4-yl | 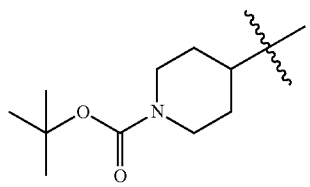 [SMILES: *C1CCN(C(=O)OC(C)(C)C)CC1] |
| 28 | Hexyn-6-yl | 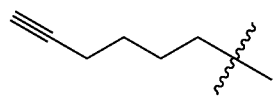 [SMILES: *CCCCC#C] |
| 29 | 5-carboxyfluorescein | 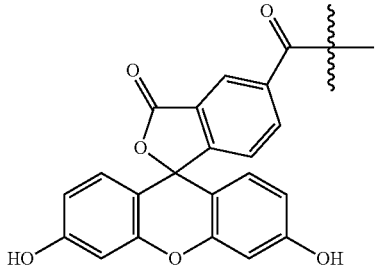 [SMILES: *C(=O)c1ccc2c(c1)C(=O)OC21c2ccc(O)cc2Oc2cc(O)ccc21] |
| 30 | Benzhydryl | 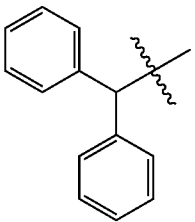 [SMILES: *C(c1ccccc1)c1ccccc1] |

TABLE 2-continued

Representative Terminal Groups

| No. | Name | Structure |
|---|---|---|
| 31 | p-Chlorobenzhydryl | |
| 32 | Piperazinyl (pip) | |
| 33 | Triphenylphos | |
| 34 | Acetamide | CH$_3$CO— |
| 35 | Methylurea | CH$_3$NHCO— |

1. Peptide Transporters

In some embodiments, the subject oligomer is conjugated to a peptide transporter moiety, for example a cell-penetrating peptide transport moiety, which is effective to enhance transport of the oligomer into cells. For example, in some embodiments the peptide transporter moiety is an arginine-rich peptide. In further embodiments, the transport moiety is attached to either the 5' or 3' terminus of the oligomer. When such peptide is conjugated to either termini, the opposite termini is then available for further conjugation to a modified terminal group as described herein.

In some embodiments of the foregoing, the peptide transport moiety comprises 6 to 16 subunits selected from X' subunits, Y' subunits, and Z' subunits, where (a) each X' subunit independently represents lysine, arginine or an arginine analog, said analog being a cationic α-amino acid comprising a side chain of the structure R$^{33}$N=C(NH$_2$)R$^{34}$, where R$^{33}$ is H or R; R$^{34}$ is R$^{35}$, NH$_2$, NHR, or NR$^4$, where R$^{35}$ is lower alkyl or lower alkenyl and may further include oxygen or nitrogen; R$^{33}$ and R$^{34}$ may together form a ring; and the side chain is linked to said amino acid via R$^{33}$ or R$^{34}$;

(b) each Y' subunit independently represents a neutral amino acid —C(O)—(CHR)$_n$—NH—, where n is 2 to 7 and each R is independently H or methyl; and (c) each Z' subunit independently represents an α-amino acid having a neutral aralkyl side chain;

wherein the peptide comprises a sequence represented by one of (X'Y'X')$_p$, (X'Y')$_m$, and (X'Z'Z')$_p$, where p is 2 to 5 and m is 2 to 8.

In selected embodiments, for each X', the side chain moiety is guanidyl, as in the amino acid subunit arginine (Arg). In further embodiments, each Y' is —CO—(CH$_2$)$_n$—CHR—NH—, where n is 2 to 7 and R is H. For example, when n is 5 and R is H, Y' is a 6-aminohexanoic acid subunit, abbreviated herein as Ahx; when n is 2 and R is H, Y' is a β-alanine subunit.

In certain embodiments, peptides of this type include those comprising arginine dimers alternating with single Y' subunits, where Y' is Ahx. Examples include peptides having the formula (RY'R)$_p$ or the formula (RRY')$_p$, where Y' is Ahx. In one embodiment, Y' is a 6-aminohexanoic acid subunit, R is arginine and p is 4.

In a further embodiment, each Z' is phenylalanine, and m is 3 or 4.

In some embodiments, the conjugated peptide is linked to a terminus of the oligomer via a linker Ahx-B, where Ahx is a 6-aminohexanoic acid subunit and B is a β-alanine subunit.

In selected embodiments, for each X', the side chain moiety is independently selected from the group consisting of guanidyl (HN=C(NH$_2$)NH—), amidinyl (HN=C(NH$_2$)C—), 2-aminodihydropyrimidyl, 2-aminotetrahydropyrimidyl, 2-aminopyridinyl, and 2-aminopyrimidonyl, and it is preferably selected from guanidyl and amidinyl. In one embodiment, the side chain moiety is guanidyl, as in the amino acid subunit arginine (Arg).

In some embodiments, the Y' subunits are either contiguous, in that no X' subunits intervene between Y' subunits, or interspersed singly between X' subunits. However, in some embodiments the linking subunit may be between Y' subunits. In one embodiment, the Y' subunits are at a terminus of the peptide transporter; in other embodiments, they are flanked by X' subunits. In further embodiments, each Y' is —CO—(CH$_2$)$_n$—CHR—NH—, where n is 2 to 7 and R is H. For example, when n is 5 and R is H, Y' is a 6-aminohexanoic acid subunit, abbreviated herein as Ahx. In selected embodiments of this group, each X' comprises a guanidyl side chain moiety, as in an arginine subunit. Exemplary peptides of this type include those comprising arginine dimers alternating with single Y' subunits, where Y' is preferably Ahx. Examples include peptides having the formula (RY'R)$_4$ or the formula (RRY')$_4$, where Y' is preferably Ahx. In some embodiments, the nucleic acid analog is linked to a terminal Y' subunit, preferably at the C-terminus. In other embodiments, the linker is of the structure AhxB, where Ahx is a 6-aminohexanoic acid subunit and B is a β-alanine subunit.

The peptide transport moieties as described above have been shown to greatly enhance cell entry of attached oligomers, relative to uptake of the oligomer in the absence of the attached transport moiety, and relative to uptake by an attached transport moiety lacking the hydrophobic subunits Y'. Such enhanced uptake may be evidenced by at least a two-fold increase, or in other embodiments a four-fold increase, in the uptake of the compound into mammalian cells relative to uptake of the agent by an attached transport moiety lacking the hydrophobic subunits Y'. In some embodiments, uptake is enhanced at least twenty fold or at least forty fold, relative to the unconjugated compound.

A further benefit of the peptide transport moiety is its expected ability to stabilize a duplex between an antisense oligomer and its target nucleic acid sequence. While not wishing to be bound by theory, this ability to stabilize a duplex may result from the electrostatic interaction between the positively charged transport moiety and the negatively charged nucleic acid. In some embodiments, the number of charged subunits in the transporter is less than 14, as noted above, or in other embodiments between 8 and 11, since too high a number of charged subunits may lead to a reduction in sequence specificity.

Exemplary arginine-rich cell-penetrating peptide transporters are given below in Table 3.

TABLE 3

Arginine-Rich Cell-Penetrating Peptide Transporters

| Name | Sequence (Amino to Carboxy Terminus, 5' to 3') | SEQ ID NO |
|---|---|---|
| (RFF)$_3$; CP0407 | N-RFFRFFRFFAhxβAla-COOH | 1 |
| RTR | N-RTRTRFLRRTAhxβAla-COOH | 2 |
| RFFR | N-RFFRFFRFFRAhxβAla-COOH | 3 |
| KTR | N-KTRTKFLKKTAhxβAla-COOH | 4 |
| KFF | N-KFFKFFKFFAhxβAla-COOH | 5 |
| KFFK | N-KFFKFFKFFKAhxβAla-COOH | 6 |
| (RFF)$_2$ | N-RFFRFFAhxβAla-COOH | 7 |
| (RFF)$_2$R | N-RFFRFFRAhxβAla-COOH | 8 |
| RAhx | N-RAhxAhxRAhxAhxRAhxAhx βAla-COOH | 9 |
| (RAhxR)$_4$; P007 | N-RAhxRRAhxRRAhxRRAhx RAhxβAla- | 10 |
| rTat | RRRQRRKKRC | 11 |
| R$_9$F$_2$ | RRRRRRRRRFFC | 12 |
| (RRAhx)$_4$B | RRAhxRRAhxRRAhxRRAhxβAla | 13 |
| (RAhxR)$_4$Ahx13; | RAhxRRAhxRRAhxRRAhxRAhxβAla | 14 |
| (AhxRR)$_4$AhxB | AhxRRAhxRRAhxRRAhxRRAhxβAla | 15 |
| (RAhx)$_6$B | RAhxRAhxRAhxRAhxRAhxRAhxβAla | 16 |
| (RAhx)$_8$B | RAhxRAhxRAhxRAhxRAhxRAhx RAhxβAla | 17 |
| (RAhxR)$_5$AhxB | RAhxRRAhxRRAhxRRAhxRRAhx RAhxβAla | 18 |
| (RAhxRRBR)$_2$Ah | RAhxRRβAla RRAhxRRβAla RAhxβAla | 19 |
| R$_4$G | RRRRG | 20 |
| R$_5$G | RRRRRG | 21 |
| R$_6$G | RRRRRRG | 22 |
| R$_7$G | RRRRRRRG | 23 |
| R$_8$G | RRRRRRRRG | 24 |
| R$_5$GR$_4$G | RRRRRGRRRRG | 25 |
| R$_5$F$_2$R$_4$G | RRRRRFFRRRRG | 26 |
| Tat-G | RKKRRQRRRG | 27 |
| rTat-G | RRRQRRKKRG | 28 |
| (RAhxR$_2$G$_2$)$_2$ | RAhxRRGGRAhxRGG | 29 |
| (RAhxR$_3$Ahx)$_2$G | RAhxRRRAhxRAhxRRRG | 30 |
| R$_4$P | RRRRP | 31 |
| R$_5$P | RRRRRP | 32 |
| R$_6$P | RRRRRRP | 33 |
| R$_7$P | RRRRRRRP | 34 |
| R$_8$P | RRRRRRRRP | 35 |

βAla = beta-alanine;
Ahx = 6-aminohexanoiC acid

In some embodiments is a compound of Formula (I) wherein Z$^5$ is -(L$^{11}$)-(L$^{12}$)-(R$^{17}$) and R$^{17}$ is a drug, protein or toxin. In some embodiments is a compound of Formula (I) wherein L$^{12}$ is a linker cleaveable under biological conditions. In some embodiments is a compound of Formula (I) wherein L$^{12}$ is selected from:
 a) —(C$_1$-C$_{10}$ alkylene)-OC(O)O—CH$_2$O—;
 b) —C(O)—(C$_1$-C$_{10}$ alkylene)-OC(O)O—CH$_2$O—;
 c) —C(O)—(CH=CH)—C(O)O—CH$_2$O—;
 d) —(C$_1$-C$_{10}$ alkylene)-S—S—CH$_2$CH$_2$O—; or
 e) C(O) (C$_1$-C$_{10}$ alkylene)-S—S—CH$_2$CH$_2$O—.

In some embodiments is a compound of Formula (I) wherein R$^{17}$ is a DNA-binding protein. In some embodiments is a compound of Formula (I) wherein $R^{17}$ is a transcription factor. In some embodiments is a compound of Formula (I) wherein $R^{17}$ is a zinc finger protein. In some embodiments is a compound of Formula (I) wherein $R^{17}$ is a drug, protein or toxin selected from the listing provided in Table 4.

TABLE 4

ANTIANDROGEN
Bicalutamide, Bifluranol, Cioteronel, Cyproterone, Delmadinone
Acetate, Flutamide, Nilutamide, Osaterone, Oxendolone
ANTIBACTERIAL (ANTIBIOTICS)
Aminoglycosides
Amikacin, Arbekacin, Bambermycins, Butirosin, Dibekacin,
Dihydrostreptomycin, Fortimicins, Gentamicin, Isepamicin, Kanamycin,
Micronomicin, Neomycin, Netilmicin, Paromomycin, Ribostamycin, Sisomicin,
Spectinomycin, Streptomycin, Tobramycin, Trospectomycin
Amphenicols
Azidamfenicol, Chloramphenicol, Thiamphenicol
Ansamycins
Rifamide, Rifampin, Rifamycin SV, Rifapentine, Rifaximin
β-Lactams
Carbacephems
Loracarbef
Carbapenems
Biapenem, Ertapenem, Fropenem, Imipenem, Meropenem, Panipenem
Cephalosporins
Cefaclor, Cefadroxil, Cefamandole, Cefatrizine, Cefazedone, Cefazolin,
Cefcapene Pivoxil, Cefclidin, Cefdinir, Cefditoren, Cefepime, Cefetamet, Cefixime,
Cefmenoxime, Cefodizime, Cefonicid, Cefoperazone, Ceforanide, Cefoselis,
Cefotaxime, Cefotiam, Cefozopran, Cefpimizole, Cefpiramide, Cefpirome,
Cefpodoxime Proxetil, Cefprozil, Cefroxadine, Cefsulodin, Ceftazidime, Cefteram,
Ceftezole, Ceftibuten, Ceftizoxime, Ceftriaxone, Cefuroxime, Cefuzonam, Cephacetrile
Sodium, Cephalexin, Cephaloglycin, Cephaloridine, Cephalosporin C, Cephalothin,
Cephapirin Sodium, Cephradine, Pivcefalexin
Cephamycins
Cefbuperazone, Cefmetazole, Cefminox, Cefotetan, Cefoxitin
Monobactams
Aztreonam, Carumonam, Tigemonam
Oxacephems
Flomoxef, Moxalactam
Penicillins
Amdinocillin, Amdinocillin Pivoxil, Amoxicillin, Ampicillin, Apalcillin,
Aspoxicillin, Azidocillin, Azlocillin, Bacampicillin, Carbenicillin, Carindacillin,
Clometocillin, Cloxacillin, Cyclacillin, Dicloxacillin, Epicillin, Fenbenicillin,
Floxacillin, Hetacillin, Lenampicillin, Metampicillin, Methicillin Sodium, Mezlocillin,
Nafcillin, Oxacillin, Penamecillin, Penethamate Hydriodide, Penicillin G, Penicillin G
Benzathine, Penicillin G Procaine, Penicillin N, Penicillin O, Penicillin V,
Penimepicycline, Phenethicillin Potassium, Piperacillin, Pivampicillin, Propicillin,
Quinacillin, Sulbenicillin, Sultamicillin, Talampicillin, Temocillin, Ticarcillin
Other
Ritipenem
Lincosamides
Clindamycin, Lincomycin
Macrolides
Azithromycin, Carbomycin, Clarithromycin, Dirithromycin,
Erythromycin, Erythromycin Acistrate, Erythromycin Estolate, Erythromycin
Glucoheptonate, Erythromycin Lactobionate, Erythromycin Propionate, Erythromycin
Stearate, Josamycin, Leucomycins, Midecamycins, Miokamycin, Oleandomycin,
Primycin, Rokitamycin, Rosaramicin, Roxithromycin, Spiramycin, Telithromycin,
Troleandomycin
Polypeptides
Amphomycin, Bacitracin, Bacitracin Zinc, Capreomycin, Colistin,
Enduracidin, Enviomycin, Fusafungine, Gramicidin(s), Gramicidin S, Polymyxin,
Quinupristin, Ristocetin, Teicoplanin, Thiostrepton, Tuberactinomycin, Tyrocidine,
Tyrothricin, Vancomycin, Viomycin
Tetracyclines
Chlortetracycline, Clomocycline, Demeclocycline, Doxycycline,
Guamecycline, Lymecycline, Meclocycline, Methacycline, Minocycline,
Oxytetracycline, Penimepicycline, Pipacycline, Rolitetracycline, Sancycline,
Tetracycline
Others
Cycloserine, Dalfopristin, Mupirocin, Pristinamycin, Virginiamycin
ANTIBACTERIAL (SYNTHETIC)
2,4-Diaminopyrimidines
Brodimoprim, Tetroxoprim, Trimethoprim, Nitrofurans
Furaltadone, Furazolium Chloride, Nifuratel, Nifurfoline, Nifurpirinol,
Nifurprazine, Nifurtoinol, Nitrofurantoin, Oxazolidinones
Linezolid
Quinolones and Analogs
Balofloxacin, Cinoxacin, Ciprofloxacin, Clinafloxacin, Enoxacin,
Fleroxacin, Flumequine, Gatifloxacin, Gemifloxacin, Grepafloxacin, Lomefloxacin,
Miloxacin, Moxifloxacin, Nadifloxacin, Nalidixic Acid, Norfloxacin, Ofloxacin, TABLE 4-continued Oxolinic Acid, Pazufloxacin, Pefloxacin, Pipemidic Acid, Piromidic Acid, Rosoxacin, Rufloxacih, Sitafloxacin, Sparfloxacin, Tosufloxacin, Trovafloxacin
Sulfonamides
Acetyl Sulfamethoxypyrazine, Chloramine-B, Chloramine-T, Dichloramine T, $N^2$-Formylsulfisomidine, $N^4$-β-D-Glucosylsulfanilamide, Mafenide, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanole, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine, Sulfamoxole, Sulfanilamide, 4-Sulfanilamidosalicylic Acid, $N^4$-Sulfanilylsulfanilamide, Sulfanilylurea, N-SulfanilyI-3,4-xylamide, Sulfaperine, Sulfaphenazole, Sulfaproxyline, Sulfapyrazine, Sulfapyridine, Sulfasomizole, Sulfasymazine, Sulfathiazole, Sulfathiourea, Sulfisomidine, Sulfisoxazole
Sulfones
Acedapsone, Acediasulfone, Acetosulfone Sodium, Dapsone, Diathymosulfone, Glucosulfone Sodium, Solasulfone, Succisulfone, Sulfanilic Acid, p-Sulfanilylbenzylamine, Sulfoxone Sodium, Thiazolsulfone
Others
Clofoctol, Hexedine, Methenamine, Metronidazole, Nitroxoline, Pexiganan, Taurolidine, Xibornol
ANTIBACTERIAL (LEPROSTATIC)
Acedapsone, Acetosulfone Sodium, Qofazimine, Dapsone, Diathymosulfone, Glucosulfone Sodium, Hydnocarpic Acid, Solasulfone, Succisulfone, Sulfoxone Sodium
ANTIBACTERIAL (TUBERCULOSTATIC)
p-Aminosalicylic Acid, p-Aminosalicylic Acid Hydrazide, Benzoylpas, 5-Bromosalicylhydroxamic Acid, Capreomycin, Clofazimine, Cyacetacide, Cycloserine, Dihydrostreptomycin, Enviomycin, Ethambutol, Ethionamide, Furonazide, Glyconiazide, Isoniazid, Morphazinamide, Opiniazide, Phenyl Aminosalicylate, Protionamide, Pyrazinamide, Rifabutin, Rifalazil, Rifampin, Rifapentine, Salinazid, Streptomycin, Streptonicozid, Sulfoniazide, Thiacetazone, Tiocarlide, Tuberactinomycin, Tubercidin, Viomycin, Dimethazan, Fencamine, Indalpine, Indeloxazine Hydrochloride, Nefopam, Nomifensine, Oxitriptan see 4873 Oxypertine, Paroxetine, Sertraline, Thiazesim, Trazodone
Hydrazides/Hydrazines
Iproclozide, Iproniazid, Isocarboxazid, Nialamide, Octamoxin, Phenelzine
Phenyloxazolidinones
Befloxatone, Toloxatone
Pyrrolidones
Cotinine
Tetracydics
Maprotiline, Metralindole, Mianserin, Mirtazapine
Tricyclics
Adinazolam, Amineptine, Amitriptyline, Amitriptylinoxide, Amoxapine, Butriptyline, Clomipramine, Demexiptiline, Desipramine, Dibenzepin, Dimetaciine, Dothiepin, Doxepin, Fluacizine, Imipramine, Imipramine N-Oxide, Iprindole, Lofepramine, Melitracen, Metapramine, Nortriptyline, Noxiptilin, Opipramol, Pizotyline, Propizepine, Protriptyline, Quinupramine, Tianeptine, Trimipramine
Others
Adrafinil, Bupropion, Butacetin, Dioxadrol, Duloxetine, Etoperidone, Femoxetine, Fenpentadiol, Fluoxetine, Fluvoxamine, Hematoporphyrin, Hypericin, Levophacetoperane, Medifoxamine, Milnacipran, Minaprine, Moclobemide, Nefazodone, Oxaflozane, Piberaline, Prolintane, Pyrisuccideanol, Reboxetine, Ritanserin, Roxindole, Rubidium Chloride, Sulphide, Tandospirone, Thozalinone, Tofenacin, Tranylcypromine, Tryptophan, Venlafaxine, Viloxazine, Zimeldine
ANTIDIABETIC
Biguanides
Buformin, Metformin, Phenformin
Hormones/Analogs
Amylin, Insulin, Insulin Aspart, Insulin Glargine, Insulin Lispro, Pramlintide
Sulfonylurea Derivatives
Acetohexamide, Carbutamide, Chlorpropamide, Glibomuride, Gliclazide, Glimepiride, Glipizide, Gliquidone, Glisoxepid, Glyburide, Glybuthiazol(e), Glybuzole, Glyhexamide, Glymidine, Glypinamide, Phenbutamide, Tolazamide, Tolbutamide, Tolcyclamide
Thiazolidinediones
Pioglitazone, Rosiglitazone, Troglitazone
Others
Acarbose, Calcium Mesoxalate, Miglitol, Nateglinide, Repaglinide, Voglibose
ANTIESTROGEN
Centchroman, Delmadinone Acetate, Tamoxifen, Toremifene
ANTIFUNGAL (ANTIBIOTICS)
Polyenes
Amphotericin B, Candicidin, Dermostatin, Filipin, Fungichromin, Hachimycin, Hamycin, Lucensomycin, Klepartricin, Natamycin, Nystatin, Pecilocin, TABLE 4-continued Perimycin
Others
Azaserine, Caspofungin, Griseofulvin, Ohgomycins, Pyrrolnitrin,
Siccanin, Tubercidin, Viridin
ANTIFUNGAL (SYNTHETIC)
Allylamines
Butenafine, Naftifine, Terbinafine
Imidazoles
Bifonazole, Butoconazole, Chlordantoin, Chlormidazole, Cloconazole,
Clotrimazole, Econazole, Enilconazole, Fenticonazole, Flutrimazole, Isoconazole,
Ketoconazole, Lanoconazole, Miconazole, Neticonazole, Omoconazole, Oxiconazole
Nitrate, Sertaconazole, Sulconazole, Tioconazole
Thiocarbamates
Liranaftate, Tolciclate, Tolindate, Tolnaftate, Triazoles Fluconazole,
Itraconazole, Posaconazole, Saperconazole, Terconazole, Voriconazole
Others
Acrisorcin, Amorolfine, Biphenamine, Bromosalicylchloranilide,
Buclosamide, Calcium Propionate, Chlorphenesin, Ciclopirox, Cloxyquin,
Coparaffinate, Diamthazole Dihydrochloride, Exalamide, Flucytosine, Hexetidine,
Loflucarban, Nifuratel, Potassium Iodide, Propionic Acid, Pyrithione, Salicylanilide,
Sodium Propionate, Sulbentine, Tenonitrozole, Triacetin, Undecylenic Acid, Zinc
Propionate
ANTIGONADOTROPIN
Danazol, Gestrinone, Paroxypropione
ANTINEOPLASTIC
Alkaloids
9-Aminocamptothecin, Docetaxel, Ecteinascidins, Etoposide, Irinotecan,
Paclitaxel, Rubitecan, Teniposide, Topotecan, Vinblastine, Vincristine, Vindesine
Alkylating Agents
Alkyl Sulfonates
Busulfan, Improsulfan, Piposulfan
Aziridines
Carboquone, Uredepa
Ethylenimines and Methylmelamines
Altretamine, Triethylenemelamine, Triethylenephosphoramide,
Triethylenethiophosphoramide
Nitrogen Mustards
Chlorambucil, Chlornaphazine, Cyclophosphamide, Estramustine,
Ifosfamide, Mechlorethamine, Mechlorethamine Oxide Hydrochloride, Melphalan,
Novembichin, Perfosfamide, Phenesterine, Prednimustine, Trichlonnethine,
Trofosfamide, Uracil Mustard
Nitrosoureas
Carmustine, Chlorozotocin, Fotemustine, Lomustine, Nimustine,
Ranimustine
Others
Dacarbazine, Mannomustine, Mitobronitol, Mitolactol, Pipobroman,
Temozolomide
Antibiotics and Analogs
Aclacinomycins, Anthramycin, Azaserine, Bleomycins, Cactinomycin,
Carubicin, Chromomycins, Dactinomycin, Daunorubicin, 6-Diazo-5-oxo-L-norleucine,
Doxorubicin, Epirubicin, Idarubicin, Menogaril, Mitomycins, Mycophenolic Acid,
Nogalamycin, Olivomycins, Peplomycin, Pirarubicin, Plicamycin, Porfiromycin,
Puromycin, Streptonigrin, Streptozocin, TNP-470, Tubercidin, Valrubicin, Zinostatin,
Zorobicin
Antimetabolites
Folk Acid Analogs/Antagonists
Denopterin, Edatrexate, Methotrexate, Nolatrexed, Pemetrexed,
Piritrexim, Pteropterin, Raltitrexed, Trimetrexate
Purine Analogs
Cladribine, Fludarabine, 6-Mercaptopurine, Thiamiprine, Thioguanine,
Tiazofurin
Pyrimidine Analogs
Ancitabine, Azacitidine, 6-Azauridine, Capecitabine, Carmofur,
Cytarabine, Decitabine, Doxifluridine, Emitefur, Enocitabine, Floxuridine,
Fluorouracil, Gemcitabine, Tegafur
Enzymes
L-Asparaginase, Ranpirnase
Immunomodulators
Bropirimine, Interferon-α, Interferon-γ, Interleukin-2, Lentinan,
Propagermanium, PSK ®, Roquinimex, Sizofiran, Ubenimex
Immunotoxins
Denilcukin Diftitox
Monoclonal Antibodies
Alemtuzumab, Edrecolomab, Gemtuzumab Ozogamicin, Ibritumomab
Tiuxetan, Rituximab, Tositumomab $^{131}$I, Trastuzumab
Platinum Complexes
Carbopiatin, Cisplatin, Lobaplatin, Miboplatin, Oxaliplatin
Others
Amsacrine, Arsenic Trioxide, Bisantrene, Defosfamide, Demecoline,
Diaziquone, Eflornithine, Elliptinium Acetate, Etoglucid, Fenretinide, Flavopridol, TABLE 4-continued Gallium Nitrate, Hydroxyurea, Imatinib, Liarozole, Lonidamine, Miltefosine,
Mitoguazone, Mitoxantrone, Mopidamol, Nietracrine, Pentostatin, Phenamet,
Podophyllinic Acid 2-Ethylhydrazide, Procarbazine, Razoxane, Sobuzoxane,
Spirogermanium, Tenuazonic Acid, Tirapazamine, Triaziquone, Urethan
ANTINEOPLASTIC (HORMONAL)
Androgens
Calusterone, Dromostanolone, Epitiostanol, Mepitiostane, Testolactone
Antiadrenals
Aminoglutethimide, Mitotane, Trilostane
Antiandrogens
Bicalutamide, Flutamide, Nilutamide
Antiestrogens
Droloxifene, Idoxifene, Tamoxifen, Toremifene
Antiprogestins
Onapristone
Aromatase Inhibitors
Aminoglutethimide, Anastrozole, Exemestane, Fadrozole, Formestane,
Letrozole, Vorozole
Estrogens
Diethylstilbestrol, Fosfestrol, Hexestrol, Polyestradiol Phosphate
LH-RH Analogs
Buserelin, Cetrorelix, Goserelin, Leuprolide, Triptorelin
Progestogens
Chlormadinone Acetate, Medroxyprogesterone, Megestrol Acetate,
Melengestrol
Retinoids and Analogs
Alitretinoin, Bexarotene, Mofarotene
Somatostatin Analog
Lanreotide
ANTINEOPLASTIC (PHOTOSENSITIZER)
Porfimer Sodium, Temoporfin, Tin Ethyl Etiopurpurin
ANTINEOPLASTIC (RADIATION SOURCE)
Americium, Chromic Phosphate, Radioactive, Cobalt, Gold,
Radioactive, Colloidal, Ibritumomab Tiuxetan, $^{131}$I-Ethiodized Oil Iobenguane,
Radium, Radon, Samarium $^{153}$Sm Lexidronam, Sodium Iodide, Radioactive, Sodium
Phosphate, Radioactive, Strontium Chloride, Radioactive, Tositumomab $^{131}$I
ANTINEOPLASTIC ADJUNCT
Antimetastatic Agent
Batimastat, Prinomastat
Chemomodulator
Eniluracil
Chemosensitizer
Biricodar, Valspodar
Radioprotective
Amifostine
Radiosensitjzer
Broxuridine, Etanidazole, RSR-13
Uroprotective
Mesna
ANTINEUTROPENIC
Granulocyte Colony-Stimulating Factor, Granulocyte-Macrophage
Colony-Stimulating Factor, Interleukin-3
ANTEPHEOCHROMOCYTOMA
Metyrosine, Phenoxybenzamine, Phentolamine
ANTIPNEUMOCYSTIC
Atovaquone, Eflornithine, Pentamidine, Sulfamethoxazole
ANTIPROGESTIN
Onapristone
ANTIPROSTATIC HYPERTROPHY
Doxazosin, Dutasteride, Epristeride, Finasteride, Gestonorone Caproate,
Mepartricin, Osaterone, Oxendolone, Tamsulosin, Terazosin
ANTIPROTOZOAL (CRYPTOSPORIDIUM)
Nitazoxanide
ANTIPROTOZOAL (LEISHMANIA)
Ethylstibamine, Hydroxystilbamidine, N-Methylglucamine,
Pentamidine, Sodium Stibogluconate see 707 Stilbamidine, Urea Stibamine
ANTIPROTOZOAL (TOXO-PLASMA)
Pyrimethamine
ANTIPROTOZOAL (TRICHO-MONAS)
Acetarsone, Aminitrozole, Anisomycin, Azanidazole, Furazolidone,
Hachimycin, Lauroguadine, Mepartricin, Metronidazole, Nifuratel, Nifuroxime,
Nimorazole, Secnidazole, Silver Picrate, Tenonitrozole, Tinidazole
ANTIPROTOZOAL (TRYPANO-SOMA)
Benznidazole, Eflomithine, Melarsoprol, Nifurtimox, Oxophenarsine TABLE 4-continued Hydrochloride, Pentamidine, Propamidine, Puromycjn, Quinapyramine, Stilbamidine,
Suramin Sodium, Trypan Red, Tryparsamide
ANTIVIRAL
Monoclonal Antibodies
Palivizumab
Peptidomimetics
Amprenavir, Indinavir, Lopinavir, Nelfinavir, Ritonavir, Saquinavir
Polynucleotides
Ampligen, Fomivirsen
Purines/Pyrimidinones
Abacavir, Acyclovir, Adefovir, Cidofovir, Cytarabine, Didanosine,
Dideoxyadenosine, Edoxudine, Emtricitabine, Famciclovir, Floxuridine, Ganciclovir,
Idoxuridine, Inosine Pranobex, Lamivudine, MADU, Penciclovir, Sorivudine,
Stavudine, Tenofovir, Trifluridine, Valacyclovir, Valganciclovir, Vidarabine,
Zalcitabine, Zidovudine
Sialic Acid Analogs
Oseltamivir, Zanamivir
Others
Acemannan, Acetylleucine Monoethanolamine, Amantadine,
Amidinomycin, Atevirdine, Capravirine, Delavirdine, n-Docosanol, Efavirenz,
Foscarnet Sodium, Interferon-∀, Interferon-Ǝ, Interferon-y, Kethoxal, Lysozyme,
Methisazone, Moroxydine, Nevirapine, Pentafiiside, Pleconaril, Podophyllotoxin,
Ribavirin, Rimantadine, Stallimycin, Statolon, Tremacamra, Tromantadine
AROMATASE INHIBITORS
Aminoglutethimide, Anastrozole, Exemestane, Fadrozole, Formestane,
Letrozole, Vorozole
DIAGNOSTIC AID (MRI CONTRAST AGENT)
Ferumoxides, Ferumoxsil, Gadobenate Dimeglumine, Gadobutrol,
Gadodiamide, Gadopentetic Acid, Gadoteridol, Gadoversetamide, Gadoxetic Acid,
Mangafodipir, MS-325, Perflubron
DIAGNOSTIC AID (RADIOACTIVE IMAGING AGENT)
Arcitumomab Complex with Tc, Butedronic Acid Complex, Capromab
Pendetide, Depreotide Complex with Tc, Disofenin Complex with Tc, Exametazime
Complex with Tc, Fludeoxyglucose F18, o-Iodohippurate Sodium $^{131}$I, Iofetamine $^{123}$I
GLUCOCORTOCOID
21-Acetoxypregnenolone, Alclometasone, Algestone, Amcinonide,
Beclomethasone, Betamethasone, Budesonide, Chloroprednisone, Ciclesonide,
Clobetasol, Clobetasone, Clocortolone, Cloprednol, Corticosterone, Cortisone,
Cortivazol, Deflazacort,
Prednisolone Sodium Phosphate, Prednisone, Prednival, Prednylidene,
Rimexolone, Tixocortol, Triamcinolone, Triamcinolone Acetonide, Triamcinolone
Benetonide, Triamcinolone Hexacetonide
GROWTH HORMONE ANTAGONIST/INHIBITOR
Octreotide, Pegvisomant, Somatostatin
GROWTH HORMONE RELEASING FACTOR
Sermorelin
GROWTH STIMULANT
Somatotropin
REVERSE TRANSCRIPTASE INHIBITOR
Abacavir, Atevirdine, Capravirine, Delavirdine, Didanosine,
Dideoxyadenosine, Efavirenz, Emtricitabine, Foscarnet Sodium, Lamivudine,
Nevirapine, Stavudine, Suramin Sodium, Tenofovir, Zalcitabine, Zidovudine
TOPOISOMERASEI INHIBITOR
9-Aminocamptothecin, Irinotecan, Topotecan
TOPOISOMERASE II INHIBITOR
Daunorubicin, Doxorubicin, Etoposide, Sobuzoxane, Teniposide C. Properties of the Oligomers As noted above, the present disclosure is directed to oligomer comprising various modifications which impart desirable properties (e.g., increased antisense activity) to the oligomers. In certain embodiments, the oligomer comprises a backbone comprising a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligomer can bind in a sequence-specific manner to a target nucleic acid. The morpholino ring structures may have the following structure (i):

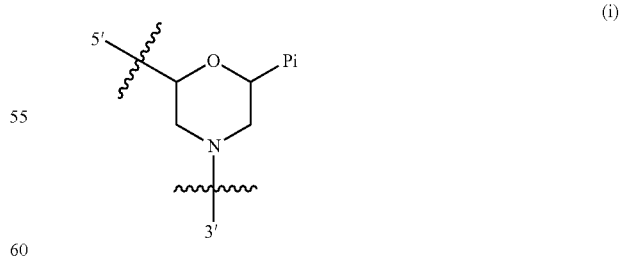

(i)

wherein B is, at each occurrence, independently a base-pairing moiety.

Each morpholino ring structure supports a base pairing moiety (Pi), to form a sequence of base pairing moieties which is typically designed to hybridize to a selected antisense target in a cell or in a subject being treated. The base pairing moiety may be a purine or pyrimidine found in native DNA or RNA (A, G, C, T, or U) or an analog, such as hypoxanthine (the base component of the nucleoside inosine) or 5-methyl cytosine. Analog bases that confer improved binding affinity to the oligomer can also be utilized. Exemplary analogs in this regard include C5-propynyl-modified pyrimidines, 9-(aminoethoxy)phenoxazine (G-clamp) and the like.

Further examples of base pairing moieties include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, *RNA*, 2003, 9, 1034-1048, Limbach et al. *Nucleic Acids Research*, 1994, 22, 2183-2196 and Revankar and Rao, *Comprehensive Natural Products Chemistry*, vol. 7, 313, are also contemplated.

Further examples of base pairing moieties include, but are not limited to, expanded-size nucleobases in which one or more benzene rings has been added. Nucleic base replacements described in the Glen Research catalog (www.glenresearch.com); Krueger A T et al, *Acc. Chem. Res.*, 2007, 40, 141-150; Kool, ET, *Acc. Chem. Res.*, 2002, 35, 936-943; Benner S. A., et al., *Nat. Rev. Genet.*, 2005, 6, 553-543; Romesberg, F. E., et al., *Curr. Opin. Chem. Biol.*, 2003, 7, 723-733; Hirao, I., *Curr. Opin. Chem. Biol.*, 2006, 10, 622-627, are contemplated as useful for the synthesis of the oligomers described herein. Some examples of these expanded-size nucleobases are shown below:

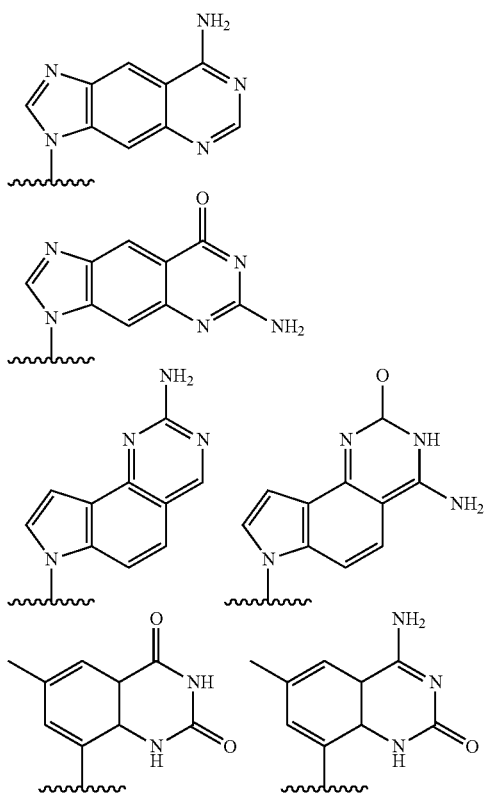

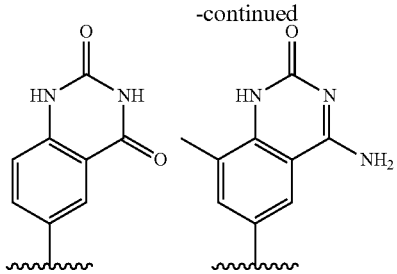

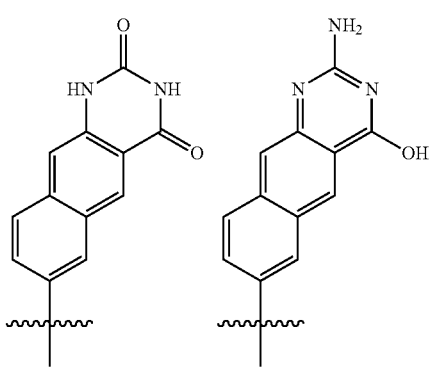

As noted above, the oligomer may be modified, in accordance with an aspect of the invention, to include one or more X2-X8 groups. In some embodiments, a compound of Formula I contains at least one X3-X8 group and no X2 group. In some embodiments, a compound of Formula I contains at least one X2, X4, X5, X6, X7, or X8 group and no X3 group. In some embodiments, a compound of Formula I contains at least one X2, X3, X5, X6, X7, or X8 group and no X4 group. In some embodiments, a compound of Formula I contains at least one X2, X3, X4, X6, X7, or X8 group and no X5 group. In some embodiments, a compound of Formula I contains at least one X2, X3, X4, X5, X7, or X8 group and no X6 group. In some embodiments, a compound of Formula I contains at least one X2, X3, X4, X5, X6, or X8 group and no X7 group. In some embodiments, a compound of Formula I contains at least one X2-X7 group and no X8 group. In some embodiments is a compound of Formula I wherein X is not

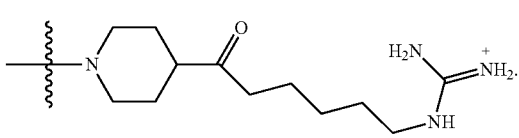

In some embodiments is a compound of Formula I wherein $R^{13}$ is acetyl and X is not

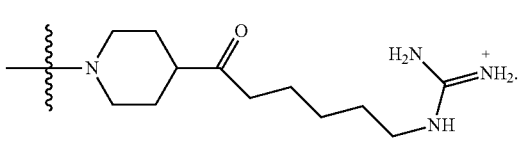

In some embodiments is a compound of Formula I wherein X is not

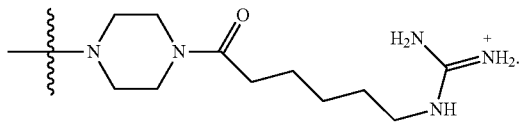

In some embodiments is a compound of Formula I wherein $R^{13}$ is acetyl and X is not

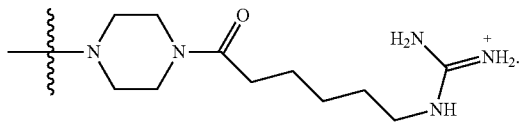

In some embodiments is a compound of Formula I wherein X is not

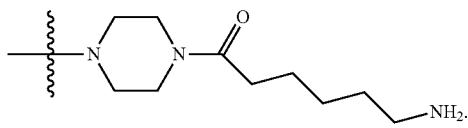 [SMILES: *N1CCN(C(=O)CCCCCN)CC1]

In some embodiments is a compound of Formula I wherein $R^{13}$ is acetyl and X is not

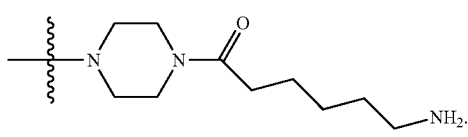 [SMILES: *N1CCN(C(=O)CCCCCN)CC1]

In some embodiments is a compound of Formula I wherein X is not

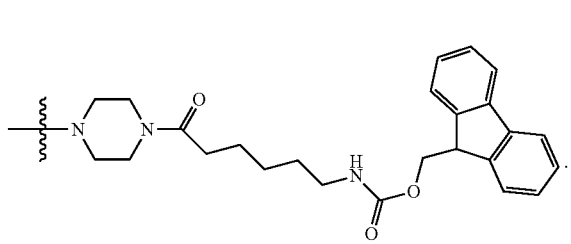 [SMILES: *N1CCN(C(=O)CCCCCNC(=O)OCC2c3ccccc3-c3ccccc32)CC1 ; "."]

In some embodiments is a compound of Formula I wherein $R^{13}$ is acetyl and X is not

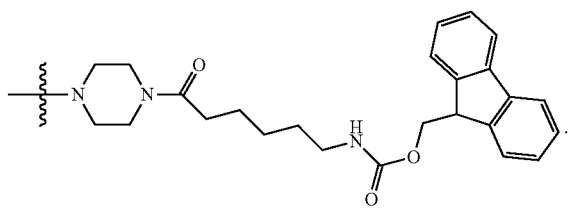 [SMILES: *N1CCN(C(=O)CCCCCNC(=O)OCC2c3ccccc3-c3ccccc32)CC1 ; "."]

In some embodiments is a compound of Formula I wherein X is not

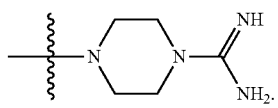 [SMILES: *N1CCN(C(=N)N)CC1]

In some embodiments is a compound of Formula I wherein $R^{13}$ is acetyl and X is not

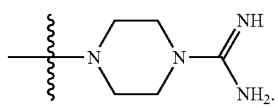 [SMILES: *N1CCN(C(=N)N)CC1]

In some embodiments is a compound of Formula I wherein X is not

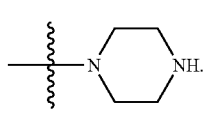

In some embodiments is a compound of Formula I wherein $R^{13}$ is acetyl and X is not

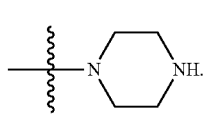 [SMILES: *N1CCNCC1]

In some embodiments is a compound of Formula I wherein X is not

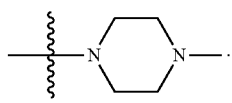

In some embodiments is a compound of Formula I wherein $R^{13}$ is acetyl and X is not

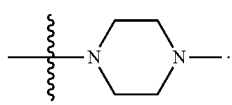

In some embodiments is a compound of Formula I wherein X is not

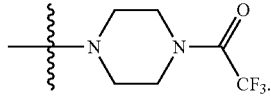

In some embodiments is a compound of Formula I wherein R[13] is acetyl and X is not

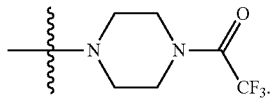

In some embodiments is a compound of Formula I wherein X is not

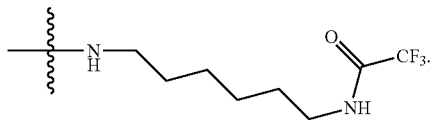 [SMILES: *NCCCCCCNC(=O)C(F)(F)F]

In some embodiments is a compound of Formula I wherein R[13] is acetyl and X is not

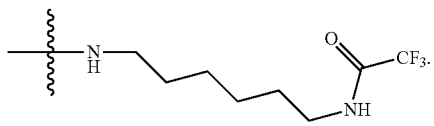

In some embodiments is a compound of Formula I wherein X is not

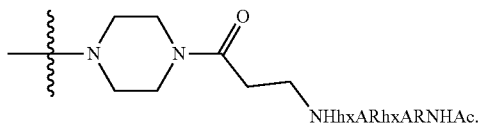

In some embodiments is a compound of Formula I wherein R[13] is acetyl and X is not

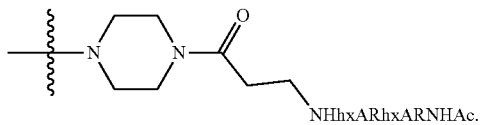

In some embodiments is a compound of Formula I wherein each X group is independently selected as described above with the provision that if the X group on the phosphorous linkage proximal to the 3' terminus is

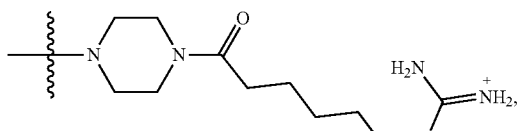

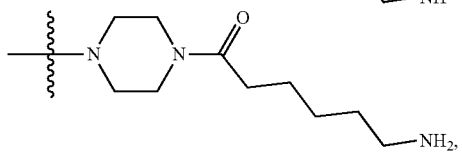

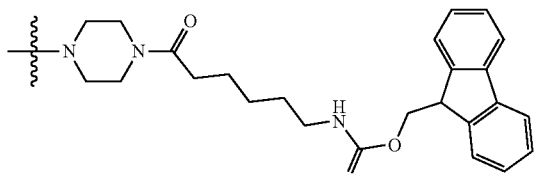

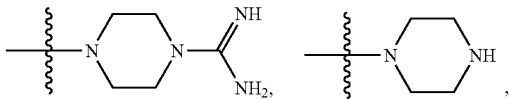

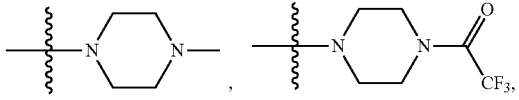

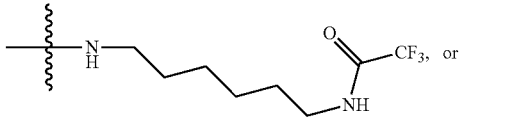

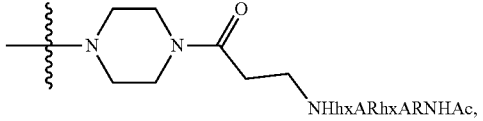

then at least one other X group is not X1.

In some embodiments is a compound of Formula I wherein each X group is independently selected as described above with the provision that if the X group on the phosphorous linkage proximal to the 3' terminus is

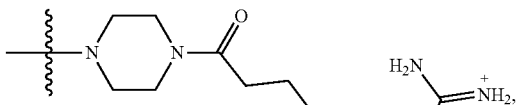

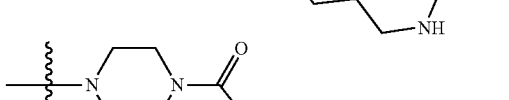

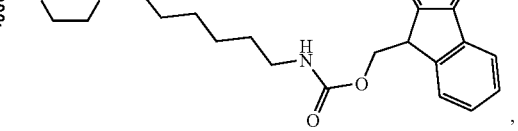

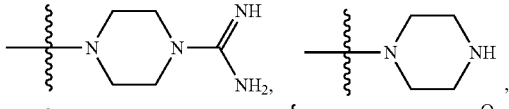

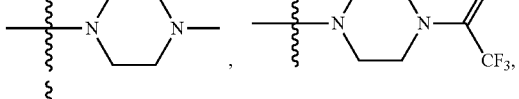

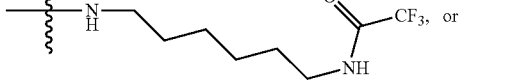

-continued

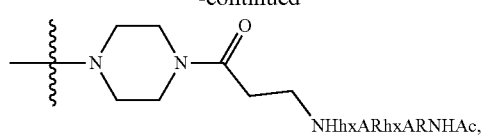
NHhxARhxARNHAc, then at least two other X groups are not X1.

In some embodiments is a compound of Formula I wherein each X group is independently selected as described above with the provision that if the X group on the phosphorous linkage proximal to the 3' terminus is

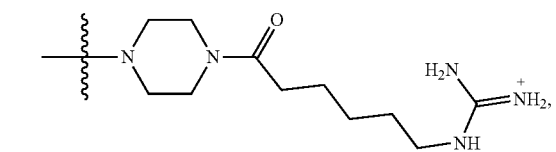

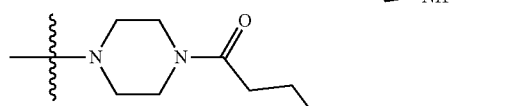
NH₂,

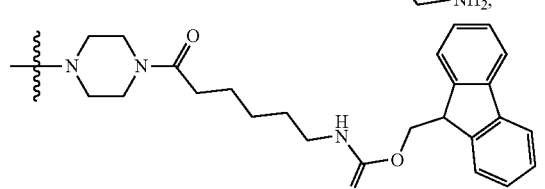

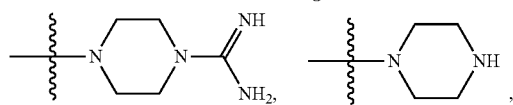

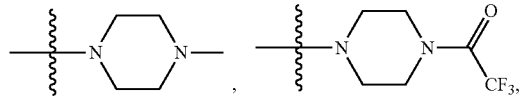

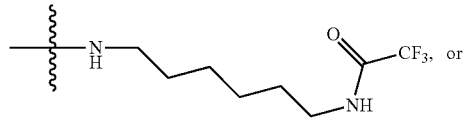

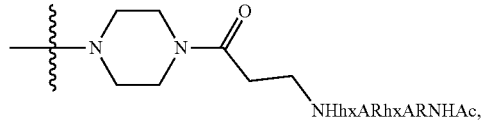
NHhxARhxARNHAc, then at least three other X groups are not X1.

In some embodiments is a compound of Formula I wherein each X group is independently selected as described above with the provision that if the X group on the phosphorous linkage proximal to the 3' terminus is

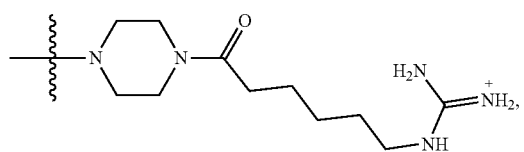

-continued

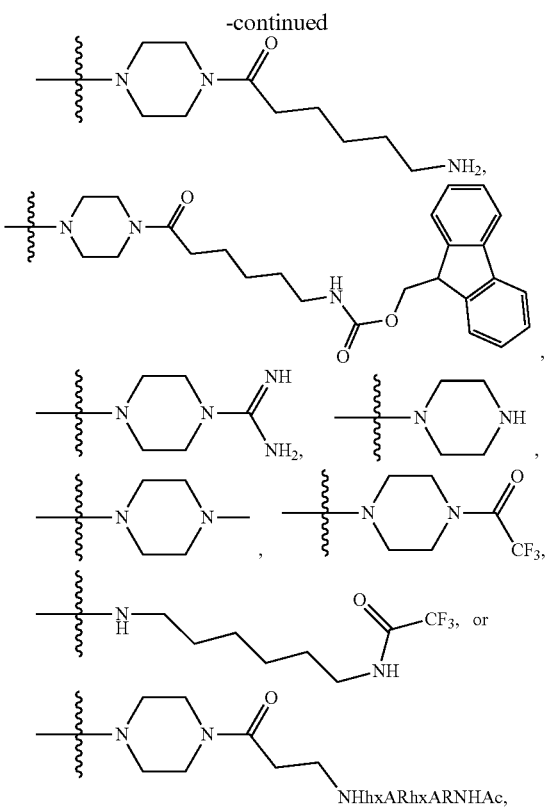

then all other X groups are not X1.

In some embodiments is a compound of Formula I wherein each X group is independently selected as described above with the provision that if X1 is present as N(CH₃)₂, and X3 is present as

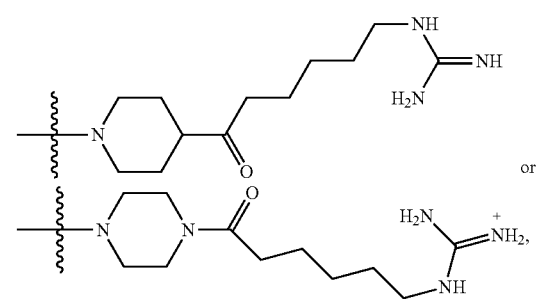

then X7 is not piperdinyl.

In some embodiments is a compound of Formula I wherein each X group is independently selected as described above with the provision that if X1 is present as N(CH₃)₂, and X7 is present as piperidinyl, then X3 is not

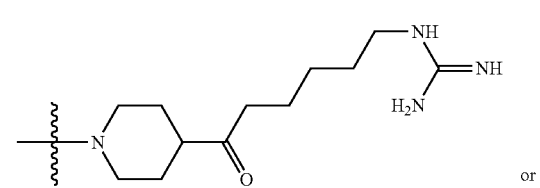

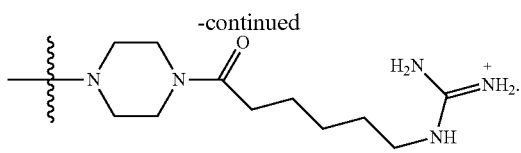

In some embodiments, a compound of Formula I contains one X2-X8 group per every 2-5 X1 groups. In some embodiments, a compound of Formula I contains 3-5 X2-X8 groups per every 10 X1 groups. In some embodiments, a compound of Formula I contains 3-5 X2-X8 groups per every 10 X1 groups. In some embodiments, a compound of Formula I contains 100% X2-X8 groups. In some embodiments, a compound of Formula I contains 95-100% X2-X8 groups. In some embodiments, a compound of Formula I contains 90-95% X2-X8 groups. In some embodiments, a compound of Formula I contains 85-90% X2-X8 groups. In some embodiments, a compound of Formula I contains 80-85% X2-X8 groups. In some embodiments, a compound of Formula I contains 75-80% X2-X8 groups. In some embodiments, a compound of Formula I contains 70-75% X2-X8 groups. In some embodiments, a compound of Formula I contains 65-70% X2-X8 groups. In some embodiments, a compound of Formula I contains 60-65% X2-X8 groups. In some embodiments, a compound of Formula I contains 55-60% X2-X8 groups. In some embodiments, a compound of Formula I contains 50-55% X2-X8 groups. In some embodiments, a compound of Formula I contains 45-50% X2-X8 groups. In some embodiments, a compound of Formula I contains 40-45% X2-X8 groups. In some embodiments, a compound of Formula I contains 35-40% X2-X8 groups. In some embodiments, a compound of Formula I contains 30-35% X2-X8 groups. In some embodiments, a compound of Formula I contains 25-30% X2-X8 groups. In some embodiments, a compound of Formula I contains 20-25% X2-X8 groups. In some embodiments, a compound of Formula I contains 15-20% X2-X8 groups. In some embodiments, a compound of Formula I contains 10-15% X2-X8 groups. In some embodiments, a compound of Formula I contains 5-10% X2-X8 groups. In some embodiments, a compound of Formula I contains less than 5% X2-X8 groups.

In some embodiments is a compound of Formula I wherein the X1 groups and the X2-X8 groups are interspersed along the backbone. In some embodiments is a compound of Formula I wherein the X1 groups and the X2-X8 groups have a strictly alternating pattern along the backbone. In some embodiments is a compound of Formula I wherein the X1 groups and the X2-X8 groups do not have a strictly alternating pattern along the backbone. In some embodiments is a compound of Formula I having blocks of X1 groups and blocks of X2-X8 groups. In some embodiments is a compound of Formula I having a central block of X1 groups flanked by blocks of X2-X8 groups. In some embodiments is a compound of Formula I having a central block of X2-X8 groups flanked by blocks of X1 groups.

In any of the aforementioned embodiments of Formula (I) wherein at least one X is selected from X2-X8 is another embodiment wherein n is an integer from 30-35. In further embodiments of the aforementioned embodiments of Formula (I) wherein at least one X is selected from X2-X8, n is an integer from 25-29. In further embodiments of the aforementioned embodiments of Formula (I) wherein at least one X is selected from X2-X8, n is an integer from 20-24. In further embodiments of any of the aforementioned embodiments of Formula (I) wherein at least one X is selected from X2-X8, n is an integer from 15-19. In further embodiments of the aforementioned embodiments of Formula (I) wherein at least one X is selected from X2-X8, n is an integer from 10-14. In further embodiments of the aforementioned embodiments of Formula (I) wherein at least one X is selected from X2-X8, n is an integer from 5-9. In yet further embodiments of the aforementioned embodiments of Formula (I) wherein at least one X is selected from X2-X8, n is an integer from 1-4.

In any of the aforementioned embodiments of Formula (I) wherein n is an integer from 30-35 is another embodiment wherein one X is X2-X8. In any of the aforementioned embodiments of Formula (I) wherein n is an integer from 30-35 is another embodiment wherein two X are independently selected from X2-X8. In any of the aforementioned embodiments of Formula (I) wherein n is an integer from 30-35 is another embodiment wherein three X are independently selected from X2-X8. In any of the aforementioned embodiments of Formula (I) wherein n is an integer from 30-35 is another embodiment wherein four X are independently selected from X2-X8. In any of the aforementioned embodiments of Formula (I) wherein n is an integer from 30-35 is another embodiment wherein five X are independently selected from X2-X8. In any of the aforementioned embodiments of Formula (I) wherein n is an integer from 30-35 is another embodiment wherein six X are independently selected from X2-X8. In any of the aforementioned embodiments of Formula (I) wherein n is an integer from 30-35 is another embodiment wherein seven X are independently selected from X2-X8. In any of the aforementioned embodiments of Formula (I) wherein n is an integer from 30-35 is another embodiment wherein eight X are independently selected from X2-X8. In any of the aforementioned embodiments of Formula (I) wherein n is an integer from 30-35 is another embodiment wherein nine X are independently selected from X2-X8. In any of the aforementioned embodiments of Formula (I) wherein n is an integer from 30-35 is another embodiment wherein ten X are independently selected from X2-X8. In any of the aforementioned embodiments of Formula (I) wherein n is an integer from 30-35 is another embodiment wherein eleven X are independently selected from X2-X8. In any of the aforementioned embodiments of Formula (I) wherein n is an integer from 30-35 is another embodiment wherein twelve X are independently selected from X2-X8. In any of the aforementioned embodiments of Formula (I) wherein n is an integer from 30-35 is another embodiment wherein thirteen X are independently selected from X2-X8. In any of the aforementioned embodiments of Formula (I) wherein n is an integer from 30-35 is another embodiment wherein fourteen X are independently selected from X2-X8. In any of the aforementioned embodiments of Formula (I) wherein n is an integer from 30-35 is another embodiment wherein fifteen X are independently selected from X2-X8. In any of the aforementioned embodiments of Formula (I) wherein n is an integer from 30-35 is another embodiment wherein sixteen X are independently selected from X2-X8. In any of the aforementioned embodiments of Formula (I) wherein n is an integer from 30-35 is another embodiment wherein seventeen X are independently selected from X2-X8. In any of the aforementioned embodiments of Formula (I) wherein n is an integer from 30-35 is another embodiment wherein eighteen X are independently selected from X2-X8. In any of the aforementioned embodiments of Formula (I) wherein n is an integer from 30-35 is another embodiment wherein nineteen X are independently selected from X2-X8. In any of the aforementioned embodiments of Formula (I) wherein n is an integer from 30-35 is another embodiment wherein twenty X are independently selected from X2-X8.

In any of the aforementioned embodiments of Formula (I) wherein n is an integer from 25-30 is another embodiment wherein one X is X2-X8. In any of the aforementioned embodiments of Formula (I) wherein n is an integer from 25-30 is another embodiment wherein two X are independently selected from X2-X8. In any of the aforementioned embodiments of Formula (I) wherein n is an integer from 25-30 is another embodiment wherein three X are independently selected from X2-X8. In any of the aforementioned embodiments of Formula (I) wherein n is an integer from 25-30 is another embodiment wherein four X are independently selected from X2-X8. In any of the aforementioned embodiments of Formula (I) wherein n is an integer from 25-30 is another embodiment wherein five X are independently selected from X2-X8. In any of the aforementioned embodiments of Formula (I) wherein n is an integer from 25-30 is another embodiment wherein six X are independently selected from X2-X8. In any of the aforementioned embodiments of Formula (I) wherein n is an integer from 25-30 is another embodiment wherein seven X are independently selected from X2-X8. In any of the aforementioned embodiments of Formula (I) wherein n is an integer from 25-30 is another embodiment wherein eight X are independently selected from X2-X8. In any of the aforementioned embodiments of Formula (I) wherein n is an integer from 25-30 is another embodiment wherein nine X are independently selected from X2-X8. In any of the aforementioned embodiments of Formula (I) wherein n is an integer from 25-30 is another embodiment wherein ten X are independently selected from X2-X8. In any of the aforementioned embodiments of Formula (I) wherein n is an integer from 25-30 is another embodiment wherein eleven X are independently selected from X2-X8. In any of the aforementioned embodiments of Formula (I) wherein n is an integer from 25-30 is another embodiment wherein twelve X are independently selected from X2-X8. In any of the aforementioned embodiments of Formula (I) wherein n is an integer from 25-30 is another embodiment wherein thirteen X are independently selected from X2-X8. In any of the aforementioned embodiments of Formula (I) wherein n is an integer from 25-30 is another embodiment wherein fourteen X are independently selected from X2-X8. In any of the aforementioned embodiments of Formula (I) wherein n is an integer from 25-30 is another embodiment wherein fifteen X are independently selected from X2-X8. In any of the aforementioned embodiments of Formula (I) wherein n is an integer 25-30 is another embodiment wherein sixteen X are independently selected from X2-X8. In any of the aforementioned embodiments of Formula (I) wherein n is an integer from 25-30 is another embodiment wherein seventeen X are independently selected from X2-X8. In any of the aforementioned embodiments of Formula (I) wherein n is an integer from 25-30 is another embodiment wherein eighteen X are independently selected from X2-X8. In any of the aforementioned embodiments of Formula (I) wherein n is an integer from 25-30 is another embodiment wherein nineteen X are independently selected from X2-X8. In any of the aforementioned embodiments of Formula (I) wherein n is an integer from 25-30 is another embodiment wherein twenty X are independently selected from X2-X8.

In any of the aforementioned embodiments of Formula (I) wherein n is an integer from 20-25 is another embodiment wherein one X is X2-X8. In any of the aforementioned embodiments of Formula (I) wherein n is an integer from 20-25 is another embodiment wherein two X are independently selected from X2-X8. In any of the aforementioned embodiments of Formula (I) wherein n is an integer from 20-25 is another embodiment wherein three X are independently selected from X2-X8. In any of the aforementioned embodiments of Formula (I) wherein n is an integer from 20-25 is another embodiment wherein four X are independently selected from X2-X8. In any of the aforementioned embodiments of Formula (I) wherein n is an integer from 20-25 is another embodiment wherein five X are independently selected from X2-X8. In any of the aforementioned embodiments of Formula (I) wherein n is an integer from 20-25 is another embodiment wherein six X are independently selected from X2-X8. In any of the aforementioned embodiments of Formula (I) wherein n is an integer from 20-25 is another embodiment wherein seven X are independently selected from X2-X8. In any of the aforementioned embodiments of Formula (I) wherein n is an integer from 20-25 is another embodiment wherein eight X are independently selected from X2-X8. In any of the aforementioned embodiments of Formula (I) wherein n is an integer from 20-25 is another embodiment wherein nine X are independently selected from X2-X8. In any of the aforementioned embodiments of Formula (I) wherein n is an integer from 20-25 is another embodiment wherein ten X are independently selected from X2-X8. In any of the aforementioned embodiments of Formula (I) wherein n is an integer from 20-25 is another embodiment wherein eleven X are independently selected from X2-X8. In any of the aforementioned embodiments of Formula (I) wherein n is an integer from 20-25 is another embodiment wherein twelve X are independently selected from X2-X8. In any of the aforementioned embodiments of Formula (I) wherein n is an integer from 20-25 is another embodiment wherein thirteen X are independently selected from X2-X8. In any of the aforementioned embodiments of Formula (I) wherein n is an integer from 20-25 is another embodiment wherein fourteen X are independently selected from X2-X8. In any of the aforementioned embodiments of Formula (I) wherein n is an integer from 20-25 is another embodiment wherein fifteen X are independently selected from X2-X8. In any of the aforementioned embodiments of Formula (I) wherein n is an integer 20-25 is another embodiment wherein sixteen X are independently selected from X2-X8. In any of the aforementioned embodiments of Formula (I) wherein n is an integer from 20-25 is another embodiment wherein seventeen X are independently selected from X2-X8. In any of the aforementioned embodiments of Formula (I) wherein n is an integer from 20-25 is another embodiment wherein eighteen X are independently selected from X2-X8. In any of the aforementioned embodiments of Formula (I) wherein n is an integer from 20-25 is another embodiment wherein nineteen X are independently selected from X2-X8. In any of the aforementioned embodiments of Formula (I) wherein n is an integer from 20-25 is another embodiment wherein twenty X are independently selected from X2-X8.

In any of the aforementioned embodiments of Formula (I) wherein n is an integer from 15-20 is another embodiment wherein one X is X2-X8. In any of the aforementioned embodiments of Formula (I) wherein n is an integer from 15-20 is another embodiment wherein two X are independently selected from X2-X8. In any of the aforementioned embodiments of Formula (I) wherein n is an integer from 15-20 is another embodiment wherein three X are independently selected from X2-X8. In any of the aforementioned embodiments of Formula (I) wherein n is an integer from 15-20 is another embodiment wherein four X are independently selected from X2-X8. In any of the aforementioned embodiments of Formula (I) wherein n is an integer from 15-20 is another embodiment wherein five X are independently selected from X2-X8. In any of the aforementioned embodiments of Formula (I) wherein n is an integer from 15-20 is another embodiment wherein six X are independently selected from X2-X8. In any of the aforementioned embodiments of Formula (I) wherein n is an integer from 15-20 is another embodiment wherein seven X are independently selected from X2-X8. In any of the aforementioned embodiments of Formula (I) wherein n is an integer from 15-20 is another embodiment wherein eight X are independently selected from X2-X8. In any of the aforementioned embodiments of Formula (I) wherein n is an integer from 15-20 is another embodiment wherein nine X are independently selected 15-20 is another embodiment wherein ten X are independently selected from X2-X8. In any of the aforementioned embodiments of Formula (I) wherein n is an integer from 15-20 is another embodiment wherein eleven X are independently selected from X2-X8. In any of the aforementioned embodiments of Formula (I) wherein n is an integer from 15-20 is another embodiment wherein twelve X are independently selected from X2-X8. In any of the aforementioned embodiments of Formula (I) wherein n is an integer from 15-20 is another embodiment wherein thirteen X are independently selected from X2-X8. In any of the aforementioned embodiments of Formula (I) wherein n is an integer from 15-20 is another embodiment wherein fourteen X are independently selected from X2-X8. In any of the aforementioned embodiments of Formula (I) wherein n is an integer from 15-20 is another embodiment wherein fifteen X are independently selected from X2-X8. In any of the aforementioned embodiments of Formula (I) wherein n is an integer 16-20 is another embodiment wherein sixteen X are independently selected from X2-X8. In any of the aforementioned embodiments of Formula (I) wherein n is an integer from 17-20 is another embodiment wherein seventeen X are independently selected from X2-X8. In any of the aforementioned embodiments of Formula (I) wherein n is an integer from 18-20 is another embodiment wherein eighteen X are independently selected from X2-X8. In any of the aforementioned embodiments of Formula (I) wherein n is an integer from 19-20 is another embodiment wherein nineteen X are independently selected from X2-X8. In any of the aforementioned embodiments of Formula (I) wherein n is 20 is another embodiment wherein twenty X are independently selected from X2-X8.

In any of the aforementioned embodiments of Formula (I) wherein n is an integer from 10-15 is another embodiment wherein one X is X2-X8. In any of the aforementioned embodiments of Formula (I) wherein n is an integer from 10-15 is another embodiment wherein two X are independently selected from X2-X8. In any of the aforementioned embodiments of Formula (I) wherein n is an integer from 10-15 is another embodiment wherein three X are independently selected from X2-X8. In any of the aforementioned embodiments of Formula (I) wherein n is an integer from 10-15 is another embodiment wherein four X are independently selected from X2-X8. In any of the aforementioned embodiments of Formula (I) wherein n is an integer from 10-15 is another embodiment wherein five X are independently selected from X2-X8. In any of the aforementioned embodiments of Formula (I) wherein n is an integer from 10-15 is another embodiment wherein six X are independently selected from X2-X8. In any of the aforementioned embodiments of Formula (I) wherein n is an integer from 10-15 is another embodiment wherein seven X are independently selected from X2-X8. In any of the aforementioned embodiments of Formula (I) wherein n is an integer from 10-15 is another embodiment wherein eight X are independently selected from X2-X8. In any of the aforementioned embodiments of Formula (I) wherein n is an integer from 10-15 is another embodiment wherein nine X are independently selected from X2-X8. In any of the aforementioned embodiments of Formula (I) wherein n is an integer from 10-15 is another embodiment wherein ten X are independently selected from X2-X8. In any of the aforementioned embodiments of Formula (I) wherein n is an integer from 11-15 is another embodiment wherein eleven X are independently selected from X2-X8. In any of the aforementioned embodiments of Formula (I) wherein n is an integer from 12-15 is another embodiment wherein twelve X are independently selected from X2-X8. In any of the aforementioned embodiments of Formula (I) wherein n is an integer from 13-15 is another embodiment wherein thirteen X are independently selected from X2-X8. In any of the aforementioned embodiments of Formula (I) wherein n is an integer from 14-15 is another embodiment wherein fourteen X are independently selected from X2-X8. In any of the aforementioned embodiments of Formula (I) wherein n is 15 is another embodiment wherein fifteen X are independently selected from X2-X8.

In any of the aforementioned embodiments of Formula (I) wherein n is an integer from 5-10 is another embodiment wherein one X is X2-X8. In any of the aforementioned embodiments of Formula (I) wherein n is an integer from 5-10 is another embodiment wherein two X are independently selected from X2-X8. In any of the aforementioned embodiments of Formula (I) wherein n is an integer from 5-10 is another embodiment wherein three X are independently selected from X2-X8. In any of the aforementioned embodiments of Formula (I) wherein n is an integer from 5-10 is another embodiment wherein four X are independently selected from X2-X8. In any of the aforementioned embodiments of Formula (I) wherein n is an integer from 5-10 is another embodiment wherein five X are independently selected from X2-X8. In any of the aforementioned embodiments of Formula (I) wherein n is an integer from 6-10 is another embodiment wherein six X are independently selected from X2-X8. In any of the aforementioned embodiments of Formula (I) wherein n is an integer from 7-10 is another embodiment wherein seven X are independently selected from X2-X8. In any of the aforementioned embodiments of Formula (I) wherein n is an integer from 8-10 is another embodiment wherein eight X are independently selected from X2-X8. In any of the aforementioned embodiments of Formula (I) wherein n is an integer from 9-10 is another embodiment wherein nine X are independently selected from X2-X8. In any of the aforementioned embodiments of Formula (I) wherein n is 10 is another embodiment wherein ten X are independently selected from X2-X8.

In any of the aforementioned embodiments of Formula (I) wherein n is an integer from 1-5 is another embodiment wherein one X is X2-X8. In any of the aforementioned embodiments of Formula (I) wherein n is an integer from 2-5 is another embodiment wherein two X are independently selected from X2-X8. In any of the aforementioned embodiments of Formula (I) wherein n is an integer from 3-5 is another embodiment wherein three X are independently selected from X2-X8. In any of the aforementioned embodiments of Formula (I) wherein n is an integer from 4-5 is another embodiment wherein four X are independently selected from X2-X8. In any of the aforementioned embodiments of Formula (I) wherein n is 5 is another embodiment wherein five X are independently selected from X2-X8.

In some embodiments for antisense applications, the oligomer may be 100% complementary to the nucleic acid target sequence, or it may include mismatches, e.g., to accommodate variants, as long as a heteroduplex formed between the oligomer and nucleic acid target sequence is sufficiently stable to withstand the action of cellular nucleases and other modes of degradation which may occur in vivo. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the nucleic acid target sequence, it is effective to stably and specifically bind to the target sequence, such that a biological activity of the nucleic acid target, e.g., expression of encoded protein(s), is modulated.

The stability of the duplex formed between an oligomer and the target sequence is a function of the binding $T_m$ and the susceptibility of the duplex to cellular enzymatic cleavage. The $T_m$ of an antisense compound with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide hybridization techniques, *Methods Enzymol.* Vol. 154 pp. 94-107.

In some embodiments, each antisense oligomer has a binding $T_m$, with respect to a complementary-sequence RNA, of greater than body temperature or in other embodiments greater than 50° C. In other embodiments $T_m$'s are in the range 60-80° C. or greater. According to well known principles, the $T_m$ of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high $T_m$ (50° C. or greater) at a length of 20 bases or less are generally preferred over those requiring greater than 20 bases for high $T_m$ values. For some applications, longer oligomers, for example longer than 20 bases may have certain advantages. For example, in certain embodiments longer oligomers may find particular utility for use in exon skippin or splice modulation.

The targeting sequence bases may be normal DNA bases or analogues thereof, e.g., uracil and inosine that are capable of Watson-Crick base pairing to target-sequence RNA bases.

The oligomers may also incorporate guanine bases in place of adenine when the target nucleotide is a uracil residue. This is useful when the target sequence varies across different viral species and the variation at any given nucleotide residue is either cytosine or uracil. By utilizing guanine in the targeting oligomer at the position of variability, the well-known ability of guanine to base pair with uracil (termed C/U:G base pairing) can be exploited. By incorporating guanine at these locations, a single oligomer can effectively target a wider range of RNA target variability.

The compounds (e.g., oligomers, intersubunit linkages, terminal groups) may exist in different isomeric forms, for example structural isomers (e.g., tautomers). With regard to stereoisomers, the compounds may have chiral centers and may occur as racemates, enantiomerically enriched mixtures, individual enantiomers, mixture or diastereomers or individual diastereomers. All such isomeric forms are included within the present invention, including mixtures thereof. The compounds may also possess axial chirality which may result in atropisomers. Furthermore, some of the crystalline forms of the compounds may exist as polymorphs, which are included in the present invention. In addition, some of the compounds may also form solvates with water or other organic solvents. Such solvates are similarly included within the scope of this invention.

The oligomers described herein may be used in methods of inhibiting production of a protein or replication of a virus. Accordingly, in one embodiment a nucleic acid encoding such a protein is exposed to an oligomer as disclosed herein. In further embodiments of the foregoing, the antisense oligomer comprises either a 5' or 3' modified terminal group or combinations thereof, as disclosed herein, and the base pairing moieties B form a sequence effective to hybridize to a portion of the nucleic acid at a location effective to inhibit production of the protein. In one embodiment, the location is an ATG start codon region of an mRNA, a splice site of a pre-mRNA, or a viral target sequence as described below.

In one embodiment, the oligomer has a $T_m$ with respect to binding to the target sequence of greater than about 50° C., and it is taken up by mammalian cells or bacterial cells. In another embodiment, the oligomer may be conjugated to a transport moiety, for example an arginine-rich peptide, as described herein to facilitate such uptake. In another embodiment, the terminal modifications described herein can function as a transport moiety to facilitate uptake by mammalian and/or bacterial cells.

The preparation and properties of morpholino oligomers is described in more detail below and in U.S. Pat. No. 5,185,444 and WO/2009/064471, each of which is hereby incorporated by reference in their entirety.

D. Formulation and Administration of the Oligomers

The present disclosure also provides for formulation and delivery of the disclosed oligomer. Accordingly, in one embodiment the present disclosure is directed to a composition comprising an oligomer as disclosed herein and a pharmaceutically acceptable vehicle.

Effective delivery of the antisense oligomer to the target nucleic acid is an important aspect of treatment. Routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of an antisense oligomer in the treatment of a viral infection of the skin is topical delivery, while delivery of a antisense oligomer for the treatment of a viral respiratory infection is by inhalation. The oligomer may also be delivered directly to the site of viral infection, or to the bloodstream.

The antisense oligomer may be administered in any convenient vehicle which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

The compounds (e.g., oligomers) of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

In some instances, liposomes may be employed to facilitate uptake of the antisense oligonucleotide into cells. (See, e.g., Williams, S. A., Leukemia 10(12):1980-1989, 1996; Lappalainen et al., Antiviral Res. 23:119, 1994; Uhlmann et al., antisense oligonucleotides: a new therapeutic principle, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747. Sustained release compositions may also be used. These may include semipermeable polymeric matrices in the form of shaped articles such as films or microcapsules.

In one embodiment, antisense inhibition is effective in treating infection of a host animal by a virus, by contacting a cell infected with the virus with an antisense agent effective to inhibit the replication of the specific virus. The antisense agent is administered to a mammalian subject, e.g., human or domestic animal, infected with a given virus, in a suitable pharmaceutical carrier. It is contemplated that the antisense oligonucleotide arrests the growth of the RNA virus in the host. The RNA virus may be decreased in number or eliminated with little or no detrimental effect on the normal growth or development of the host.

In one aspect of the method, the subject is a human subject, e.g., a patient diagnosed as having a localized or systemic viral infection. The condition of a patient may also dictate prophylactic administration of an antisense oligomer of the invention, e.g. in the case of a patient who (1) is immunocompromised; (2) is a burn victim; (3) has an indwelling catheter; or (4) is about to undergo or has recently undergone surgery. In one preferred embodiment, the oligomer is a phosphorodiamidate morpholino oligomer, contained in a pharmaceutically acceptable carrier, and is delivered orally. In another preferred embodiment, the oligomer is a phosphorodiamidate morpholino oligomer, contained in a pharmaceutically acceptable carrier, and is delivered intravenously (i.v.).

In another application of the method, the subject is a livestock animal, e.g., a chicken, turkey, pig, cow or goat, etc, and the treatment is either prophylactic or therapeutic. The invention also includes a livestock and poultry food composition containing a food grain supplemented with a subtherapeutic amount of an antiviral antisense compound of the type described above. Also contemplated is, in a method of feeding livestock and poultry with a food grain supplemented with subtherapeutic levels of an antiviral, an improvement in which the food grain is supplemented with a subtherapeutic amount of an antiviral oligonucleotide composition as described above.

In one embodiment, the antisense compound is administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-1000 mg oligomer per 70 kg. In some cases, doses of greater than 1000 mg oligomer/patient may be necessary. For i.v. administration, preferred doses are from about 0.5 mg to 1000 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

An effective in vivo treatment regimen using the antisense oligonucleotides of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of viral infection under treatment, and corresponding adjustments in the dose or treatment regimen, in order to achieve an optimal therapeutic outcome. Treatment may be monitored, e.g., by general indicators of disease and/or infection, such as complete blood count (CBC), nucleic acid detection methods, immunodiagnostic tests, viral culture, or detection of heteroduplex.

The efficacy of an in vivo administered antiviral antisense oligomer of the invention in inhibiting or eliminating the growth of one or more types of RNA virus may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of viral protein production, as determined by standard techniques such as ELISA or Western blotting, or (3) measuring the effect on viral titer, e.g. by the method of Spearman-Karber. (See, for example, Pari, G. S. et al., Antimicrob. Agents and Chemotherapy 39(5):1157-1161, 1995; Anderson, K. P. et al., Antimicrob. Agents and Chemotherapy 40(9):2004-2011, 1996, Cottral, G. E. (ed) in: Manual of Standard Methods for Veterinary Microbiology, pp. 60-93, 1978).

In some embodiments, the oligomer is actively taken up by mammalian cells. In further embodiments, the oligomer may be conjugated to a transport moiety (e.g., transport peptide) as described herein to facilitate such uptake.

E. Preparation of the Oligomers

The morpholino subunits, the modified intersubunit linkages and oligomers comprising the same can be prepared as described in the examples and in U.S. Pat. Nos. 5,185,444 and 7,943,762 which are hereby incorporated by reference in their entirety. The morpholino subunits can be prepared according to the following general Reaction Scheme I.

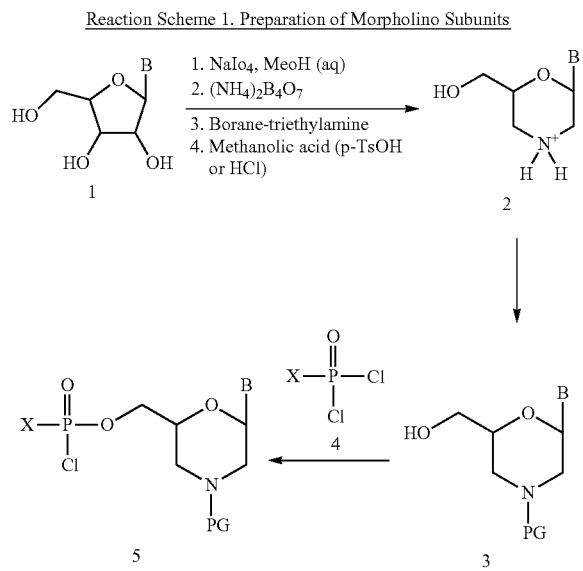

Referring to Reaction Scheme 1, wherein B represents a base pairing moiety and PG represents a protecting group, the morpholino subunits may be prepared from the corresponding ribonucleoside (1) as shown. The morpholino subunit (2) may be optionally protected by reaction with a suitable protecting group precursor, for example trityl chloride. The 3' protecting group is generally removed during solid-state oligomer synthesis as described in more detail below. The base pairing poiety may be suitable protected for sold phase oligomer synthesis. Suitable protecting groups include benzoyl for adenine and cytosine, phenylacetyl for guanine, and pivaloyloxymethyl for hypoxanthine (I). The pivaloyloxymethyl group can be introduced onto the N1 position of the hypoxanthine heterocyclic base. Although an unprotected hypoxanthine subunit, may be employed, yields in activation reactions are far superior when the base is protected. Other suitable protecting groups include those disclosed in co-pending U.S. application Ser. No. 12/271,040, which is hereby incorporated by reference in its entirety.

Reaction of 3 with the activated phosphorous compound 4, results in morpholino subunits having the desired linkage moiety 5. Compounds of structure 4 can be prepared using any number of methods known to those of skill in the art. For example, such compounds may be prepared by reaction of the corresponding amine and phosphorous oxychloride. In this regard, the amine starting material can be prepared using any method known in the art, for example those methods described in the Examples and in U.S. Pat. No. 7,943,762.

Figure 2:
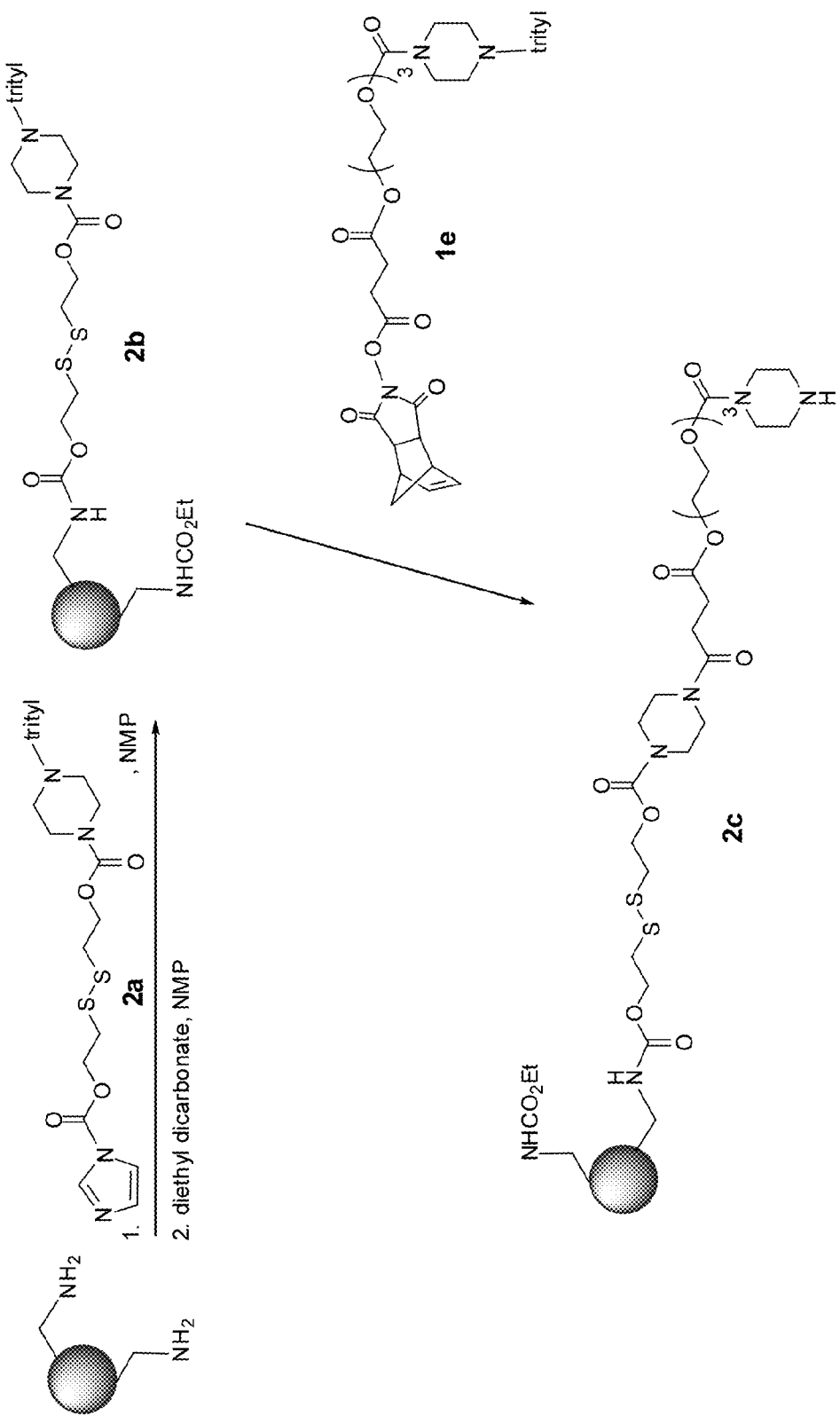
FIG. 2 illustrates preparation of a solid support for oligomer synthesis.
Figure 3:
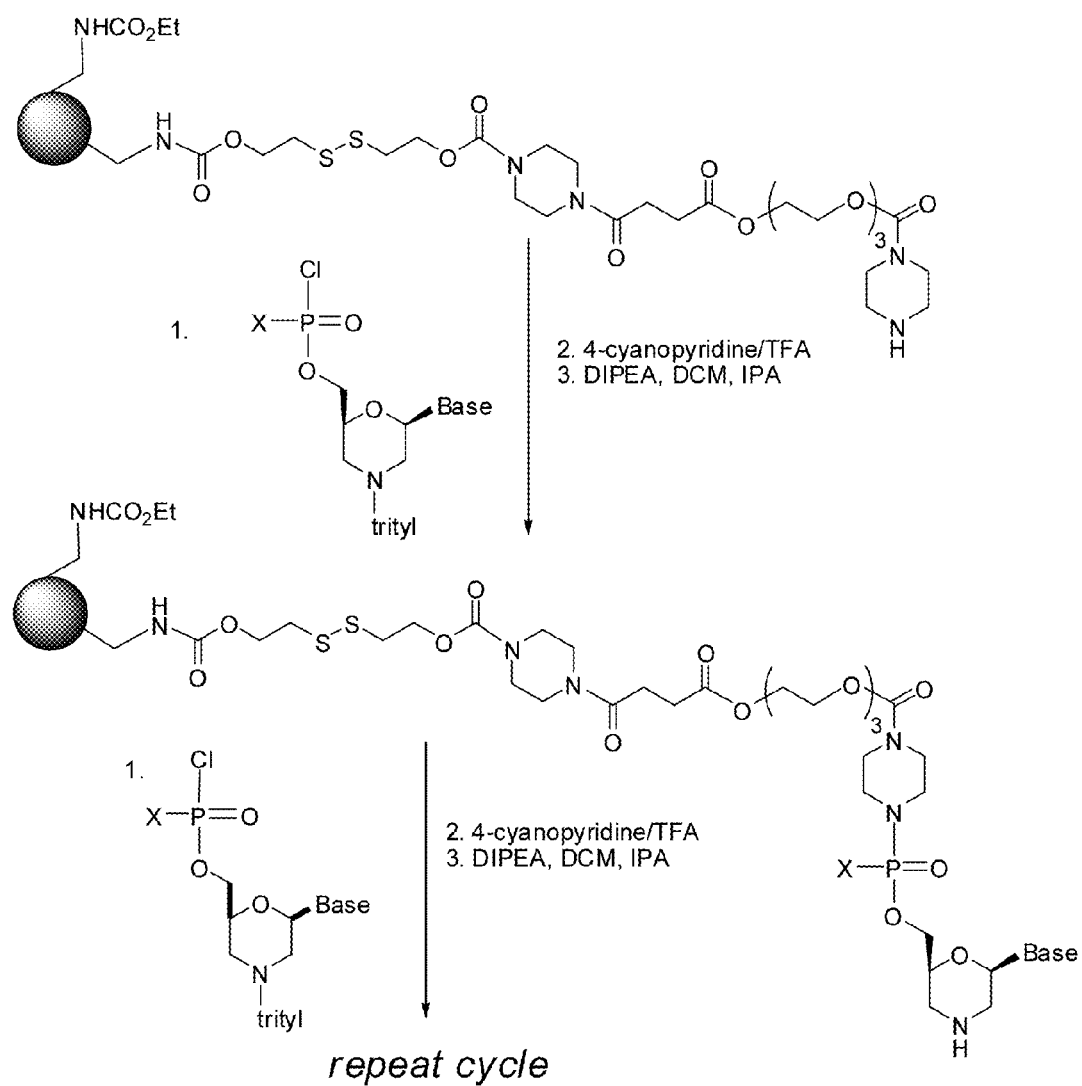
FIG. 3 illustrates solid phase synthesis of oligomers.
Figure 4:
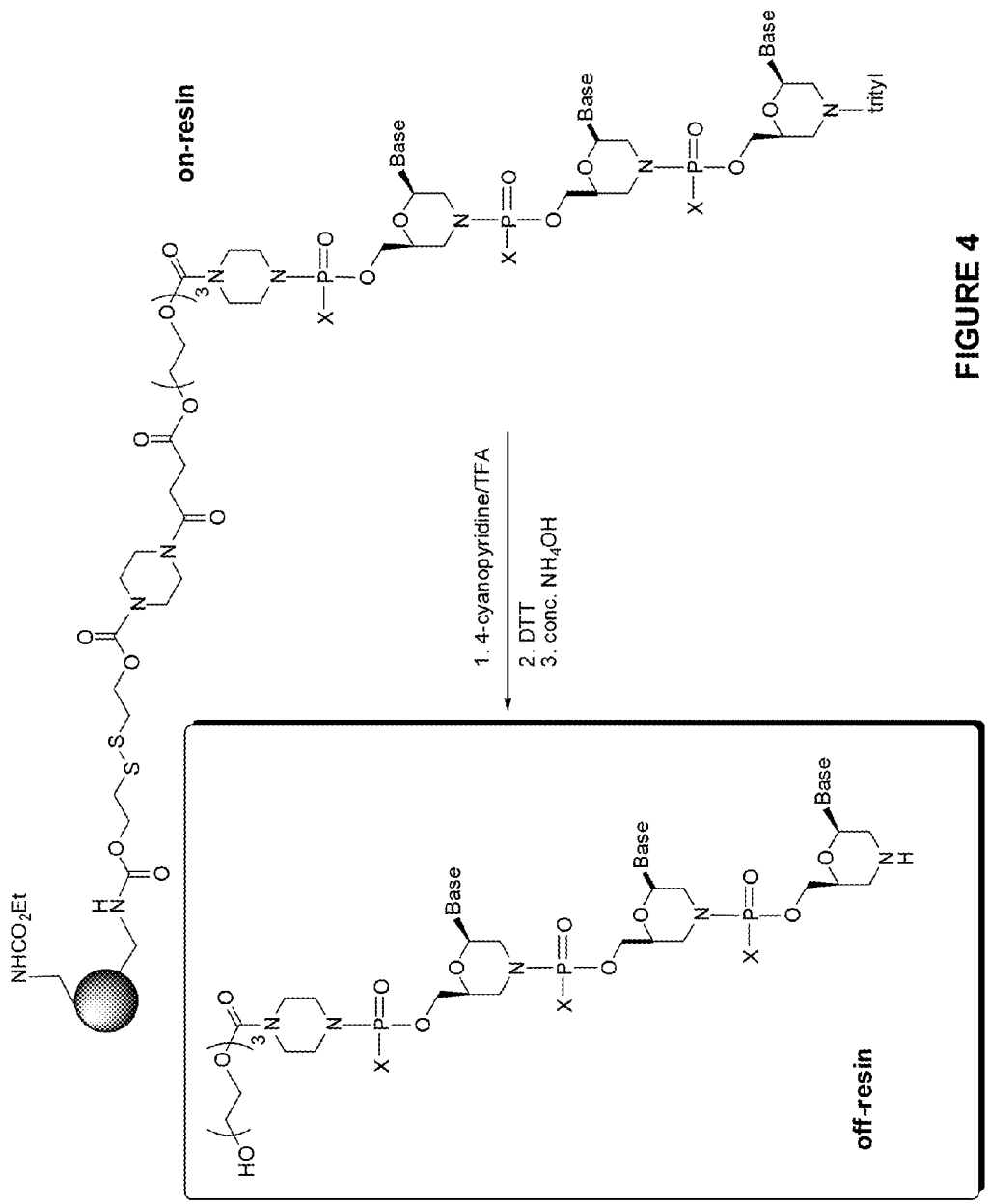
FIG. 4 illustrates cleavage of oligomer from solid support.

Compounds of structure 5 can be used in solid-phase automated oligomer synthesis for preparation of oligomers comprising the intersubunit linkages. Such methods are well known in the art. Briefly, a compound of structure 5 may be modified at the 5' end to contain a linker to a solid support. For example, compound 5 may be linked to a solid support by a linker comprising $L^{11}$ and $L^{15}$. An exemplary method is demonstrated in FIGS. 1 and 2. Once supported, the protecting group (e.g., trityl) is removed and the free amine is reacted with an activated phosphorous moiety of a second compound of structure 5. This sequence is repeated until the desired length oligo is obtained. The protecting group in the terminal 5' end may either be removed or left on if a 5'-modification is desired. The oligo can be removed from the solid support using any number of methods, for example treatment with DTT followed by ammonium hydroxide as depicted in FIG. 3.

The preparation of modified morpholino subunits and morpholino oligomers are described in more detail in the Examples. The morpholino oligomers containing any number of modified linkages may be prepared using methods described herein, methods known in the art and/or described by reference herein. Also described in the examples are global modifications of morpholino oligomers prepared as previously described (see e.g., PCT publication WO2008036127).

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups may be blocked with base labile groups such as Fmoc. A particularly useful amine protecting group for the synthesis of compounds of Formula (I) is the trifluoroacetamide. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups are known in the art and include, but are not limited to the following moieties:

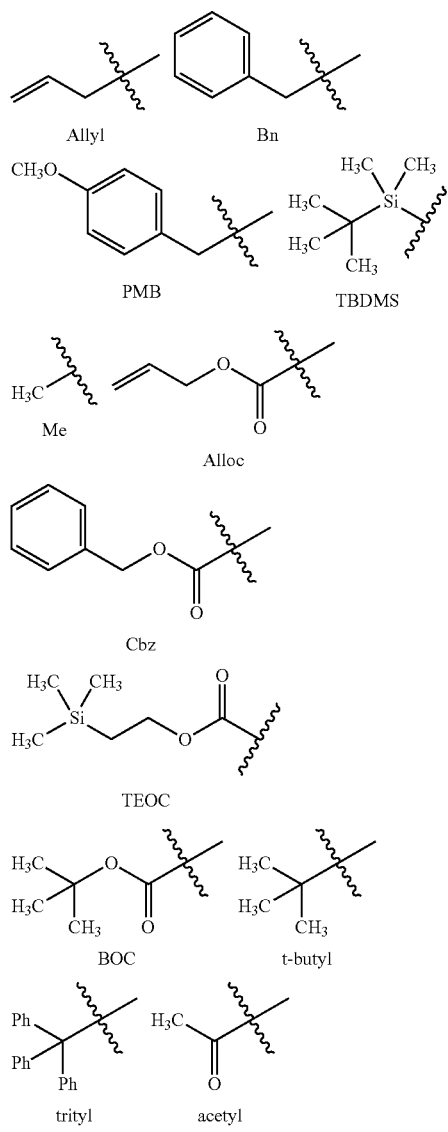

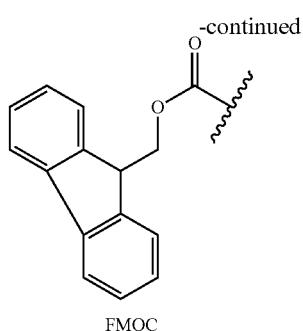

FMOC

F. Antisense Activity of the Oligomers

RNAi

RNA interference (RNAi) is a method of modulating gene expression. RNAi is a naturally occurring process. RNAi can also be induced by delivery of exogenous RNA sequences.

Naturally occurring RNAi is initiated by the recognition of double-stranded RNA sequences (dsRNA) by an RNase III enzyme (e.g., Dicer), followed by cleavage of the dsRNA into short fragments of ~20 nucleotides called small interfering RNAs (siRNAs). Dicer is an RNase III enzyme with ATPase/RNA helicase, a DUF283 (Domain of unknown function) domain, a PAZ (Piwi, Argonaut and Zwille) domain which can bind the characteristic two-base 3' overhangs of microRNA (miRNA) and siRNA, two catalytic RNase III domains (RIIIa and RIIIb), and a C-terminal double-stranded RNA-binding domain (dsRBD). Following cleavage, each siRNA molecule is unwound into two single-stranded RNA sequences (ssRNAs). One strand, the passenger, is degraded. The other stand, the guide, is incorporated into the RNA-induced silencing complex (RISC). RISC is a ribonucleoprotein complex containing members of the Argonaute (Ago) family of proteins. Argonaute proteins have endonuclease activity. RNAi occurs when the guide strand base binds to a complementary RNA sequence (for example, mRNA or pre-mRNA). The binding of the guide sequence induces cleavage of the guide sequence and the complementary sequence by Argonaute.

RNAi can also be initiated by the introduction of exogenous RNA sequences, for example siRNA sequences, miRNA sequences, and antisense oligonucleotides. Antisense oligonucleotides (AONs) are single-stranded oligonucleotides that are complementary to a target pre-mRNA or mRNA sequence. Once contacted with the complementary sequence, the AON will bind to the complementary sequence by Watson-Crick base-pair binding. In certain instances, an exogenous AON enters a cell. The AON binds to a complementary RNA sequence (e.g., pre-mRNA or mRNA), and the binding of the antisense sequence molecule induces cleavage of the complementary RNA sequence (e.g., by RNase-H).

Alternatively, AONs can be designed so that their binding does not induce cleavage of the complementary RNA strand, but instead disrupts processing of pre-mRNA (e.g., splicing, capping, polyadenylation), or changes or prevents the translation of mRNA sequences (e.g., by sterically interfering with the binding of one or more enzymes). For example, generating an AON as a morpholino results in an AON that does not support RNase-H mediated cleavage of the complementary strand. Instead, the binding of the morpholino AON to a target pre-mRNA sequence results in a stable complex that can (a) disrupt the ability of the splice some to splice the pre-mRNA (e.g., by blocking a splice acceptor site or a splice donor site), (b) disrupt capping the pre-mRNA, or (c) disrupt poly-adenylation of the pre-mRNA (e.g., by blocking the binding site for CPSF, CstF, or CFI).

The present disclosure provides a method of inhibiting or altering expression of a target nucleic acid sequence, the method comprising exposing a nucleic acid encoding the protein to an oligomer as disclosed herein. Accordingly, in one embodiment a target nucleic acid sequence is exposed to an antisense oligomer as described herein, or in other embodiments 10% to 50% such modified linkages, as disclosed herein, where the base pairing moieties Pi form a sequence effective to hybridize to a portion of the target nucleic acid sequence at a location effective to inhibit or alter expression of the target nucleic acid sequence. The oligomer may target, for example, an ATG start codon region of an mRNA, a splice site of a pre-mRNA, or a viral target sequence as described below. In another embodiment, the method comprises exposing a target nucleic acid sequence to an antisense oligomer comprising at least one terminal modification. In another embodiment, the method comprises exposing a target nucleic acid sequence to an antisense oligomer comprising a peptide transporter moiety.

In another embodiment, the disclosure provides a method of enhancing antisense activity of an oligomer having a sequence of morpholino subunits, joined by intersubunit linkages, supporting base-pairing moieties, the method comprises modifying an oligomer as described herein to contain at least one of the modified terminal groups, at least one intersubunit linkage wherein X does not equal X1 or combinations thereof.

In some embodiments, enhancement of antisense activity may be evidenced by:

(i) a decrease in expression of a target nucleic acid sequence, relative to that provided by a corresponding unmodified oligomer, or (ii) an increase in expression of a target nucleic acid sequence, relative to that provided by a corresponding unmodified oligomer. Assays suitable for measurement of these effects are described further below. In one embodiment, modification provides this activity in a cell-free translation assay, a splice correction translation assay in cell culture, or a splice correction gain of function animal model system as described herein. In one embodiment, activity is enhanced by a factor of at least two, at least five or at least ten.

Described below are various exemplary applications of the oligomers of the invention including antimicrobial (e.g., antivirals and antibacterials) applications, treatment by altering gene expression, cancer treatment, and treatment of inflammatory, cardiovascular, and metabolic disorders. This description is not meant to limit the invention in any way but serves to exemplify the range of diseases and disorders that can be addressed using oligomers comprising the modified intersubunit linkages described herein.

Antisense oligonucleotides have been used as antimicrobial drugs (e.g., antivirals and antibacterials). In some embodiments, a compound of Formula (I) as disclosed herein is used as an antiviral drug. In some embodiments, a compound of Formula (I) as disclosed herein is used to inhibit the expression of virally-encoded proteins. In some embodiments, inhibiting the expression of virally-encoded proteins treats a viral infection. In some embodiments, the oligomers can be used in methods of inhibiting in a mammalian host cell, replication of an infecting RNA virus having a single-stranded, positive-sense genome. The method includes administering to the infected host cells, a virus-inhibitory amount of an oligomer as described herein, having a targeting sequence of at least 12 subunits that is complementary to a target nucleic acid sequence of the virus. The compound may be administered to a mammalian subject infected with the virus, or at risk of infection with the virus. In some embodiments, the target sequence encodes a polyprotein containing non-structural proteins such as polymerases, helicases and proteases. In some embodiments, the target sites include targets that are conserved between a variety of viral isolates. Other favored sites include the IRES (internal ribosome entry site), transactivation protein binding sites, and sites of initiation of replication.

In some embodiments, a compound of Formula (I) as disclosed herein is used as an antibacterial drug. In some embodiments, a compound of Formula (I) as disclosed herein inhibits the expression of a bacterial virulence factor (e.g., a toxin or a protein that inhibits a host immune response). In some embodiments, inhibiting the expression of a bacterial virulence factor treats a bacterial infection.

In some embodiments, a compound of Formula (I) as disclosed herein is used treat a disease or disorder (e.g., cancer, inflammatory, metabolic, neurological, cardiovascular) by altering the expression of a gene. In some embodiments, a compound of Formula (I) as disclosed herein is used treat a disease or disorder characterized by undesired or excessive expression of a gene. For example, disorders characterized by undesired angiogenesis may be treated by using a compound of Formula (I) as disclosed herein to inhibit the expression of VEGF or any other gene implicated in angiogenesis. In some embodiments, disorders characterized by mutated (e.g., non-functional) gene products are treated by a compound of Formula (I) as disclosed herein. For example, Duchenne Muscular Dystrophy (DMD) is characterized by somatic mutations that lead to truncated and non-functional dystrophin. Antisense oligonucleotides have been used to alter the splicing of mutant dystrophin pre-mRNA such that a truncated but functional dystrophin protein is produced.

In some embodiments, a compound of Formula (I) as disclosed herein is used treat a cancer. In some embodiments, a compound of Formula (I) as disclosed herein is used to decrease the expression of a gene that inhibits apoptosis, inhibits cell adhesion, promotes angiogenesis, promotes cell proliferation, promotes cell growth, or participates in DNA repair. For example, some cancers are associated with the over-expression of anti-apoptotic genes. Inhibiting the expression of these genes by use of a compound of Formula (I) as disclosed herein may result in an increase in apoptosis of cancer cells or an increased sensitivity to chemotherapeutic agents.

In some embodiments, a compound of Formula (I) as disclosed herein is used treat an inflammatory disorder. In some embodiments, a compound of Formula (I) as disclosed herein is used to decrease the expression of cytokines or cell surface molecules involved in chemotaxis. For example, autoimmune disorders are associated with the undesired and excessive immune cell migration. Inhibiting the expression of cytokines or cell surface molecules associated with chemotaxis may result in a decrease in immune cell migration and inflammation.

In some embodiments, a compound of Formula (I) as disclosed herein is used treat a cardiovascular disorder. In some embodiments, a compound of Formula (I) as disclosed herein is used to inhibit the expression of lipoproteins, or inhibit the expression of proteins or enzymes that decrease the levels of cardioprotective molecules (e.g., HDL).

In some embodiments, a compound of Formula (I) as disclosed herein is used treat a metabolic disorder. In some embodiments, a compound of Formula (I) as disclosed herein is used to inhibit the expression of gene products that lead to decreased insulin sensitivity or decreased metabolic rates.

In some embodiments, a compound of Formula (I) as disclosed herein is used treat a neurological disorder. In some embodiments, a compound of Formula (I) as disclosed herein is used to inhibit the expression of gene products that lead to decreased neural transmission (e.g., gene products that decrease myelin).

In some embodiments, a compound of Formula (I) as disclosed herein is used to modulate expression of nuclear hormone receptors (NHR) from the nuclear hormone receptor superfamily (NHRSF). Examples of particular NHRs include glucocorticoid receptor (GR), progesterone receptor (PR) and androgen receptor (AR). In certain embodiments, the antisense oligonucleotides and agents described herein lead to increased expression of ligand-independent or other selected forms of the receptors, and decreased expression of their inactive forms.

NHR modulators may be useful in treating NHR-associated diseases, including diseases associated with the expression products of genes whose transcription is stimulated or repressed by NHRs. Compounds that antagonize transactivation can be useful in treating metabolic diseases associated with increased levels of glucocorticoid, such as diabetes, osteoporosis and glaucoma, among others. Also, compounds that agonize transactivation can be useful in treating metabolic diseases associated with a deficiency in a nuclear hormone receptor.

Modifications

The function of an antisense oligonucleotide is dependent on both the sequence of the AON and the chemical structure of the AON. Various modifications may be made by adding moieties to or replacing portions of the nucleotides not involved in Watson-Crick base-pair binding. Modifications to the chemical structure can affect the affinity, stability, solubility, toxicity, and stability of the AON.

Different modifications may increase the affinity of the AON for the complementary sequence. They may also decrease affinity for non-complementary sequences. Changes to the charge or chirality of a backbone may also affect affinity.

Modifications may increase resistance to undesired degradation by nucleases. Modifications may also increase or decrease the affinity of the AON for RNase H. For example, morpholino oligonucleotides and peptide nucleic acids (PNAs) do not activate RNase H.

Modifications may be designed such that they increase the size of the AON such that it is not readily filtered by the glomerulus. For example, PEGylation of an AON increases the size of an AON such that renal filtration is reduced. Modifications can increase the ability of the AON to bind to plasma proteins in vivo such that they are not rapidly filtered from the blood.

The toxicity of the AON can also be affected by modifications to the chemical structure of the AON. Where it is desirable, toxicity may be increased by certain modifications (e.g., when using the AON as an antimicrobial). Alternatively, toxicity may be decreased by certain modifications. Phosphorodithioate analogs have increased toxicity as compared to other analogs.

Further, modifications to the chemical structure of AONs may result in the AON being directed to specific tissues, organs, or cells. An AON can be directed to a specific tissue by modifying the AON such that it recognizes tissue-specific proteins expressed by the cells of the targeted tissues. The conjugation of a ligand may target an AON to a specific cell. For example, an AON may be conjugated to a ligand that recognizes and binds to a specific receptor only found on specific cells (e.g., hepatocytes). The AON/ligand conjugate bonds to the receptor and accesses the cell by receptor-mediated endocytosis. Conjugating cholesterol to an AON may target the AON to the liver. Further, modifications that promote cell/tissue-specific uptake include the conjugation of polymers, carbohydrate- or peptide-labeled nanoparticles, or liposomes capable of recognizing cell-specific proteins.

Modifications to the chemical structure may also enhance the ability of the AON to enter a cell. In certain instances, conjugating lipids to an AON may increase cellular uptake. Additional conjugates may include protein transduction signals and nuclear localization signals.

Additionally, AONs may be modified to carry cargo. Therapeutic or prophylactic agents may be conjugated to AONs. For example, an AON targeting a cancer cell may further comprise a known chemotherapeutic agent or an AON targeting a bacterial cell may be conjugated to an antibacterial agent. Labels may also be conjugated to AONs, for example so that proper targeting may be monitored or progress of treatment may be monitored. AONs may be conjugated to radiolabels, contrast agents (e.g., gadolinium), or fluorophores.

Modifications to the chemical structure of the AON may also affect the method of administering the AON. Modifications may promote transdermal or transmucosal penetration such that the AON may be administered topically (e.g., as a nasal spray, ear drop, eye drop, oral spray). As discussed above, modifications may increase resistance to renal filtration such that the AON may be administered parenterally. Modifications may result in an AON that may be orally administered by increasing the AON's resistance to degradation by the acidic environment of the stomach or the basic environment of the intestines.

In certain instances, varying the modifications to individual nucleotides may result in an increase in desirable properties or a decrease in undesirable properties.

EXAMPLES

I. Chemical Synthesis

Unless otherwise noted, all chemicals were obtained from Sigma-Aldrich-Fluka. Benzoyl adenosine, benzoyl cytidine, and phenylacetyl guanosine were obtained from Carbosynth Limited, UK.

Synthesis of PMO, PMO+, PPMO and PMO containing further linkage modifications as described herein was done using methods known in the art and described in pending U.S. application Ser. Nos. 12/271,036 and 12/271,040 and PCT publication number WO/2009/064471, which are hereby incorporated by reference in their entirety.

PMO with a 3' trityl modification are synthesized essentially as described in PCT publication number WO/2009/064471 with the exception that the detrytilation step is omitted.

Procedure a for the Preparation of Activated Subunits

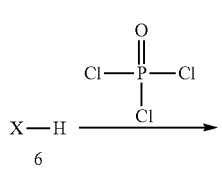

-continued

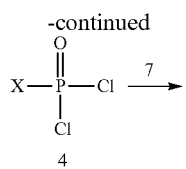

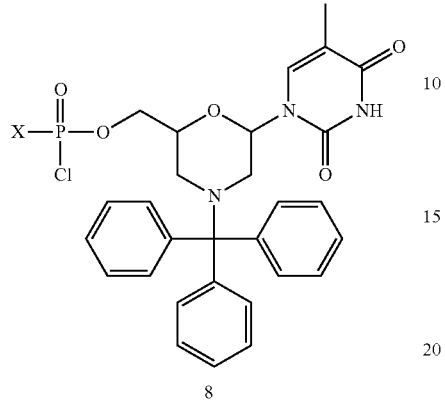

-continued

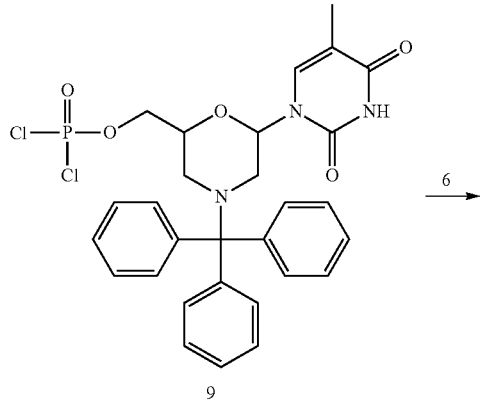

To a stirred solution of 6 (1 eq) in dichloromethane was added POCl₃ (1.1 eq), followed by diisopropylethylamine (3 eq) at 0° C., cooled by an ice-bath. After 15 minutes, the ice-bath was removed and the solution was allowed to warm to room temperature for one hour. Upon reaction completion, the reaction solution was diluted with dichloromethane, washed with 10% aqueous citric acid three times. After drying over MgSO₄, the organic layer was passed through a plug of silica gel and concentrated in vacuo. The resulting phosphoroamidodichloride (4) was used directly for the next step without further purification.

To a solution of the phosphoroamidodichloride (4) (1 eq), 2,6-lutidine (1 eq) in dichloromethane was added Mo(Tr)T (7) (0.5 eq)/dichloromethane solution, followed by N-methylimidazole (0.2 eq). The reaction stirred at room temperature overnight. Upon reaction completion, the reaction solution was diluted with dichloromethane, and washed with 10% aqueous citric acid three times. After drying over MgSO₄, the organic layer was filtered, then concentrated. The product (8) was purified by silica gel chromatography (eluting with a gradient of ethyl acetate/hexanes), and then stored at −20° C. The structure was confirmed by LCMS analysis.

Procedure B for the Preparation of Activated Subunits

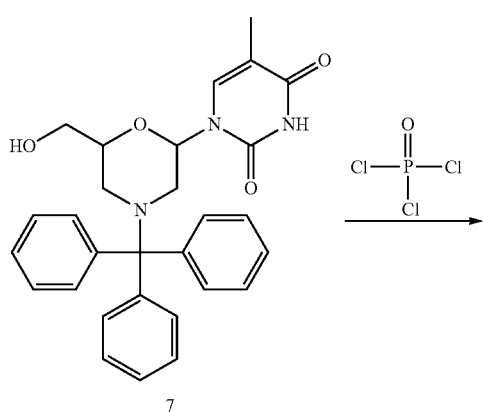

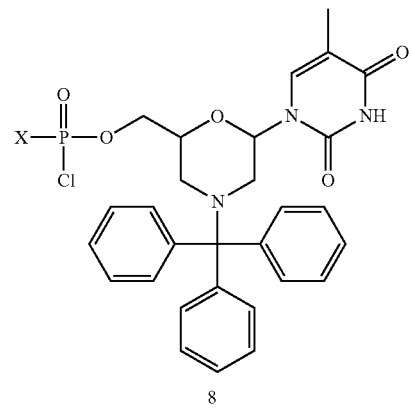

To a solution of POCl₃ (1.1 eq) in dichloromethane was added 2,6-lutidine (2 eq), followed by dropwise addition of Mo(Tr)T (7) (1 eq)/dichloromethane solution at 0° C. After 1 hour, the reaction solution was diluted with dichloromethane, and quickly washed three times with 10% aqueous citric acid. The desired phosphodichloridate (9) was obtained after drying over MgSO₄ and evaporation of solvent.

To a solution of the phosphodichloridate (1 eq) in dichloromethane was added 6 (1 eq)/dichloromethane dropwise to the solution at 0° C. After 15 minutes, the reaction mixture was allowed to warm to room temperature for about an hour. Upon reaction completion, the product (8) as a white solid was collected by precipitation with the addition of hexanes, followed by filtration. The product was stored at −20° C. after drying under vacuum. The structure was confirmed by LCMS analysis.

Example 1

((2S,6R)-6-(5-methyl-2,4-dioxo-3,4-dihydropyrimidin-1(2H)-yl)-4-tritylmorpholin-2-yl)methyl phosphorodichloridate

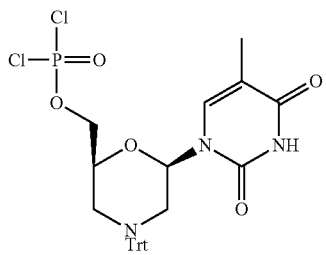 [SMILES: Cc1cn([C@H]2CNC[C@@H](COP(=O)(Cl)Cl)O2)c(=O)[nH]c1=O]

To a cooled (ice/water bath) DCM solution (20 mL) of phosphorus oxychloride (2.12 mL, 22.7 mmol) was added dropwise 2,6-lutidine (4.82 mL, 41.4 mmol) then a DCM solution (20 mL) Mo(Tr)T (2) (10.0 g, 20.7 mmol) was added dropwise over 15 min (int. temp. 0-10° C.) then bath was removed a stirring continued at ambient temperature for 20 min. The reaction was washed with citric acid solution (40 mL×3, 10% w/v aq), dried (MgSO$_4$), filtered and concentrated to a white foam (9.79 g) then used directly for the following procedure.

Example 2

(6-(5-methyl-2,4-dioxo-3,4-dihydropyrimidin-1(2H)-yl)-4-tritylmorpholin-2-yl)methyl (4-(dimethylamino)piperidin-1-yl)phosphonochloridate

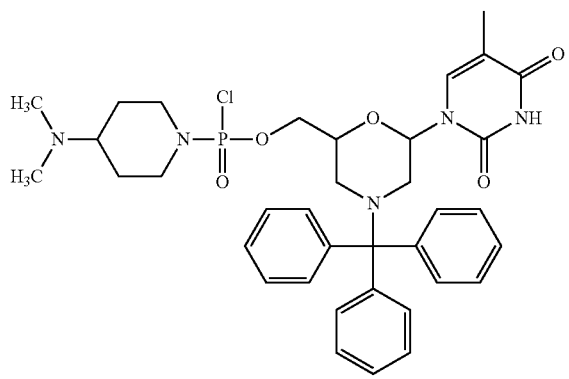 [SMILES: Cc1cn(C2CN(C(c3ccccc3)(c3ccccc3)c3ccccc3)CC(COP(=O)(Cl)N3CCC(N(C)C)CC3)O2)c(=O)[nH]c1=O]

To a cooled (ice/water bath) DCM solution (5 mL) of the dichlorophosphate from example 1 (5.00 g, 5.00 mmol) was added a DCM solution (5 mL) of the piperidine (0.61 g, 4.76 mmol) dropwise then the bath was removed and stirring continued at ambient temperature for 30 min. The reaction was loaded directly onto column. Chromatography [SiO$_2$ column (40 g), DCM/EtOH eluant (gradient 1:0 to 1:1)] to afford the title compound (2.5 g) as a white foam. ESI/MS calcd. for 1-(4-nitrophenyl)piperazine derivative C$_{46}$H$_{55}$N$_8$O$_7$P 862.4. found m/z=863.6 (M+1).

Example 3

1-(1-(chloro((6-(5-methyl-2,4-dioxo-3,4-dihydropyrimidin-1(2H)-yl)-4-tritylmorpholin-2-yl)methoxy)phosphoryl)piperidin-4-yl)-1-methylpyrrolidin-1-ium chloride

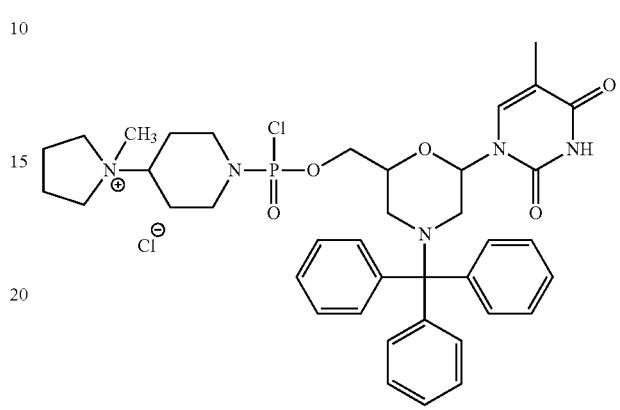

The title compound was synthesized in a manner analogous to that described in Example 2 to afford the title compound (0.6 g) as a white solid. ESI/MS calcd. for 1-(4-nitrophenyl)piperazine derivative C$_{49}$H$_{60}$N$_8$O$_7$P 903.4. found m/z=903.7 (M+).

Example 4

((2S,6R)-6-(5-methyl-2,4-dioxo-3,4-dihydropyrimidin-1(2H)-yl)-4-tritylmorpholin-2-yl)methyl (4-methylpiperazin-1-yl)phosphonochloridate

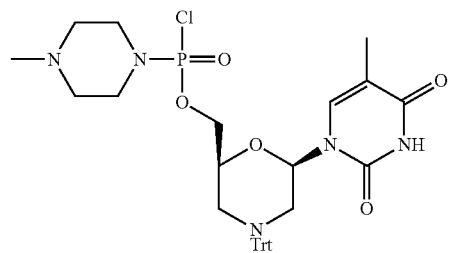

To a cooled (ice/water bath) DCM solution (10 mL) of phosphorus oxychloride (1.02 mL, 11.0 mmol) was added dropwise 2,6-lutidine (3.49 mL, 29.9 mmol) then a DCM solution (10 mL) of methyl piperazine (1.00 g, 10.0 mmol) was added dropwise and stirring continued for 1 h. A DCM solution (10 mL) of Mo(Tr)T (2) (4.82, 10.0 mmol) and NMI (79 µL, 1.0 mmol) was added and stirred 4 h then loaded directly onto column. Chromatography [SiO$_2$ column (80 g), DCM/Acetone with 2% TEA eluant (gradient 1:0 to 0:1)] to afford the title compound (0.8 g) as a white foam. ESI/MS calcd. for 1-(4-nitrophenyl)piperazine derivative C$_{43}$H$_{48}$N$_7$O$_8$P 834.4. found m/z=835.5 (M+1).

Example 5

((2S,6R)-6-(5-methyl-2,4-dioxo-3,4-dihydropyrimidin-1(2H)-yl)-4-tritylmorpholin-2-yl)methyl morpholinophosphonochloridate

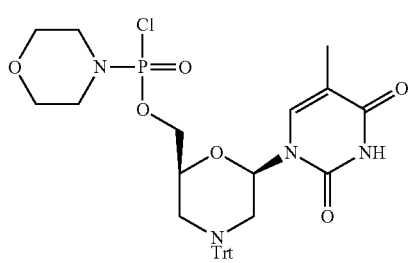

To a cooled solution (ice/water bath) of phosphorus oxychloride (19.1 mL, 205 mmol) in DCM (410 mL) was added dropwise 2,6-lutidine (54.2 mL, 465 mmol) then Mo(Tr)T (2) (90.0 g, 186 mmol) portionwise over 15 min (int. temp. 0-10° C.) and stirred. After 5 min, a DCM solution (205 mL) of morpholine (17.9 mL, 205 mmol) was added dropwise over 15 min (int. temp. 0-8° C.) and stirred. After 15 min, additional DCM solution (10 mL) of morpholine (0.500 mL) was added, stirred 5 min then washed with citric acid solution (300 mL×3, 10% w/v aq), dried (MgSO$_4$), filtered and concentrated to a viscous oil which was loaded directly onto column. Chromatography [SiO$_2$ column (330 g), hexanes/EtOAc eluant (gradient 1:0 to 0:1)] to afford the title compound (78.5 g, 65% yield) as a white foam. ESI/MS calcd. for 1-(4-nitrophenyl)piperazine derivative $C_{43}H_{48}N_7O_8P$ 821.3. found m/z=844.4 (M+Na).

Example 6

(9-((2R,6S)-6-((((chloro(morpholino)phosphoryl)oxy)methyl)-4-tritylmorpholin-2-yl)-6-oxo-6,9-dihydro-1H-purin-1-yl)methyl pivalate

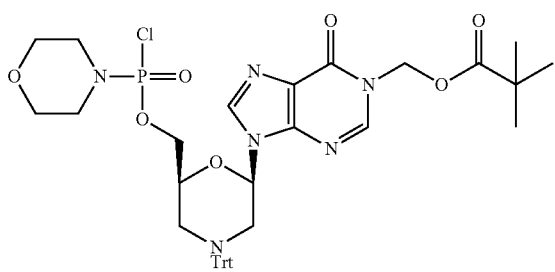

The title compound was synthesized in a manner analogous to that described in Example 5 to afford the title compound (6.35 g, 79% yield) as a white foam. ESI/MS calcd. for 1-(4-nitrophenyl)piperazine derivative $C_{49}H_{56}N_9O_9P$ 945.4. found m/z=1891.9 (2M+1).

Example 7

((2S,6R)-6-(5-methyl-2,4-dioxo-3,4-dihydropyrimidin-1(2H)-yl)-4-tritylmorpholin-2-yl)methyl (4-ethylpiperazin-1-yl)phosphonochloridate

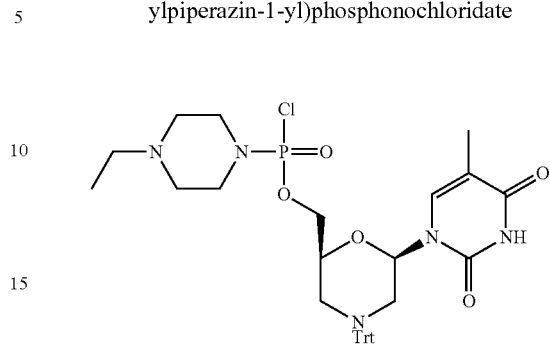

The title compound was synthesized in a manner analogous to that described in Example 5 to afford the title compound (11.5 g) as a white foam. ESI/MS calcd. for 1-(4-nitrophenyl)piperazine derivative $C_{45}H_{53}N_8O_7P$ 848.4. found m/z=849.7 (M+1).

Example 8

((2S,6R)-6-(6-benzamido-9H-purin-9-yl)-4-tritylmorpholin-2-yl)methyl (4-ethylpiperazin-1-yl)phosphonochloridate

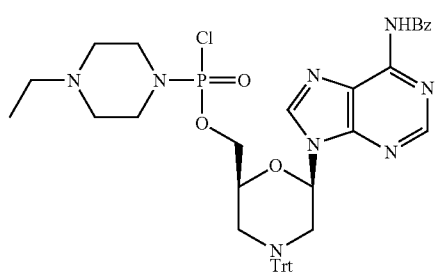

The title compound was synthesized in a manner analogous to that described in Example 5 to afford the title compound (4.5 g) as a white foam. ESI/MS calcd. for 1-(4-nitrophenyl)piperazine derivative $C_{52}H_{56}N_{11}O_6P$ 961.4. found m/z=962.8 (M+1).

Example 9

((2S,6R)-6-(5-methyl-2,4-dioxo-3,4-dihydropyrimidin-1(2H)-yl)-4-tritylmorpholin-2-yl)methyl (4-isopropylpiperazin-1-yl)phosphonochloridate

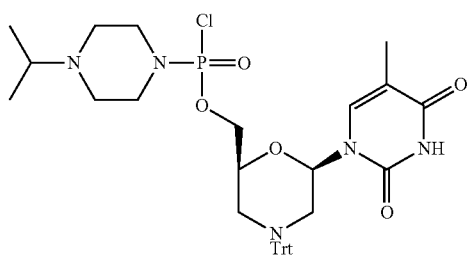

The title compound was synthesized in a manner analogous to that described in Example 5 to afford the title compound (3.5 g) as a white foam. ESI/MS calcd. for 1-(4-nitrophenyl)piperazine derivative $C_{46}H_{55}N_8O_7P$ 862.4. found m/z=863.7 (M+1).

Example 10

((2S,6R)-6-(5-methyl-2,4-dioxo-3,4-dihydropyrimidin-1(2H)-yl)-4-tritylmorpholin-2-yl)methyl methyl (2-(2,2,2-trifluoroacetamido)ethyl)phosphoramidochloridate

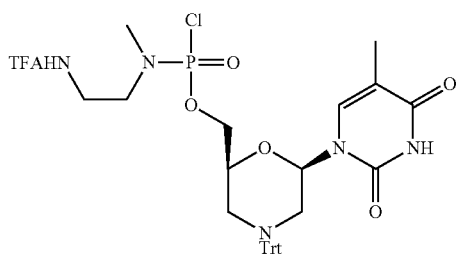

The title compound was synthesized in a manner analogous to that described in Example 5 to afford the title compound (1.0 g) as a white foam. ESI/MS calcd. for 1-(4-nitrophenyl)piperazine derivative $C_{44}H_{48}F_3N_8O_8P$ 904.3. found n/z=903.7 (M−1).

Example 11

((2S,6R)-6-(5-methyl-2,4-dioxo-3,4-dihydropyrimidin-1(2H)-yl)-4-tritylmorpholin-2-yl)methyl methyl (2-(2,2,2-trifluoro-n-methylacetamido)ethyl)phosphoramidochloridate

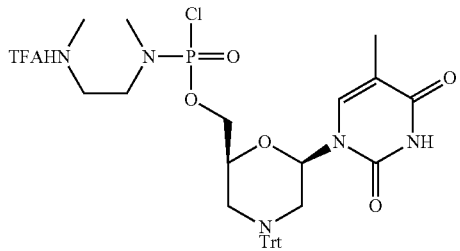

The title compound was synthesized in a manner analogous to that described in Example 5 to afford the title compound (1.8 g) as a white foam. ESI/MS calcd. for 1-(4-nitrophenyl)piperazine derivative $C_{45}H_{50}F_3N_8O_8P$ 918.3. found m/z=1836.6 (2M+).

Example 12

((2S,6R)-6-(5-methyl-2,4-dioxo-3,4-dihydropyrimidin-1(2H)-yl)-4-tritylmorpholin-2-yl)methyl (4-(2,2,2-trifluoroacetamido)piperidin-1-yl)phosphonochloridate

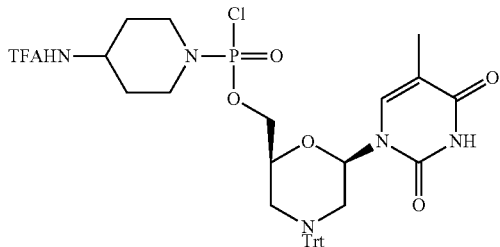

To a cooled solution (ice/water bath) of phosphorus oxychloride (17.7 mL, 190 mmol) in DCM (190 mL) was added dropwise 2,6-lutidine (101 mL, 864 mmol) then Mo(Tr)T (2) (83.5 g, 173 mmol) portionwise over 15 min (int. temp. 0-10° C.) and stirred. After 30 min, the piperidine (48.9 g, ~190 mmol) was added dropwise over 15 min (int. temp. 0-8° C.) and stirred. After 1 h, DIPEA (50 mL) was added dropwise (int. temp. 0-10° C.) and stirred 1 h. The reaction was washed with citric acid solution (500 mL×3, 10% w/v aq), dried (MgSO$_4$), filtered and concentrated to a viscous oil which was loaded directly onto column. Chromatography [SiO$_2$ column (330 g), hexanes/EtOAc eluant (gradient 1:0 to 0:1)] to afford the title compound (91.3 g, 70% yield) as a white foam. ESI/MS calcd. for 1-(4-nitrophenyl)piperazine derivative $C_{43}H_{48}N_7O_8P$ 930.9. found m/z=954.4 (M+Na).

Examples 13-37 were prepared via procedure A described above.

Example 13

(6-(5-methyl-2,4-dioxo-3,4-dihydropyrimidin-1(2H)-yl)-4-tritylmorpholin-2-yl)methyl (4-(1-(2,2,2-trifluoroacetyl)piperidin-4-yl)piperazin-1-yl)phosphonochloridate

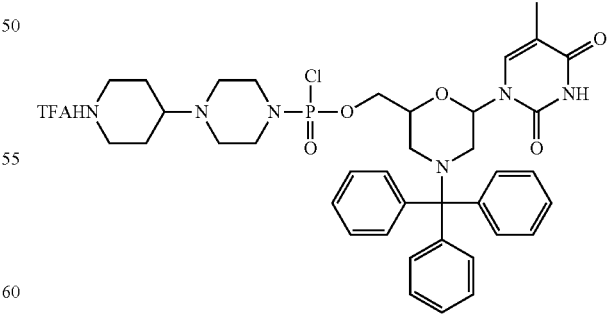

The title compound was synthesized in a manner analogous to that described in procedure A to afford the title compound (1.09 g, 23% yield). ESI/MS calcd. for 1-(4-nitrophenyl)piperazine derivative $C_{51}H_{58}F_3N_8O_8P$ 998.41. found m/z=997.5 (M−1).

Example 14

(6-(5-methyl-2,4-dioxo-3,4-dihydropyrimidin-1(2H)-yl)-4-tritylmorpholin-2-yl)methyl (4-morpholinopiperidin-1-yl)phosphonochloridate

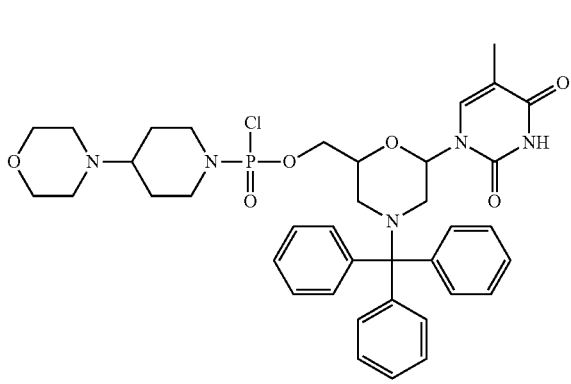 [SMILES: Cc1cn(C2CN(C(c3ccccc3)(c3ccccc3)c3ccccc3)CC(COP(=O)(Cl)N3CCC(N4CCOCC4)CC3)O2)c(=O)[nH]c1=O]

The title compound was synthesized in a manner analogous to that described in procedure A to afford the title compound (0.98 g, 84% yield). ESI/MS calcd. for 1-(4-nitrophenyl)piperazine derivative $C_{48}H_{57}N_8O_8P$ 904.40. found m/z=903.5 (M−1).

Example 15

(6-(5-methyl-2,4-dioxo-3,4-dihydropyrimidn-1(2H)-yl)-4-tritylmorpholin-2-yl)methyl bis(3-(2,2,2-trifluoroacetamido)propyl)phosphoramidochloridate

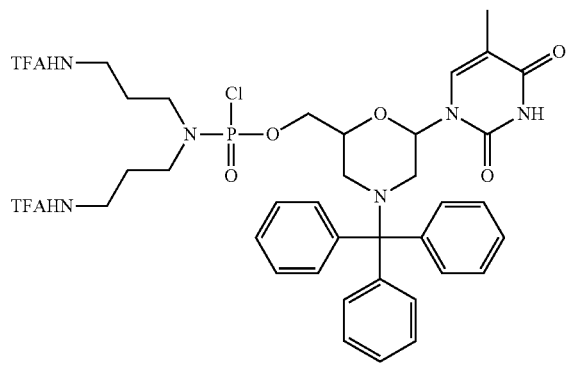

The title compound was synthesized in a manner analogous to that described in procedure A to afford the title compound (7.52 g). ESI/MS calcd. for 1-(4-nitrophenyl)piperazine derivative $C_{49}H_{54}F_6N_9O_9P$ 1057.37. found m/z=1056.4 (M−1).

Example 16

(6-(5-methyl-2,4-dioxo-3,4-dihydropyrimidin-1(2H)-yl)-4-tritylmorpholin-2-yl)methyl methyl(6,7,9,10,17,18,20,21-octahydrodibenzo [b,k][1,4,7,10,13,16]hexaoxacyclooctadecin-2-yl)phosphoramidochloridate

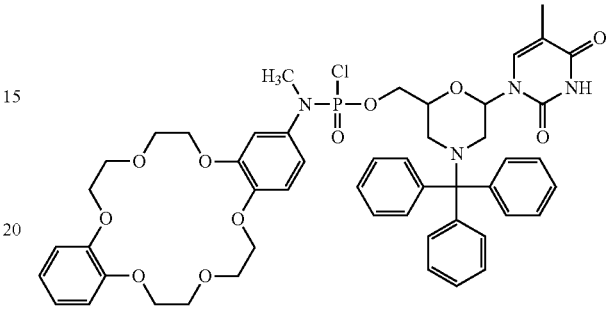

The title compound was synthesized in a manner analogous to that described in procedure A to afford the title compound (0.30 g). ESI/MS calcd. for $C_{50}H_{56}ClN_4O_{11}P$ 952.32. found m/z=951 (M−1).

Example 17

(6-(5-methyl-2,4-dioxo-3,4-dihydropyrimidin-1(2H)-yl)-4-tritylmorpholin-2-yl)methyl 1,4,7,10-tetraoxa-13-azacyclopentadecan-13-ylphosphonochloridate

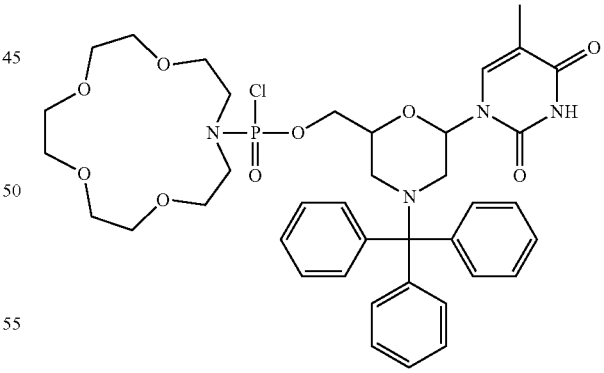

The title compound was synthesized in a manner analogous to that described in procedure A to afford the title compound (4.26 g, 25% yield). ESI/MS calcd. for 1-(4-nitrophenyl)piperazine derivative $C_{49}H_{60}N_7O_{11}P$ 953.41. found m/z=952.7 (M−1).

Example 18

(6-(5-methyl-2,4-dioxo-3,4-dihydropyrimidin-1(2H)-yl)-4-tritylmorpholin-2-yl)methyl 1,4,7,10,13-pentaoxa-16-azacyclooctadecan-16-ylphosphonochloridate

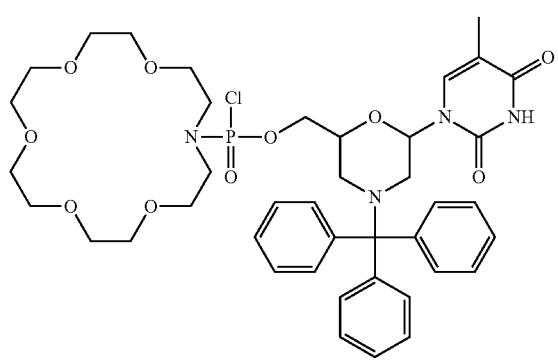 [SMILES: Cc1cn(C2CN(C(c3ccccc3)(c3ccccc3)c3ccccc3)CC(COP(=O)(Cl)N3CCOCCOCCOCCOCCOCC3)O2)c(=O)[nH]c1=O]

The title compound was synthesized in a manner analogous to that described in procedure A to afford the title compound (1.11 g, 18% yield). ESI/MS calcd. for 1-(4-nitrophenyl)piperazine derivative $C_{51}H_{64}N_7O_{12}P$ 997.44. found m/z=996.6 (M−1).

Example 19

(6-(5-methyl-2,4-dioxo-3,4-dihydropyrimidin-1(2H)-yl)-4-tritylmorpholin-2-yl)methyl (4-oxopiperidin-1-yl)phosphonochloridate

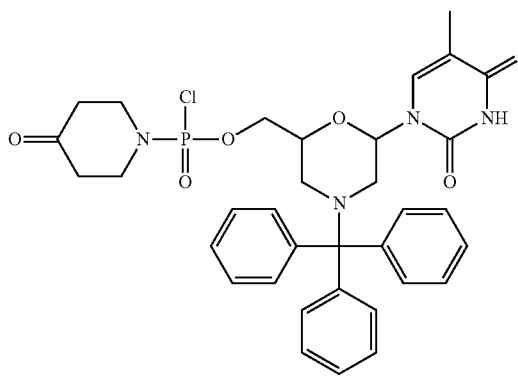

The title compound was synthesized in a manner analogous to that described in procedure A to afford the title compound (1.03 g, 14% yield). ESI/MS calcd. for 1-(4-nitrophenyl)piperazine derivative $C_{44}H_{48}N_7O_8P$ 833.33. found m/z=832.4 (M−1).

Example 20

(6-(5-methyl-2,4-dioxo-3,4-dihydropyrimidin-1(2H)-yl)-4-tritylmorpholin-2-yl)methyl (octahydroisoquinolin-2(1H)-yl)phosphonochloridate

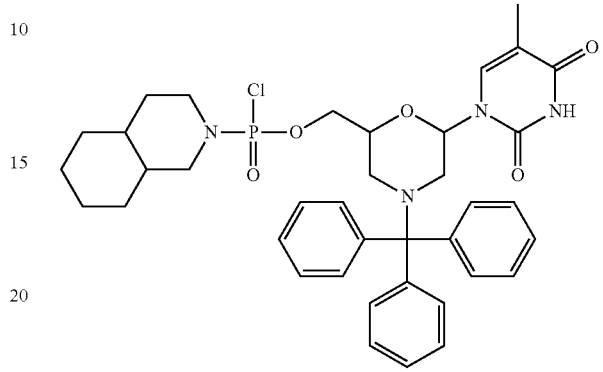

The title compound was synthesized in a manner analogous to that described in procedure A to afford the title compound (4.87 g, 32% yield). ESI/MS calcd. for 1-(4-nitrophenyl)piperazine derivative $C_{48}H_{56}N_7O_7P$ 873.40. found m/z=872.7 (M−1).

Example 21

(6-(5-methyl-2,4-dioxo-3,4-dihydropyrimidin-1(2H)-yl)-4-tritylmorpholin-2-yl)methyl (4-(trifluoromethyl)piperidin-1-yl)phosphonochloridate

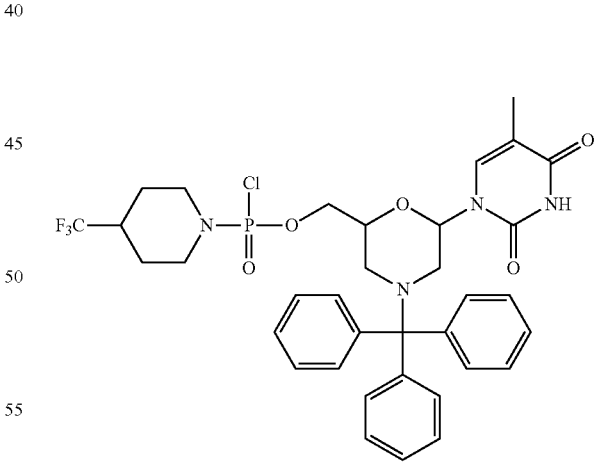

The title compound was synthesized in a manner analogous to that described in procedure A to afford the title compound (1.59 g, 42% yield). ESI/MS calcd. for 1-(4-nitrophenyl)piperazine derivative $C_{45}H_{49}F_3N_7O_7P$ 887.34. found m/z=886.6 (M−1).

Example 22

(6-(5-methyl-2,4-dioxo-3,4-dihydropyrimidin-1(2H)-yl)-4-tritylmorpholin-2-yl)methyl (4-(4-nitrophenyl)piperazin-1-yl)phosphonochloridate

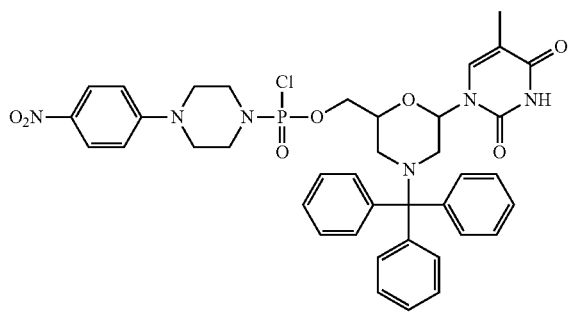 [SMILES: Cc1cn(C2CN(C(c3ccccc3)(c3ccccc3)c3ccccc3)CC(COP(=O)(Cl)N3CCN(c4ccc([N+](=O)[O-])cc4)CC3)O2)c(=O)[nH]c1=O]

The title compound was synthesized in a manner analogous to that described in procedure A to afford the title compound (2.27 g, 24% yield). ESI/MS calcd. for 1-(4-nitrophenyl)piperazine derivative $C_{49}H_{52}N_9O_9P$ 941.36. found m/z=940.7 (M−1).

Example 23

(6-(5-methyl-2,4-dioxo-3,4-dihydropyrimidin-1(2H)-yl)-4-tritylmorpholin-2-yl)methyl (4-acetyl-1,4-diazepan-1-yl)phosphonochloridate

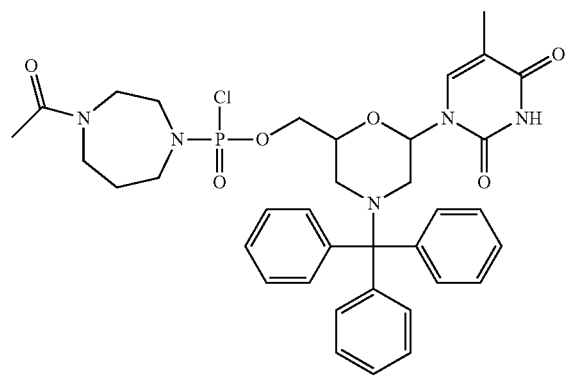 [SMILES: CC(=O)N1CCCN(P(=O)(Cl)OCC2CN(C(c3ccccc3)(c3ccccc3)c3ccccc3)CC(n3cc(C)c(=O)[nH]c3=O)O2)CC1]

The title compound was synthesized in a manner analogous to that described in procedure A to afford the title compound (6.08 g, 20% yield). ESI/MS calcd. for 1-(4-nitrophenyl)piperazine derivative $C_{46}H_{53}N_8O_8P$ 876.37. found m/z=875.9 (M−1).

Example 24

(6-(5-methyl-2,4-dioxo-3,4-dihydropyrimidin-1(2H)-yl)-4-tritylmorpholin-2-yl)methyl (4-acetylpiperazin-1-yl)phosphonochloridate

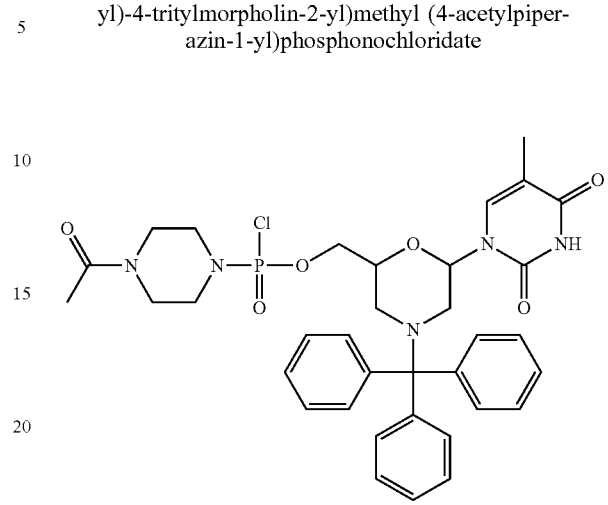

The title compound was synthesized in a manner analogous to that described in procedure A to afford the title compound (3.30 g, 20% yield). ESI/MS calcd. for 1-(4-nitrophenyl)piperazine derivative $C_{45}H_{51}N_8O_8P$ 862.36. found m/z=861.7 (M−1).

Example 25

(6-(5-methyl-2,4-dioxo-3,4-dihydropyrimidin-1(2H)-yl)-4-tritylmorpholin-2-yl)methyl (4-cyanopiperidin-1-yl)phosphonochloridate

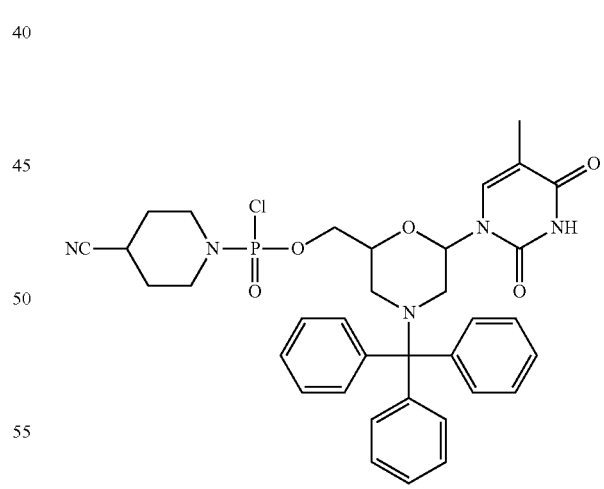

The title compound was synthesized in a manner analogous to that described in procedure A to afford the title compound (0.84 g, 25% yield). ESI/MS calcd. for 1-(4-nitrophenyl)piperazine derivative $C_{45}H_{49}N_8O_7P$ 844.35. found m/z=843.6 (M−1).

Example 26

(6-(5-methyl-2,4-dioxo-3,4-dihydropyrimidin-1(2H)-yl)-4-tritylmorpholin-2-yl)methyl hex-5-yn-1-yl (methyl)phosphoramidochloridate

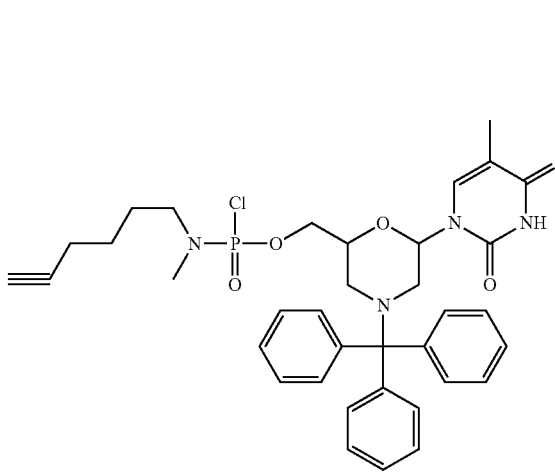

The title compound was synthesized in a manner analogous to that described in procedure A to afford the title compound (0.53 g). ESI/MS calcd. for $C_{36}H_{40}ClN_4O_5P$ 674.24. found m/z=673 (M−1).

Example 27

(6-(5-methyl-2,4-dioxo-3,4-dihydropyrimidin-1(2H)-yl)-4-tritylmorpholin-2-yl)methyl hex-5-en-1-yl (methyl)phosphoramidochloridate

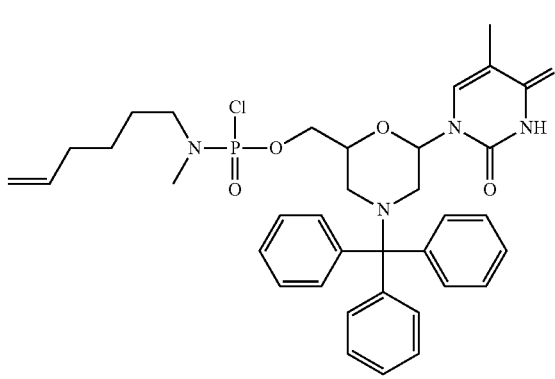

The title compound was synthesized in a manner analogous to that described in procedure A to afford the title compound (1.58 g). ESI/MS calcd. for $C_{36}H_{42}ClN_4O_5P$ 676.26. found m/z=675 (M−1).

Example 28

(6-(5-methyl-2,4-dioxo-3,4-dihydropyrimidin-1(2H)-yl)-4-tritylmorpholin-2-yl)methyl (4-([1,1'-biphenyl]-3-ylcarboxamido)piperidin-1-yl)phosphonochloridate

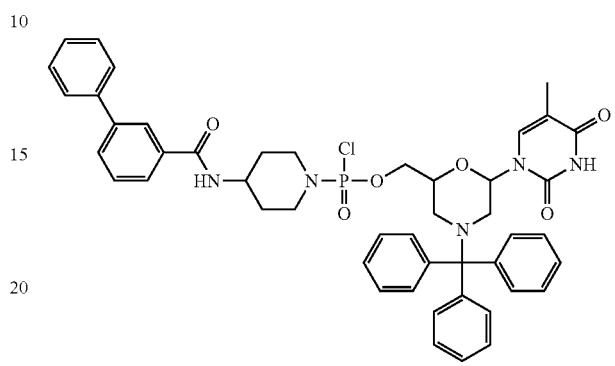

The title compound was synthesized in a manner analogous to that described in procedure A to afford the title compound (2.78 g). ESI/MS calcd. for $C_{47}H_{47}ClN_5O_6P$ 843.30. found m/z=842 (M−1).

Example 29

(6-(5-methyl-2,4-dioxo-3,4-dihydropyrimidin-1(2H)-yl)-4-tritylmorpholin-2-yl)methyl (4-(3-cyanobenzamido)piperidin-1-yl)phosphonochloridate

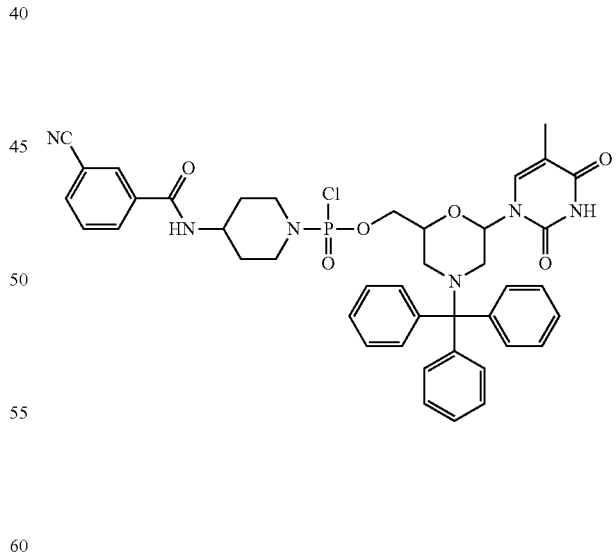

The title compound was synthesized in a manner analogous to that described in procedure A to afford the title compound (4.89 g). ESI/MS calcd. for $C_{42}H_{42}ClN_6O_6P$ 792.26. found m/z=793 (M−1).

Example 30

(6-(5-methyl-2,4-dioxo-3,4-dihydropyrimidin-1(2H)-yl)-4-tritylmorpholin-2-yl)methyl [1,4'-bipiperidin]-1'-ylphosphonochloridate

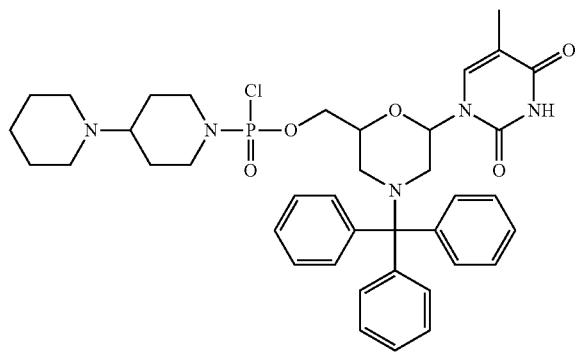 [SMILES: Cc1cn(C2CN(C(c3ccccc3)(c3ccccc3)c3ccccc3)CC(COP(=O)(Cl)N3CCC(N4CCCCC4)CC3)O2)c(=O)[nH]c1=O]

The title compound was synthesized in a manner analogous to that described in procedure A to afford the title compound (0.83 g). ESI/MS calcd. for $C_{39}H_{47}ClN_5O_5P$ 731.30. found m/z=730 (M−1).

Example 31

(6-(5-methyl-2,4-dioxo-3,4-dihydropyrimidin-1(2H)-yl)-4-tritylmorpholin-2-yl)methyl (4-(2',4'-dimethoxy-[1,1'-biphenyl]-3-ylcarboxamido)piperidin-1-yl)phosphonochloridate

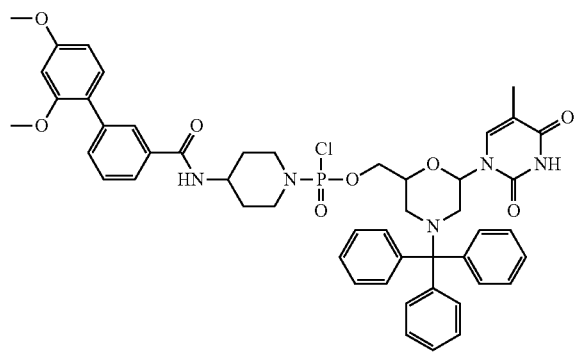 [SMILES: COc1ccc(-c2cccc(C(=O)NC3CCN(P(=O)(Cl)OCC4CN(C(c5ccccc5)(c5ccccc5)c5ccccc5)CC(n5cc(C)c(=O)[nH]c5=O)O4)CC3)c2)c(OC)c1]

The title compound was synthesized in a manner analogous to that described in procedure A to afford the title compound (0.34 g). ESI/MS calcd. for $C_{49}H_{51}ClN_5O_8P$ 903.32. found m/z=902 (M−1).

Example 32

(6-(5-methyl-2,4-dioxo-3,4-dihydropyrimidin-1(2H)-yl)-4-tritylmorpholin-2-yl)methyl but-3-en-1-yl (methyl)phosphoramidochloridate

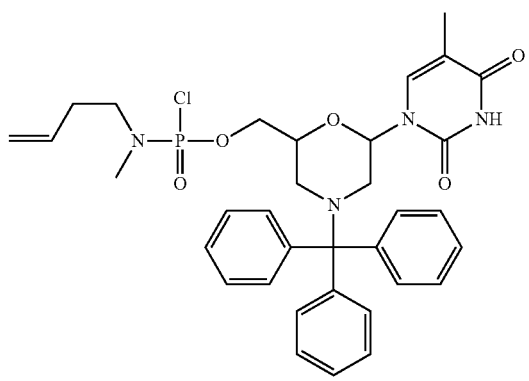 [SMILES: C=CCCN(C)P(=O)(Cl)OCC1CN(C(c2ccccc2)(c2ccccc2)c2ccccc2)CC(n2cc(C)c(=O)[nH]c2=O)O1]

The title compound was synthesized in a manner analogous to that described in procedure A to afford the title compound (0.66 g). ESI/MS calcd. for $C_{34}H_{38}ClN_4O_5P$ 648.23. found m/z=671 (M+Na).

Example 33

(6-(5-methyl-2,4-dioxo-3,4-dihydropyrimidin-1(2H)-yl)-4-tritylmorpholin-2-yl)methyl (4-(2',3'-dimethoxy-[1,1'-biphenyl]-3-ylcarboxamido)piperidin-1-yl)phosphonochloridate

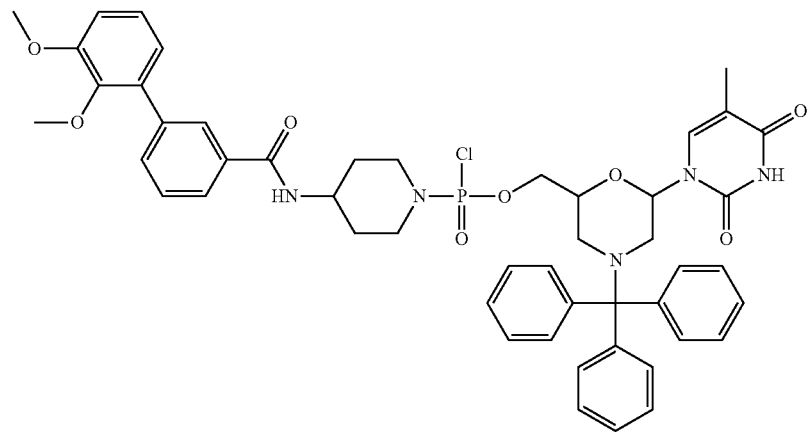 [SMILES: COc1cccc(-c2cccc(C(=O)NC3CCN(P(=O)(Cl)OCC4CN(C(c5ccccc5)(c5ccccc5)c5ccccc5)CC(n5cc(C)c(=O)[nH]c5=O)O4)CC3)c2)c1OC]

The title compound was synthesized in a manner analogous to that described in procedure A to afford the title compound (0.62 g). ESI/MS calcd. for $C_{49}H_{51}ClN_5O_8P$ 903.32. found m/z=902 (M−1).

Example 34

(6-(5-methyl-2,4-dioxo-3,4-dihydropyrimidin-1(2H)-yl)-4-tritylmorpholin-2-yl)methyl (4-(3'-(trifluoromethoxy)-[1,1'-biphenyl]-3-ylcarboxamido)piperidin-1-yl)phosphonochloridate

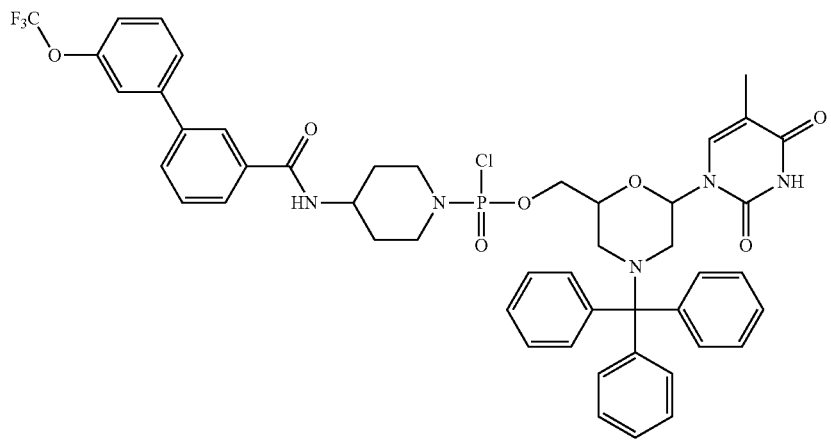 [SMILES: Cc1cn(C2CN(C(c3ccccc3)(c3ccccc3)c3ccccc3)CC(COP(=O)(Cl)N3CCC(NC(=O)c4cccc(-c5cccc(OC(F)(F)F)c5)c4)CC3)O2)c(=O)[nH]c1=O]

The title compound was synthesized in a manner analogous to that described in procedure A to afford the title compound (0.44 g). ESI/MS calcd. for $C_{48}H_{46}ClF_3N_5O_7P$ 927.28. found m/z=926 (M−1).

Example 35

(6-(5-methyl-2,4-dioxo-3,4-dihydropyrimidin-1(2H)-yl)-4-tritylmorpholin-2-yl)methyl (4-(4'-(trifluoromethoxy)-[1,1'-biphenyl]-3-ylcarboxamido)piperidin-1-yl)phosphonochloridate

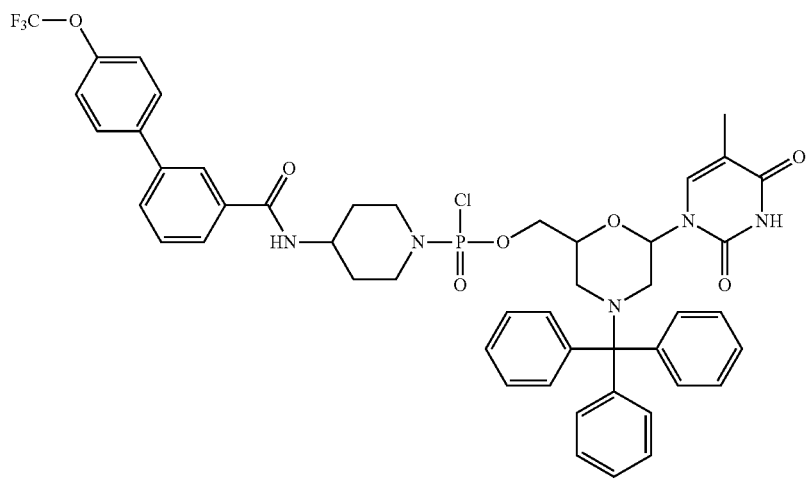 [SMILES: Cc1cn(C2CN(C(c3ccccc3)(c3ccccc3)c3ccccc3)CC(COP(=O)(Cl)N3CCC(NC(=O)c4cccc(-c5ccc(OC(F)(F)F)cc5)c4)CC3)O2)c(=O)[nH]c1=O]

The title compound was synthesized in a manner analogous to that described in procedure A to afford the title compound (0.51 g). ESI/MS calcd. for $C_{48}H_{46}ClF_3N_5O_7P$ 927.28. found m/z=926 (M−1).

Example 36

(6-(5-methyl-2,4-dioxo-3,4-dihydropyrimidin-1(2H)-yl)-4-tritylmorpholin-2-yl)methyl (4-(4'-chloro-3'-(trifluoromethyl)-[1,1'-biphenyl]-3-ylcarboxamido)piperidin-1-yl)phosphonochloridate

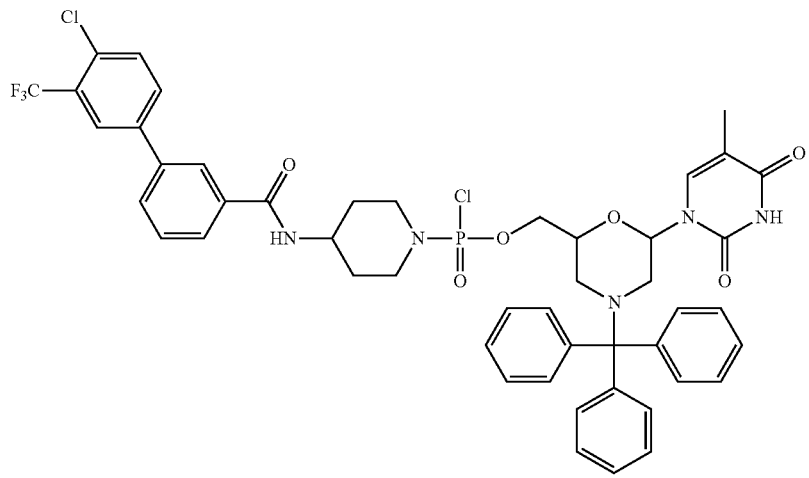 [SMILES: Cc1cn(C2CN(C(c3ccccc3)(c3ccccc3)c3ccccc3)CC(COP(=O)(Cl)N3CCC(NC(=O)c4cccc(-c5ccc(Cl)c(C(F)(F)F)c5)c4)CC3)O2)c(=O)[nH]c1=O]

The title compound was synthesized in a manner analogous to that described in procedure A to afford the title compound (0.56 g). ESI/MS calcd. for $C_{48}H_{45}Cl_2F_3N_5O_6P$ 945.24. found m/z=944 (M−1).

Example 37

(6-(5-methyl-2,4-dioxo-3,4-dihydropyrimidin-1(2H)-yl)-4-tritylmorpholin-2-yl)methyl (4-(3',5'-dichloro-[1,1'-biphenyl]-3-ylcarboxamido)piperidin-1-yl)phosphonochloridate

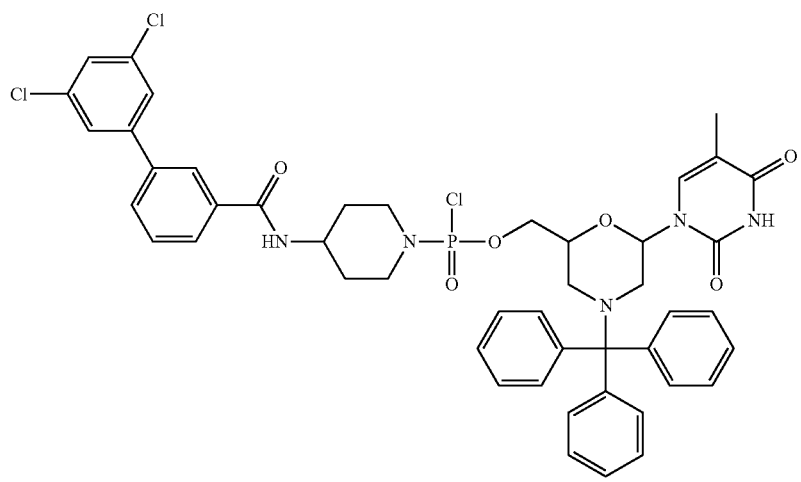 [SMILES: Cc1cn(C2CN(C(c3ccccc3)(c3ccccc3)c3ccccc3)CC(COP(=O)(Cl)N3CCC(NC(=O)c4cccc(-c5cc(Cl)cc(Cl)c5)c4)CC3)O2)c(=O)[nH]c1=O]

The title compound was synthesized in a manner analogous to that described in procedure A to afford the title compound (0.42 g). ESI/MS calcd. for $C_{47}H_{45}Cl_3N_5O_6P$ 911.22. found m/z=910 (M−1).

Examples 38-40 were prepared via procedure B described above.

Example 38

(6-(5-methyl-2,4-dioxo-3,4-dihydropyrimidin-1(2H)-yl)-4-tritylmorpholin-2-yl)methyl (4-(pyrimidin-2-yl)piperazin-1-yl)phosphonochloridate

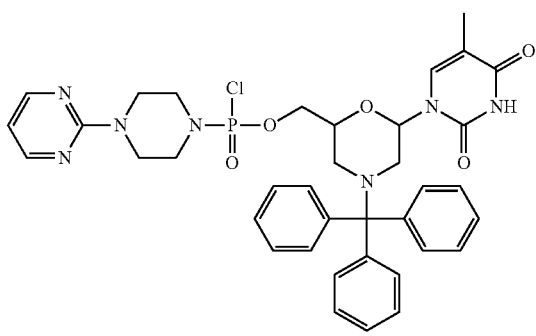 [SMILES: Cc1cn(C2CN(C(c3ccccc3)(c3ccccc3)c3ccccc3)CC(COP(=O)(Cl)N3CCN(c4ncccn4)CC3)O2)c(=O)[nH]c1=O]

The title compound was synthesized in a manner analogous to that described in procedure B to afford the title compound (3.13 g, 24% yield). ESI/MS calcd. for 1-(4-nitrophenyl)piperazine derivative $C_{47}H_{51}N_{10}O_7P$ 898.37. found m/z=897.7 (M−1).

Example 39

(6-(5-methyl-2,4-dioxo-3,4-dihydropyrimidin-1(2H)-yl)-4-tritylmorpholin-2-yl)methyl (4-(2-(dimethylamino)ethyl)piperazin-1-yl)phosphonochloridate

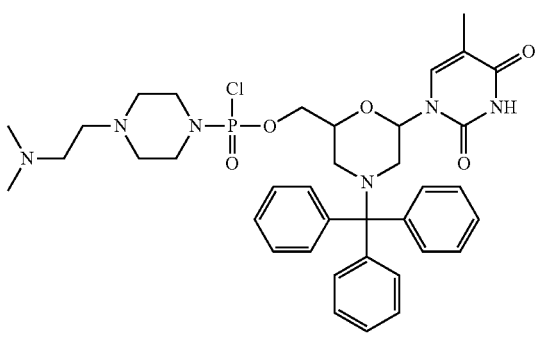 [SMILES: Cc1cn(C2CN(C(c3ccccc3)(c3ccccc3)c3ccccc3)CC(COP(=O)(Cl)N3CCN(CCN(C)C)CC3)O2)c(=O)[nH]c1=O]

The title compound was synthesized in a manner analogous to that described in procedure B to afford the title compound (1.0 g, 79% yield). ESI/MS calcd. for 1-(4-nitrophenyl)piperazine derivative $C_{47}H_{58}N_9O_7P$ 891.42. found m/z=890.8 (M−1).

Example 40

(6-(5-methyl-2,4-dioxo-3,4-dihydropyrimidin-1(2H)-yl)-4-tritylmorpholin-2-yl)methyl (4-phenylpiperazin-1-yl)phosphonochloridate

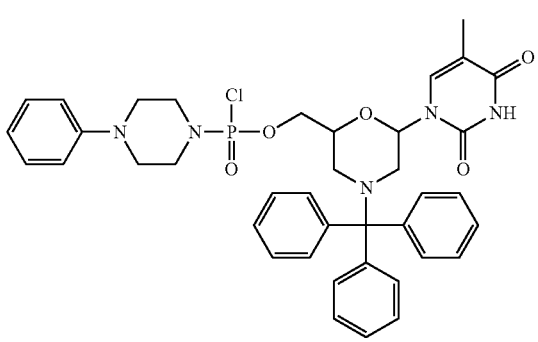 [SMILES: Cc1cn(C2CN(C(c3ccccc3)(c3ccccc3)c3ccccc3)CC(COP(=O)(Cl)N3CCN(c4ccccc4)CC3)O2)c(=O)[nH]c1=O]

The title compound was synthesized in a manner analogous to that described in procedure B to afford the title compound (0.72 g, 67% yield). ESI/MS calcd. for 1-(4-nitrophenyl)piperazine derivative $C_{49}H_{53}N_8O_7P$ 896.38. found m/z=895.6 (M−1).

The activated subunits of the foregoing examples can be modified by incorporating A, G, and C nucleobases by applying procedure A and substituting the appropriate A, G, and C morpholino derivatives for Mo(Tr)T. The structures of suitably protected A, G, and C morpholinos are shown in Examples 41-51.

Example 41

N-(9-(6-(hydroxymethyl)-4-tritylmorpholin-2-yl)-9H-purin-6-yl)benzamide (Protected A)

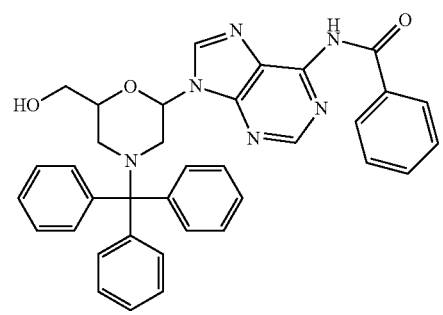 [SMILES: O=C(Nc1ncnc2c1ncn2C1CN(C(c2ccccc2)(c2ccccc2)c2ccccc2)CC(CO)O1)c1ccccc1]

Example 42

9-(6-(hydroxymethyl)-4-tritylmorpholin-2-yl)-2-(2-phenylacetamido)-9H-purin-6-yl pivalate (Protected G)

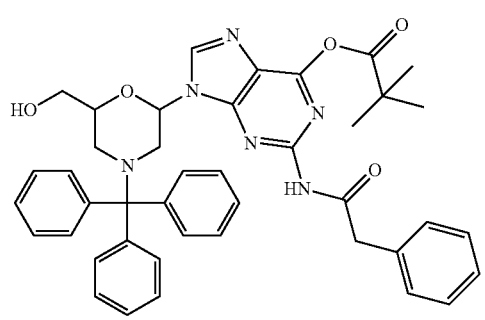 [SMILES: CC(C)(C)C(=O)Oc1nc(NC(=O)Cc2ccccc2)nc2c1ncn2C1CN(C(c2ccccc2)(c2ccccc2)c2ccccc2)CC(CO)O1]

Example 43

N-(1-(6-(hydroxymethyl)-4-tritylmorpholin-2-yl)-2-oxo-1,2-dihydropyrimidin-4-yl)benzamide (Protected C)

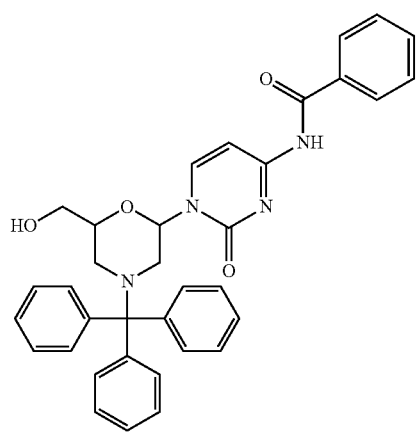 [SMILES: O=C(Nc1ccn(C2CN(C(c3ccccc3)(c3ccccc3)c3ccccc3)CC(CO)O2)c(=O)n1)c1ccccc1]

Example 44

(6-(5-methyl-2,4-dioxo-3,4-dihydropyrimidin-1(2H)-yl)-4-tritylmorpholin-2-yl)methyl (4-(2,2,2-trifluoro-N-methylacetamido)piperidin-1-yl)phosphonochloridate

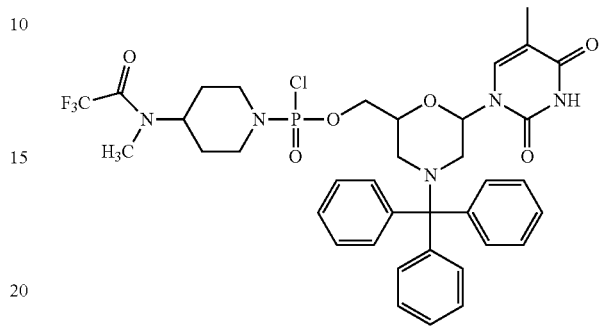

Example 45

(6-(5-methyl-2,4-dioxo-3,4-dihydropyrimidin-1(2H)-yl)-4-tritylmorpholin-2-yl)methyl methyl(3-(2,2,2-trifluoro-n-methylacetamido)propyl)phosphoramidochloridate

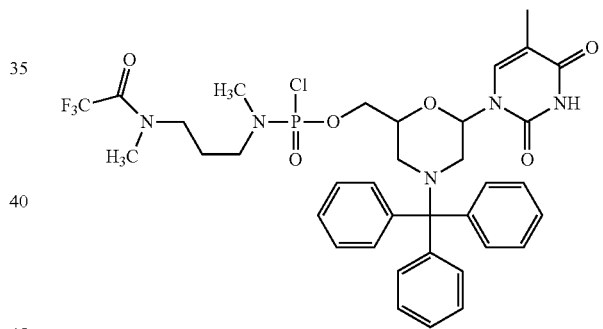

Example 46

(6-(6-benzamido-9H-purin-9-yl)-4-tritylmorpholin-2-yl)methyl morpholinophosphonochloridate

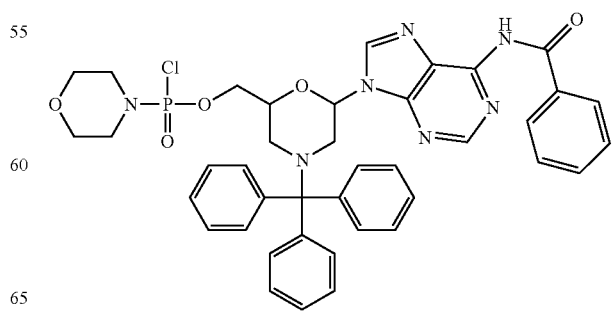

The title compound was synthesized to afford the title compound (10.81 g). ESI/MS calcd. for $C_{40}H_{39}ClN_7O_5P$ 763.24. found m/z=762 (M−1).

Example 47

(6-(6-benzamido-9H-purin-9-yl)-4-tritylmorpholin-2-yl)methyl (4-acetylpiperazin-1-yl)phosphonochloridate

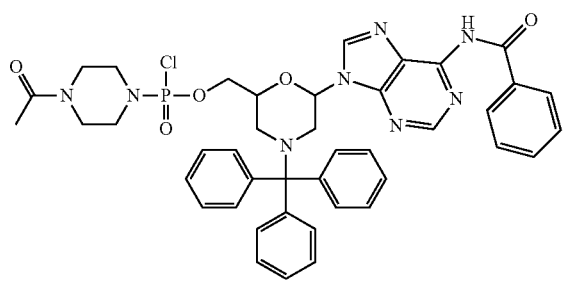 [SMILES: CC(=O)N1CCN(P(=O)(Cl)OCC2CN(C(c3ccccc3)(c3ccccc3)c3ccccc3)CC(n3cnc4c(NC(=O)c5ccccc5)ncnc43)O2)CC1]

The title compound was synthesized to afford the title compound (8.67 g). ESI/MS calcd. for $C_{42}H_{42}ClN_8O_5P$ 804.27. found m/z=803 (M−1).

Example 48

9-(6-((((chloro(morpholino)phosphoryl)oxy)methyl)-4-tritylmorpholin-2-yl)-2-(2-phenylacetamido)-9H-purin-6-yl pivalate

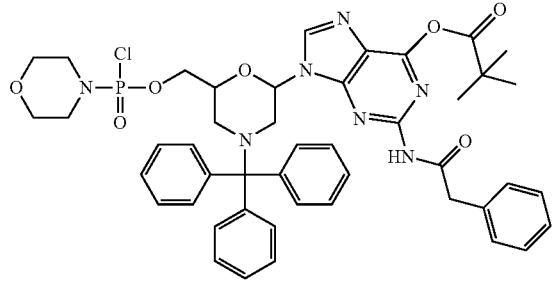 [SMILES: CC(C)(C)C(=O)Oc1nc(NC(=O)Cc2ccccc2)nc2c1ncn2C1CN(C(c2ccccc2)(c2ccccc2)c2ccccc2)CC(COP(=O)(Cl)N2CCOCC2)O1]

The title compound was synthesized to afford the title compound (9.88 g). ESI/MS calcd. for $C_{53}H_{55}ClN_7O_8P$ 983.35. found m/z=985 (M−1).

Example 49

9-(6-((((4-acetylpiperazin-1-yl)chlorophosphoryl)oxy)methyl)-4-tritylmorpholin-2-yl)-2-(2-phenylacetamido)-9H-purin-6-yl pivalate

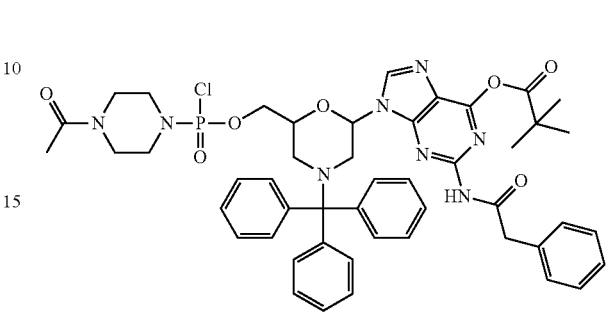

The title compound was synthesized to afford the title compound (8.40 g). ESI/MS calcd. for $C_{55}H_{58}ClN_8O_8P$ 1024.38. found m/z=1023 (M−1).

Example 50

(6-(4-benzamido-2-oxopyrimidin-1(2H)-yl)-4-tritylmorpholin-2-yl)methyl (4-acetylpiperazin-1-yl)phosphonochloridate

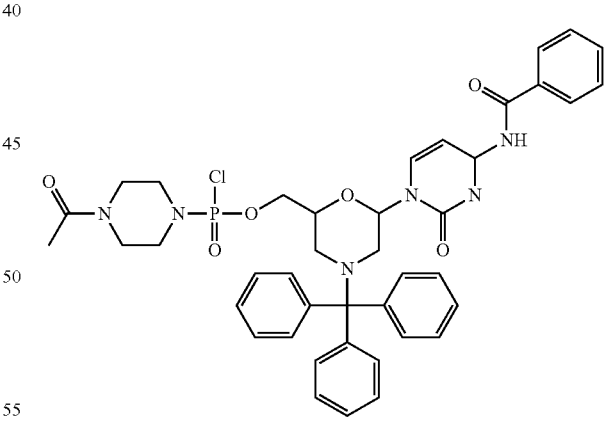

The title compound was synthesized to afford the title compound (6.36 g). ESI/MS calcd. for $C_{41}H_{42}ClN_6O_6P$ 780.26. found m/z=779 (M−1).

Example 51

(6-(4-benzamido-2-oxopyrimidin-1(2H)-yl)-4-trityl-morpholin-2-yl)methyl morpholinophosphonochloridate

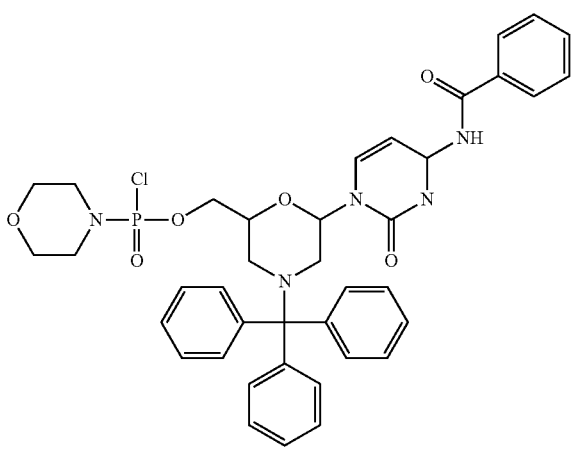 [SMILES: O=C(NC1C=CN(C2CN(C(c3ccccc3)(c3ccccc3)c3ccccc3)CC(COP(=O)(Cl)N3CCOCC3)O2)C(=O)N1)c1ccccc1]

The title compound was synthesized to afford the title compound (10.29 g). ESI/MS calcd. for $C_{39}H_{39}ClN_5O_6P$ 739.23. found m/z=738 (M−1).

Example 52

((2S,6R)-6-(6-benzamido-9H-purin-9-yl)-4-trityl-morpholin-2-yl)methyl (4-(2,2,2-trifluoroacetamido)piperidin-1-yl)phosphonochloridate

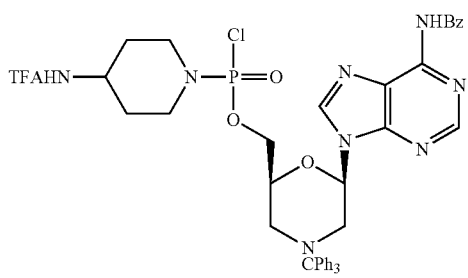

The title compound was synthesized in a manner analogous to that described in procedure A to afford the title compound (15.4 g, 66% yield) as a white solid. ESI/MS calcd. for 1-(4-nitrophenyl)piperazine derivative $C_{53}H_{53}F_3N_{11}O_7P$ 1043.4. found m/z=1042.5 (M−1).

Example 53

(R)-methyl(1-phenylethyl)phosphoramidic dichloride

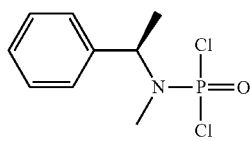

To a cooled (ice/water bath) solution of phosphorus oxychloride (2.83 mL, 30.3 mmol) in DCM (30 mL) was added sequentially, dropwise, and with stirring 2,6-lutidine (7.06 mL, 60.6 mmol) and a DCM solution of (R)-(+)-N,a-dimethylbenzylamine (3.73 g, 27.6 mmol). After 5 minutes, the bath was removed and reaction mixture allowed to warm to ambient temperature. After 1 hour, the reaction solution was washed with a citric acid solution (50 mL×3, 10% w/v aq), dried (MgSO$_4$), filtered through SiO$_2$ and concentrated to provide the title compound (3.80 g) as a white foam. ESI/MS calcd. for 1-(4-nitrophenyl)piperazine derivative $C_{19}H_{25}N_4O_4P$ 404.2. found m/z=403.1 (M−1).

Example 54

(S)-methyl(1-phenylethyl)phosphoramidic dichloride

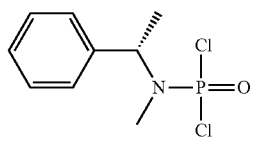

The title compound was synthesized in a manner analogous to that described in Example 53 to afford the title compound (3.95 g) as a white foam. ESI/MS calcd. for 1-(4-nitrophenyl)piperazine derivative $C_{19}H_{25}N_4O_4P$ 404.2. found m/z=403.1 (M−1).

Example 55

((2S,6R)-6-(5-methyl-2,4-dioxo-3,4-dihydropyrimidin-1(2H)-yl)-4-tritylmorpholin-2-yl)methyl methyl ((R)-1-phenylethyl)phosphoramidochloridate

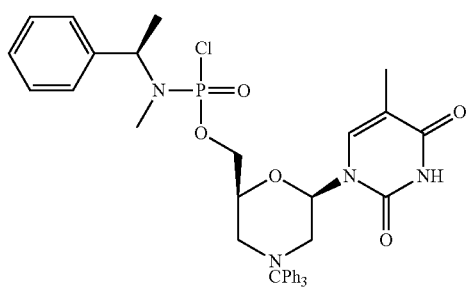

The title compound was synthesized in a manner analogous to that described in procedure A to afford the title chlorophosphoroamidate (4.46 g, 28% yield) as a white solid. ESI/MS calcd. for $C_{38}H_{40}ClN_4O_5P$ 698.2. found m/z=697.3 (M−1).

Example 56

((2S,6R)-6-(5-methyl-2,4-dioxo-3,4-dihydropyrimidin-1(2H)-yl)-4-tritylmorpholin-2-yl)methyl methyl ((S)-1-phenylethyl)phosphoramidochloridate

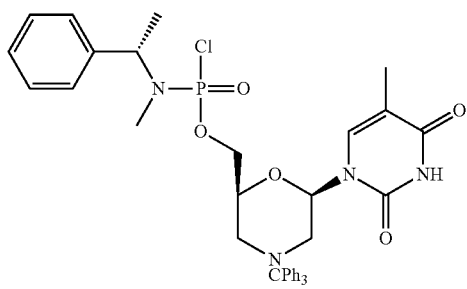

The title compound was synthesized in a manner analogous to that described in procedure A to afford the title chlorophosphoroamidate (4.65 g, 23% yield) as a white solid. ESI/MS calcd. for $C_{38}H_{40}ClN_4O_5P$ 698.2. found m/z=697.3 (M−1).

Example 57

(4-(pyrrolidin-1-yl)piperidin-1-yl)phosphonic dichloride hydrochloride

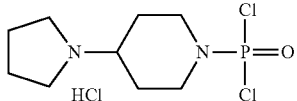 [SMILES: O=P(Cl)(Cl)N1CCC(N2CCCC2)CC1 ; Cl]

To a cooled (ice/water bath) solution of phosphorus oxychloride (5.70 mL, 55.6 mmol) in DCM (30 mL) was added 2,6-lutidine (19.4 mL, 167 mmol) and a DCM solution (30 mL) of 4-(1-pyrrolidinyl)-piperidine (8.58 g, 55.6 mmol) and stirred for 1 hour. The suspension was filtered and solid washed with excess diethyl ether to afford the title pyrrolidine (17.7 g, 91% yield) as a white solid. ESI/MS calcd. for 1-(4-nitrophenyl)piperazine derivative $C_{19}H_{30}N_5O_4P$ 423.2. found m/z=422.2 (M−1).

Example 58

((2S,6R)-6-(5-methyl-2,4-dioxo-3,4-dihydropyrimidin-1(2H)-yl)-4-tritylmorpholin-2-yl)methyl (4-(pyrrolidin-1-yl)piperidin-1-yl)phosphonochloridate hydrochloride

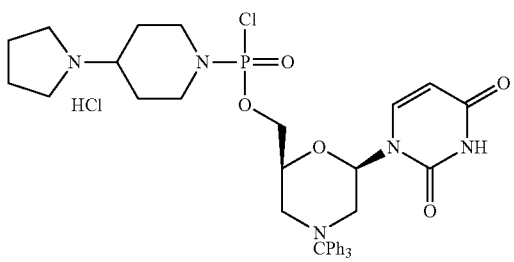

To a stirred, cooled (ice/water bath) solution of the dichlorophosphoramidate from Example 57 (17.7 g, 50.6 mmol) in DCM (100 mL) was added a DCM solution (100 mL) of Mo(Tr)T (2) (24.5 g, 50.6 mmol), 2,6-Lutidine (17.7 mL, 152 mmol), and 1-methylimidazole (0.401 mL, 5.06 mmol) dropwise over 10 minutes. The bath was allowed to warm to ambient temperature as suspension was stirred. After 6 hours, the suspension was poured onto diethyl ether (1 L), stirred 15 minutes, filtered and solid washed with additional ether to afford a white solid (45.4 g). The crude product was purified by chromatography [SiO$_2$ column (120 gram), DCM/MeOH eluant (gradient 1:0 to 6:4)], and the combined fractions were poured onto diethyl ether (2.5 L), stirred 15 min, filtered, and the resulting solid washed with additional ether to afford the title compound (23.1 g, 60% yield) as a white solid. ESI/MS calcd. for 1-(4-nitrophenyl)piperazine derivative $C_{48}H_{57}N_8O_7P$ 888.4. found m/z=887.6 (M−1).

Example 59

3-(tert-butyldisulfanyl)-2-(isobutoxycarbonylamino)propanoic acid

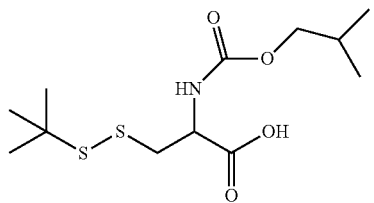 [SMILES: CC(C)COC(=O)NC(CSSC(C)(C)C)C(=O)O]

To S-tert-butylmercapto-L-cysteine (10 g, 47.8 mmol) in CH$_3$CN (40 mL) was added K$_2$CO$_3$ (16.5 g, 119.5 mmol) in H$_2$O (20 mL). After stirring for 15 minutes, iso-butyl chloroformate (9.4 mL, 72 mmol) was injected slowly. The reaction was allowed to run for 3 hours. The white solid was filtered through Celite; the filtrate was concentrated to remove CH$_3$CN. The residue was dissolved in ethyl acetate (200 mL), washed with 1N HCl (40 ml×3), brine (40×1), dried over Na$_2$SO$_4$. The title compound was obtained after chromatography (5% MeOH/DCM).

Example 60 tert-butyl 4-(3-(tert-butyldisulfanyl)-2-(isobutoxycarbonylamino)propanamido)piperidine-1-carboxylate

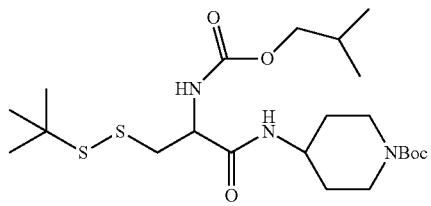 [SMILES: CC(C)COC(=O)NC(CSSC(C)(C)C)C(=O)NC1CCN(C(=O)OC(C)(C)C)CC1]

To the acid from Example 59 (6.98 g, 22.6 mmol) in DMF (50 ml was added HATU (8.58 g, 22.6 mmol). After 30 min, Hunig base (4.71 ml, 27.1 mmol) and 1-Boc-4-amino piperidine (5.43 g, 27.1 mmol) were added to the mixture. The reaction was continued stirring at RT for another 3 h. DMF was removed at high vacuum, the crude residue was dissolved in EtAc (300 ml), washed with H₂O (50 ml×3). The title compound was obtained after ISCO purification (5% MeOH/DCM).

Example 61 isobutyl 3-(isopropyldisulfanyl)-1-oxo-1-(piperidin-4-ylamino)propan-2-ylcarbamate

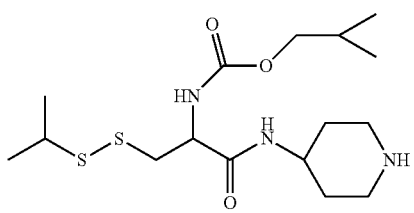 [SMILES: CC(C)COC(=O)NC(CSSC(C)C)C(=O)NC1CCNCC1]

To the compound from Example 60 (7.085 g, 18.12 mmol) was added 30 ml of 4M HCl/Dioxane. The reaction was completed after 2 h at RT. The title compound was used for the next step without further purification.

Example 62 isobutyl 3-(tert-butyldisulfanyl)-1-(1-(dichlorophosphoryl)piperidin-4-ylamino)-1-oxopropan-2-ylcarbamate

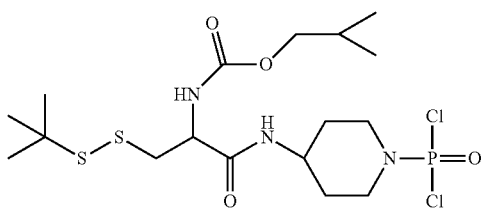 [SMILES: CC(C)COC(=O)NC(CSSC(C)(C)C)C(=O)NC1CCN(P(=O)(Cl)Cl)CC1]

To the compound from Example 61 (7.746 g, 18.12 mmol) in DCM (200 ml) at −78° C. was slowly injected POCl₃ (1.69 ml, 18.12 mmol) under Ar, followed by the addition of Et₃N (7.58 ml, 54.36 mmol). The reaction was stirred at RT for 5 h, concentrated to remove excess base and solvent. The title compound was given as white solid after ISCO purification (50% EtAc/Hexane).

Example 63 isobutyl 3-(tert-butyldisulfanyl)-1-(1-(chloro(((2S,6R)-6-(5-methyl-2,4-dioxo-3,4-dihydropyrimidin-1(2H)-yl)-4-tritylmorpholin-2-yl)methoxy)phosphoryl)piperidin-4-ylamino)-1-oxopropan-2-ylcarbamate

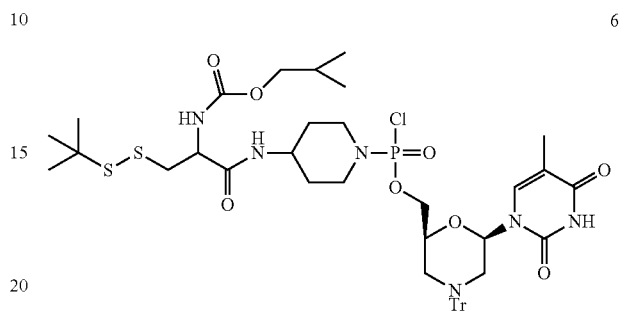

To 1-((2R,6S)-6-(hydroxymethyl)-4-tritylmorpholin-2-yl)-5-methylpyrimidine-2,4(1H,3H)-dione (moT(Tr)) (5.576 g, 10.98 mmol) in DCM (100 ml) at 0° C., was added lutidine (1.92 ml, 16.47 mmol) and DMAP (669 mg, 5.5 mmol), followed by the addition of the compound from Example 62 (6.13 g, 12.08 mmol). The reaction was left stirring at RT for 18 h. The title compound was obtained after ISCO purification (50% EtAc/Hexane).

Example 64

((2S,6R)-6-(5-methyl-2,4-dioxo-3,4-dihydropyrimidin-1(2H)-yl)-4-tritylmorpholin-2-yl)methylhexyl (methyl)phosphoramidochloridate

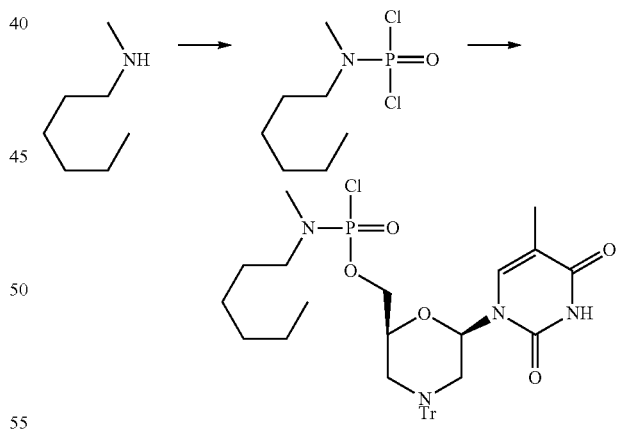

A DCM (80 ml) solution of N-hydroxylmethylamine (4.85 ml, 32 mmol) was cooled down to −78° C. under N2. A solution of phosphoryl chloride (2.98 ml, 32 mmol) in DCM (10 ml), followed by a solution of Et₃N (4.46 ml, 32 mmol) in DCM (10 ml), was added slowly. The stirring was continued while the reaction was allowed to warm to RT overnight. The desired phosphoramidodichloride was given as clear oil after ISCO purification (20% EtAc/Hexane).

To moT(Tr) (2) (5.10 g, 10.54 mmol) in DCM (100 ml) at 0° C., was added lutidine (3.68 ml, 31.6 mmol) and DMAP (642 mg, 5.27 mmol), followed by the addition of the phosphoramidodichloride (4.89 g, 21.08 mmol). The reaction was left stirring at RT for 18 h. The title compound was obtained after ISCO purification (50% EtOAc/Hexane).

Example 65

((2S,6R)-6-(5-methyl-2,4-dioxo-3,4-dihydropyrimidin-1(2H)-yl)-4-tritylmorpholin-2-yl)methyl dodecyl (methyl)phosphoramidochloridate

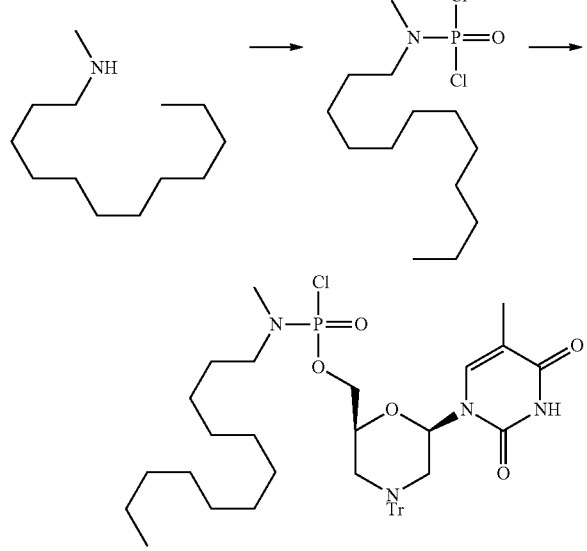

The title compound was prepared according to the general procedures described in Examples 53 and 55.

Example 66

((2S,6R)-6-(5-methyl-2,4-dioxo-3,4-dihydropyrimidin-1(2H)-yl)-4-tritylmorpholin-2-yl)methyl morpholinophosphonochloridate

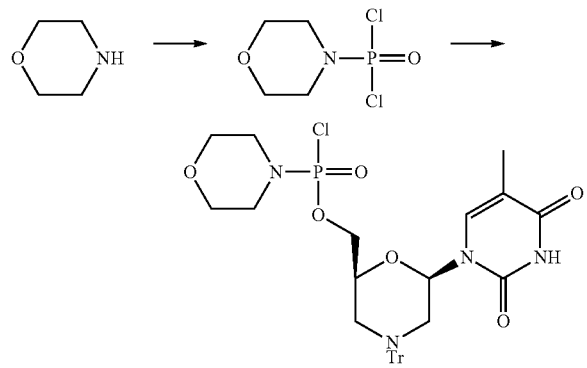

The title compound was prepared according to the general procedures described in Examples 53 and 55.

Example 67

((2S,6R)-6-(5-methyl-2,4-dioxo-3,4-dihydropyrimidin-1(2H)-yl)-4-tritylmorpholin-2-yl)methyl (S)-2-(methoxymethyl)pyrrolidin-1-ylphosphonochloridate

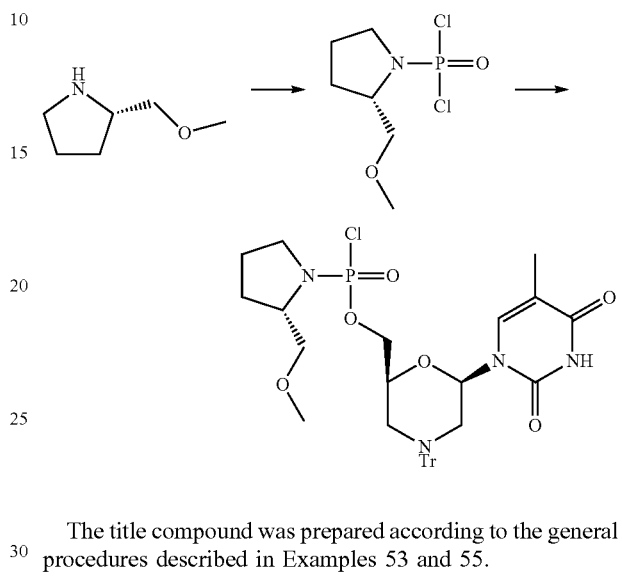

The title compound was prepared according to the general procedures described in Examples 53 and 55.

Example 68

((2S,6R)-6-(5-methyl-2,4-dioxo-3,4-dihydropyrimidin-1(2H)-yl)-4-tritylmorpholin-2-yl)methyl 4-(3,4,5-trimethoxybenzamido)piperidin-1-ylphosphonochloridate

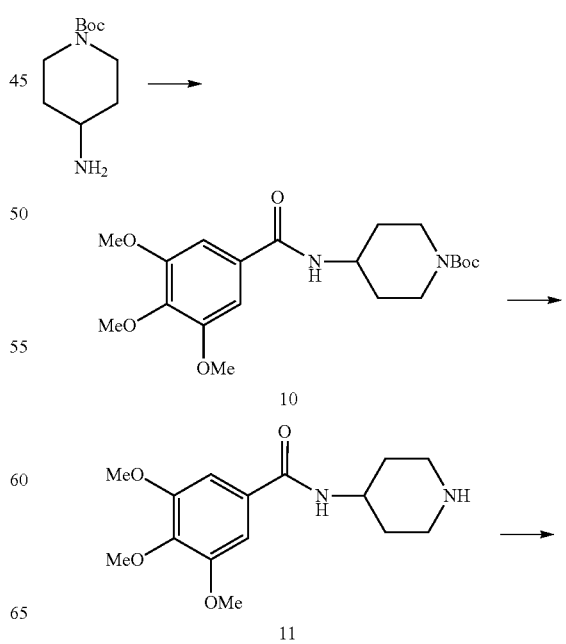

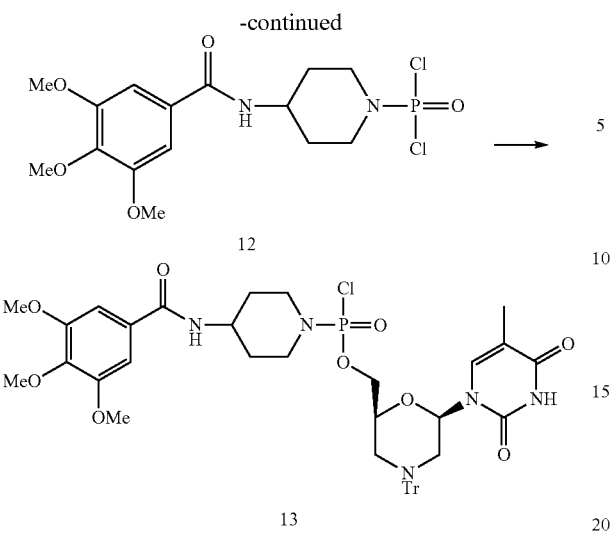

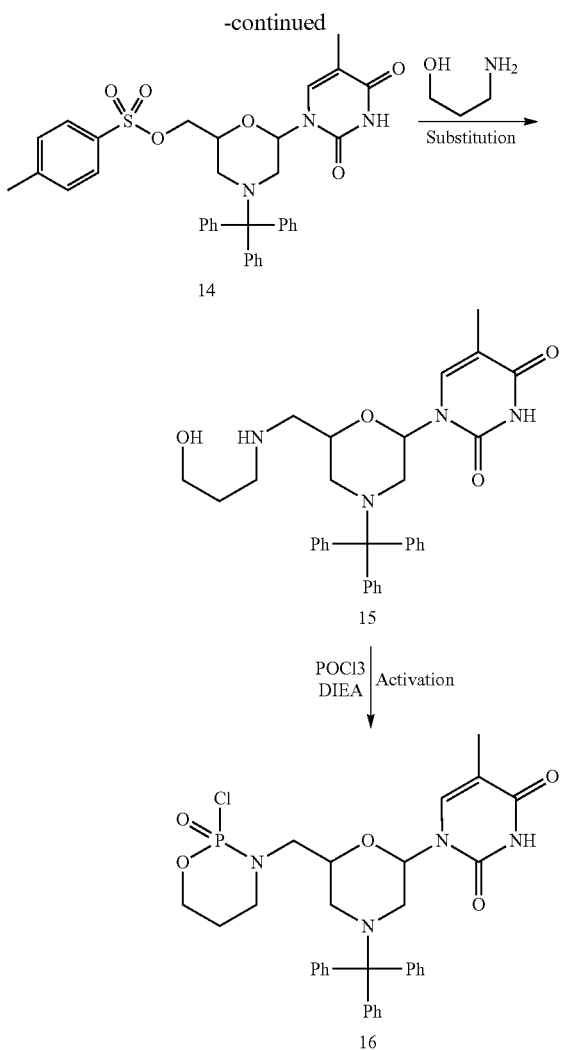

To 1-Boc-4-piperidine (1 g, 5 mmol) in DCM (20 ml) was added Hunig base (1.74 ml, 10 mmol), followed by the addition of 3,4,5-trimethoxybenzoyl chloride (1.38 g, 6 mmol). The reaction was run at RT for 3 h, concentrated to remove solvent and excess base. The residue was dissolved in EtAc (100 ml), washed with 0.05N HCl (3×15 ml), sat. NaHCO₃ (2×15 ml), dried over Na₂SO₄. Product (10) was obtained after ISCO purification (5% MeOH/DCM).

To 10 was added 15 ml of 4N HCl/Dioxane, reaction was terminated after 4 h. 11 was obtained as white solid.

A DCM (20 ml) solution of 11 (1.23 g, 4.18 mmol) was cooled down to −78° C. under N₂. A solution of phosphoryl chloride (0.39 ml, 4.18 mmol) in DCM (2 ml), followed by a solution of Et₃N (0.583 ml, 4.18 mmol) in DCM (2 ml), was added slowly. The stirring was continued while the reaction was allowed to warm to RT overnight. The desired product (12) was obtained after ISCO purification (50% EtAc/Hexane).

To moT(Tr) (1.933 g, 4.0 mmol) in DCM (20 ml) at 0° C., was added lutidine (0.93 ml, 8 mmol) and DMAP (49 mg, 0.4 mmol), followed by the addition of 12 (1.647 g, 4 mmol). The reaction was left stirring at RT for 18 h. The desired product (13) was obtained after ISCO purification (50% EtAc/Hexane).

Example 69

Synthesis of Cyclophosphoramide Containing Subunit

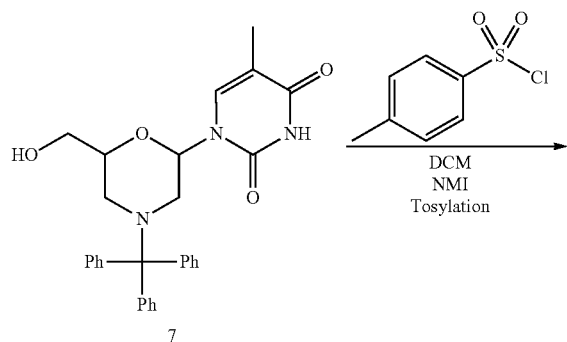

The moT subunit (7) (25 g) was suspended in DCM (175 ml) and NMI (N-methylimidazole, 5.94 g, 1.4 eq.) was added to obtain a clear solution. Tosyl chloride was added to the reaction mixture, and the reaction progress was monitored by TLC until done (about 2 hours). An aqueous workup was performed by washing with 0.5 M citric acid buffer (pH=5), followed by brine. The organic layer was separated and dried over Na2SO4. Solvent was removed with a rotavaporator to obtain the crude product (14) which was used in the next step without further purification.

The moT Tosylate (14) was mixed with propanolamine (1 g/10 ml). The reaction mixture was then placed in an oven at 45° C. overnight followed by dilution with DCM (10 ml). An aqueous workup was performed by washing with 0.5 M citric acid buffer (pH=5), followed by brine. The organic layer was separated and dried over Na₂SO₄. Solvent was removed with a rotavaporator to obtain the crude product (15) The curde product was analyzed by NMR and HPLC and determined to be ready for the next step without further purification.

The crude product (15) was dissolved in DCM (2.5 ml DCM/g, 1 eq.) and mixed with DIEA (3 eq.). This solution was cooled with dry ice-acetone and POCl₃ was added dropwise (1.5 eq.). The resultant mixture was stirred at room temperature overnight. An aqueous workup was performed by washing with 0.5 M citric acid buffer (pH=5), followed by brine. The organic layer was separated and dried over Na$_2$SO$_4$. Solvent was removed with a rotavaporator to obtain the crude product as a yellowish solid. The crude product was purified by silica gel chromatography (crude product/silica=1 to 5 ratio, gradient DCM to 50% EA/DCM), and fractions were pooled according to TLC analysis. Solvent was removed to obtain the desired product (16) as a mixture of diastereomers. The purified product was analyzed by HPLC (NPP quench) and NMR (H-1 and P-31).

The diastereomeric mixture was separated according to the following procedure. The mixture (2.6 g) was dissolved in DCM. This sample was loaded on a RediSepRf column (80 g normal phase made by Teledyne Isco) and eluted with 10% EA/DCM to 50% EA/DCM over 20 minutes. Fractions were collected and analyzed by TLC. Fractions were pooled according to TLC analysis, and solvent was removed with a rotavaporator at room temperature. The diastereomeric ratio of their pooled fractions was determined by P-31 NMR and NPP-TFA analysis. If needed, the above procedure was repeated until the diastereomeric ratio reached 97%.

Example 70

Global Cholic Acid Modification

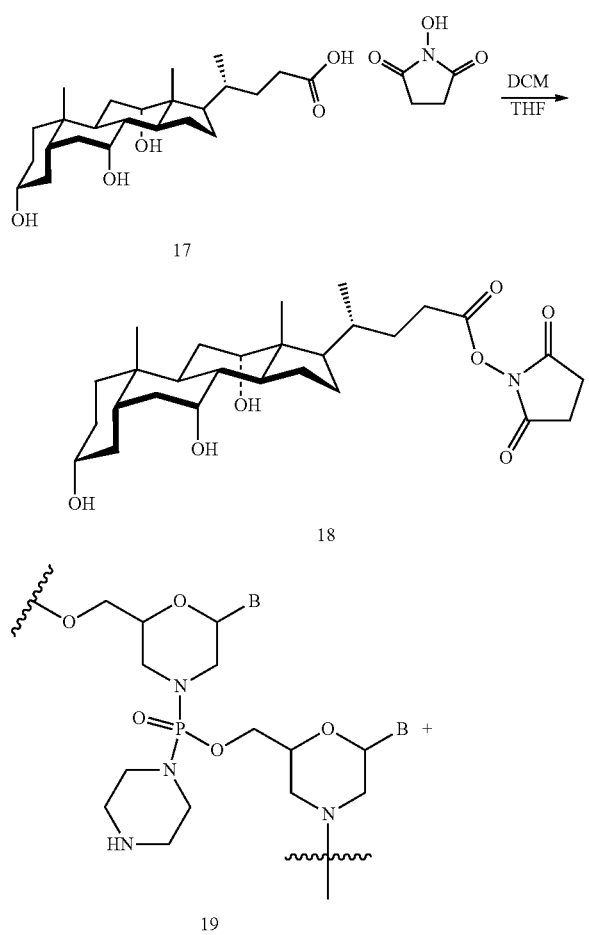

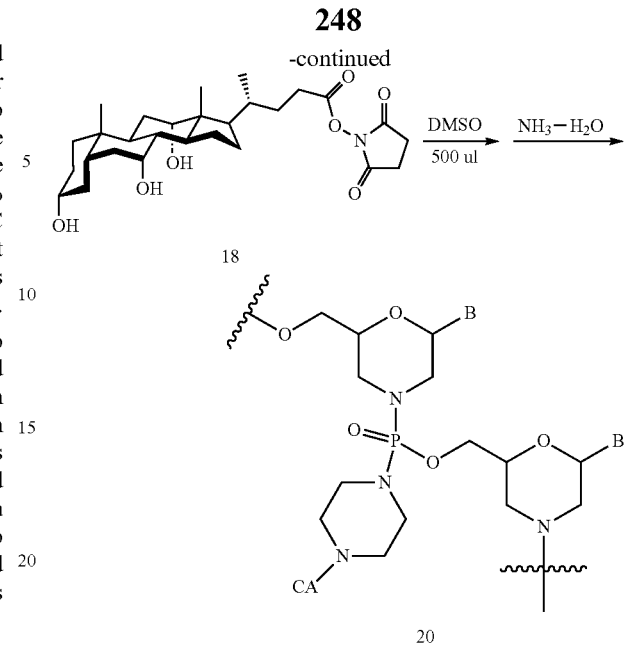

Cholic acid (17) (12 g, 29.4 mmol), N-hydroxysuccinimide (4.0 g, 34.8 mmol), EDCI (5.6 g, 29.3 mmol), and DMAP (1 g, 8.2 mmol) were charged to a round bottom flask. DCM (400 ml) and THF (40 ml) were added to dissolve. The reaction mixture was stirred at room temperature overnight. Water (400 ml) was then added to the reaction mixture, the organic layer separated and washed with water (2×400 ml), followed by sat. NaHCO$_3$ (300 ml) and brine (300 ml). The organic layer was then dried over Na$_2$SO$_4$. Solvent was removed with rotavaporator to obtain a white solid. The crude product (18) was dissolved in chloroform (100 ml) and precipitated into heptane (1000 ml). The solid was collected by filtration, analyzed by HPLC and NMR and used without further purification.

Compound 19 (20 mg, 2.8 µmol) was weighed into a vial (4 ml) and dissolved in DMSO (500 ul). The activated cholate ester (18) (13 mg, 25 µmol) was added to the reaction mixture according to the ratio of two equivalent of active ester per modification site followed by stirring at room temperature overnight. Reaction progress was determined by MALDI and HPLC (C-18 or SAX).

After the reaction was complete (as determined by disappearance of 19), 1 ml of concentrated ammonia was added to the reaction mixture once the reaction is complete. The reaction vial was then placed in an oven (45° C.) overnight (18 hours) followed by cooling to room temperature and dilution with 1% ammonia in water (10 ml). This sample was loaded on to an SPE column (2 cm), and the vial rinsed with 1% ammonia solution (2×2 ml). The SPE column was washed with 1% ammonia in water (3×6 ml), and the product eluted with 45% acetonitrile in 1% ammonia in water (6 ml). Fractions containing oligomer were identified by UV optical density measurement. Product (20) was isolated by lyophilization. Purity and identity were determined by MALDI and HPLC (C-18 and/or SAX).

This same procedure is applicable to deoxycholic acid activation and conjugation to 19.

Example 71

Global Guanidinylation

Compound 19 (25 mg, 2.8 µmol) was weighed into a vial (6 ml). 1H-Pyrozole-1-carboxamidine chloride (15 mg, 102

μmol) and potassium carbonate (20 mg, 0.15 mmol) were added to the vial. Water was added (500 ul), and the reaction mixture was stirred at room temperature overnight (about 18 hours). Reaction completion was determined by MALDI.

Once complete, the reaction was diluted with 1% ammonia in water (10 ml) and loaded on to an SPE column (2 cm). The vial was rinsed with 1% ammonia solution (2×2 ml), and the SPE column was washed with 1% ammonia in water (3×6 ml). Product was eluted with 45% acetonitrile in 1% ammonia in water (6 ml). Fractions containing oligomer were identified by UV optical density measurement. Product was isolated by lyophilization. Purity and identity were determined by MALDI and HPLC (C-18 and/or SAX).

Example 72

Global Thioacetyl Modification

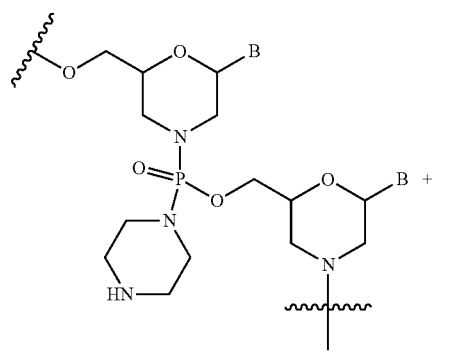

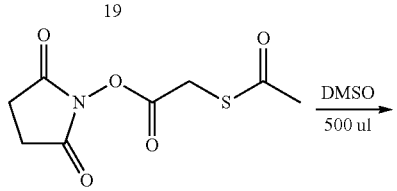

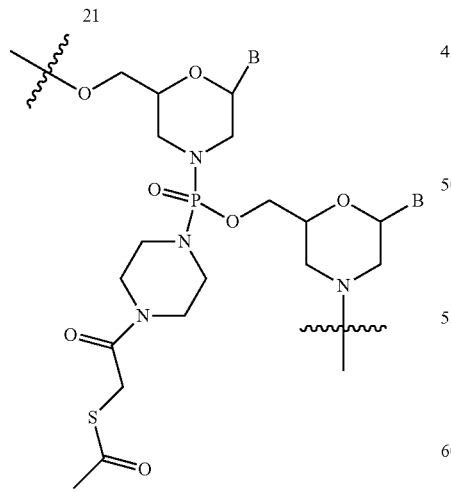

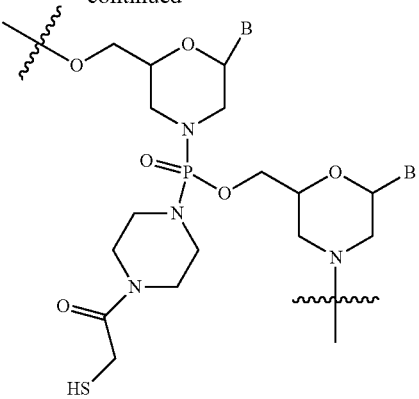

Compound 19 (20 mg, 2.3 μmol) was weighed in to a vial (4 ml) and dissolved in DMSO (500 ul). N-succinimidyl-S-acetylthioacetate (SATA) (21) (7 mg, 28 μmol) was added to the reaction mixture, and it was allowed to stir at room temperature overnight. Reaction progress was monitored by MALDI and HPLC.

Once complete, 1% ammonia in water was added to the reaction mixture, and it was stirred at room temperature for 2 hours. This solution was loaded on to an SPE column (2 cm). The vial was rinsed with 1% ammonia solution (2×2 ml), and the SPE column was washed with 1% ammonia in water (3×6 ml). Product (23) was eluted with 45% acetonitrile in 1% ammonia in water (6 ml). Fractions containing oligomer were identified by UV optical density measurement. Product was isolated by lyophilization. Purity and identity were determined by MALDI and HPLC (C-18 and/or SAX).

Example 73

Global Succinic Acid Modification

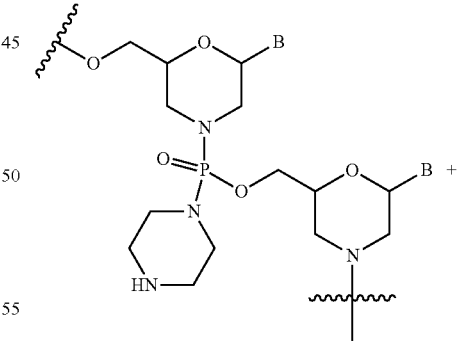

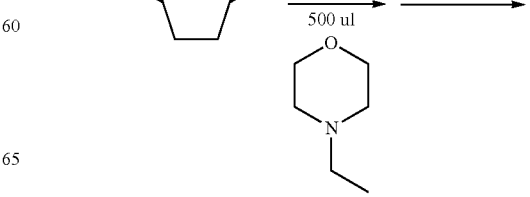

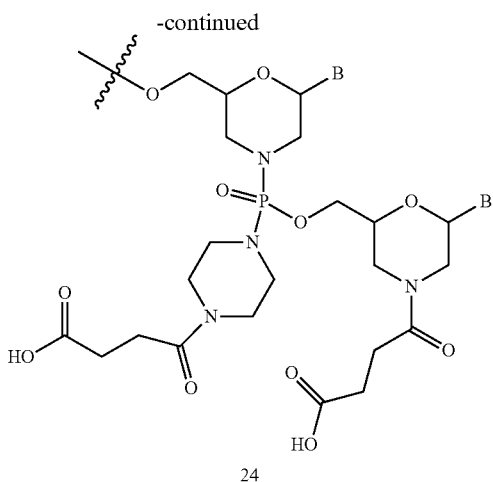

24

Compound 19 (32 mg, 3.7 µmol) was weighed in to a vial (4 ml) and dissolved in DMSO (500 ul). N-ethyl morpholino (12 mg, 100 mol) and succinic anhydride (10 mg, 100 mol) were added to the reaction mixture, and it was allowed to stir at room temperature overnight. Reaction progress was monitored by MALDI and HPLC.

Once complete, 1% ammonia in water was added to the reaction mixture, and it was stirred at room temperature for 2 hours. This solution was loaded on to an SPE column (2 cm). The vial was rinsed with 1% ammonia solution (2×2 ml), and the SPE column was washed with 1% ammonia in water (3×6 ml). Product (24) was eluted with 45% acetonitrile in 1% ammonia in water (6 ml). Fractions containing oligomer were identified by UV optical density measurement. Product was isolated by lyophilization. Purity and identity were determined by MALDI and HPLC (C-18 and/or SAX).

The above procedure is applicable to glutaric acid (glutaric anhydride) and tetramethyleneglutaric acid (tetramethyleneglutaric anhydride) modification of compound 19 as well.

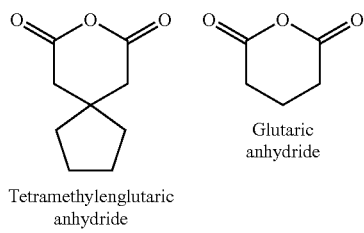

Tetramethylenglutaric anhydride

Glutaric anhydride

Example 74

Preparation of an Oligonucleotide Analogue Comprising a Modified Terminal Group To a solution of a 25-mer PMO containing a free 3'-end (27.7 mg, 3.226 µmol) in DMSO (300 µL) was added farnesyl bromide (1.75 µl, 6.452 µmol) and diisopropylethylamine (2.24 µL, 12.9 µmol). The reaction mixture was stirred at room temperature for 5 hours. The crude reaction mixture was diluted with 10 mL of 1% aqueous NH$_4$OH, and then loaded onto a 2 mL Amberchrome CG300M column. The column was then rinsed with 3 column volumes of water, and the product was eluted with 6 mL of 1:1 acetonitrile and water (v/v). The solution was then lyophilized to obtain the title compound as a white solid.

Example 75

Preparation of Morpholino Oligomers

Preparation of trityl piperazine phenyl carbamate 1b (see FIG. 1): To a cooled suspension of compound 1a in dichloromethane (6 mL/g 11) was added a solution of potassium carbonate (3.2 eq) in water (4 mL/g potassium carbonate). To this two-phase mixture was slowly added a solution of phenyl chloroformate (1.03 eq) in dichloromethane (2 g/g phenyl chloroformate). The reaction mixture was warmed to 20° C. Upon reaction completion (1-2 hr), the layers were separated. The organic layer was washed with water, and dried over anhydrous potassium carbonate. The product 1b was isolated by crystallization from acetonitrile. Yield=80%

Preparation of carbamate alcohol 1c: Sodium hydride (1.2 eq) was suspended in 1-methyl-2-pyrrolidinone (32 mL/g sodium hydride). To this suspension were added triethylene glycol (10.0 eq) and compound 1b (1.0 eq). The resulting slurry was heated to 95° C. Upon reaction completion (1-2 hr), the mixture was cooled to 20° C. To this mixture was added 30% dichloromethane/methyl tert-butyl ether (v:v) and water. The product-containing organic layer was washed successively with aqueous NaOH, aqueous succinic acid, and saturated aqueous sodium chloride. The product 1c was isolated by crystallization from dichloromethane/methyl tert-butyl ether/heptane. Yield=90%.

Preparation of Tail acid 1d: To a solution of compound 1c in tetrahydrofuran (7 mL/g 36) was added succinic anhydride (2.0 eq) and DMAP (0.5 eq). The mixture was heated to 50° C. Upon reaction completion (5 hr), the mixture was cooled to 20° C. and adjusted to pH 8.5 with aqueous NaHCO3. Methyl tert-butyl ether was added, and the product was extracted into the aqueous layer. Dichloromethane was added, and the mixture was adjusted to pH 3 with aqueous citric acid. The product-containing organic layer was washed with a mixture of pH=3 citrate buffer and saturated aqueous sodium chloride. This dichloromethane solution of 1d was used without isolation in the preparation of compound 1e.

Preparation of 1e: To the solution of compound 1d was added N-hydroxy-5-norbornene-2,3-dicarboxylic acid imide (HONB) (1.02 eq), 4-dimethylaminopyridine (DMAP) (0.34 eq), and then 1-(3-dimethylaminopropyl)-N'-ethylcarbodiimide hydrochloride (EDC) (1.1 eq). The mixture was heated to 55° C. Upon reaction completion (4-5 hr), the mixture was cooled to 20° C. and washed successively with 1:1 0.2 M citric acid/brine and brine. The dichloromethane solution underwent solvent exchange to acetone and then to N,N-dimethylformamide, and the product was isolated by precipitation from acetone/N,N-dimethylformamide into saturated aqueous sodium chloride. The crude product was reslurried several times in water to remove residual N,N-dimethylformamide and salts. Yield=70% of 1e from compound 1c. Introduction of the activated "Tail" onto the disulfide anchor-resin was performed in NMP by the procedure used for incorporation of the subunits during solid phase synthesis.

Preparation of the Solid Support for Synthesis of Morpholino Oligomers (see FIG. 2): This procedure was performed in a silanized, jacketed peptide vessel (custom made by ChemGlass, NJ, USA) with a coarse porosity (40-60 µm) glass frit, overhead stirrer, and 3-way Teflon stopcock to allow N2 to bubble up through the frit or a vacuum extraction. Temperature control was achieved in the reaction vessel by a circulating water bath.

The resin treatment/wash steps in the following procedure consist of two basic operations: resin fluidization and solvent/solution extraction. For resin fluidization, the stopcock was positioned to allow N2 flow up through the frit and the specified resin treatment/wash was added to the reactor and allowed to permeate and completely wet the resin. Mixing was then started and the resin slurry mixed for the specified time. For solvent/solution extraction, mixing and N2 flow were stopped and the vacuum pump was started and then the stopcock was positioned to allow evacuation of resin treatment/wash to waste. All resin treatment/wash volumes were 15 mL/g of resin unless noted otherwise.

To aminomethylpolystyrene resin (100-200 mesh; ~1.0 mmol/g N2 substitution; 75 g, 1 eq, Polymer Labs, UK, part #1464-X799) in a silanized, jacketed peptide vessel was added 1-methyl-2-pyrrolidinone (NMP; 20 ml/g resin) and the resin was allowed to swell with mixing for 1-2 hr. Following evacuation of the swell solvent, the resin was washed with dichloromethane (2×1-2 min), 5% diisopropylethylamine in 25% isopropanol/dichloromethane (2×3-4 min) and dichloromethane (2×1-2 min). After evacuation of the final wash, the resin was fluidized with a solution of disulfide anchor 2a in 1-methyl-2-pyrrolidinone (0.17 M; 15 mL/g resin, ~2.5 eq) and the resin/reagent mixture was heated at 45° C. for 60 hr. On reaction completion, heating was discontinued and the anchor solution was evacuated and the resin washed with 1-methyl-2-pyrrolidinone (4×3-4 min) and dichloromethane (6×1-2 min). The resin was treated with a solution of 10% (v/v) diethyl dicarbonate in dichloromethane (16 mL/g; 2×5-6 min) and then washed with dichloromethane (6×1-2 min). The resin 2b was dried under a N2 stream for 1-3 hr and then under vacuum to constant weight (+2%). Yield: 110-150% of the original resin weight.

Determination of the Loading of Aminomethylpolystyrene-disulfide resin: The loading of the resin (number of potentially available reactive sites) is determined by a spectrometric assay for the number of triphenylmethyl (trityl) groups per gram of resin.

A known weight of dried resin (25±3 mg) is transferred to a silanized 25 ml volumetric flask and ~5 mL of 2% (v/v) trifluoroacetic acid in dichloromethane is added. The contents are mixed by gentle swirling and then allowed to stand for 30 min. The volume is brought up to 25 mL with additional 2% (v/v) trifluoroacetic acid in dichloromethane and the contents thoroughly mixed. Using a positive displacement pipette, an aliquot of the trityl-containing solution (500 µL) is transferred to a 10 mL volumetric flask and the volume brought up to 10 mL with methanesulfonic acid.

The trityl cation content in the final solution is measured by UV absorbance at 431.7 nm and the resin loading calculated in trityl groups per gram resin (µmol/g) using the appropriate volumes, dilutions, extinction coefficient ($\epsilon$: 41 µmol-1 cm-1) and resin weight. The assay is performed in triplicate and an average loading calculated.

The resin loading procedure in this example will provide resin with a loading of approximately 500 µmol/g. A loading of 300-400 in µmol/g was obtained if the disulfide anchor incorporation step is performed for 24 hr at room temperature.

Tail loading: Using the same setup and volumes as for the preparation of aminomethylpolystyrene-disulfide resin, the Tail can be introduced into the molecule. For the coupling step, a solution of 1e (0.2 M) in NMP containing 4-ethylmorpholine (NEM, 0.4 M) was used instead of the disulfide anchor solution. After 2 hr at 45° C., the resin 2b was washed twice with 5% diisopropylethylamine in 25% isopropanol/dichloromethane and once with DCM. To the resin was added a solution of benzoic anhydride (0.4 M) and NEM (0.4 M). After 25 min, the reactor jacket was cooled to room temperature, and the resin washed twice with 5% diisopropylethylamine in 25% isopropanol/dichloromethane and eight times with DCM. The resin 2c was filtered and dried under high vacuum. The loading for resin 2c is defined to be the loading of the original aminomethylpolystyrene-disulfide resin 2b used in the Tail loading.

Solid Phase Synthesis: Morpholino Oligomers were prepared on a Gilson AMS-422 Automated Peptide Synthesizer in 2 mL Gilson polypropylene reaction columns (Part #3980270). An aluminum block with channels for water flow was placed around the columns as they sat on the synthesizer. The AMS-422 will alternatively add reagent/wash solutions, hold for a specified time, and evacuate the columns using vacuum.

For oligomers in the range up to about 25 subunits in length, aminomethylpolystyrene-disulfide resin with loading near 500 µmol/g of resin is preferred. For larger oligomers, aminomethylpolystyrene-disulfide resin with loading of 300-400 µmol/g of resin is preferred. If a molecule with 5'-Tail is desired, resin that has been loaded with Tail is chosen with the same loading guidelines.

The following reagent solutions were prepared:
Detrytilation Solution: 10% Cyanoacetic Acid (w/v) in 4:1 dichloromethane/acetonitrile; Neutralization Solution: 5% Diisopropylethylamine in 3:1 dichloromethane/isopropanol; Coupling Solution: 0.18 M (or 0.24 M for oligomers having grown longer than 20 subunits) activated Morpholino Subunit of the desired base and linkage type and 0.4 M N ethylmorpholine, in 1,3-dimethylimidazolidinone. Dichloromethane (DCM) was used as a transitional wash separating the different reagent solution washes.

On the synthesizer, with the block set to 42° C., to each column containing 30 mg of aminomethylpolystyrene-disulfide resin (or Tail resin) was added 2 mL of 1-methyl-2-pyrrolidinone and allowed to sit at room temperature for 30 min. After washing with 2 times 2 mL of dichloromethane, the following synthesis cycle was employed:

| Step | Volume | Delivery | Hold time |
| --- | --- | --- | --- |
| Detrytilation | 1.5 mL | Manifold | 15 seconds |
| Detrytilation | 1.5 mL | Manifold | 15 seconds |
| Detrytilation | 1.5 mL | Manifold | 15 seconds |
| Detrytilation | 1.5 mL | Manifold | 15 seconds |
| Detrytilation | 1.5 mL | Manifold | 15 seconds |
| Detrytilation | 1.5 mL | Manifold | 15 seconds |
| Detrytilation | 1.5 mL | Manifold | 15 seconds |
| DCM | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| Coupling | 350 uL-500 uL | Syringe | 40 minutes |
| DCM | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| DCM | 1.5 mL | Manifold | 30 seconds |
| DCM | 1.5 mL | Manifold | 30 seconds |

The sequences of the individual oligomers were programmed into the synthesizer so that each column receives the proper coupling solution (A,C,G,T,I) in the proper sequence. When the oligomer in a column had completed incorporation of its final subunit, the column was removed from the block and a final cycle performed manually with a coupling solution comprised of 4-methoxytriphenylmethyl chloride (0.32 M in DMI) containing 0.89 M 4-ethylmorpholine.

Cleavage from the resin and removal of bases and backbone protecting groups: After methoxytritylation, the resin was washed 8 times with 2 mL 1-methyl-2-pyrrolidinone. One mL of a cleavage solution consisting of 0.1 M 1,4-dithiothreitol (DTT) and 0.73 M triethylamine in 1-methyl-2-pyrrolidinone was added, the column capped, and allowed to sit at room temperature for 30 min. After that time, the solution was drained into a 12 mL Wheaton vial. The greatly shrunken resin was washed twice with 300 µL of cleavage solution. To the solution was added 4.0 mL conc aqueous ammonia (stored at −20° C.), the vial capped tightly (with Teflon lined screw cap), and the mixture swirled to mix the solution. The vial was placed in a 45° C. oven for 16-24 hr to effect cleavage of base and backbone protecting groups.

Initial Oligomer Isolation: The vialed ammonolysis solution was removed from the oven and allowed to cool to room temperature. The solution was diluted with 20 mL of 0.28% aqueous ammonia and passed through a 2.5×10 cm column containing Macroprep HQ resin (BioRad). A salt gradient (A: 0.28% ammonia with B: 1 M sodium chloride in 0.28% ammonia; 0-100% B in 60 min) was used to elute the methoxytrityl containing peak. The combined fractions were pooled and further processed depending on the desired product.

Demethoxytritylation of Morpholino Oligomers: The pooled fractions from the Macroprep purification were treated with 1 M H3PO4 to lower the pH to 2.5. After initial mixing, the samples sat at room temperature for 4 min, at which time they are neutralized to pH 10-11 with 2.8% ammonia/water. The products were purified by solid phase extraction (SPE).

Amberchrome CG-300M (Rohm and Haas; Philadelphia, Pa.) (3 mL) is packed into 20 mL fritted columns (BioRad Econo-Pac Chromatography Columns (732-1011)) and the resin rinsed with 3 mL of the following: 0.28% NH4OH/80% acetonitrile; 0.5M NaOH/20% ethanol; water; 50 mM H3PO4/80% acetonitrile; water; 0.5 NaOH/20% ethanol; water; 0.28% NH4OH.

The solution from the demethoxytritylation was loaded onto the column and the resin rinsed three times with 3-6 mL 0.28% aqueous ammonia. A Wheaton vial (12 mL) was placed under the column and the product eluted by two washes with 2 mL of 45% acetonitrile in 0.28% aqueous ammonia. The solutions were frozen in dry ice and the vials placed in a freeze dryer to produce a fluffy white powder. The samples were dissolved in water, filtered through a 0.22 micron filter (Pall Life Sciences, Acrodisc 25 mm syringe filter, with a 0.2 micron HT Tuffryn membrane) using a syringe and the Optical Density (OD) was measured on a UV spectrophotometer to determine the OD units of oligomer present, as well as dispense sample for analysis. The solutions were then placed back in Wheaton vials for lyophilization.

Analysis of Morpholino Oligomers: MALDI-TOF mass spectrometry was used to determine the composition of fractions in purifications as well as provide evidence for identity (molecular weight) of the oligomers. Samples were run following dilution with solution of 3,5-dimethoxy-4-hydroxycinnamic acid (sinapinic acid), 3,4,5-trihydoxyacetophenone (THAP) or alpha-cyano-4-hydroxycinnamic acid (HCCA) as matrices.

Cation exchange (SCX) HPLC was performed using a Dionex ProPac SCX-10, 4×250 mm column (Dionex Corporation; Sunnyvale, Calif.) using 25 mM pH=5 sodium acetate 25% acetonitrile (Buffer A) and 25 mM pH=5 sodium acetate 25% acetonitrile 1.5 M potassium chloride (buffer B) (Gradient 10-100% B in 15 min) or 25 mM KH2PO4 25% acetonitrile at pH=3.5 (buffer A) and 25 mM KH2PO4 25% acetonitrile at pH=3.5 with 1.5 M potassium chloride (buffer B) (Gradient 0-35% B in 15 min). The former system was used for positively charged oligomers that do not have a peptide attached, while the latter was used for peptide conjugates.

Purification of Morpholino Oligomers by Cation Exchange Chromatography: The sample is dissolved in 20 mM sodium acetate, pH=4.5 (buffer A) and applied to a column of Source 30 cation exchange resin (GE Healthcare) and eluted with a gradient of 0.5 M sodium chloride in 20 mM sodium acetate and 40% acetonitrile, pH=4.5 (buffer B). The pooled fractions containing product are neutralized with conc aqueous ammonia and applied to an Amberchrome SPE column. The product is eluted, frozen, and lyophilized as above.

I. Biological Evaluation

Example 1

Treatment of Influenza A Virus Infected Cells

A series of PMO containing various modified intersubunit linkages was prepared and used to treat influenza A virus-infected cells in culture. The PMO and PMO containing the modified intersubunit linkages of the present inventions were all designed to target the viral M1/M2 segment at the AUG start codon and have one of two base sequences. Inhibition of influenza A virus replication by antisense targeting of multiple sites within the M1/M2 segment is described in U.S. application Ser. No. 12/945,081 which is incorporated herein by reference in its entirety. In addition to inhibition of translation by targeting the common M1/M2 AUG start site, splice donor and splice acceptor sites can also be targeted using compounds of the invention.

An alveolar murine macrophage cell line (ATCC; AMJ2-C11) was infected at 0.1 MOI with H1N1 (strain PR8) and 1 hour post-infection test compound was added. Cells were incubated at 35 degrees C. overnight. Viral supernatant was then taken and incubated with VNAR protease to release viral RNA. HA RNA was quantified by quantitative real-time PCR (qRT-PCR). Cells were washed, fixed, and permeabilized. M1 and M2 proteins were then probed with monoclonal antibodies for 30 min at 37 degrees C. Cells were washed and anti-mouse IgG conjugated with Alexa 646 was added for 15 min at room temperature. M1 and M2 were then assayed by flow cytometry. To determine M1 and M2 protein levels, the percent of M1 or M2 positive cells was multiplied by the mean fluorescent intensity of M1 or M2. Each sample was then divided by the untreated control to generate the percent of M1 or M2 compared to untreated scramble controls.

A reduction in viral M2 protein levels from cells treated with various compounds of the disclosure was observed. The flow cytometry method described above was used to determine relative M2 protein expression after treatment at 60 micromolar. The compounds of the disclosure inhibited the production of the M2 protein to varying degrees.

Example 2

Treatment of Influenza A Virus Infected Mice In Vivo

Additional experiments in support of the invention were performed using Balb/c mice infected with the PR8 strain of influenza A. Mice were infected with 3.5 $TCID_{50}$ via an intranasal inoculation after being treated 4 hours prior with various compound of the invention disclosed herein. In some experiments an additional dose of test compound was administered at 96 hr post-infection. All doses consisted of 100 micrograms of test compound in 50 microliters of PBS and were administered by intranasal insufflation. The weight of the animals were monitored daily and was used as a clinical endpoint for antiviral drug activity. At day 7 post-infection the animals were sacrificed and lungs were harvested for viral load determinations using the qRT-PCR method described in Example 1.

$TCID_{50}$ determinations were made using half-log serial dilutions of the lung homogenates and plated onto AMJ-C12 macrophage cells. After 24 hr at 35 degrees C., the media was changed and incubated for an additional 72 h at 35 degrees C. 50 mL of a solution of 0.5% chicken RBC in PBS was added and incubated for 1 h at 4 degrees C. Hemagglutination pattern was read and $TCID_{50}$ were calculated using the Reed and Muench method. TCID50 values were then normalized to input tissue weight.

The compounds of the invention as disclosed herein show increased antiviral activity and decreased weight loss compared to a PMOplus compound after H1N1 infection. Balb/c mice (n=4) were infected with H1N1 and given a single 100 microgram dose of test compound 4 hours prior to infection. Mice were weighed daily and percent weight loss was determined from pre-infection weight. Lungs were harvested day 7 post-infection and assayed for viral load by $TCID_{50}$. Results are presented as the fold increase in antiviral activity over naked PMO. This experiment shows approximately 50-fold increased antiviral activity of two PMO-X compounds compared to un-modified PMO and approximately 10-fold higher activity compared to a PMOplus compound.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The present application claims the benefit under 35 U.S.C. §119(e) of U.S. Provisional Patent Application No. 61/561,806 filed on Nov. 18, 2011; which application is incorporated herein by reference in its entirety.

---

What is claimed is:

1. A compound having the structure of Formula (I):

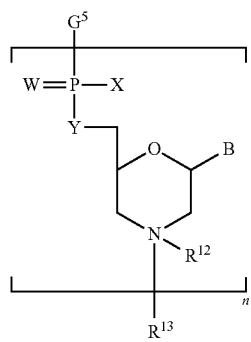
(I)

or a salt or isomer thereof,
wherein:
n is an integer from 2-35;
$G^5$ is halogen, OH, alkoxy, $OSO_2$(alkyl), $OSO_2$(aryl), or

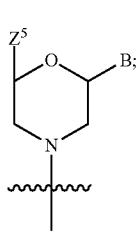

each B is an independently selected base pair moiety;
each Y is independently O or $NR^{10}$;
each W is independently S or O;
$Z^5$ is -($L^{11}$)-($R^{15}$), -($L^{11}$)-($L^{15}$)-($R^{16}$), or -($L^{11}$)-($L^{12}$)-($R^{17}$);

$L^{11}$ is selected from:

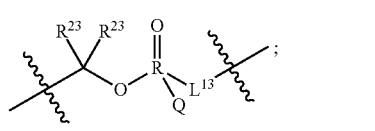
a)

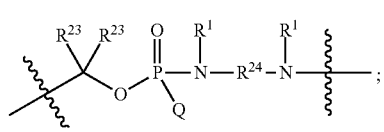
b)

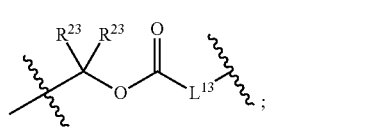
c)

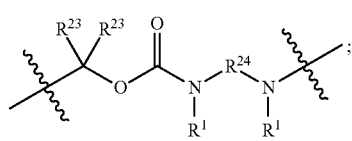
d)

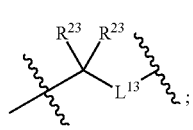
e)

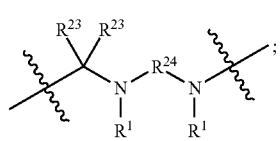
f)

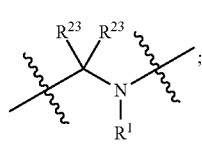
g)

-continued

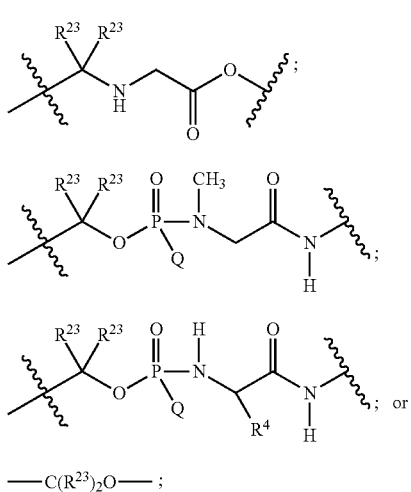

h)

i)

j)

k)

—C(R²³)₂O—;

wherein L¹³ is selected from:

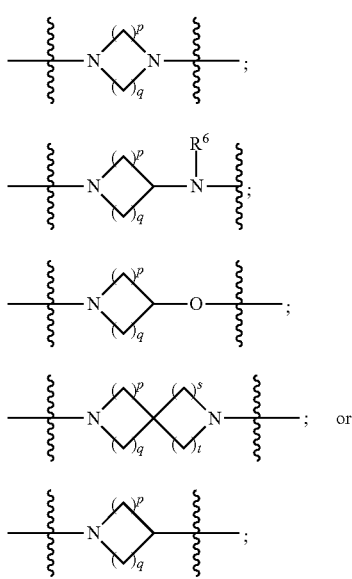

a)

b)

c)

d)

e)

$L^{12}$ is a linker cleaveable under biological conditions selected from:
a) —($C_1$-$C_{10}$ alkylene)-OC(O)O—CH₂O—;
b) —C(O)—($C_1$-$C_{10}$ alkylene)-OC(O)O—CH₂O—;
c) —C(O)—(CH=CH)—C(O)O—CH₂O—;
d) —($C_1$-$C_{10}$ alkylene)-S—S—CH₂CH₂O—; or
e) —C(O)—($C_1$-$C_{10}$ alkylene)-S—S—CH₂CH₂O—;

$L^{15}$ is divalent radical selected from $C_1$-$C_{30}$ alkylene, $C_3$-$C_8$cycloalkylene, $C_6$-$C_{30}$ arylene, —($C_6$-$C_{30}$ arylene)-($C_1$-$C_{30}$ alkylene)-, —($C_1$-$C_{30}$ alkylene)-C(=O)—, —($C_2$-$C_{30}$ alkoxy)-C(=O)—, -(3-18 membered heteroalkylene)-C(=O)—, —($C_3$-$C_8$ cycloalkylene)-C(=O)—, —($C_3$-$C_8$ cycloalkylene)-($C_1$-$C_{30}$ alkylene)-C(=O)—, —($C_1$-$C_{30}$ alkylene)($C_3$-$C_8$ cycloalkylene)-C(=O)—, —($C_6$-$C_{30}$ arylene)-C(=O)—, —($C_6$-$C_{30}$ arylene)-($C_1$-$C_{30}$ alkylene)-C(=O)—, —($C_1$-$C_{30}$ alkylene)-($C_6$-$C_{30}$ arylene)-C(=O)—, —($C_1$-$C_{30}$ alkylene)-O—C(=O)—, —($C_3$-$C_8$ cycloalkylene)-O—C(=O)—, —($C_7$-$C_{30}$ arylene)-O—C(=O)—, —($C_6$-$C_{30}$ arylene)-($C_1$-$C_{30}$ alkylene)-O—C(=O)—, —($C_6$-$C_{30}$ arylene)-($C_1$-$C_{30}$ alkylene)-O—C(=O)—, —C(=O)OR²¹, or —P(=O)(R²²)₂;

$R^{12}$ is an electron pair, with the provision that if $R^{13}$ is $C_1$-$C_{30}$ alkyl, then $R^{12}$ is an electron pair, an N-oxide, or $C_1$-$C_6$ alkyl;

each $R^{10}$ and $R^{13}$ is independently selected from hydrogen, a cell-penetrating peptide, a natural or non-natural amino acid, guanidinyl, amidinyl, heterocyclyl, $C_1$-$C_{30}$ alkyl, $C_3$-$C_8$ cycloalkyl; $C_6$-$C_{30}$ aryl, $C_7$-$C_{30}$ aralkyl, $C_1$-$C_{30}$ alkylcarbonyl, $C_3$-$C_8$ cycloalkylcarbonyl, $C_3$-$C_8$ cycloalkylalkylcarbonyl, $C_6$-$C_{30}$ arylcarbonyl, $C_7$-$C_{30}$ aralkylcarbonyl, $C_1$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, —C(=O)OR²¹, —C(=O)NHR²¹, or —P(=O)(R²²)₂;

$R^{15}$ is independently selected from a cell-penetrating peptide, a natural or non-natural amino acid, guanidinyl, amidinyl, heterocyclyl, $C_1$-$C_{30}$ alkyl, $C_3$-$C_8$ cycloalkyl; $C_6$-$C_{30}$ aryl, $C_7$-$C_{30}$ aralkyl, $C_1$-$C_{30}$ alkylcarbonyl, $C_3$-$C_8$ cycloalkylcarbonyl, $C_3$-$C_8$ cycloalkylalkylcarbonyl, $C_6$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, 3-18 membered alkoxyalkylcarbonyl, —SO₂R²¹, —C(=O)OR²¹, —P(=O)(OH)₂ or —P(=O)(R²²)₂;

$R^{16}$ is a solid support matrix suitable for solid phase synthesis of oligonucleotides;

$R^{17}$ is a drug, protein or toxin;

each $R^{21}$ is independently $C_1$-$C_{30}$ alkyl, or a 3-18 membered alkoxyalkyl group;

each $R^{22}$ is independently an $C_6$-$C_{12}$ aryloxy;

each $R^{23}$ is independently H or $C_1$-$C_6$ alkyl; or optionally two R²³ groups join to form a 3- to 8-membered ring;

$R^{24}$ is a $C_1$-$C_6$ alkylene;

Q is independently selected from X1, X2, X3, X4, X5, X6, X7, or X8;

each X is independently selected from X1, X2, X3, X4, X5, X6, X7, or X8 wherein at least two instances of X are selected from X2, X3, X4, X5, X6, X7, or X8;

wherein

X1 is N(CH₃)₂;

X2 is selected from:
a) —O-alkylene-CO₂H;
b) —O-alkylene-CHN₄;
c) —N(R¹)-alkylene-CO₂H;
d) —N(R¹)-alkylene-CHN₄;
e) -L1-CO-alkylene-CO₂H;
f) -L1-CO-alkylene-CHN₄;
g) -L1-CO-alkenylene-CO₂H;
h) -L1-CO-alkenylene-CHN₄;
i) -L1-CO-arylene-CO₂H;
j) -L1-CO-arylene-CHN₄;
k) -L1-CONH-alkylene-CO₂H;
l) -L1-CONH-alkylene-CHN₄;
m) -L1-CONH-arylene-CO₂H;
n) -L1-CONH-arylene-CHN₄;
o) -L1-SO₂-alkylene-CO₂H;
p) -L1-SO₂-alkylene-CHN₄;
q) -L1-SO₂-arylene-CO₂H;
r) -L1-SO₂-arylene-CHN₄;
s) -L1-alkylene-CO₂H;
t) -L1-alkylene-CHN₄;

u) -L1-arylene-CO$_2$H;
v) -L1-arylene-CHN$_4$; and
w) a protected form of any of the above X2 groups;

X3 is selected from:
a) -L1-alkyl;
b) -L1-heterocyclyl;
c) —O-alkylene-CNH—NH$_2$;
d) —N(R$^1$)-alkylene-CNH—NH$_2$;
e) -L1-CNH—NH$_2$;
f) -L1-alkylene-CNH—NH$_2$;
g) -L1-arylene-CNH—NH$_2$;
h) -L1-CO-alkylene-CNH—NH$_2$;
i) -L1-CO-alkenylene-CNH—NH$_2$;
j) -L1-CO-arylene-CNH—NH$_2$;
k) -L1-CONH-alkylene-CNH—NH$_2$;
l) -L1-CONH-arylene-CNH—NH$_2$;
m) -L1-SO$_2$-alkylene-CNH—NH$_2$;
n) -L1-SO$_2$-arylene-CNH—NH$_2$;
o) —O-alkylene-N(R$^1$)$_2$;
p) —N(R$^1$)-alkylene-N(R$^1$)$_2$;
q) -L1-N(R$^1$)$_2$;
r) -L1-alkylene-N(R$^1$)$_2$;
s) -L1-arylene-N(R$^1$)$_2$;
t) -L1-CO-alkylene-N(R$^1$)$_2$;
u) -L1-CO-alkenylene-N(R$^1$)$_2$;
v) -L1-CO-arylene-N(R$^1$)$_2$;
w) -L1-CONH-alkylene-N(R$^1$)$_2$;
x) -L1-CONH-arylene-N(R$^1$)$_2$;
y) -L1-SO$_2$-alkylene-N(R$^1$)$_2$;
z) —O-alkylene-N(R$^2$)$_3$;
aa) —N(R$^1$)-alkylene-N(R$^2$)$_3$;
bb) -L1-N(R$^2$)$_3$;
cc) -L1-alkylene-N(R$^2$)$_3$;
dd) -L1-arylene-N(R$^2$)$_3$;
ee) -L1-CO-alkylene-N(R$^2$)$_3$;
ff) -L1-CO-alkenylene-N(R$^2$)$_3$;
gg) -L1-CO-arylene-N(R$^2$)$_3$;
hh) -L1-CONH-alkylene-N(R$^2$)$_3$;
ii) -L1-CONH-arylene-N(R$^2$)$_3$;
jj) -L1-SO$_2$-alkylene-N(R$^2$)$_3$;
kk) —O-alkylene-heterocyclyl;
ll) —N(R$^1$)-alkylene-heterocyclyl;
mm) -L1-alkylene-heterocyclyl;
nn) -L1-arylene-heterocyclyl;
oo) -L1-CO-alkylene-heterocyclyl;
pp) -L1-CO-alkenylene-heterocyclyl;
qq) -L1-CO-arylene-heterocyclyl;
rr) -L1-CONH-alkylene-heterocyclyl;
ss) -L1-CONH-arylene-heterocyclyl;
tt) -L1-SO$_2$-alkylene-heterocyclyl;
uu) —O-alkylene-N(O)(R$^2$)$_2$;
vv) —N(R$^1$)-alkylene-N(O)(R$^2$)$_2$;
ww) -L1-N(O)(R$^2$)$_2$;
xx) -L1-alkylene-N(O)(R$^2$)$_2$;
yy) -L1-arylene-N(O)(R$^2$)$_2$;
zz) -L1-CO-alkylene-N(O)(R$^2$)$_2$;
aaa) -L1-CO-alkenylene-N(O)(R$^2$)$_{23}$;
bbb) -L1-CO-arylene-N(O)(R$^2$)$_2$;
ccc) -L1-CONH-alkylene-N(O)(R$^2$)$_2$;
ddd) -L1-CONH-arylene-N(O)(R$^2$)$_2$;
eee) -L1-SO$_2$-alkylene-N(O)(R$^2$)$_2$;
fff) —O-alkylene-NH—CNH—NH$_2$;
ggg) —N(R$^1$)-alkylene-NH—CNH—NH$_2$;
hhh) -L1-NH—CNH—NH$_2$;
iii) -L1-alkylene-NH—CNH—NH$_2$;
jjj) -L1-arylene-NH—CNH—NH$_2$;
kkk) -L1-CO-alkylene-NH—CNH—NH$_2$;
lll) -L1-CO-alkenylene-NH—CNH—NH$_2$;
mmm) -L1-CO-arylene-NH—CNH—NH$_2$;
nnn) -L1-CONH-alkylene-NH—CNH—NH$_2$;
ooo) -L1-CONH-arylene-NH—CNH—NH$_2$;
ppp) -L1-SO$_2$-alkylene-NH—CNH—NH$_2$;
qqq) -L1-SO$_2$-arylene-NH—CNH—NH$_2$; and
rrr) a protected form of any of the above X3 groups;

X4 is selected from:
a) —O-alkylene-aryl;
b) —N(R$^1$)-aryl;
c) —N(R$^1$)-alkylene-aryl;
d) -L1-CO-alkylene-aryl;
e) -L1-CO-alkenylene-aryl;
f) -L1-CO-arylene-aryl;
g) -L1-CONH-alkylene-aryl;
h) -L1-CONH-arylene-aryl;
i) -L1-SO$_2$-alkylene-aryl;
j) -L1-SO$_2$-arylene-aryl;
k) -L1-alkylene-aryl;
l) -L1-arylene-aryl;
m) —N(R$^1$)-alkylene-N(R$^1$)-aryl;
n) —N(R$^1$)-alkylene-N(R$^1$)CO-aryl;
o) —N(R$^1$)-alkylene-N(R$^1$)SO$_2$-aryl;
p) —N(R$^1$)-alkylene-N(R$^1$)CH$_2$-aryl;
q) -L1-aryl;
r) -L1-CO-aryl;
s) -L1-SO$_2$-aryl;
t) -L1-alkylene-P(aryl)$_3$;
u) -L1-CO-alkylene-P(aryl)$_3$;
v) -L1-SO$_2$-alkylene-P(aryl)$_3$; and
w) a protected form of any of the above X4 groups;

X5 is selected from:
a) —O-alkylene-heteroaryl;
b) —N(R$^1$)-alkylene-heteroaryl;
c) -L1-CO-alkylene-heteroaryl;
d) -L1-CO-alkenylene-heteroaryl;
e) -L1-CO-arylene-heteroaryl;
f) -L1-CONH-alkylene-heteroaryl;
g) -L1-CONH-arylene-heteroaryl;
h) -L1-SO$_2$-alkylene-heteroaryl;
i) -L1-SO$_2$-arylene-heteroaryl;
j) -L1-alkylene-heteroaryl;
k) -L1-arylene-heteroaryl;
l) —N(R$^1$)-alkylene-N(R$^1$)-heteroaryl;
m) —N(R$^1$)-alkylene-N(R$^1$)CO-heteroaryl;
n) —N(R$^1$)-alkylene-N(R$^1$)SO$_2$-heteroaryl;
o) —N(R$^1$)-alkylene-N(R$^1$)CH$_2$-heteroaryl;
p) -L1-heteroaryl; and
q) a protected form of any of the above X5 groups;

X6 is selected from:
a) —O-alkylene-(OCH$_2$CH$_2$)$_m$OH;
b) —O-alkylene-(OCH$_2$CH$_2$)$_m$OCH$_3$;
c) —N(R$^1$)-alkylene-(OCH$_2$CH$_2$)$_m$OH;
d) —N(R$^1$)-alkylene-(OCH$_2$CH$_2$)$_m$OCH$_3$;
e) —N(R$^1$)-arylene-(OCH$_2$CH$_2$)$_m$OH;
f) —N(R$^1$)-arylene-(OCH$_2$CH$_2$)$_m$OCH$_3$;
g) -L1-alkylene-(OCH$_2$CH$_2$)$_m$OH;
h) -L1-CO-alkylene-(OCH$_2$CH$_2$)$_m$OH;
i) -L1-CO-alkylene-(OCH$_2$CH$_2$)$_m$OCH$_3$;
j) -L1-SO$_2$-alkylene-(OCH$_2$CH$_2$)$_m$OH;
k) -L1-SO$_2$-alkylene-(OCH$_2$CH$_2$)$_m$OCH$_3$;
l) -L1-CO-arylene-(OCH$_2$CH$_2$)$_m$OH;
m) -L1-CO-arylene-(OCH$_2$CH$_2$)$_m$OCH$_3$;
n) -L1-SO$_2$-arylene-(OCH$_2$CH$_2$)$_m$OH;
o) -L1-SO$_2$-arylene-(OCH$_2$CH$_2$)$_m$OCH$_3$;
p) -L1-CO—(OCH$_2$CH$_2$)$_m$OH;
q) -L1-CO—(OCH$_2$CH$_2$)$_m$OCH$_3$;

r) —N(R¹)-(dibenzo-18-crown-6);
s) an aza-crown ether; and
t) a protected form of any of the above X6 groups;
X7 is selected from:
  a) -heterocyclyl;
  b) —N(R¹)(R³)
  c) -L1-hydrogen;
  d) -L1-alkyl;
  e) -L1-CO-alkyl;
  f) -L1-CONH-alkyl;
  g) -L1-CON(alkyl)-alkyl;
  h) -L1-SO₂-alkyl; and
  i) a protected form of any of the above X7 groups;
X8 is selected from:
  a) -L1-CA;
  b) -L1-dCA;
  c) -L1-COCH₂(R⁴)
  d) -L1-COCH(R⁴)NHCO₂-alkyl;
  e) —OR⁵;
  f) a protected form of any of the above X8 groups;
each R¹ is independently hydrogen, alkyl, or a cell-penetrating peptide;
each R² is independently $C_1$-$C_{12}$ alkyl or optionally when two R² are $C_1$-$C_{12}$ alkyl, two R² are joined to form a heterocyclic ring;
each R³ is independently $C_2$-$C_{18}$ alkyl, alkenyl, or alkynyl;
each R⁴ is independently hydrogen, alkyl, hydroxyalkyl, sulfhydrylalkyl, or arylalkyl;
each R⁵ is independently $C_1$-$C_{12}$ alkyl;
each R⁶ is independently hydrogen or $C_1$-$C_{12}$ alkyl;
L1 is selected from:

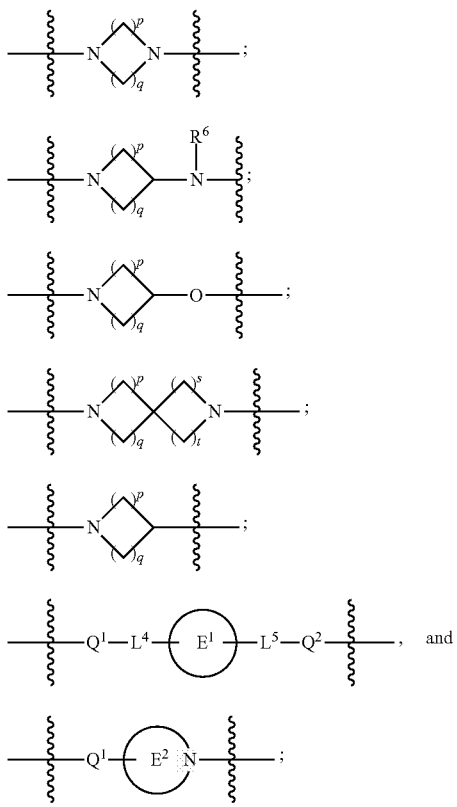

wherein
  each Q¹ and Q² are each selected from a bond, —O— or —N(R⁶)—;
  each E¹ is independently selected from optionally substituted aryl or optionally substituted heteroaryl;
  each E² is independently an optionally substituted nitrogen containing heteroaryl;
  each L⁴ and L⁵ are each independently a bond, optionally substituted $C_1$-$C_6$ alkyl, or optionally substituted heteroalkyl; and
  m, p, q, s, and t are each independently 1-4,
wherein if the X group proximal to the 3' terminus is:

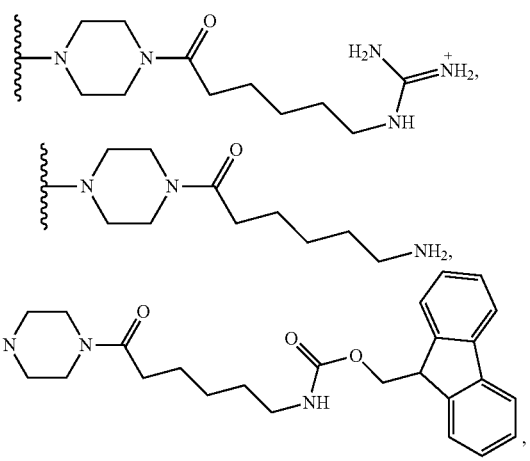

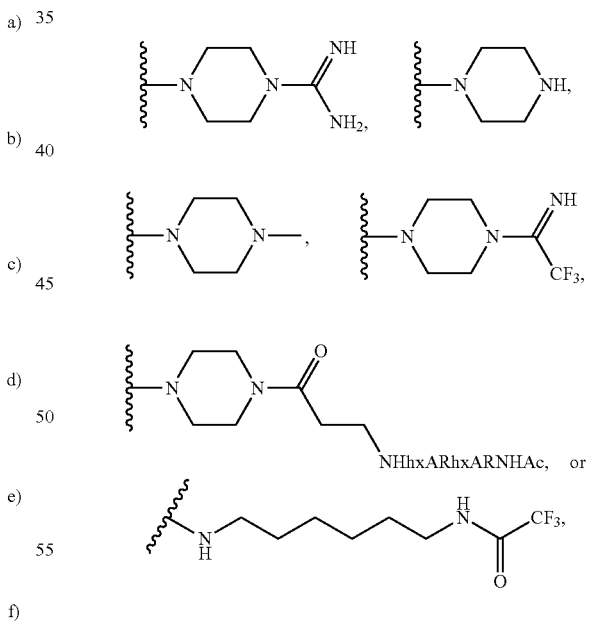

then at least three other X groups are not X1.

2. The compound of claim 1, wherein Z⁵ is -(L¹¹)-(R¹⁵); each Y is independently O, NH, or NR¹⁰; each W is O; each R¹ is independently hydrogen or alkyl; each R² is independently $C_1$-$C_{12}$ alkyl; and each X is independently selected from X1, X2, X3, X4, X5, X6, X7, or X8.

3. The compound of claim 1, wherein R¹³ is an optionally substituted triphenylmethyl group.

4. The compound of claim 2, wherein $G^5$ is
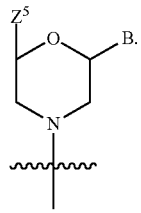
5. The compound of claim 4 wherein each W is O and each Y is O.
6. The compound of claim 5, wherein at least one X is selected from:
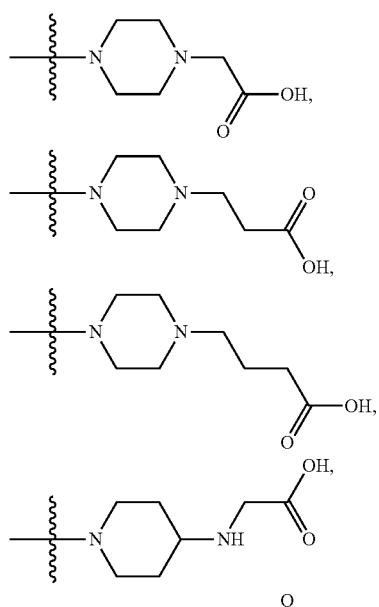
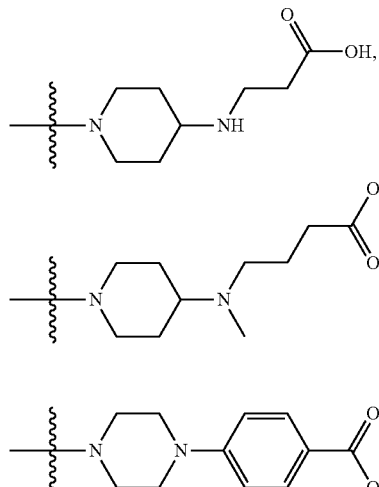
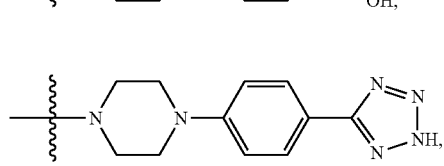
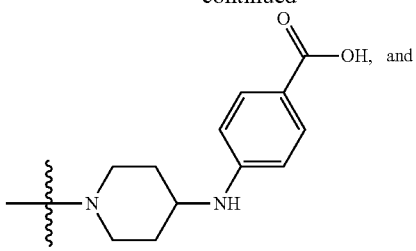
7. The compound of claim 5, wherein at least one X is selected from -L1-heterocyclyl, and wherein L1 is selected from:
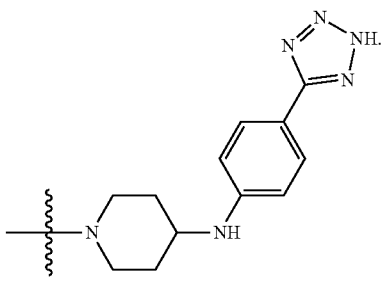 [SMILES: *N1CCC(Nc2ccc(-c3nn[nH]n3)cc2)CC1]
8. The compound of claim 5, wherein at least one X is selected from:
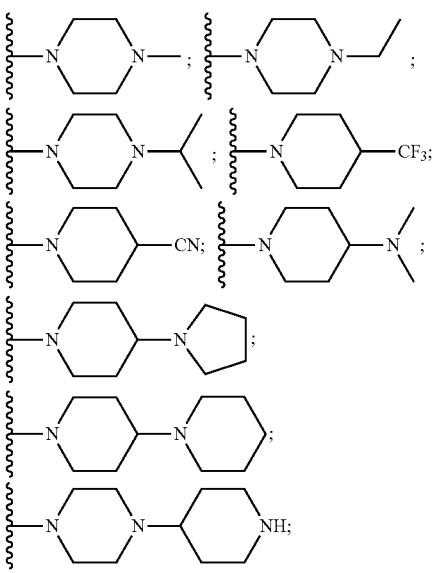

-continued

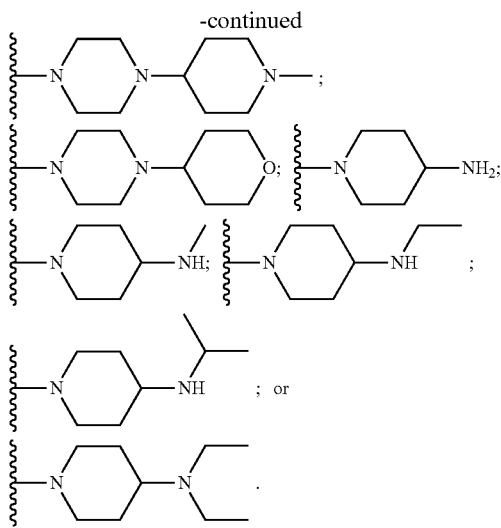

9. The compound of claim 5, wherein at least one X is selected from —N($R^1$)-alkylene-CNH—$NH_2$, —N($R^1$)-alkylene-N($R^1$)$_2$, —N($R^1$)-alkylene-N($R^2$)$_3$, —N($R^1$)-alkylene-heterocyclyl, —N($R^1$)-alkylene-N(O)($R^2$)$_2$, and —N($R^1$)-alkylene-NH—CNH—$NH_2$.

10. The compound of claim 5, wherein at least one X is selected from —O-alkylene-aryl, —N($R^1$)-aryl, —N($R^1$)-alkylene-aryl, —N($R^1$)-alkylene-N($R^1$)-aryl, —N($R^1$)-alkylene-N($R^1$)CO-aryl, —N($R^1$)-alkylene-N($R^1$)$SO_2$-aryl, and —N($R^1$)-alkylene-N($R^1$)$CH_2$-aryl.

11. The compound of claim 5, wherein at least one X is selected from —O-alkylene-heteroaryl, —N($R^1$)-alkylene-heteroaryl, —N($R^1$)-alkylene-N($R^1$)-heteroaryl, —N($R^1$)-alkylene-N($R^1$)CO-heteroaryl, —N($R^1$)-alkylene-N($R^1$)$SO_2$-heteroaryl, and —N($R^1$)-alkylene-N($R^1$)$CH_2$-heteroaryl.

12. The compound of claim 5, wherein at least one X is selected from -L1-heteroaryl, -L1-alkylene-heteroaryl, -L1-arylene-heteroaryl, -L1-CO-alkylene-heteroaryl, -L1-CO-alkenylene-heteroaryl, -L1-CO-arylene-heteroaryl, -L1-CONH-alkylene-heteroaryl, -L1-CONH-arylene-heteroaryl, -L1-$SO_2$-alkylene-heteroaryl, -L1-$SO_2$-arylene-heteroaryl.

13. The compound of claim 5, wherein at least one X is -L1-CO-alkyl.

14. The compound of claim 5, wherein at least one X is X8.

15. The compound of claim 5, wherein $Z^5$ is -($L^{11}$)-($R^{15}$) wherein $R^{15}$ is selected from —C(=O)$OCH_2CH_2OH$, —C(=O)$OCH_2CH_2OCH_2CH_2OH$, or —C(=O)$OCH_2CH_2OCH_2CH_2OCH_2CH_2OH$.

16. The compound of claim 15, wherein $Z^5$ is

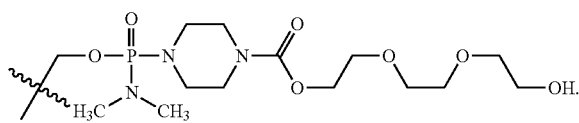

* * * * *